(12) United States Patent
Makriyannis et al.

(10) Patent No.: US 11,964,956 B2
(45) Date of Patent: *Apr. 23, 2024

(54) CANNABINERGIC COMPOUNDS AND USES THEREOF

(71) Applicant: Northeastern University, Boston, MA (US)

(72) Inventors: Alexandros Makriyannis, Watertown, MA (US); Spyridon P. Nikas, Newton, MA (US); Ganeshsingh A. Thakur, Boston, MA (US); Rishi Sharma, Revere, MA (US); Shashank Kulkarni, Billerica, MA (US)

(73) Assignee: Northeastern University, Boston, MA (US)

( * ) Notice: Subject to any disclaimer, the term of this patent is extended or adjusted under 35 U.S.C. 154(b) by 397 days.

This patent is subject to a terminal disclaimer.

(21) Appl. No.: 17/119,836

(22) Filed: Dec. 11, 2020

(65) Prior Publication Data

US 2021/0101878 A1 Apr. 8, 2021

Related U.S. Application Data

(63) Continuation-in-part of application No. 16/241,424, filed on Jan. 7, 2019, now Pat. No. 10,882,838, which is a continuation of application No. 14/426,257, filed as application No. PCT/US2012/053929 on Sep. 6, 2012, now abandoned.

(51) Int. Cl.
| | | |
|---|---|---|
| *C07D 311/80* | (2006.01) | |
| *C07C 57/58* | (2006.01) | |
| *C07C 255/57* | (2006.01) | |
| *C07D 405/12* | (2006.01) | |
| *C07D 407/04* | (2006.01) | |
| *C07D 493/04* | (2006.01) | |

(52) U.S. Cl.
CPC ............ *C07D 311/80* (2013.01); *C07C 57/58* (2013.01); *C07C 255/57* (2013.01); *C07D 405/12* (2013.01); *C07D 407/04* (2013.01); *C07D 493/04* (2013.01)

(58) Field of Classification Search
CPC ..... C07C 311/80; C07C 57/58; C07D 407/04; C07D 405/12; C07D 493/04
See application file for complete search history.

(56) References Cited

U.S. PATENT DOCUMENTS

| | | | |
|---|---|---|---|
| 5,219,747 | A | 6/1993 | McNally et al. |
| 7,115,661 | B1 | 10/2006 | Thatcher et al. |
| 7,745,424 | B2 | 6/2010 | Ralston et al. |
| 9,580,400 | B2 | 2/2017 | Makriyannis et al. |
| 10,221,164 | B2 | 3/2019 | Makriyannis et al. |
| 10,882,838 | B2 * | 1/2021 | Makriyannis ........ C07D 407/04 |
| 10,968,206 | B2 | 4/2021 | Makriyannis et al. |
| 2007/0032544 | A1 | 2/2007 | Korthout et al. |
| 2007/0060638 | A1 | 3/2007 | Olmstead et al. |
| 2010/0152283 | A1 | 6/2010 | Grant |
| 2016/0108016 | A1 | 4/2016 | Makriyannis et al. |
| 2017/0210728 | A1 | 7/2017 | Makriyannis et al. |
| 2019/0185443 | A1 | 6/2019 | Makriyannis et al. |
| 2019/0225596 | A1 | 7/2019 | Makriyannis et al. |

FOREIGN PATENT DOCUMENTS

| | | |
|---|---|---|
| WO | WO 2007/136607 | 11/2007 |
| WO | WO 2014039042 | 3/2014 |
| WO | WO 2014/134127 | 9/2014 |

OTHER PUBLICATIONS

Bodor, et al., "Soft Drug Design: General Principles and Recent Applications," Medical Research Reviews, vol. 20, No. 1, pp. 58-101, 2000.
Boehncke, et al. "Concise International Chemical Assessment Document 6: Biphenyl," World Health Organization, 41 pages, 1999.
Bolla. M. et al. "Therapeutic Potential of Nitrate Esters of Commonly Used Drugs." Current Topics in Medicinal Chemistry. 2005. vol. 5. pp. 707-720.
Buchwald, A., et al., "Soft cannabinoid analogues as potential anti-glaucoma agents," Pharmazie, vol. 55, No. 3, pp. 196-201, Mar. 2000.
Buchwald, A., et al., "Soft cannabinoid analogues as potential anti-glaucoma agents," Pharmazie, vol. 57, No. 2, pp. 108-114, Feb. 2002.
Chang, C. A. et al. "Homology Modeling of Cannabinoid Receptors: Discovery of Cannabinoid Analogues for Therapeutic Use." Computational Drug Discovery and Design, Methods in Molecular Biology, Riccardo Baron (ed.). 2012. vol. 819. Chapter 35. pp. 595-611.
Database Registry Chemical Abstracts Service, Columbus, Ohio, Accession No. RN 36235-17-3, Entered STN: Nov. 16, 1984.
Database Registry Chemical Abstracts Service, Columbus, Ohio, Accession No. RN 131318-15-5, 131318-16-6, 131318-17-7, Entered STN: Jan. 11, 1991.
Davis, M.P., "Oral nabilone capsules in the treatement of chemotherapy-induced nausea and vomiting and pain", 17:1, 85-95, 2007.
Fattore, L. et al. "Beyond THC: the new generation of cannabinoid designer drugs." Frontiers in Behavioral Neuroscience. 2011. vol. 5. Article 60, pp. 1-12.
Final Office Action for U.S. Appl. No. 14/426,257, entitled: "Novel Cannabinergic Compounds and Uses Thereof," dated Nov. 1, 2017.
Final Office Action for U.S. Appl. No. 15/401,791, entitled: "Cannabinergic Nitrate Esters and Related Analogs," dated Feb. 21, 2018.

(Continued)

*Primary Examiner* — Theodore R. Howell
*Assistant Examiner* — George W Kosturko
(74) *Attorney, Agent, or Firm* — Hamilton, Brook, Smith & Reynolds, P.C.

(57) ABSTRACT

Disclosed are compounds and compositions that modulate cannabinoid receptors, methods of modulating cannabinoid receptors, and methods of treating various disorders related to the modulation of cannabinoid receptors. This disclosure is directed to methods of treating cannabinoid dependence, neuropathy, inflammation, glaucoma, a neurodegenerative disorder, a motor function disorder, a gastrointestinal disorder, hypothermia, emesis, loss of appetite, or anorexia associated with AIDS.

30 Claims, 4 Drawing Sheets

(56) References Cited

OTHER PUBLICATIONS

Final Office Action for U.S. Appl. No. 16/240,190, entitled: "Cannabinergic Nitrate Esters and Related Analogs," dated Sep. 30, 2020.
Final Office Action for U.S. Appl. No. 16/240,190, entitled: "Cannabinergic Nitrate Esters and Related Analogs," dated May 28, 2020.
International Preliminary Report on Patentability for International Application No. PCT/US2012/053929, entitled: "Novel Cannabinergic Compounds and Uses Thereof," dated Mar. 10, 2015.
International Preliminary Report on Patentability for International Application No. PCT/US2014/018582, entitled: "Cannabinergic Nitrate Esters and Related Analogs," dated Sep. 11, 2015.
International Search Report and Written Opinion for International Application No. PCT/US2012/053929, entitled: "Novel Cannabinergic Compounds and Uses Thereof," dated Nov. 13, 2012.
International Search Report and Written Opinion for International Application No. PCT/US2014/018582, entitled: "Cannabinergic Nitrate Esters and Related Analogs," dated Jun. 27, 2014.
Ito, N., et al., "A medium-term rat liver bioassay for rapid in vivo detection of carcinogenic potential of chemicals", Cancer Sci, 94(1): 3-8 (Jan. 2003).
Khanolkar, A. D. et al. "Cannabilactones: A Novel Class of CB2 Selective Agonists with Peripheral Analgesic Activity." J. Med. Chem. 2007. vol. 50. pp. 6493-6500.
Kulkarni, S., et al., "Novel C-Ring-Hydroxy-Substituted Controlled Deactivation Cannabinergic Analogue", J. Med. Chem., 2016, 59-6903-6919.
Mercier, R. IV. et al. "Human Cannabinoid 2 GPCR Ligand-interaction Landscape: Cysteine Residues Critical to Biarylpyrazole Antagonist Binding Motif and Receptor Modulation." Chem Biol. 2010. vol. 17, No. 10, pp. 1132-1142.
Minutolo, F., et al., "Metabolically labile cannabinoid esters: A 'soft drug' approach for the development of cannabinoid-based therapeutic drugs," Bioorganic & Medicinal Chemistry Letters, vol. 17, No. 17, pp. 4878-4881, 2007.

Non-Final Office Action for U.S. Appl. No. 14/426,257, entitled: "Novel Cannabinergic Compounds and Uses Thereof ," dated Aug. 8, 2018.
Non-Final Office Action for U.S. Appl. No. 14/426,257, entitled: "Novel Cannabinergic Compounds and Uses Thereof ," dated Apr. 18, 2017.
Non-Final Office Action for U.S. Appl. No. 15/401,791, entitled: "Cannabinergic Nitrate Esters and Related Analogs," dated May 29, 2018.
Non-Final Office Action for U.S. Appl. No. 15/401,791, entitled: "Cannabinergic Nitrate Esters and Related Analogs," dated Aug. 31, 2017.
Non-Final Office Action for U.S. Appl. No. 16/240,190, entitled: "Cannabinergic Nitrate Esters and Related Analogs," dated Nov. 27, 2019.
Non-Final Office Action for U.S. Appl. No. 16/241,424 entitled: "Novel Cannabinergic Compounds and Uses Thereof," dated Dec. 30, 2019.
Notice of Allowance for U.S. Appl. No. 16/241,424 entitled: "Novel Cannabinergic Compounds and Uses Thereof," dated Aug. 12, 2020.
Notice of Allowance for U.S. Appl. No. 14/770,331, entitled: "Cannabinergic Nitrate Esters and Related Analogs," dated Oct. 11, 2016.
Notice of Allowance for U.S. Appl. No. 15/401,791, entitled: "Cannabinergic Nitrate Esters and Related Analogs," dated Oct. 11, 2018.
Stark, P., et al. "Cannabinoids. I. Behavioral Effects," The Journal of Pharmacology and Experimental Therapeutics, vol. 214, No. 1, pp. 124-130, 1980.
Sullivan, H.R., et al., "Pharmacokinetics of Nabilone, a Psychotropically Active 9-Ketocannabinoid, in the Dog. Utilization of Quantitative Selected Ion Monitoring and Deuterium Labeling," Biomedical Mass Spectrometry, vol. 5, No. 4, pp. 296-301, 1978.
Wey, S.J., et al., "Structure-Based Design, Synthesis, and Biological Evaluation of Indomethacin Derivatives as Cyclooxygenase-2 Inhibiting Nitric Oxide Donors", J. Med. Chem., 2007, 50, 6367-6382.
Notice of Allowance for U.S. Appl. No. 16/240,190 entitled: "Cannabinergic Nitrate Esters and Related Analogs," dated Nov. 25, 2020.

* cited by examiner

CANNABINERGIC COMPOUNDS AND USES THEREOF

RELATED APPLICATIONS

This application is a continuation-in-part of U.S. application Ser. No. 16/241,424, filed Jan. 7, 2019, which is a continuation of U.S. application Ser. No. 14/426,257, filed Nov. 25, 2015, now abandoned, which is the U.S. National Stage application of International Patent Application No. PCT/US2012/053929, filed Sep. 6, 2012. The entire teachings of these applications are incorporated herein by reference.

STATEMENT REGARDING FEDERALLY SPONSORED RESEARCH

This invention was made with government support under Grant DA026795 awarded by the National Institutes of Health. The government has certain rights in the invention.

FIELD OF THE INVENTION

The present disclosure is in the field of medicinal chemistry. More specifically, this disclosure relates to cannabinoid derivatives and the use of such compounds in methods for treating cannabinoid dependence, pain, inflammation, neuropathy, neurodegenerative disease, anxiety disorder, motor function disorder, fertility disorder, gastrointestinal disorder, appetite disorder, metabolic disorder, movement disorder, and cancer.

BACKGROUND

Presently, two $G_{i/o}$ protein coupled cannabinoid receptors have been characterized in mammals and other organisms: CB1, a central receptor found in the mammalian brain and a number of other sites in peripheral tissues; and CB2, a peripheral receptor found principally in cells related to the immune system. Compounds known as cannabinergic ligands bind to CB1 and/or CB2 receptors in a subject. In vitro methods for assaying the ability of a compound to bind to CB1 and/or CB2 receptors are known and results from these assays correlate with, and predict, the in vivo ability of that compound to bind to, and thereby modulate, CB1 and/or CB2 receptors.

Despite having a rapid onset of action, the magnitude and duration of in vivo CB1 and/or CB2 receptor modulation by many cannabinergic ligands such as Dronabinol and Nabilone are unpredictable due to pharmacokinetic liabilities and erratic pharmacodynamic profiles. For example, Dronabinol and Nabilone have high lipophilicity (c log P>7), leading to large volume of distribution ($V_d$), high levels of protein binding (≥97%) and unpredictable time course of action. Dronabinol exhibits slow and erratic absorption (up to 2-6 h) and is metabolized to yield active cannabinergic ligands (e.g., 11-OH-$\Delta^9$-THC), leading to unpredictable and long half life. As a result, dose titration for such drugs is complicated. In addition, both Dronabinol and Nabilone produce physiological effects comparable to those of marijuana, and can confer tolerance that may be associated with increased dependence liability. A need exists for compounds that modulate cannabinoid receptors with improved pharmacokinetic and pharmacodynamic properties.

SUMMARY OF THE INVENTION

It has been discovered that certain chemical compounds can modulate the cannabinoid receptors. It has also been shown that drug molecules can be modified so that they have controlled duration of action. These discoveries have been exploited to develop the present application, which includes novel compounds and therapeutic compositions for modulating cannabinoid receptors, methods for modulating cannabinoid receptors, methods for modulating the duration of action of these compositions, and methods for treating various disorders in a subject.

One aspect of the application is directed to cannabinoid derivatives according to formula (I), (II), or (III):

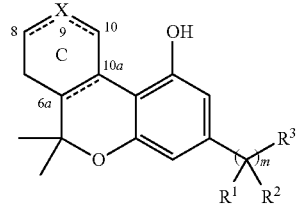

(I)

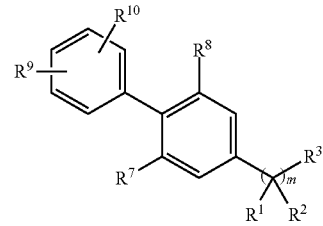

(II)

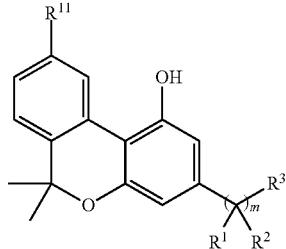

(III)

wherein, '-----' can be a single bond or a double bond, provided that no more than one double bond is present in C ring of Formula (I);

when, '-----' between C8-C9 or C9-C10 is a single bond, X is —C(O)—, —CH(OH)—, —C(O)O—, —OC(O)—, —CHCH$_2$OR$^{12}$, —CHOCOR$^{12}$, CHCO$_2$R$^{12}$, or CHR$^{12}$;

when, '-----' between C8-C9 or C9-C10 is a double bond, X is —C(CH$_3$)—, —CCH$_2$OH, —COCOH, or —CCO$_2$R$^4$ R$^1$ and R$^2$ are independently H, —(C$_1$-C$_2$)-alkyl, —OH, or —CH$_2$CO$_2$H, wherein R$^1$ and R$^2$ are both not simultaneously OH, or R$^1$ and R$^2$ together with the carbon to which they are attached form a —(C$_3$-C$_6$)-cycloalkyl or a —(C$_3$-C$_6$)-lactone;

R$^3$ is R$^4$, —CH$_2$OH, —CO$_2$H, —C(O)SR$^4$, —C(O)N(R$^6$) R$^4$, —OC(O)R$^4$, —(C$_1$-C$_3$ alkyl)-OC(O)R$^4$, —C(O) OR$^4$, or —(C$_1$-C$_3$ alkyl)-C(O)OR$^4$, provided that when R$^3$ is R$^4$, then either X is —C(O)O— or —OC(O)—, or R$^1$ and R$^2$ together with the carbon to which they are attached form a —(C$_3$-C$_6$)-lactone so that at least one ester group is present in Formula (I);

R$^4$ is —(C$_1$-C$_8$)-alkyl-R$^5$, —(C$_1$-C$_8$)-alkenyl-R$^5$, or —(C$_1$-C$_8$)-alkynyl-R$^5$;

$R^5$ is H, halogen, —OH, —O—$(C_1$-$C_6)$-alkyl, —O—$(C_1$-$C_6)$-alkenyl, —O—$(C_1$-$C_6)$-alkynyl, —CN, —$N_3$, —NCS, —$SO_2NH_2$, —$SO_2CF_3$, imidazole, oxazole, isoxazole, 1,2,3-triazole, 1,2,4-triazole, morpholine, thiomorpholine, $$-N\diagdown S=O, \quad -N\diagdown S\diagup_O^O, \quad \text{or}$$

$$-N\diagdown N-\text{H, Me, or Et,}$$

wherein —O—$(C_1$-$C_6)$-alkyl, —O—$(C_1$-$C_6)$-alkenyl, and —O—$(C_1$-$C_6)$-alkynyl are optionally substituted with —CN, —$N_3$, or —NCS;

$R^6$ is H or —$(C_1$-$C_2)$-alkyl;

$R^7$ and $R^8$ are independently H, halogen, CN, —$(C_1$-$C_2)$-alkyl, OH, or —O—$(C_1$-$C_2)$-alkyl;

$R^9$ and $R^{10}$ are independently H, halogen, —OH, —O—$(C_1$-$C_6)$-alkyl, —O—$(C_1$-$C_6)$-alkenyl, —O—$(C_1$-$C_6)$-alkynyl, —CN, —$N_3$, —NCS, —$SO_2NH_2$, —$SO_2CF_3$, imidazole, oxazole, isoxazole, 1,2,3-triazole, 1,2,4-triazole, morpholine, thiomorpholine, $$-N\diagdown S=O, \quad -N\diagdown S\diagup_O^O, \quad \text{or}$$

$$-N\diagdown N-\text{H, Me, or Et,}$$

wherein —O—$(C_1$-$C_6)$-alkyl, —O—$(C_1$-$C_6)$-alkenyl, and —O—$(C_1$-$C_6)$-alkynyl are optionally substituted with —CN, —$N_3$, or —NCS;

$R^{11}$ is H, —$(CH_2)_p$-halogen, —$(CH_2)_p$—CN, —$(CH_2)_p$OH, or —$(C_1$-$C_2)$-alkyl, in which p is 0, 1, or 2;

$R^{12}$ is H or $(C_1$-$C_6)$-alkyl; and m is 0, 1, or 2;

or a pharmaceutically acceptable salt thereof;

with the proviso that when X is —C($CH_3$)—, $R^3$ is $CO_2H$ and $R^1$ is H or methyl, then $R^2$ is not hydrogen; and when X is —C($CH_2OH$)—, $R^1$ and $R^2$ are —$(C_1$-$C_2)$-alkyl, and $R^3$ is —C(O)$OR^4$, —$(C_1$-$C_3$ alkyl)C(O)$OR^4$, —OC(O)$R^4$, or —$(C_1$-$C_3$ alkyl)OC(O)$R^4$, then $R^5$ is not hydrogen.

In some embodiments, the cannabinoid derivatives are compounds of formula (I). In some embodiments, the cannabinoid derivatives are compounds of formula (II). In some embodiments, the cannabinoid derivatives are compounds of formula (III).

One aspect of the application is directed to compounds according to formula (Id) or (Ie):

(Id)

(Ie)

or a pharmaceutically acceptable salt thereof, wherein:
R is

A is —C(O)—O—, —O—C(O)—, —C(O)—S—, —S—C(O)—, —C(O)—NH—, —NH—C(O)—, —$NHSO_2$—, or —$SO_2$—NH—;

$R^{13}$ and $R^{14}$ are independently H, methyl or fluoro, or $R^{13}$ and $R^{14}$ together with the carbon to which they are attached form a ($C_3$-$C_6$)cycloalkyl or ($C_3$-$C_6$) heterocyclyl containing one or two heteroatoms independently selected from O, S or N, wherein each N, when present, is optionally and independently substituted with methyl;

$R^{15}$ is H, fluoro, methyl or ethyl;

$R^{16}$ is H, halo, ($C_1$-$C_3$)alkyl, ($C_1$-$C_3$)haloalkyl, —NCS, —$N_3$, —CN, —$NO_2$, —$ONO_2$, —$SO_2F$, —OH, —O—($C_1$-$C_6$)alkyl, —SH, —S—($C_1$-$C_6$)alkyl, —$NH_2$, —N(H)($C_1$-$C_6$)alkyl, —N[($C_1$-$C_6$)alkyl]$_2$, or ($C_3$-$C_6$)heterocyclyl;

i is 0, 1, 2, 3, 4 or 5; and j is 0, 1, 2, 3, 4, 5 or 6.

In some embodiments, the CB1 receptor, the CB2 receptor or both receptors are modulated. In some embodiments, the CB1 receptor is modulated. In some embodiments, the CB2 receptor is modulated. In some embodiments, both receptors are modulated.

In still further embodiments, the compounds of formula (I), (II), or (III) are compounds listed in the below Examples. In still further embodiments, the compounds of formula (Id) or (Ie) are compounds listed in the below Examples.

In another aspect, the disclosure is directed to methods of treating cannabinoid dependence, neuropathy, inflammation, glaucoma, a neurodegenerative disorder, a motor function disorder, a gastrointestinal disorder, hypothermia, emesis, loss of appetite, or anorexia associated with AIDS in a subject comprising administration of a compound of formula (I), (II) or (III). In some embodiments, a therapeutically effective amount of a compound of formula (I) is administered. In some embodiments, a therapeutically effective amount of a compound of formula (II) is administered. In some embodiments, a therapeutically effective amount of a compound of formula (III) is administered.

A further aspect of the disclosure is directed to methods of treating neuropathy in a subject. In these methods, a therapeutically effective amount of a compound of formula (I), (II) or (III) is administered to the subject. In some embodiments, a therapeutically effective amount of a compound of formula (I) is administered. In some embodiments, a therapeutically effective amount of a compound of formula (II) is administered. In some embodiments, a therapeutically effective amount of a compound of formula (III) is administered. In some embodiments, administration of the compound treats neuropathy in the subject. In some embodiments, the neuropathy is inflammation, pain, neuropathic pain, neuropathic low back pain, complex regional pain syndrome, post trigeminal neuralgia, causalgia, toxic neuropathy, reflex sympathetic dystrophy, diabetic neuropathy, chronic neuropathy caused by chemotherapeutic agents, central pain, peripheral pain, pellagric neuropathy, alcoholic neuropathy, Beriberi neuropathy, or burning feet syndrome.

In yet other embodiments, the neuropathy is a neurodegenerative disorder. In particular embodiments, the neurodegenerative disease is multiple sclerosis, Parkinson's disease, Huntington's chorea, Alzheimer's disease, amyotrophic lateral sclerosis (ALS), memory disorder, mood disorder, sleep disorder, gastrointestinal motility disorder, irritable bowel syndrome, diarrhea, cardiovascular disease, hypertension, osteoporosis, osteoarthritis, emesis, epilepsy, a mental disorder, schizophrenia, depression, glaucoma, cachexia, insomnia, traumatic brain injury, spinal cord injury, seizures, excitotoxin exposure, ischemia, or AIDS wasting syndrome.

An additional aspect of the application is directed to methods of treating a motor function disorder in a subject. The methods comprise administering to the subject a therapeutically effective amount of a compound of formula (I), (II) or (III). The administration of the compound treats the motor function disorder of the subject. In some embodiments, a therapeutically effective amount of a compound of formula (I) is administered. In some embodiments, a therapeutically effective amount of a compound of formula (II) is administered. In some embodiments, a therapeutically effective amount of a compound of formula (III) is administered. In some embodiments, the motor function disorder is Tourette's syndrome.

Another aspect of the application is directed to methods of treating an anxiety disorder in a subject. The methods comprise administering to the subject a therapeutically effective amount of a compound of formula (I), (II) or (III). The administration of the compound treats the anxiety disorder of the subject. In some embodiments, a therapeutically effective amount of a compound of formula (I) is administered. In some embodiments, a therapeutically effective amount of a compound of formula (II) is administered. In some embodiments, a therapeutically effective amount of a compound of formula (III) is administered. In certain embodiments, the anxiety disorder is panic disorder, acute stress disorder, posttraumatic stress disorder, substance-induced anxiety disorder, obsessive compulsive disorder, agoraphobia, specific phobia, or social phobia.

In yet another aspect, the disclosure is directed to methods of treating an appetite disorder in a subject. The methods comprise administering to the subject a therapeutically effective amount of a compound of formula (I), (II) or (III). The administration of the compound treats the appetite disorder, the metabolic disorder, or the movement disorder of the subject. In some embodiments, a therapeutically effective amount of a compound of formula (I) is administered. In some embodiments, a therapeutically effective amount of a compound of formula (II) is administered. In some embodiments, a therapeutically effective amount of a compound of formula (III) is administered.

In another aspect, the disclosure is directed to a method of treating a metabolic disorder in a subject. The methods comprise administering to the subject a therapeutically effective amount of a compound of formula (I), (II) or (III). The administration of the compound treats the metabolic disorder of the subject. In some embodiments, a therapeutically effective amount of a compound of formula (I) is administered. In some embodiments, a therapeutically effective amount of a compound of formula (II) is administered. In some embodiments, a therapeutically effective amount of a compound of formula (III) is administered.

In still another aspect, the disclosure is directed to methods of treating a movement disorder in a subject. The methods comprise administering to the subject a therapeutically effective amount of a compound of formula (I), (II) or (III). The administration of the compound treats the movement disorder of the subject. In some embodiments, a therapeutically effective amount of a compound of formula (I) is administered. In some embodiments, a therapeutically effective amount of a compound of formula (II) is administered. In some embodiments, a therapeutically effective amount of a compound of formula (III) is administered.

In another aspect, the disclosure is directed to methods of treating pain; central pain; peripheral pain; neuropathic pain; a neuropathy; inflammatory pain; diabetes; a neurodegenerative disease; multiple sclerosis; Parkinson's disease; Huntington's chorea; Alzheimer's disease; amyotrophic lateral sclerosis; a mental disorder; schizophrenia; depression; a mood disorder; an addiction disorder; a sleep disorder; a memory disorder; a gastrointestinal motility disorder; irritable bowel syndrome; diarrhea; dyskinesia; migraine; headache; brain injury; traumatic brain injury; post-traumatic stress disorder, osteoporosis; osteoarthritis; high blood pressure disease or hypertension; peripheral vascular disease; coronary artery disease; abnormal heart rate; cardiac insufficiency; pulmonary hypertension; ocular hypertension or glaucoma; endotoxic shock; hypotensive shock; an appetite disorder; an immune system disorder; a fertility disorder; a disease associated with motor dysfunction; Tourette's syndrome; inflammation; a neurological disorder; epilepsy; nausea; nausea associated with cancer chemotherapy; AIDS wasting syndrome; or cancer in a subject (e.g., a subject in need thereof). The methods comprise administration of a compound of formula (Id) or (Ie), or a pharmaceutically acceptable salt thereof, (e.g., a therapeutically effective amount of a compound of formula (Id) or (Ie), or a pharmaceutically acceptable salt thereof), to the subject. In some embodiments, a therapeutically effective amount of a compound of formula (Id), or a pharmaceutically acceptable salt thereof, is administered. In some embodiments, a therapeutically effective amount of a compound of formula (Ie), or a pharmaceutically acceptable salt thereof, is administered.

Still other objects and advantages of the invention will become apparent to those of skill in the art from the disclosure herein, which is simply illustrative and not restrictive. Thus, other embodiments will be recognized by the skilled artisan without departing from the spirit and scope of the invention

BRIEF DESCRIPTION OF THE FIGURES

The following figures are illustrative only and not intended to be limiting.

DETAILED DESCRIPTION

Figure 1A:
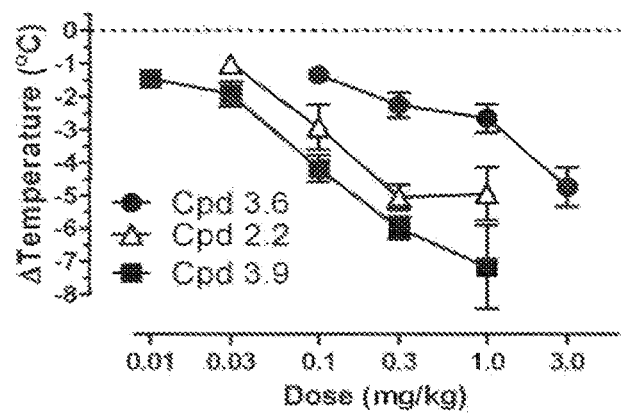
FIGS. 1A-1E show rat hypothermia test results for compounds 2.2, 3.6, and 3.9 (FIG. 1A); 1.1, 1.2, 1.3, and 1.33 (FIG. 1B); 1.14 and 1.16 (FIG. 1C); 1.20, 1.28, and 1.35 (FIG. 1D); and 1.1, 1.6, 1.10, and 1.1, 1.6, 1.10, and 1.25 (FIG. 1E).

This application relates to compounds that modulate cannabinoid receptors, to methods for modulating cannabinoid receptors, methods for modulating the duration of action of the compound to processes for the preparation of these compounds, to pharmaceutical compositions comprising these compounds, and to methods for treating cannabinoid dependence, inflammation, pain, neuropathy, glaucoma, central nervous system disorders, gastrointestinal disorders, and neurodegenerative disorders; brain trauma, post traumatic stress disorders (PTSD).

1. Definitions

The compounds of this disclosure include any and all possible isomers including but not limited to stereoisomers, enantiomers, diastereomers, and tautomers thereof. The compounds of this disclosure also include any and all pharmaceutically-acceptable salts thereof. Thus, the terms "compound" and "compounds" as used in this disclosure refer to the compounds of this disclosure and any and all possible isomers, stereoisomers, enantiomers, diastereomers, tautomers, and pharmaceutically-acceptable salts thereof.

In general, the compositions of the disclosure can be alternately formulated to comprise, consist of, or consist essentially of, any appropriate components disclosed in this application. The compositions of the disclosure can additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The articles "a" and "an" are used in this disclosure to refer to one or more than one (i.e., to at least one) of the grammatical object of the article. By way of example, "an element" means one element or more than one element.

The term "or" is used in this disclosure to mean, and is used interchangeably with, the term "and/or," unless indicated otherwise.

The term "about" is used in this disclosure to mean a value − or +20% of a given numerical value. Thus, "about 60%" means a value between 60-20% of 60 and 60+20% of 60 (i.e., between 48% and 72%).

Unless otherwise specifically defined, "alcohol" refers to the general formula alkyl-OH and includes primary, secondary and tertiary variations.

Unless otherwise specifically defined, the terms "alkyl" and "alk" refer to a straight or branched chain alkane (hydrocarbon) radical containing from 1 to 15 carbon atoms. Exemplary "alkyl" groups include, but are not limited to, methyl ("Me"), ethyl ("Et"), propyl, isopropyl, n-butyl, t-butyl, sec-butyl, isobutyl, pentyl, hexyl, isohexyl, heptyl, 4,4-dimethylpentyl, 1,1-dimethylpentyl, 1,2-dimethylheptyl, octyl, 2,2,4-trimethylpentyl, nonyl, decyl, undecyl, dodecyl, and the like. The alkyl group may be optionally substituted with one or more substituents, e.g., 1 to 5 substituents, at any available point of attachment. Exemplary substituents include, but are not limited to, one or more of the following groups: hydrogen, halogen (e.g., a single halogen substituent or multiple halo substituents forming, in the latter case, groups such as $CF_3$), cyano, nitro, $CHF_2$, $OCHF_2$, $CH_2F$, $OCH_2F$, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each $R_a$ is hydrogen, alkyl, cycloalkyl, alkenyl, cycloalkenyl, alkynyl, heterocycle, or aryl; $R_b$, $R_c$ and $R_d$ are each independently hydrogen, alkyl, cycloalkyl, heterocycle, aryl, or said $R_b$ and $R_c$ together with the N to which they are bonded optionally form a heterocycle or substituted heterocycle; and each $R_e$ is alkyl, cycloalkyl, alkenyl, cycloalkenyl, alkynyl, heterocycle, or aryl. In the aforementioned exemplary substituents, groups such as alkyl, cycloalkyl, alkenyl, alkynyl, cycloalkenyl, heterocycle and aryl can themselves be optionally substituted. The term "$C_1$-$C_n$-alkyl" refers to a straight or branched chain alkane (hydrocarbon) radical containing from 1 to n carbon atoms. For example, the term "$C_1$-$C_5$-alkyl" refers to a straight or branched chain alkane (hydrocarbon) radical containing from 1 to 5 carbon atoms, such as methyl, ethyl, propyl, isopropyl, n-butyl, t-butyl, isobutyl, etc.

Unless otherwise specifically defined, the term "alkenyl" refers to a straight or branched chain hydrocarbon radical containing from 2 to 15 carbon atoms and at least one carbon-carbon double bond. Exemplary such groups include, but are not limited to, ethenyl (also called "vinyl"), allyl, propenyl, crotyl, 2-isopentenyl, allenyl, butenyl, butadienyl, pentenyl, pentadienyl, 3(1,4-pentadienyl), hexenyl and hexadienyl. The alkenyl group may be optionally substituted with one or more substituents, e.g., 1 to 5 substituents, at any available point of attachment. Exemplary substituents include, but are not limited to, alkyl or substituted alkyl, as well as those groups recited above as exemplary alkyl substituents. The exemplary substituents can themselves be optionally substituted.

Unless otherwise specifically defined, the term "alkynyl" refers to a straight or branched chain hydrocarbon radical containing from 2 to 15 carbon atoms and at least one carbon-carbon triple bond. Exemplary such groups include, but are not limited to, ethynyl, propynyl and butynyl. The alkynyl group may be optionally substituted with one or more substituents, e.g., 1 to 5 substituents, at any available point of attachment. Exemplary substituents include, but are not limited to, alkyl or substituted alkyl, as well as those groups recited above as exemplary alkyl substituents. The exemplary substituents can themselves be optionally substituted.

Unless otherwise specifically defined, the term "aryl" refers to cyclic, aromatic hydrocarbon groups that have 1 to 5 aromatic rings, including monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). The aryl group may be optionally substituted by one or more substituents, e.g., 1 to 5 substituents, at any point of attachment. Exemplary substituents include, but are not limited to, halogen, nitro, cycloalkyl or substituted cycloalkyl, cycloalkenyl or substituted cycloalkenyl, cyano, alkyl, fused cyclic groups, fused cycloalkyl, fused cycloalkenyl, fused heterocycle, and fused aryl, and those groups recited above as exemplary alkyl substituents. The substituents can themselves be optionally substituted.

Unless otherwise specifically defined, the term "cycloalkyl" refers to a fully saturated cyclic hydrocarbon group containing from 1 to 4 rings and 3 to 8 carbons per ring. Exemplary such groups include, but are not limited to, cyclopropyl, cyclobutyl, cyclopentyl, cyclohexyl, cycloheptyl, adamantyl, etc. The cycloalkyl group may be optionally substituted with one or more substituents, e.g., 1 to 5 substituents, at any available point of attachment. Exemplary substituents include, but are not limited to, halogen, nitro, cyano, alkyl, spiro-attached or fused cyclic substituents, spiro-attached cycloalkyl, spiro-attached cycloalkenyl, spiro-attached heterocycle, fused cycloalkyl, fused cycloalkenyl, fused heterocycle, fused aryl, and those groups recited above as exemplary alkyl substituents. The substituents can themselves be optionally substituted.

Unless otherwise specifically defined, the terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms independently selected from nitrogen, oxygen and/or sulfur, where the nitrogen and sulfur heteroatoms may optionally be oxidized and the nitrogen heteroatoms may optionally be quaternized. The heterocyclic group may be attached to the remainder of the molecule at any heteroatom or carbon atom of the ring or ring system. Exemplary monocyclic heterocyclic groups include, but are not limited to, azetidinyl, pyrrolidinyl, pyrrolyl, pyrazolyl, oxetanyl, dioxanyl, dioxolanyl, oxathiolanyl, pyrazolinyl, imidazolyl, imidazolinyl, imidazolidinyl, oxazolyl, oxazolidinyl, isoxazolinyl, isoxazolyl, thietanyl, azetidine, diazetidine, thiolanyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, purinyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, and the like. Exemplary bicyclic heterocyclic groups include, but are not limited to, indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include, but are not limited to, carbazolyl, benzidolyl, phenanthrolinyl, acridinyl, phenanthridinyl, xanthenyl and the like.

A heterocyclic group may be optionally substituted with one or more substituents, e.g., 1 to 5 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl or substituted alkyl, spiro-attached or fused cyclic substituents at any available point or points of attachment, spiro-attached cycloalkyl, spiro-attached cycloalkenyl, spiro-attached heterocycle (excluding heteroaryl), fused cycloalkyl, fused cycloalkenyl, fused heterocycle, fused aryl, and those groups recited above as exemplary alkyl substituents. The substituents can themselves be optionally substituted.

A "pharmaceutical composition", as used herein, refers to a mixture of one or more of the compounds described herein, or pharmaceutically acceptable salts thereof, along with other chemical components, such as physiologically acceptable carriers and excipients. The purpose of a pharmaceutical composition is to facilitate administration of a compound to an organism.

The term "carrier", as used herein, refers to a diluent, adjuvant, excipient, or vehicle with which a compound is administered, and encompasses a material or materials involved in carrying or transporting a pharmaceutical agent from one organ, or portion of the body, to another organ, or portion of the body. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in "Remington's Pharmaceutical Sciences" by E. W. Martin (hereby incorporated by reference in its entirety).

The phrase "pharmaceutically acceptable" is employed in this disclosure to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids. Pharmaceutically acceptable salt forms may also include forms wherein the ratio of molecules comprising the salt is not 1:1. For example, the salt may comprise more than one inorganic or organic acid molecule per molecule of base, such as two hydrochloric acid molecules per molecule of compound of formula (I) or (II). As another example, the salt may comprise less than one inorganic or organic acid molecule per molecule of base, such as two molecules of compound of formula (I) or (II) per molecule of tartaric acid. Other exemplary pharmaceutically acceptable salts are described herein.

The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids, tricarboxylic acids, and fatty acids. Preferred acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, alpha-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tartaric acid and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The term "disorder" is used in this disclosure to mean, and is used interchangeably with, the terms disease, condition, or illness, unless otherwise indicated.

The terms "effective amount" and "therapeutically effective amount" as used in this disclosure refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

As used in this disclosure, the terms "subject" and "patient" include, without limitation, a human or an animal. Exemplary animals include, but are not limited to, mammals such as mouse, rat, guinea pig, dog, cat, horse, cow, pig, monkey, chimpanzee, baboon, or rhesus monkey.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used herein, means a compound which is convertible in vivo by metabolic means (e.g., by hydrolysis) to a compound of formula (I), (II) or (III).

The terms "isolated" and "purified" as used in this disclosure refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

2. Cannabinoid Compounds

Certain chemical compounds have been found to modulate cannabinergic receptors. These compounds may have selective affinity for the CB1 and/or CB2 cannabinoid receptors.

Examples of cannabinergic ligands that bind to CB1 and/or CB2 include, but are not limited to, N-arachidonoyl ethanolamine (also known as anandamide or AEA) and 2-arachidonoylglycerol (2-AG) (both endogenous ligands for the cannabinoid CB1 and CB2 receptors), (−)-$\Delta^9$-tetrahydrocannabinol (the principal bioactive constituent of cannabis and exogenous ligand for the cannabinoid CB1 and CB2 receptors) and other synthetic cannabinergic analogs.

Marijuana-like cannabinoids, in addition to acting at cannabinoid receptors, also affect cellular membranes, and are known to cause undesirable side effects such as drowsiness, impairment of monoamide oxidase function, and impairment of non-receptor mediated brain function. Thus, the addictive and psychotropic properties of some cannabinoids limit their therapeutic value. Compounds that modulate cannabinoid receptor activity may provide desirable pharmacological properties without the undesirable properties associated with conventional cannabinoids.

Herein, novel compounds were developed incorporating a soft-drug approach and modulation of polarity to discover novel cannabinergic ligands with controlled duration of action. Compounds developed using the dual approach have controlled duration of action and thus reduced potential for drug dependence and/or abuse. Soft drugs are isosteric variations of the longer acting prototypes that incorporate a moiety that is susceptible to metabolic action. The soft drugs incorporate key pharmacophoric features required for biological activity, coupled with suitable structural modifications to permit enzymatic transformation of the active soft drug to inactive or substantially less active metabolites. Soft-cannabinoid analogs have been reported wherein the only reported soft spot is an ester group in the side chain of the $\Delta^{6a-10a}$ tricyclic cannabinoid structure (See, e.g., *Med. Res. Rev.* 2000, 20(1), 58-101; Pharmazie 2000, 55(3), 196-201; and Pharmazie 2002, 57(2), 108-114; each herein incorporated by reference in its entirety), or in a biaryl cannabinoid derivative (See, e.g., *Bioorg. Med. Chem. Lett.* 2007, 17(17), 4878-4881; herein incorporated by reference in its entirety). However, these compounds exhibit sub-optimal affinity and potency at cannabinoid receptors with no demonstrated control of action. Exemplary soft drugs include remifentanil (Ultiva®), etomidate (Amidate®) and esmolol (Brevibloc®). Herein, exemplary labile moieties incorporated into the compounds are esters, thioesters or amide groups that can be targeted by ubiquitous carboxyesterase or amdiase enzymes that are expressed throughout the body in both organs and in the bloodstream.

However, modulation of polarity has not previously been studied in conjunction with the soft-drug approach. Incorporation of polar features within key pharmacophoric sides of cannabinoids reduce the depot effect and permit metabolic deactivation to proceed in a controlled manner. Thus, incorporation of a dual approach using a metabolic soft spot such as, for example, an ester, amide or thioester in key pharmacophoric sites such that inactivation occurs by non-tissue specific enzymes such as, for example, esterases and/or amidases, via an organ independent elimination mechanism provides for metabolic deactivation in a controlled manner after the desired pharmacological response is obtained. This provides potent cannabinergic ligands that demonstrate a less variable pharmacodynamic profile, conferring a reduced dependence and abuse potential.

The present disclosure provides novel chemical compounds of formulae (I), (II) and (III).

In some embodiments, ══ is a single bond. In some embodiments, ══ is a double bond. In some embodiments, ══ between C8-C9 is a single bond. In some embodiments, ══ between C8-C9 is a double bond. In some embodiments, ══ between C9-C10 is a single bond. In some embodiments, ══ between C9-C10 is a double bond. In some embodiments, ══ between C6a-C10a is a single bond. In some embodiments, ══ between C6a-C10a is a double bond.

In some embodiments, X is —C(O)—, —CH(OH)—, —C(O)O—, —OC(O)—, —CH(CH$_2$OR$^{12}$), CHOCOR$^{12}$, CHCO$_2$R$^{12}$, or CHR$^{12}$. In some embodiments, X is —C(O)—, —CH(OH)—, —C(O)O—, —OC(O)—, or —CH(CH$_2$OH). In some embodiments, X is —C(CH$_3$)—, —CCH$_2$OH, COCOH, or CCO$_2$R$^4$. In some embodiments, X is —C(CH$_3$)— or —C(CH$_2$OH)—. In some embodiments, X is —CH(OH)—, —C(O)O—, —OC(O)—, or —CH(CH$_2$OH)—. In some embodiments, X is —C(CH$_3$)—. In some embodiments, X is —C(CH$_2$OH)—.

In some embodiments, R$^1$ and R$^2$ are independently H, —(C$_1$-C$_2$)-alkyl, —OH, or —CH$_2$CO$_2$H, wherein R$^1$ and R$^2$ are both not simultaneously OH. In some embodiments, R$^1$ and R$^2$ together with the carbon to which they are attached form a —(C$_3$-C$_6$)-cycloalkyl or a —(C$_3$-C$_6$)-lactone. In some embodiments, R$^1$ and R$^2$ together with the carbon to which they are attached form a —(C$_3$-C$_6$)-cycloalkyl. In some embodiments, R$^1$ and R$^2$ together with the carbon to which they are attached form a —(C$_3$-C$_6$)-lactone. In some embodiments, R$^1$ and R$^2$ are independently H, methyl, —OH, or —CH$_2$CO$_2$H. In some embodiments, R$^1$ and R$^2$ are independently H or methyl. In some embodiments, R$^1$ and R$^2$ are each methyl. In some embodiments, R$^1$ and R$^2$ are each H.

In some embodiments, R$^3$ is R$^4$, —CH$_2$OH, —CO$_2$H, —C(O)SR$^4$, —C(O)N(R$^6$)R$^4$—OC(O)R$^4$, —(C$_1$-C$_3$ alkyl)-OC(O)R$^4$, —C(O)OR$^4$, or —(C$_1$-C$_3$ alkyl)-C(O)OR$^4$, provided that when R$^3$ is R$^4$, then either X is —C(O)O— or —OC(O)—, or R$^1$ and R$^2$ together with the carbon to which they are attached form a —(C$_3$-C$_6$)-lactone so that at least one ester group is present in Formula (I).

In some embodiments, R$^3$ is R$^4$, —CH$_2$OH, —C(O)SR$^4$, —C(O)N(R$^6$)R$^4$, —OC(O)R$^4$, —(C$_1$-C$_3$ alkyl)-OC(O)R$^4$, —C(O)OR$^4$, or —(C$_1$-C$_3$ alkyl)-C(O)OR$^4$, provided that when R$^3$ is R$^4$, then either X is —C(O)O— or —OC(O)—, or R$^1$ and R$^2$ together with the carbon to which they are attached form a —(C$_3$-C$_6$)-lactone so that at least one ester group is present in Formula (I).

In some embodiments, R$^3$ is R$^4$, —CH$_2$OH, —C(O)SR$^4$, —C(O)N(R$^6$)R$^4$, —OC(O)R$^4$, —(C$_1$-C$_3$ alkyl)-OC(O)R$^4$, —C(O)OR$^4$, or —(C$_1$-C$_3$ alkyl)-C(O)OR$^4$, provided that when R$^3$ is R$^4$, then either X is —C(O)O— or —OC(O)—, or R$^1$ and R$^2$ together with the carbon to which they are attached form a —(C$_3$-C$_6$)-lactone so that at least one ester group is present in Formula (I), and provided that when R$^3$ is —OC(O)R$^4$, —(C$_1$-C$_3$ alkyl)-OC(O)R$^4$, —C(O)OR$^4$, or —(C$_1$-C$_3$ alkyl)-C(O)OR$^4$, then R$^5$ is not hydrogen.

In some embodiments, R$^3$ is R$^4$, —CH$_2$OH, —C(O)SR$^4$, —C(O)N(R$^6$)R$^4$, —OC(O)R$^4$, —(C$_1$-C$_3$ alkyl)-OC(O)R$^4$, —C(O)OR$^4$, or —(C$_1$-C$_3$ alkyl)-C(O)OR$^4$, provided that when R$^3$ is R$^4$, then either X is —C(O)O— or —OC(O)—, or R$^1$ and R$^2$ together with the carbon to which they are attached form a —(C$_3$-C$_6$)-lactone so that at least one ester group is present in Formula (I), and provided that when R$^3$ is —OC(O)R$^4$, —(C$_1$-C$_3$ alkyl)-OC(O)R$^4$, —C(O)OR$^4$, or —(C$_1$-C$_3$ alkyl)-C(O)OR$^4$, then R$^5$ is not hydrogen.

In some embodiments, R$^3$ is R$^4$, —C(O)OR$^4$, —(CH$_2$)C(O)OR$^4$, —C(O)SR$^4$, —C(O)N(R$^6$)R$^4$, —OC(O)R$^4$, or —(CH$_2$)OC(O)R$^4$. In some embodiments, R$^3$ is R$^4$, —C(O)OR$^4$, —(C$_1$-C$_3$ alkyl)-C(O)OR$^4$, —C(O)SR$^4$, —C(O)N(R$^6$)R$^4$, —OC(O)R$^4$, or —(C$_1$-C$_3$ alkyl)-OC(O)R$^4$. In some embodiments, R$^3$ is R$^4$, —CO$_2$H, —C(O)OR$^4$, or —(C$_1$-C$_3$ alkyl)-C(O)OR$^4$. In some embodiments, R$^3$ is R$^4$, —C(O)OR$^4$, or —(C$_1$-C$_3$ alkyl)-C(O)OR$^4$.

In some embodiments, R$^4$ is —(C$_1$-C$_8$)-alkyl-R$^5$, —(C$_1$-C$_8$)-alkenyl-R$^5$, or —(C$_1$-C$_8$)-alkynyl-R$^5$. In some embodiments, R$^4$ is —(C$_1$-C$_6$)-alkyl-R$^5$, —(C$_1$-C$_6$)-alkenyl-R$^5$, or —(C$_1$-C$_6$)-alkynyl-R$^5$. In some embodiments, R$^4$ is —(C$_1$-C$_4$)-alkyl-R$^5$, —(C$_1$-C$_4$)-alkenyl-R$^5$, or —(C$_1$-C$_4$)-alkynyl-R$^5$.

In some embodiments, R$^5$ is H, halogen, —OH, —O—(C$_1$-C$_6$)-alkyl, —O—(C$_1$-C$_6$)-alkenyl, —O—(C$_1$-C$_6$)-alkynyl, —CN, —N$_3$, —NCS, —SO$_2$NH$_2$, —SO$_2$CF$_3$, imidazole, oxazole, isoxazole, 1,2,3-triazole, 1,2,4-triazole, morpholine, thiomorpholine,

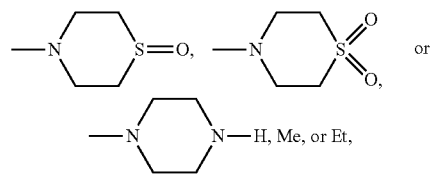

wherein —O—(C$_1$-C$_6$)-alkyl, —O—(C$_1$-C$_6$)-alkenyl, and —O—(C$_1$-C$_6$)-alkynyl are optionally substituted with —CN, —N$_3$, or —NCS.

In some embodiments, R$^5$ is halogen, —OH, —O—(C$_1$-C$_6$)-alkyl, —O—(C$_1$-C$_6$)-alkenyl, —O—(C$_1$-C$_6$)-alkynyl, —CN, —N$_3$, —NCS, —SO$_2$NH$_2$, —SO$_2$CF$_3$, imidazole, oxazole, isoxazole, 1,2,3-triazole, 1,2,4-triazole, morpholine, thiomorpholine,

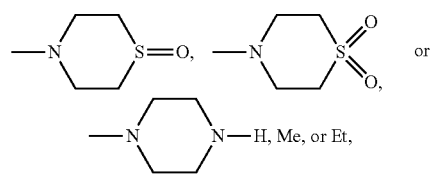

wherein —O—$(C_1-C_6)$-alkyl, —O—$(C_1-C_6)$-alkenyl, and —O—$(C_1-C_6)$-alkynyl are optionally substituted with —CN, —$N_3$, or —NCS.

In some embodiments, $R^5$ is H, halogen, —OH, —O—$(C_1-C_6)$-alkyl, —O—$(C_1-C_6)$-alkenyl, —O—$(C_1-C_6)$-alkynyl, —CN, —$N_3$, imidazole, oxazole, 1,2,3-triazole, 1,2,4-triazole, morpholine, thiomorpholine,

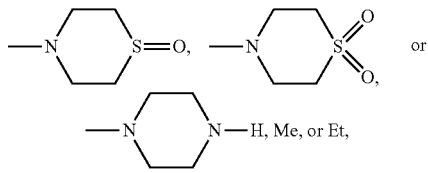

wherein —O—$(C_1-C_6)$-alkyl, —O—$(C_1-C_6)$-alkenyl, and —O—$(C_1-C_6)$-alkynyl are optionally substituted with —CN, —$N_3$, or —NCS.

In some embodiments, $R^5$ is halogen, —OH, —O—$(C_1-C_6)$-alkyl, —O—$(C_1-C_6)$-alkenyl, —O—$(C_1-C_6)$-alkynyl, —CN, —$N_3$, imidazole, oxazole, isoxazole, 1,2,3-triazole, 1,2,4-triazole, morpholine, thiomorpholine,

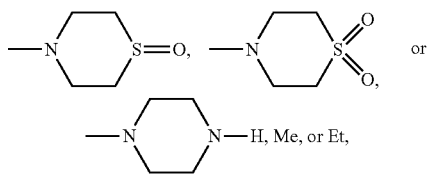

wherein —O—$(C_1-C_6)$-alkyl, —O—$(C_1-C_6)$-alkenyl, and —O—$(C_1-C_6)$-alkynyl are optionally substituted with —CN, —$N_3$, or —NCS.

In some embodiments, $R^5$ is halogen, —CN, —$N_3$, imidazole, oxazole, isoxazole, 1,2,3-triazole, 1,2,4-triazole, morpholine, thiomorpholine,

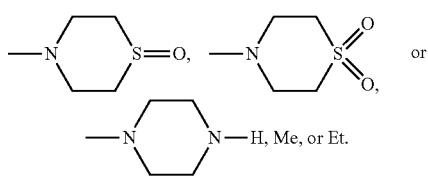

In some embodiments, $R^5$ is halogen, —CN, —$N_3$, imidazole, oxazole, isoxazole, 1,2,3-triazole, 1,2,4-triazole, morpholine, thiomorpholine, or

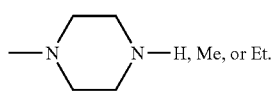

In some embodiments, $R^5$ is halogen, —CN, —$N_3$, imidazole, oxazole, isoxazole, 1,2,3-triazole, or 1,2,4-triazole.

In some embodiments, $R^6$ is H or —$(C_1-C_2)$-alkyl. In some embodiments, $R^6$ is H or methyl. In some embodiments, $R^6$ is H. In some embodiments, $R^6$ is methyl.

In some embodiments, $R^7$ and $R^8$ are independently H, halogen, CN, —$(C_1-C_2)$-alkyl, OH, or —O—$(C_1-C_2)$-alkyl. In some embodiments, $R^7$ and $R^8$ are independently halogen, CN, OH, —$(C_1-C_2)$-alkyl, or —O—$(C_1-C_2)$-alkyl. In some embodiments, $R^7$ and $R^8$ are independently OH or —O—$(C_1-C_2)$-alkyl. In some embodiments, $R^7$ and $R^8$ are each OH. In some embodiments, $R^7$ and $R^8$ are each —O—$(C_1-C_2)$-alkyl.

In some embodiments, $R^9$ and $R^{10}$ are independently H, halogen, —OH, —O—$(C_1-C_6)$-alkyl, —O—$(C_1-C_6)$-alkenyl, —O—$(C_1-C_6)$-alkynyl, —CN, —$N_3$, —NCS, —$SO_2NH_2$, —$SO_2CF_3$, imidazole, oxazole, isoxazole, 1,2,3-triazole, 1,2,4-triazole, morpholine, thiomorpholine,

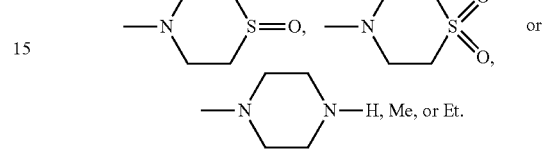

In some embodiments, $R^9$ and $R^{10}$ are independently halogen, —OH, —O—$(C_1-C_6)$-alkyl, —O—$(C_1-C_6)$-alkenyl, —O—$(C_1-C_6)$-alkynyl, —CN, —$N_3$, —NCS, —$SO_2NH_2$, —$SO_2CF_3$, imidazole, oxazole, isoxazole, 1,2,3-triazole, 1,2,4-triazole, morpholine, thiomorpholine,

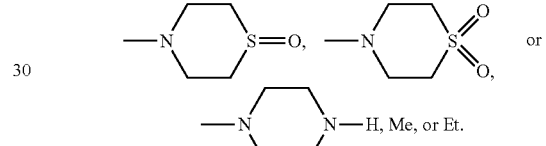

In some embodiments, $R^9$ and $R^{10}$ are independently halogen, —OH, —O—$(C_1-C_6)$-alkyl, —O—$(C_1-C_6)$-alkenyl, —O—$(C_1-C_6)$-alkynyl, —CN, —$N_3$, —NCS, —$SO_2NH_2$, —$SO_2CF_3$, imidazole, oxazole, isoxazole, 1,2,3-triazole, 1,2,4-triazole, morpholine, thiomorpholine,

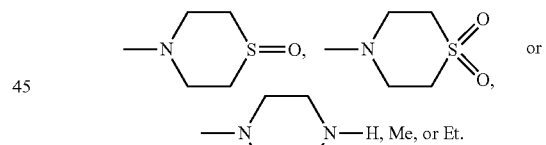

In some embodiments, $R^9$ and $R^{10}$ are independently halogen, —O—$(C_1-C_6)$-alkyl, —O—$(C_1-C_6)$-alkenyl, —O—$(C_1-C_6)$-alkynyl, —CN, —$N_3$, —NCS, —$SO_2NH_2$, —$SO_2CF_3$, imidazole, oxazole, isoxazole, 1,2,3-triazole, 1,2,4-triazole, morpholine, thiomorpholine,

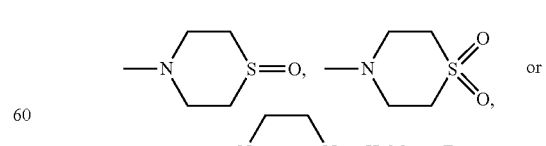

In some embodiments, $R^9$ and $R^{10}$ are independently halogen, —O—$(C_1-C_6)$-alkyl, —O—$(C_1-C_6)$-alkenyl, —O—$(C_1-C_6)$-alkynyl, —CN, —$N_3$, —NCS, —$SO_2NH_2$, —SO$_2$CF$_3$, imidazole, oxazole, isoxazole, 1,2,3-triazole, 1,2,4-triazole, morpholine, thiomorpholine,

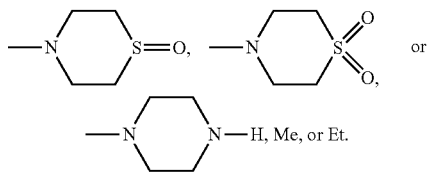

In some embodiments, R$^9$ and R$^{10}$ are independently H, halogen, —CN, NCS, N$_3$, —SO$_2$NH$_2$, —SO$_2$CF$_3$, or —(C$_1$-C$_2$)-alkyl. In some embodiments, R$^9$ and R$^{10}$ are independently H, halogen, —CN, —SO$_2$NH$_2$, —SO$_2$CF$_3$, or —(C$_1$-C$_2$)-alkyl. In some embodiments, R$^9$ and R$^{10}$ are independently H, halogen, —CN, or —(C$_1$-C$_2$)-alkyl. In some embodiments, R$^9$ and R$^{10}$ are independently halogen, —CN, or —(C$_1$-C$_2$)-alkyl. In some embodiments, R$^9$ and R$^{10}$ are independently H, halogen, —CN, or methyl. In some embodiments, R$^9$ and R$^{10}$ are independently H, halogen, or methyl. In some embodiments, R$^9$ and R$^{10}$ are independently halogen, or —CN. In some embodiments, R$^9$ and R$^{10}$ are independently H or halogen. In some embodiments, R$^9$ and R$^{10}$ are independently H or —CN. In some embodiments, R$^9$ and R$^{10}$ are each methyl. In some embodiments, R$^9$ and R$^{10}$ are each —CN. In some embodiments, R$^9$ and R$^{10}$ are each halogen.

In some embodiments, R$^{11}$ is H, —(CH$_2$)$_p$-halogen, —(CH$_2$)$_p$—CN, —(CH$_2$)$_p$OH, or —(C$_1$-C$_2$)-alkyl, in which p is 0, 1, or 2. In some embodiments, R$^{11}$ is —(CH$_2$)$_p$-halogen, —(CH$_2$)$_p$—CN, —(CH$_2$)$_p$—H, or —(C$_1$-C$_2$)-alkyl, in which p is 0, 1, or 2. In some embodiments, R$^1$ is H, —(CH$_2$)$_p$-halogen, —(CH$_2$)$_p$—CN, —(CH$_2$)$_p$—H, or —(C$_1$-C$_2$)-alkyl, in which p is 0. In some embodiments, R$^{11}$ is H, —(CH$_2$)$_p$-halogen, —(CH$_2$)$_p$—CN, or —(C$_1$-C$_2$)-alkyl. In some embodiments, R$^{11}$ is —(CH$_2$)P-halogen, —(CH$_2$)$_p$—CN, or —(C$_1$-C$_2$)-alkyl.

In some embodiments, R$^{12}$ is independently H or —(C$_1$-C$_6$)-alkyl. In some embodiments, R$^{12}$ is independently H or —(C$_1$-C$_3$)-alkyl. In some embodiments, R$^{12}$ is independently H or —(C$_1$-C$_2$)-alkyl. In some embodiments, R$^{12}$ is H. In some embodiments, R$^{12}$ is —(C$_1$-C$_2$)-alkyl. In some embodiments, R$^{12}$ is methyl.

In some embodiments, p is 0, 1, or 2. In some embodiments, p is 0 or 1. In some embodiments, p is 0. In some embodiments, p is 1.

In some embodiments, m is 0, 1, or 2. In some embodiments, m is 0 or 1. In some embodiments, m is 0. In some embodiments, m is 1.

In some embodiments, when X is —C(CH$_3$)—, R$^3$ is CO$_2$H and R$^1$ is H or methyl, then R$^2$ is not hydrogen; and when X is —C(CH$_2$OH)—, R$^1$ and R$^2$ are —(C$_1$-C$_2$)-alkyl, and R$^3$ is —C(O)OR$^4$, —(C$_1$-C$_3$ alkyl)-C(O)OR$^4$, —OC(O)R$^4$, or —(C$_1$-C$_3$ alkyl)-OC(O)R$^4$, then R$^5$ is not hydrogen.

In some embodiments, ' ═══ between C8-C9 or C9-C10 is a double bond, R$^3$ is R$^4$, —CH$_2$OH, —C(O)SR$^4$, —C(O)N(R$^6$)R$^4$, —OC(O)R$^4$, —(C$_1$-C$_3$ alkyl)-OC(O)R$^4$, —C(O)OR$^4$, or —(C$_1$-C$_3$ alkyl)-C(O)OR$^4$, provided that when R$^3$ is R$^4$, then either X is —C(O)O— or —OC(O)—, or R$^1$ and R$^2$ together with the carbon to which they are attached form a —(C$_3$-C$_6$)-lactone so that at least one ester group is present in Formula (I), and provided that when R$^3$ is —OC(O)R$^4$, —(C$_1$-C$_3$ alkyl)-OC(O)R$^4$, —C(O)OR$^4$, or —(C$_1$-C$_3$ alkyl)-C(O)OR$^4$, then R$^5$ is not hydrogen.

In some embodiments, when ═══ between C8-C9 or C9-C10 is a single bond, R$^3$ is R$^4$, —C(O)OR$^4$, or —(C$_1$-C$_3$ alkyl)-C(O)OR$^4$;
R$^5$ is H, halogen, —OH, —O—(C$_1$-C$_6$)-alkyl, —O—(C$_1$-C$_6$)-alkenyl, —O—(C$_1$-C$_6$)-alkynyl, —CN, —N$_3$, —NCS, —SO$_2$NH$_2$, —SO$_2$CF$_3$, imidazole, oxazole, isoxazole, 1,2,3-triazole, 1,2,4-triazole, morpholine, thiomorpholine,

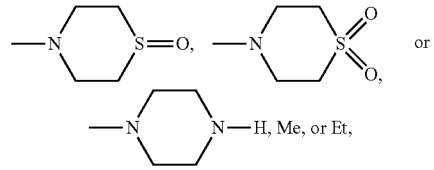

wherein —O—(C$_1$-C$_6$)-alkyl, —O—(C$_1$-C$_6$)-alkenyl, and —O—(C$_1$-C$_6$)-alkynyl are optionally substituted with —CN, —N$_3$, or —NCS; and
when ' ═══ between C8-C9 or C9-C10 is a double bond, R$^3$ is R$^4$, —C(O)OR$^4$, —(C$_1$-C$_3$ alkyl)-C(O)OR$^4$, —C(O)SR$^4$, —C(O)N(R$^6$)R$^4$, —OC(O)R$^4$, or —(C$_1$-C$_3$ alkyl)-OC(O)R$^4$; and
R$^5$ is halogen, —OH, —O—(C$_1$-C$_6$)-alkyl, —O—(C$_1$-C$_6$)-alkenyl, —O—(C$_1$-C$_6$)-alkynyl, —CN, —N$_3$, —NCS, —SO$_2$NH$_2$, —SO$_2$CF$_3$, imidazole, oxazole, isoxazole, 1,2,3-triazole, 1,2,4-triazole, morpholine, thiomorpholine,

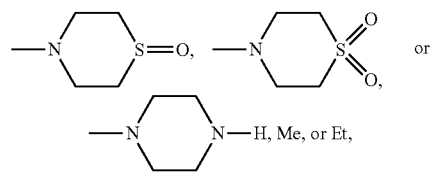

wherein —O—(C$_1$-C$_6$)-alkyl, —O—(C$_1$-C$_6$)-alkenyl, and —O—(C$_1$-C$_6$)-alkynyl are optionally substituted with —CN, —N$_3$, or —NCS.

In some embodiments, when ═══ between C8-C9 or C9-C10 is a single bond,
R$^1$ and R$^2$ are independently H, —(C$_1$-C$_2$)-alkyl;
R$^3$ is R$^4$, —C(O)OR$^4$, or —(C$_1$-C$_3$ alkyl)-C(O)OR$^4$;
R$^5$ is H, halogen, —OH, —O—(C$_1$-C$_6$)-alkyl, —O—(C$_1$-C$_6$)-alkenyl, —O—(C$_1$-C$_6$)-alkynyl, —CN, —N$_3$, —NCS, —SO$_2$NH$_2$, —SO$_2$CF$_3$, imidazole, oxazole, isoxazole, 1,2,3-triazole, 1,2,4-triazole, morpholine, thiomorpholine,

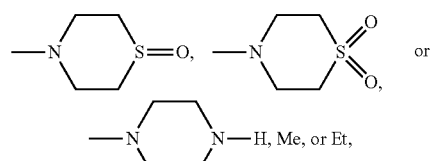

wherein —O—(C$_1$-C$_6$)-alkyl, —O—(C$_1$-C$_6$)-alkenyl, and —O—(C$_1$-C$_6$)-alkynyl are optionally substituted with —CN, —N$_3$, or —NCS; and
when ═══ between C8-C9 or C9-C10 is a double bond, R$^3$ is R$^4$, —C(O)OR$^4$, —(C$_1$-C$_3$ alkyl)-C(O)OR$^4$, —C(O)SR$^4$, —C(O)N(R$^6$)R$^4$, —OC(O)R$^4$, or —(C$_1$-C$_3$ alkyl)-OC(O)R$^4$; and R⁵ is halogen, —OH, —O—(C₁-C₆)-alkyl, —O—(C₁-C₆)-alkenyl, —O—(C₁-C₆)-alkynyl, —CN, —N₃, —NCS, —SO₂NH₂, —SO₂CF₃, imidazole, oxazole, isoxazole, 1,2,3-triazole, 1,2,4-triazole, morpholine, thiomorpholine,

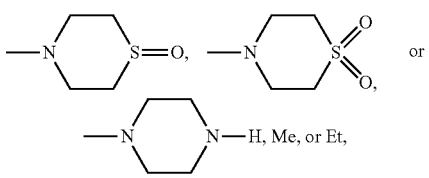

wherein —O—(C₁-C₆)-alkyl, —O—(C₁-C₆)-alkenyl, and —O—(C₁-C₆)-alkynyl are optionally substituted with —CN, —N₃, or —NCS.

In some embodiments, when '⋯' between C8-C9 or C9-C10 is a single bond,
R¹ and R² are independently H or —(C₁-C₂)-alkyl;
R³ is R⁴, —C(O)OR⁴, or —(C₁-C₃ alkyl)-C(O)OR⁴;
R⁵ is halogen, —OH, —O—(C₁-C₆)-alkyl, —O—(C₁-C₆)-alkenyl, —O—(C₁-C₆)-alkynyl, —CN, —N₃, —NCS, —SO₂NH₂, —SO₂CF₃, imidazole, oxazole, isoxazole, 1,2,3-triazole, 1,2,4-triazole, morpholine, thiomorpholine,

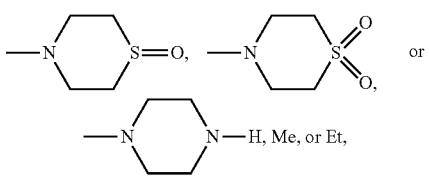

wherein —O—(C₁-C₆)-alkyl, —O—(C₁-C₆)-alkenyl, and —O—(C₁-C₆)-alkynyl are optionally substituted with —CN, —N₃, or —NCS; and
When '⋯' between C8-C9 or C9-C10 is a double bond,
R¹ and R² are independently H or —(C₁-C₂)-alkyl, or R¹ and R² together with the carbon to which they are attached form a —(C₃-C₅)-cycloalkyl or a —(C₃-C₅)-lactone;
R³ is R⁴, —C(O)OR⁴, —(C₁-C₃ alkyl)-C(O)OR⁴, —C(O)SR⁴, —C(O)N(R⁶)R⁴, —OC(O)R⁴, or —(C₁-C₃ alkyl)-OC(O)R⁴; and
R⁵ is halogen, —OH, —O—(C₁-C₆)-alkyl, —O—(C₁-C₆)-alkenyl, —O—(C₁-C₆)-alkynyl, —CN, —N₃, —NCS, —SO₂NH₂, —SO₂CF₃, imidazole, oxazole, isoxazole, 1,2,3-triazole, 1,2,4-triazole, morpholine, thiomorpholine,

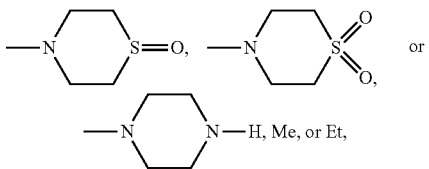

wherein —O—(C₁-C₆)-alkyl, —O—(C₁-C₆)-alkenyl, and —O—(C₁-C₆)-alkynyl are optionally substituted with —CN, —N₃, or —NCS.

In some embodiments, when '⋯' between C8-C9 or C9-C10 is a single bond,
R¹ and R² are independently H or methyl;
R³ is R⁴, —C(O)OR⁴, or —(C₁-C₃ alkyl)-C(O)OR⁴;
R⁵ is halogen, —CN, —N₃, —NCS, —SO₂NH₂, —SO₂CF₃, imidazole, oxazole, isoxazole, 1,2,3-triazole, 1,2,4-triazole, morpholine, thiomorpholin,

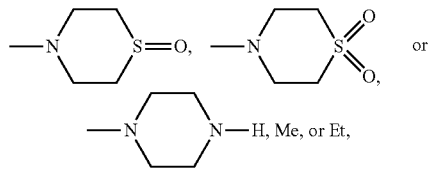

wherein —O—(C₁-C₆)-alkyl, —O—(C₁-C₆)-alkenyl, and —O—(C₁-C₆)-alkynyl are optionally substituted with —CN, —N₃, or —NCS; and
when ⋯' between C8-C9 or C9-C10 is a double bond,
R¹ and R² are independently H or methyl, or R¹ and R² together with the carbon to which they are attached form a —(C₃-C₅)-cycloalkyl or a —(C₃-C₅)-lactone;
R³ is R⁴, —C(O)OR⁴, —(C₁-C₃ alkyl)-C(O)OR⁴, —C(O)SR⁴, —C(O)N(R⁶)R⁴, or —OC(O)R⁴, or —(C₁-C₃ alkyl)-OC(O)R⁴; and
R⁵ is halogen, —CN, —N₃, —NCS, —SO₂NH₂, —SO₂CF₃, imidazole, oxazole, isoxazole, 1,2,3-triazole, 1,2,4-triazole, morpholine, thiomorpholine,

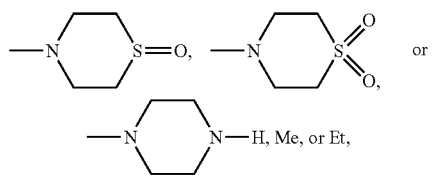

wherein —O—(C₁-C₆)-alkyl, —O—(C₁-C₆)-alkenyl, and —O—(C₁-C₆)-alkynyl are optionally substituted with —CN, —N₃, or —NCS.

In some embodiments, when ⋯' between C8-C9 or C9-C10 is a single bond,
R¹ and R² are independently H or methyl;
R³ is R⁴, —C(O)OR⁴, or —(C₁-C₃ alkyl)-C(O)OR⁴;
R⁵ is halogen, —CN, —N₃, —NCS, —SO₂NH₂, —SO₂CF₃, imidazole, oxazole, isoxazole, 1,2,3-triazole, 1,2,4-triazole, morpholine, thiomorpholine,

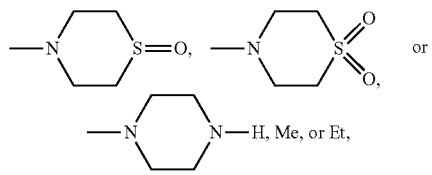

wherein —O—(C₁-C₆)-alkyl, —O—(C₁-C₆)-alkenyl, and —O—(C₁-C₆)-alkynyl are optionally substituted with —CN, —N₃, or —NCS; and
when ⋯' between C8-C9 or C9-C10 is a double bond,
R¹ and R² are independently H or methyl, or R¹ and R² together with the carbon to which they are attached form a —(C₃-C₅)-cycloalkyl or a —(C₃-C₅)-lactone;

R³ is R⁴, —C(O)OR⁴, —(C₁-C₃ alkyl)-C(O)OR⁴, —C(O)SR⁴, —C(O)N(R⁶)R⁴, —OC(O)R⁴, or —(C₁-C₃ alkyl)-OC(O)R⁴; and R⁵ is halogen, —CN, —N₃, —NCS, —SO₂NH₂, —SO₂CF₃, imidazole, oxazole, isoxazole, 1,2,3-triazole, 1,2,4-triazole, morpholine, thiomorpholine,

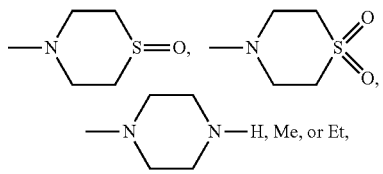

wherein —O—(C₁-C₆)-alkyl, —O—(C₁-C₆)-alkenyl, and —O—(C₁-C₆)-alkynyl are optionally substituted with —CN, —N₃, or —NCS.

In some embodiments, when '⁓' between C8-C9 or C9-C10 is a single bond,
R¹ and R² are independently H or methyl;
R³ is R⁴, —C(O)OR⁴, or —(C₁-C₃ alkyl)-C(O)OR⁴;
R⁵ is halogen, —CN, —N₃, —NCS, —SO₂NH₂, —SO₂CF₃, imidazole, oxazole, isoxazole, 1,2,3-triazole, 1,2,4-triazole, morpholine, thiomorpholine,

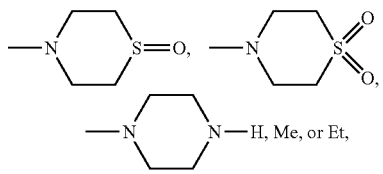

wherein —O—(C₁-C₆)-alkyl, —O—(C₁-C₆)-alkenyl, and —O—(C₁-C₆)-alkynyl
are optionally substituted with —CN, —N₃, or —NCS; and
when '⁓' between C8-C9 or C9-C10 is a double bond,
R¹ and R² are independently H or methyl, or R¹ and R² together with the carbon to which they are attached form a —(C₃-C₅)-cycloalkyl or a —(C₃-C₅)-lactone;
R³ is R⁴, —C(O)OR⁴, —(C₁-C₃ alkyl)-C(O)OR⁴, —C(O)SR⁴, —C(O)N(R⁶)R⁴, —OC(O)R⁴, or —(C₁-C₃ alkyl)-OC(O)R⁴; and
R⁵ is halogen, —CN, —N₃, —NCS, —SO₂NH₂, —SO₂CF₃, imidazole, oxazole, isoxazole, 1,2,3-triazole, 1,2,4-triazole, morpholine, thiomorpholine,

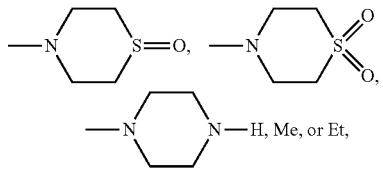

wherein —O—(C₁-C₆)-alkyl, —O—(C₁-C₆)-alkenyl, and —O—(C₁-C₆)-alkynyl are optionally substituted with —CN, —N₃, or —NCS.

In some embodiments, when '⁓' between C8-C9 or C9-C10 is a single bond,
R¹ and R² are independently H or methyl;
R³ is R⁴ or —C(O)OR⁴;

R⁵ is halogen, —CN, —N₃, —NCS, —SO₂NH₂, —SO₂CF₃, imidazole, oxazole, isoxazole, 1,2,3-triazole, 1,2,4-triazole, morpholine, thiomorpholine,

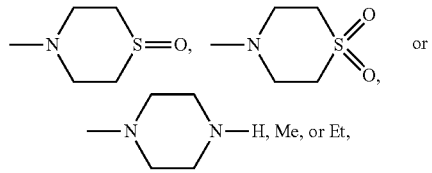

wherein —O—(C₁-C₂)-alkyl, —O—(C₁-C₆)-alkenyl, and —O—(C₁-C₆)-alkynyl are optionally substituted with —CN, —N₃, or —NCS; and
when '⁓' between C8-C9 or C9-C10 is a double bond,
R¹ and R² are independently H or methyl, or R¹ and R² together with the carbon to which they are attached form a —(C₃-C₅)-cycloalkyl or a —(C₃-C₅)-lactone;
R³ is R⁴, —C(O)OR⁴, —C(O)SR⁴, —C(O)N(R⁶)R⁴, or —OC(O)R⁴; and
R⁵ is halogen, —CN, —N₃, —NCS, —SO₂NH₂, —SO₂CF₃, imidazole, oxazole, isoxazole, 1,2,3-triazole, 1,2,4-triazole, morpholine, thiomorpholine,

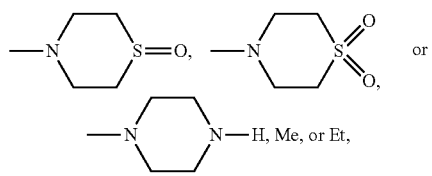

wherein —O—(C₁-C₆)-alkyl, —O—(C₁-C₆)-alkenyl, and —O—(C₁-C₆)-alkynyl are optionally substituted with —CN, —N₃, or —NCS.

In some embodiments of formula (I), the compound is of formula (Ia):

(Ia)

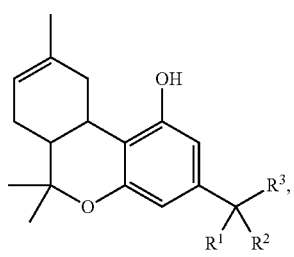

In some embodiments of formula (I), the compound is of formula Ib):

(Ib)

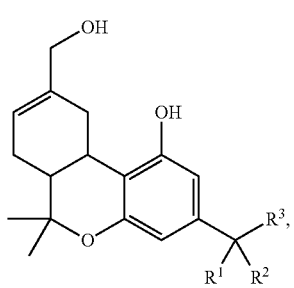

In some embodiments of formula (I), the compound is of formula (Ic):

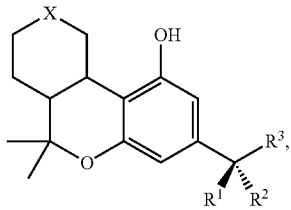

(Ic)

In some embodiments, the compound is formula (II).
In some embodiments of formula (II), the compound is of formula (IIa):

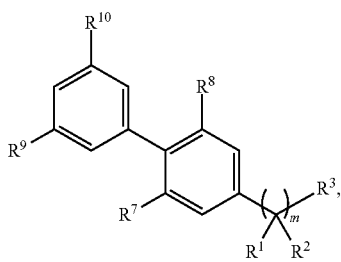

(IIa)

In some embodiments, the compound is of formula (II), wherein $R^1$ and $R^2$ are independently H or methyl;
$R^3$ is —C(O)O—$(C_1-C_4)$-alkyl; and
$R^7$ and $R^8$ are independently OH or $OCH_3$; and
$R^9$ and $R^{10}$ are independently H, halogen, —CN, NCS, $N_3$, —$SO_2NH_2$, —$SO_2CF_3$, or —$(C_1-C_2)$-alkyl.

In some embodiments, the compound is of formula (II), wherein $R^1$ and $R^2$ are each methyl;
$R^3$ is —C(O)O-ethyl;
$R^7$ and $R^8$ are independently OH or $OCH_3$; and
$R^9$ and $R^{10}$ are independently H, halogen, —CN, NCS, $N_3$, —$SO_2NH_2$, —$SO_2CF_3$, or —$(C_1-C_2)$-alkyl.

In some embodiments, the compound is of formula (II), wherein $R^1$ and $R^2$ are each methyl;
$R^3$ is —C(O)O-ethyl;
$R^7$ and $R^8$ are independently OH or $OCH_3$; and
$R^9$ and $R^{10}$ are independently halogen, or methyl.

In some embodiments, the compound is of formula (II), wherein $R^1$ and $R^2$ are each methyl;
$R^3$ is —C(O)O-ethyl;
$R^7$ and $R^8$ are independently OH or $OCH_3$; and
$R^9$ and $R^{10}$ are each methyl or $R^9$ and $R^{10}$ are each halogen.

In some embodiments, the compound is of formula (III).
In some embodiments of the compound of formula (III), $R^1$ and $R^2$ are independently H, —$(C_1-C_2)$-alkyl, —OH, or —$CH_2CO_2H$, wherein $R^1$ and $R^2$ are both not simultaneously OH, or $R^1$ and $R^2$ together with the carbon to which they are attached form a —$(C_3-C_6)$-cycloalkyl or a —$(C_3-C_6)$-lactone;
$R^3$ is $R^4$, —$CH_2OH$, —$CO_2H$, —C(O)$SR^4$, —C(O)N($R^6$)$R^4$, —OC(O)$R^4$, —$(C_1-C_3$ alkyl)-OC(O)$R^4$, —C(O)$OR^4$, or —$(C_1-C_3$ alkyl)-C(O)$OR^4$, provided that when $R^3$ is $R^4$, then $R^1$ and $R^2$ together with the carbon to which they are attached form a —$(C_3-C_6)$-lactone so that at least one ester group is present in Formula (III);

$R^4$ is —$(C_1-C_8)$-alkyl-$R^5$, —$(C_1-C_8)$-alkenyl-$R^5$, or —$(C_1-C_8)$-alkynyl-$R^5$; and
$R^5$ is H, halogen, —OH, —O—$(C_1-C_6)$-alkyl, —O—$(C_1-C_6)$-alkenyl, —O—$(C_1-C_6)$-alkynyl, —CN, —$N_3$, —NCS, —$SO_2NH_2$, —$SO_2CF_3$, imidazole, oxazole, isoxazole, 1,2,3-triazole, 1,2,4-triazole, morpholine, thiomorpholine,

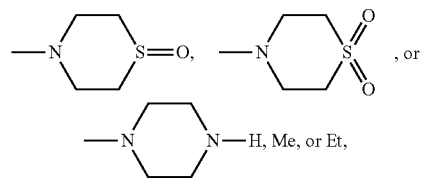

wherein —O—$(C_1-C_6)$-alkyl, —O—$(C_1-C_6)$-alkenyl, and —O—$(C_1-C_6)$-alkynyl are optionally substituted with —CN, —$N_3$, or —NCS; and
$R^{19}$ is —$(CH_2)_p$-halogen, —$(CH_2)_p$—CN, —$(CH_2)$POH, or —$(C_1-C_2)$-alkyl, in which p is 0, 1, or 2.

Specific embodiments of compounds of formula (I)a are shown in Table 1.

Table 1: Compounds of Formula (I)a:

TABLE 1

Compounds of Formula (I)a:

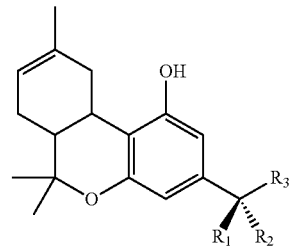

(I)a

| No. | $R^1$ | $R^2$ | $R^3$ |
|---|---|---|---|
| 1.1 | $CH_3$ | $CH_3$ | $CO_2H$ |
| 1.2 | $CH_3$ | $CH_3$ | ![](structure: -C(O)O(CH2)4Br) |
| 1.3 | $CH_3$ | $CH_3$ | ![](structure: -C(O)O(CH2)4CN) |
| 1.4 | $CH_3$ | $CH_3$ | ![](structure: -C(O)O-butyl) |
| 1.5 | $CH_3$ | $CH_3$ | ![](structure: -C(O)O(CH2)5Br) |
| 1.6 | $CH_3$ | $CH_3$ | ![](structure: -C(O)O(CH2)4-imidazole) |

TABLE 1-continued

Compounds of Formula (I)a:

(I)a

| No. | R¹ | R² | R³ |
|---|---|---|---|
| 1.7 | CH₃ | CH₃ | -C(=O)O-(CH₂)₃-Br |
| 1.8 | CH₃ | CH₃ | -C(=O)O-(CH₂)₃-CN |
| 1.9 | CH₃ | CH₃ | -C(=O)O-(CH₂)₃-N₃ |
| 1.10 | CH₃ | CH₃ | -C(=O)O-(CH₂)₃-imidazolyl |
| 1.11ᵃ | isopropyl (spiro) | | CO₂H |
| 1.12ᵃ | isopropyl (spiro) | | -C(=O)O-butyl |
| 1.13 | H | CH₃ | CO₂H |
| 1.14 | H | CH₃ | -C(=O)O-butyl |
| 1.15 | CH₃ | H | CO₂H |
| 1.16 | CH₃ | H | -C(=O)O-butyl |
| 1.17 | cyclobutyl (spiro) | | CO₂H |
| 1.18 | cyclobutyl (spiro) | | -C(=O)O-(CH₂)₄-Br |
| 1.19 | cyclobutyl (spiro) | | -C(=O)O-(CH₂)₄-CN |
| 1.20 | cyclobutyl (spiro) | | -C(=O)O-butyl |
| 1.21 | cyclobutyl (spiro) | | -C(=O)O-(CH₂)₄-N₃ |
| 1.22 | HOCH₂, HO₂C (quaternary) | | n-hexyl |
| 1.23 | β-lactone (spiro oxetanone) | | n-hexyl |
| 1.24 | CH₃ | CH₃ | -C(=O)O-(CH₂)₄-morpholinyl |
| 1.25 | CH₃ | CH₃ | -C(=O)O-(CH₂)₃-morpholinyl |
| 1.26 | H | H | CO₂H |
| 1.27 | H | H | -C(=O)O-(CH₂)₄-Br |

TABLE 1-continued

Compounds of Formula (I)a:

(I)a

[Structure: tricyclic cannabinoid core with OH group, and R3 substituent with R1, R2 on the chiral carbon attached to the aromatic ring]

| No. | R¹ | R² | R³ |
|---|---|---|---|
| 1.28 | H | H | –C(=O)O–(CH₂)₃–CN |
| 1.29 | H | H | –C(=O)O–butyl |
| 1.30 | CH₃ | CH₃ | –C(=O)S–ethyl |
| 1.31 | CH₃ | CH₃ | –C(=O)NH–butyl |
| 1.32 | CH₃ | CH₃ | CH₂OH |
| 1.33 | CH₃ | CH₃ | –CH₂–O–C(=O)–propyl |
| 1.34 | CH₃ | CH₃ | CO₂CH₃ |
| 1.35 | CH₃ | CH₃ | CO₂CH₂CH₃ |
| 1.36 | CH₃ | CH₃ | –C(=O)O–CH₂CH₂–Br |

ᵃThe compound is a mixture of diastereomers. Thus, compound 1.11 is a racemic mixture of compounds 1.13 and 1.15; and compound 1.12 is a racemic mixture of compounds 1.14 and 1.16.

Specific embodiments of compounds of formula (I)b are shown in Table 2.

Table 2: Compounds of Formula (I)b:

TABLE 2

Compounds of Formula (I)b:

(I)b

[Structure: tricyclic cannabinoid core with CH₂OH group on the cyclohexene ring, phenolic OH, and R3 substituent with R1, R2 on the chiral carbon attached to the aromatic ring]

| No. | R¹ | R² | R³ |
|---|---|---|---|
| 2.1 | CH₃ | CH₃ | CO₂H |
| 2.2 | CH₃ | CH₃ | –C(=O)O–butyl |
| 2.3 | CH₃ | CH₃ | –C(=O)O–(CH₂)₄–N(imidazolyl) |
| 2.4 | CH₃ | CH₃ | –C(=O)O–(CH₂)₃–Br |
| 2.5 | CH₃ | CH₃ | –C(=O)O–(CH₂)₂–CN |
| 2.6 | CH₃ | CH₃ | –C(=O)O–(CH₂)₃–N(imidazolyl) |
| 2.7 | CH₃ | CH₃ | –C(=O)O–(CH₂)₃–N(morpholinyl) |

Specific embodiments of compounds of formula (I)c are shown in Table 3.

Table 3: Compounds of Formula (I)c:

TABLE 3

Compounds of Formula (I)c:

(I)c

| No. | X | $R^1$ | $R^2$ | $R^3$ |
|---|---|---|---|---|
| 3.1 | C(O) | H | H | $CO_2H$ |
| 3.2 | C(O) | H | H | $CO_2$-n-butyl |
| 3.3 | C(O) | $CH_3$ | $CH_3$ | CO2H |
| 3.4 | C(O) | $CH_3$ | $CH_3$ | $CO_2$-n-butyl |
| 3.5 | OH (wedge) | $CH_3$ | $CH_3$ | $CO_2H$ |
| 3.6 | OH (wedge) | $CH_3$ | $CH_3$ | $CO_2$-n-butyl |
| 3.7 | OH (dashed) | $CH_3$ | $CH_3$ | $CO_2H$ |
| 3.8 | OH (dashed) | $CH_3$ | $CH_3$ | $CO_2$-n-butyl |
| 3.9 | CH<sub>2</sub>OH | $CH_3$ | $CH_3$ | $CO_2$-n-butyl |
| 3.10 | —$CO_2$— | $CH_3$ | $CH_3$ | n-hexyl |
| 3.11 | —$O_2C$— | $CH_3$ | $CH_3$ | n-hexyl |

Specific embodiments of compounds of formula (IIa) are shown in Table 4.

Table 4: Compounds of Formula (IIa):

TABLE 4

Compounds of Formula (IIa):

(IIa)

| No. | $R^7$ | $R^8$ | $R^9$ | $R^{10}$ |
|---|---|---|---|---|
| 4.1 | $OCH_3$ | $OCH_3$ | H | CN |
| 4.2 | OH | OH | H | CN |
| 4.3 | $OCH_3$ | $OCH_3$ | $CH_3$ | $CH_3$ |
| 4.4 | OH | OH | $CH_3$ | $CH_3$ |
| 4.5 | OH | $OCH_3$ | $CH_3$ | $CH_3$ |
| 4.6 | $OCH_3$ | $OCH_3$ | Cl | Cl |
| 4.7 | $OCH_3$ | OH | Cl | Cl |
| 4.8 | OH | OH | Cl | Cl |

The present disclosure also provides chemical compounds of formulae (Id) and (Ie), and pharmaceutically acceptable salts thereof. In some embodiments, the compound is of formula (Id):

(Id)

or a pharmaceutically acceptable salt thereof. In some embodiments, the compound is of formula (Ie):

(Ie)

or a pharmaceutically acceptable salt thereof. R is

In some embodiments, A is —C(O)—O—, —O—C(O)—, —C(O)—S—, —S—C(O)—, —C(O)—NH—, —NH—C(O)—, —NHSO$_2$—, or —SO$_2$—NH—. In some embodiments, A is —C(O)—O— or —C(O)—S—. In some embodiments, A is A is —C(O)—O—.

In some embodiments, R$^{13}$ and R$^{14}$ are independently H, methyl or fluoro, or R$^{13}$ and R$^{14}$ together with the carbon to which they are attached form a (C$_3$-C$_6$)cycloalkyl or (C$_3$-C$_6$)heterocyclyl containing one or two heteroatoms independently selected from O, S or N, wherein each N, when present, is optionally and independently substituted with methyl.

In some embodiments, R$^{13}$ and R$^{14}$ are independently H, methyl or fluoro. In some embodiments, R$^{13}$ and R$^{14}$ are each methyl.

In some embodiments, R$^{13}$ and R$^{14}$ together with the carbon to which they are attached form a (C$_3$-C$_6$)cycloalkyl or (C$_3$-C$_6$)heterocyclyl containing one or two heteroatoms independently selected from O, S or N, wherein each N, when present, is optionally and independently substituted with methyl. In some embodiments, R$^{13}$ and R$^{14}$ together with the carbon to which they are attached form a (C$_3$-C$_6$) cycloalkyl.

In some embodiments, R$^{15}$ is H, fluoro, methyl or ethyl. In some embodiments, R$^{15}$ is H or methyl.

In some embodiments, R$^{16}$ is H, halo, (C$_1$-C$_3$)alkyl, (C$_1$-C$_3$)haloalkyl, —NCS, —N$_3$, —CN, —NO$_2$, —ONO$_2$, —SO$_2$F, —OH, —O—(C$_1$-C$_6$)alkyl, —SH, —S—(C$_1$-C$_6$)alkyl, —NH$_2$, —N(H)(C$_1$-C$_6$)alkyl, —N[(C$_1$-C$_6$)alkyl]$_2$, or (C$_3$-C$_6$)heterocyclyl. In some embodiments, R$^{16}$ is halo, (C$_1$-C$_3$)alkyl, (C$_1$-C$_3$)haloalkyl, —NCS, —N$_3$, —CN, —NO$_2$, —ONO$_2$, —SO$_2$F, —OH, —O—(C$_1$-C$_6$)alkyl, —SH, —S—(C$_1$-C$_6$)alkyl, —NH$_2$, —N(H)(C$_1$-C$_6$)alkyl, —N[(C$_1$-C$_6$)alkyl]$_2$, or (C$_3$-C$_6$)heterocyclyl. In some embodiments, R$^{16}$ is H, halo, —NCS, —N$_3$, —CN, —ONO$_2$, or saturated (C$_3$-C$_6$)heterocyclyl. In some embodiments, R$^{16}$ is halo, —NCS, —N$_3$, —CN, —ONO$_2$, or saturated (C$_3$-C$_6$)heterocyclyl.

In some embodiments, i is 0, 1, 2, 3, 4 or 5. In some embodiments, i is 0, 1 or 2. In some embodiments, i is 0 or 1. In some embodiments, i is 0.

In some embodiments, j is 0, 1, 2, 3, 4, 5, or 6. In some embodiments, j is 0, 1, 2, 3, 4, or 5. In some embodiments, j is 0, 1, 2, or 3. In some embodiments, j is 2 or 3. In some embodiments, j is 3.

Specific embodiments of compounds of formula (Id) are shown in Table 4A.

TABLE 4A

Compounds of Formula (Id):

(Id)

| No. | R |
|---|---|
| 4.1A | [structure: pivalate ethyl ester] |
| 4.2A | [structure: pivalate propyl ester] |
| 4.3A | [structure: pivalate butyl ester] |
| 4.4A | [structure: pivalate pentyl ester] |
| 4.5A | [structure: pivalate (S)-sec-butyl ester] |
| 4.6A | [structure: pivalate (R)-sec-butyl ester] |
| 4.7A | [structure: pivalate 3-iodopropyl ester] |
| 4.8A | [structure: pivalate 3-cyanopropyl ester] |
| 4.9A | [structure: pivalate 3-morpholinopropyl ester] |
| 4.10A | [structure: pivalate 2-oxopropyl ester] |

TABLE 4A-continued

Compounds of Formula (Id):

| No. | R |
|---|---|
| 4.11A | (3,3-dimethyl-4-methoxy-4-oxobutanoyl group) |
| 4.12A | (2,2-dimethylpropanoic acid / pivalic acid) |
| 4.13A | (3,3-dimethyl-4-hydroxy-4-oxobutanoyl) |
| 4.14A | (S-butyl 2,2-dimethylthioester) |
| 4.15A | (N-butyl 2,2-dimethylamide) |
| 4.16A | (3-azidopropyl 2,2-dimethylester) |
| 4.17A | (3-isothiocyanatopropyl 2,2-dimethylester) |
| 4.18A | (4-bromobutyl 2,2-dimethylester) |
| 4.19A | (4-azidobutyl 2,2-dimethylester) |
| 4.20A | (4-isothiocyanatobutyl 2,2-dimethylester) |
| 4.21A | (4-nitrooxybutyl 2,2-dimethylester / ONO2) |
| 4.22A | (butyl 1-methylcyclopentane-1-carboxylate) |
| 4.23A | (1-methylcyclopentane-1-carboxylic acid) |

The compounds can be synthesized by illustrative synthetic means as described in the Examples below. The ordinarily skilled artisan appreciates that additional methods of making the compounds exist, and understands that general synthetic schemes for the compounds disclosed herein can be understood from the illustrative schemes below.

In another aspect, the invention comprises methods of modulating a cannabinoid receptor in a subject comprising administration of a compound of formula (I), (II), or (III). In another aspect, the invention comprises methods of modulating a cannabinoid receptor in a subject comprising administration of a compound of formula (Id) or (Ie), or a pharmaceutically acceptable salt thereof (e.g., a therapeutically effective amount of a compound of formula (Id) or (Ie), or a pharmaceutically acceptable salt thereof).

In another aspect, the invention comprises methods of treating cannabinoid dependence, neuropathy, inflammation, glaucoma, a neurodegenerative disorder, a motor function disorder, anxiety disorder, a gastrointestinal disorder, hypothermia, emesis, loss of appetite, or anorexia associated with AIDS in a subject comprising administration of a compound of formula (I), (II) or (III). In some embodiments, the methods treat cannabinoid dependence, neuropathy, inflammation, glaucoma, a neurodegenerative disorder, a motor function disorder, anxiety disorder, a gastrointestinal disorder, hypothermia, emesis, loss of appetite, or anorexia associated with AIDS. In some embodiments, the methods treat cannabinoid dependence, neuropathy, inflammation, glaucoma, a neurodegenerative disorder, a motor function disorder, anxiety disorder, hypothermia, emesis, loss of appetite, or anorexia associated with AIDS. In some embodiments, the methods treat cannabinoid dependence, neuropathy, glaucoma, a neurodegenerative disorder, a motor function disorder, anxiety disorder, hypothermia, emesis, loss of appetite, or anorexia associated with AIDS. In some embodiments, the methods treat cannabinoid dependence. In some embodiments, the methods treat neuropathy. In some embodiments, the methods treat a neurodegenerative disorder. In some embodiments, the methods treat a motor function disorder. In some embodiments, the methods treat anxiety disorder. In some embodiments, the methods treat hypothermia. In some embodiments, the methods treat emesis. In some embodiments, the methods treat loss of appetite. In some embodiments, the methods treat anorexia associated with AIDS.

In another aspect, the invention comprises methods of treating pain; central pain; peripheral pain; neuropathic pain; a neuropathy; inflammatory pain; diabetes; a neurodegenerative disease; multiple sclerosis; Parkinson's disease; Huntington's chorea; Alzheimer's disease; amyotrophic lateral sclerosis; a mental disorder; schizophrenia; depression; a mood disorder; an addiction disorder; a sleep disorder; a memory disorder; a gastrointestinal motility disorder; irritable bowel syndrome; diarrhea; dyskinesia; migraine; headache; brain injury; traumatic brain injury; post-traumatic stress disorder, osteoporosis; osteoarthritis; high blood pressure disease or hypertension; peripheral vascular disease; coronary artery disease; abnormal heart rate; cardiac insufficiency; pulmonary hypertension; ocular hypertension or glaucoma; endotoxic shock; hypotensive shock; an appetite disorder; an immune system disorder; a fertility disorder; a disease associated with motor dysfunction; Tourette's syndrome; inflammation; a neurological disorder; epilepsy; nausea; nausea associated with cancer chemotherapy; AIDS wasting syndrome; or cancer in a subject, comprising administration of a compound of formula (I), (II) or (III), or (Id) or (Ie), or a pharmaceutically acceptable salt thereof (e.g., a therapeutically effective amount of a compound of formula (I), (II) or (III), or (Id) or (Ie), or a pharmaceutically acceptable salt thereof), to the subject. In some embodiments, the methods treat pain, for example, central pain, peripheral pain or neuropathic pain.

In some embodiments, neuropathy comprises inflammation, pain, neuropathic pain, neuropathic low back pain, complex regional pain syndrome, post trigeminal neuralgia, causalgia, toxic neuropathy, reflex sympathetic dystrophy, diabetic neuropathy, chronic neuropathy caused by chemotherapeutic agents, central pain, peripheral pain, pellagric neuropathy, alcoholic neuropathy, Beriberi neuropathy, or burning feet syndrome. In some embodiments, neuropathy comprises a neurodegenerative disease.

In some embodiments, the neurodegenerative disease is multiple sclerosis, Parkinson's disease, Huntington's chorea, Alzheimer's disease, amyotrophic lateral sclerosis, memory disorder, mood disorder, sleep disorder, gastrointestinal motility disorder, irritable bowel syndrome, diarrhea, cardiovascular disease, hypertension, osteoporosis, osteoarthritis, emesis, epilepsy, a mental disorder, schizophrenia, depression, glaucoma, cachexia, insomnia, traumatic brain injury, spinal cord injury, seizures, excitotoxin exposure, ischemia, or AIDS wasting syndrome.

In some embodiments, the anxiety disorder is panic disorder, acute stress disorder, post-traumatic stress disorder, substance-induced anxiety disorder, obsessive compulsive disorder, agoraphobia, specific phobia, or social phobia.

In some embodiments, the motor function disorder is Tourette's syndrome.

In some embodiments, the methods comprise administration of a compound of formula (I). In some embodiments, the methods comprise administration of a compound of formula (II). In some embodiments, the methods comprise administration of a compound of formula (III).

Some of the physiological effects provided by modulation of the cannabinoid receptors by cannabinergic ligands are useful to treat a disorder in a subject. Such treatable physiological effects include, but are not limited to, neuroprotection; reduction of inflammation; reduction of pain; reduction of central pain; reduction of peripheral pain; modulation of memory; sleep inducement; modulation of the immune system; hypotension; reduction of emesis; effects on gastrointestinal motility; effects on motor function; effects on intestinal transit and colonic propulsion; modulation of appetite; and modulation of fertility.

Disorders that can be treated by modulation of cannabinoid receptors include, for example: appetite disorders, metabolic disorders, movement disorders, inflammation, pain, neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy caused by chemotherapeutic agents), central pain, peripheral pain, neuropathy (e.g., diabetic neuropathy, pellagric neuropathy, alcoholic neuropathy, Beriberi neuropathy, burning feet syndrome), neurodegenerative diseases including multiple sclerosis, Parkinson's disease, Huntington's chorea, Alzheimer's disease, amyotrophic lateral sclerosis; memory disorders, mood disorders, sleep disorders, gastrointestinal motility disorders such as irritable bowel syndrome and diarrhea; cardiovascular disease, hypertension, osteoporosis, osteoarthritis, emesis, epilepsy, mental disorders such as schizophrenia and depression; glaucoma, cachexia, insomnia, traumatic brain injury, spinal cord injury, seizures, excitotoxin exposure, ischemia, AIDS wasting syndrome, psychological disorders including anxiety disorders (e.g., panic disorder, acute stress disorder, post-traumatic stress disorder, substance-induced anxiety disorders, obsessive-compulsive disorder, agoraphobia, specific phobia, social phobia), to modulate the immune system; to regulate fertility; to prevent or reduce diseases associated with motor function such as Tourette's syndrome; to provide neuroprotection, to produce peripheral vasodilation; to slow down intestinal transit and colonic propulsion; to treat several types of cancer, as well as other ailments in which a growing family of bioactive lipid mediators is implicated.

The compounds of formula (I), (II) and/or (III) and pharmaceutical formulations thereof can also be used in combination with one or more agents treating and/or targeting the disorder or the endogenous cannabinergic system. The compounds of formula (Id) and/or (Ie), or a pharmaceutically acceptable salt thereof, and pharmaceutical formulations thereof can also be used in combination with one or more agents treating and/or targeting the disorder or the endogenous cannabinergic system. Such agents include, but are not limited to, CB1 cannabinoid receptor agonists, CB2 cannabinoid receptor agonists, analgesics, FAAH inhibitors, anandamide transport inhibitors, COX-2 enzyme inhibitors, anxiolytics, antidepressants, and opioids. For example, these compounds and pharmaceutical formulations can be used in conjunction with other cannabinergic ligands that act directly or indirectly on the CB1 and CB2 receptors.

The disclosed compounds can also be used to prepare prodrugs. Prodrugs are known to those skilled in the art of pharmaceutical chemistry, and provide benefits such as increased adsorption and half-life. Those skilled in the art of drug delivery will readily appreciate that the pharmacokinetic properties of formula (I), (II) and/or (III) can be controlled by an appropriate choice of moieties to produce prodrug derivatives.

This disclosure is also directed to pharmaceutical formulations comprising at least one compound of formula (I), (II) and/or (III), and a pharmaceutically acceptable carrier. Such formulations are suitable for administration to a subject. This disclosure is also directed to pharmaceutical formulations comprising at least one compound of formula (Id) or (Ie), or a pharmaceutically acceptable salt thereof, and a pharmaceutically acceptable carrier. The pharmaceutical formulation can be used for treating a disorder described herein.

Any suitable pharmaceutically acceptable carrier known in the art can be used as long as it does not affect the inhibitory activity of a compound of formula (I), (II) and/or (III). Carriers may be used that efficiently solubilize the agents. Carriers include, but are not limited to, a solid, liquid, or a mixture of a solid and a liquid. The carriers can take the form of capsules, tablets, pills, powders, lozenges, suspensions, emulsions, or syrups. The carriers can include substances that act as flavoring agents, lubricants, solubilizers, suspending agents, binders, stabilizers, tablet disintegrating agents, and encapsulating materials. Other examples of suitable physiologically acceptable carriers are described in *Remington's Pharmaceutical Sciences* (21st ed. 2005), incorporated into this disclosure by reference.

Non-limiting examples of materials which can serve as pharmaceutically-acceptable carriers include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline, (18) Ringer's solution, (19) ethyl alcohol; (20) phosphate buffer solutions; and (21) other non-toxic compatible substances employed in pharmaceutical formulations.

The formulations can conveniently be presented in unit dosage form and can be prepared by any methods known in the art of pharmacy. The amount of compound of formula (I), (II) and/or (III) that can be combined with a carrier material to produce a single-dosage form will vary depending upon the subject being treated, the particular mode of administration, the particular condition being treated, among others. Similarly, the amount of compound of formula (Id) and/or (Ie) that can be combined with a carrier material to produce a single-dosage form will vary depending upon the subject being treated, the particular mode of administration, the particular condition being treated, among others. The amount of active ingredient that can be combined with a carrier material to produce a single-dosage form will generally be that amount of the compound that produces a therapeutic effect. Generally, out of one hundred percent, this amount will range from about 1 percent to about ninety-nine percent of active ingredient, in some instances from about 5 percent to about 70 percent, in other instances from about 10 percent to about 30 percent.

Methods of preparing these formulations or compositions include the step of bringing into association a compound disclosed in this application with a carrier and, optionally, one or more accessory ingredients. In general, the formulations are prepared by uniformly and intimately bringing into association a compound of formula (I), (II) and/or (III) with liquid carriers, or timely divided solid carriers, or both, and then, if necessary, shaping the product.

In solid dosage forms of the disclosed compounds for oral administration (e.g., capsules, tablets, pills, dragees, powders, granules, and the like), the active ingredient is mixed with one or more additional ingredients, such as sodium citrate or dicalcium phosphate, and/or any of the following: (1) fillers or extenders, such as, but not limited to, starches, lactose, sucrose, glucose, mannitol, and/or silicic acid; (2) binders, such as, but not limited to, carboxymethylcellulose, alginates, gelatin, polyvinyl pyrrolidone, sucrose, and/or acacia; (3) humectants, such as, but not limited to, glycerol; (4) disintegrating agents, such as, but not limited to, agar, calcium carbonate, potato or tapioca starch, alginic acid, certain silicates, and sodium carbonate; (5) solution retarding agents, such as, but not limited to, paraffin; (6) absorption accelerators, such as, but not limited to, quaternary ammonium compounds; (7) wetting agents, such as, but not limited to, cetyl alcohol and glycerol monostearate; (8) absorbents, such as, but not limited to, kaolin and bentonite clay; (9) lubricants, such as, but not limited to, talc, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols, and the like.

In powders, the carrier is a finely-divided solid, which is mixed with an effective amount of a finely-divided agent. Powders and sprays can contain, in addition to a compound of formula (I), (II) and/or (III), excipients, such as lactose, talc, silicic acid, aluminum hydroxide, calcium silicates and polyamide powder, or mixtures of these substances. Powders and sprays can contain, in addition to a compound of formula (Id) and/or (Ie), excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Tablets for systemic oral administration can include one or more excipients as known in the art, such as, for example, calcium carbonate, sodium carbonate, sugars (e.g., lactose, sucrose, mannitol, sorbitol), celluloses (e.g., methyl cellulose, sodium carboxymethyl cellulose), gums (e.g., arabic, tragacanth), together with one or more disintegrating agents (e.g., maize, starch, or alginic acid, binding agents, such as, for example, gelatin, collagen, or acacia), lubricating agents (e.g., magnesium stearate, stearic acid, or talc), inert diluents, preservatives, disintegrants (e.g., sodium starch glycolate), surface-active and/or dispersing agent. A tablet can be made by compression or molding, optionally with one or more accessory ingredients.

In solutions, suspensions, emulsions or syrups, an effective amount of a disclosed compound is dissolved or suspended in a carrier, such as sterile water or an organic solvent, such as aqueous propylene glycol. Other compositions can be made by dispersing the agent in an aqueous starch or sodium carboxymethyl cellulose solution or a suitable oil known to the art. The liquid dosage forms can contain inert diluents commonly used in the art, such as, for example, water or other solvents, solubilizing agents and emulsifiers, such as, but not limited to, ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols, and fatty acid esters of sorbitan, and mixtures thereof.

Besides inert diluents, the oral compositions can also include adjuvants, such as wetting agents, emulsifying and suspending agents, sweetening, flavoring, coloring, perfuming, and preservative agents.

Suspensions can contain, in addition to the active compound, suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Formulations of the pharmaceutical compositions for rectal or vaginal administration can be presented as a suppository, which can be prepared by mixing one or more compounds of this disclosure with one or more suitable non-irritating excipients or carriers comprising, for example, cocoa butter, polyethylene glycol, a suppository wax or a salicylate, and which is solid at RT but liquid at body temperature and, thus, will melt in the rectum or vaginal cavity and release the agents. Formulations suitable for vaginal administration also include, but are not limited to, pessaries, tampons, creams, gels, pastes, foams, or spray formulations containing such carriers as are known in the art to be appropriate.

Dosage forms for the topical or transdermal administration of a compound of this disclosure include, but are not limited to, powders, sprays, ointments, pastes, creams, lotions, gels, solutions, patches, and inhalants. The active compound can be mixed under sterile conditions with a pharmaceutically-acceptable carrier, and with any preservatives, buffers, or propellants.

Ointments, pastes, creams, and gels can contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound of formula (I), (II) and/or (III) to the body. Transdermal patches can also provide controlled delivery of a compound of formula (Id) and/or (Ie) to the body. Such dosage forms can be made by dissolving or dispersing the agents in the proper medium. Absorption enhancers can also be used to increase the flux of the agents across the skin. The rate of such flux can be controlled by either providing a rate controlling membrane or dispersing the compound in a polymer matrix or gel.

The compounds of formula (I), (II) and/or (III) are administered in a therapeutically effective amount to a patient in need of such treatment. The compounds of formula (Id) and/or (Ie) are administered in a therapeutically effective amount to a patient in need of such treatment. Such an amount is effective in treating a disorder of the patient. This amount can vary, depending on the activity of the agent utilized, the nature of the disorder, and the health of the patient. A skilled practitioner will appreciate that the therapeutically-effective amount of a compound of formula (I), (II) and/or (III) can be lowered or increased by fine-tuning and/or by administering more than one compound of formula (I), (II) and/or (III), or by administering a compound of formula (I), (II) and/or (III) together with a second agent (e.g., antibiotics, antifungals, antivirals, NSAIDS, DMARDS, steroids, etc.). Likewise, a skilled practitioner will appreciate that the therapeutically-effective amount of a compound of formula (Id) and/or (Ie) can be lowered or increased by fine-tuning and/or by administering more than one compound of formula (Id) and/or (Ie), or by administering a compound of formula (Id) and/or (Ie) together with a second agent (e.g., antibiotics, antifungals, antivirals, NSAIDS, DMARDS, steroids, etc.). Therapeutically-effective amounts can be easily determined, for example, empirically by starting at relatively low amounts and by step-wise increments with concurrent evaluation of beneficial effect (e.g., reduction in symptoms). The actual effective amount will be established by dose/response assays using methods standard in the art. As is known to those in the art, the effective amount will depend on bioavailability, bioactivity, and biodegradability of the compound of formula (I), (II) and/or (III). The effective amount of a compound of formula (Id) and/or (Ie) will likewise depend on bioavailability, bioactivity, and biodegradability of the compound of formula (Id) and/or (Ie).

A therapeutically effective amount is an amount that is capable of reducing a symptom of a disorder in a subject. Accordingly, the amount will vary with the subject being treated. Administration of the compound of formula (I), (II) and/or (III) can be hourly, daily, weekly, monthly, yearly, or a single event. Administration of the compound of formula (Id) and/or (Ie) can be hourly, daily, weekly, monthly, yearly, or a single event. For example, the effective amount of the compound can comprise from about 1 µg/kg body weight to about 100 mg/kg body weight. In some embodiments, the effective amount of the compound comprises from about 1 µg/kg body weight to about 50 mg/kg body weight. In some embodiments, the effective amount of the compound comprises from about 10 µg/kg body weight to about 10 mg/kg body weight. When one or more compounds of formula (I), (II) and/or (III) or agents are combined with a carrier, they can be present in an amount of about 1 weight percent to about 99 weight percent, the remainder being composed of the pharmaceutically-acceptable carrier. When one or more compounds of formula (Id) and/or (Ie) or agents are combined with a carrier, they can be present in an amount of about 1 weight percent to about 99 weight percent, the remainder being composed of the pharmaceutically-acceptable carrier.

Methods of administration of the therapeutic formulations comprising the compounds of formula (I), (II) and/or (III) can be by any of a number of methods known in the art. Methods of administration of the therapeutic formulations comprising the compounds of formula (Id) and/or (Ie) can be by any of a number of methods known in the art. These methods include, but are not limited to, local or systemic administration. Exemplary routes of administration include, but are not limited to, oral, parenteral, transdermal, intradermal, intramuscular, intraperitoneal, intravenous, subcutaneous, intranasal (e.g., nebulizer, inhaler, aerosol dispenser), colorectal, rectal, intravaginal, and any combinations thereof. In addition, it may be desirable to introduce pharmaceutical compositions of the disclosed compounds into the central nervous system by any suitable route, including intraventricular and intrathecal injection. Intraventricular injection can be facilitated by an intraventricular catheter, for example, attached to a reservoir, such as an Ommaya reservoir. Methods of introduction can be provided by rechargeable or biodegradable devices, e.g., depots. Furthermore, administration can occur by coating a device, implant, stent, or prosthetic. The compounds of formula (I), (II) and/or (III) can also be used to coat catheters in any situation where catheters are inserted in the body. The compounds of formula (Id) and/or (Ie) can also be used to coat catheters in any situation where catheters are inserted in the body.

The therapeutic formulations containing a compound of formula (I), (II) and/or (III) can also be administered as part of a combinatorial therapy with other agents. The therapeutic formulations containing a compound of formula (Id) and/or (Ie) can also be administered as part of a combinatorial therapy with other agents. Combination therapy refers to any form of administration combining two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either simultaneously or sequentially. Thus, an individual who receives such treatment can have a combined (conjoint) effect of different therapeutic compounds.

In other instances, for example, in the case of inflammatory conditions, a therapeutic formulation containing a compound of formula (I), (II) and/or (III) can be administered in combination with one or more other agents useful in the treatment of inflammatory diseases or conditions. In other instances, for example, in the case of inflammatory conditions, a therapeutic formulation containing a compound of formula (Id) and/or (Le) can be administered in combination with one or more other agents useful in the treatment of inflammatory diseases or conditions. Agents useful in the treatment of inflammatory diseases or conditions include, but are not limited to, anti-inflammatory agents, or antiphlogistics. Exemplary antiphlogistics include, but are not limited to, glucocorticoids, such as cortisone, hydrocortisone, prednisone, prednisolone, fluorcortolone, triamcinolone, methylprednisolone, prednylidene, paramethasone, dexamethasone, betamethasone, beclomethasone, fluprednylidene, desoxymethasone, fluocinolone, flunethasone, diflucortolone, clocortolone, clobetasol and fluocortin butyl ester; immunosuppressive agents such as anti-TNF agents (e.g., etanercept, infliximab) and IL-1 inhibitors; penicillamine; non-steroidal anti-inflammatory drugs (NSAIDs) which encompass anti-inflammatory, analgesic, and antipyretic drugs such as salicyclic acid, celecoxib, difunisal and from substituted phenylacetic acid salts or 2-phenylpropionic acid salts, such as alclofenac, ibutenac, ibuprofen, clindanac, fenclorac, ketoprofen, fenoprofen, indoprofen, fenclofenac, diclofenac, flurbiprofen, piprofen, naproxen, benoxaprofen, carprofen and ciclorofen; oxican derivatives, such as piroxican; anthranilic acid derivatives, such as mefenamic acid, flufenamic acid, tolfenamic acid and meclofenamic acid, anilino-substituted nicotinic acid derivatives, such as the fenamates miflumic acid, clonixin and flunixin; heteroarylacetic acids wherein heteroaryl is a 2-indol-3-yl or pyrrol-2-yl group, such as indomethacin, oxmetacin, intrazol, acemetazin, cinmetacin, zomepirac, tolmetin, colpirac and tiaprofenic acid; idenylacetic acid of the sulindac type; analgesically active heteroaryloxyacetic acids, such as benzadac; phenylbutazone; etodolac; nabunetone; and disease modifying antirheumatic drugs (DMARDs) such as methotrexate, gold salts, hydroxychloroquine, sulfasalazine, ciclosporin, azathioprine, and leflunomide. Other therapeutics useful in the treatment of inflammatory diseases or conditions include antioxidants. Antioxidants can be natural or synthetic. Antioxidants are, for example, superoxide dismutase (SOD), 21-aminosteroids/aminochromans, vitamin C or E, etc. Many other antioxidants are known to those of skill in the art. The compounds of formula (I), (II) and/or (III) can serve as part of a treatment regimen for an inflammatory condition, which may combine many different anti-inflammatory agents. The compounds of formula (Id) and/or (Ie) can serve as part of a treatment regimen for an inflammatory condition, which may combine many different anti-inflammatory agents. For example, the subject compounds can be administered in combination with one or more of an NSAID, DMARD, or immunosuppressant. The subject compounds can also be administered in combination with methotrexate. The subject antibodies can also be administered in combination with a TNF-α inhibitor.

In the case of cardiovascular disease conditions, and particularly those arising from atherosclerotic plaques, which are thought to have a substantial inflammatory component, the therapeutic formulation including a compound of formula (I), (II) and/or (III) can be administered in combination with one or more other agents useful in the treatment of cardiovascular diseases. In the case of cardiovascular disease conditions, and particularly those arising from atherosclerotic plaques, which are thought to have a substantial inflammatory component, the therapeutic formulation including a compound of formula (Id) and/or (Ie) can be administered in combination with one or more other agents useful in the treatment of cardiovascular diseases. Agents useful in the treatment of cardiovascular diseases include, but are not limited to, β-blockers such as carvedilol, metoprolol, bucindolol, bisoprolol, atenolol, propranolol, nadolol, timolol, pindolol, and labetalol; antiplatelet agents such as aspirin and ticlopidine; inhibitors of angiotensin-converting enzyme (ACE) such as captopril, enalapril, lisinopril, benazopril, fosinopril, quinapril, ramipril, spirapril, and moexipril; and lipid-lowering agents such as mevastatin, lovastatin, simvastatin, pravastatin, fluvastatin, atorvastatin, and rosuvastatin.

In the case of cancer, the subject compounds can be administered in combination with one or more anti-angiogenic factors, chemotherapeutics, or as an adjuvant to radiotherapy. It is further envisioned that the administration of the subject compounds will serve as part of a cancer treatment regimen, which may combine many different cancer therapeutic agents.

The disclosure is further illustrated by the following examples, which are not to be construed as limiting this disclosure in scope or spirit to the specific procedures described in this disclosure. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

It will be recognized that one or more features of any embodiments disclosed herein may be combined and/or rearranged within the scope of the invention to produce further embodiments that are also within the scope of the invention.

EXAMPLES

Preparation of Compounds of Formula 1b.

Example 1: Synthesis of Tricyclic Acid (1.1)

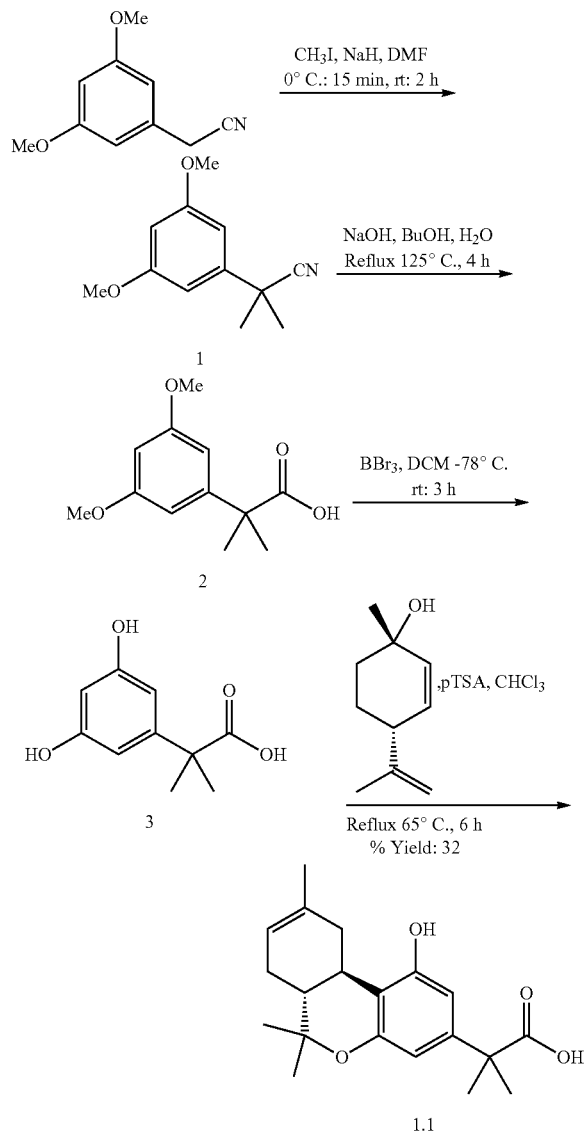

Scheme 1

Procedure:

2-(3, 5-dimethoxyphenyl)-2-methylpropanenitrile (1)

To the stirring suspension of sodium hydride (169.2 mmol) in dry DMF (40 ml) under argon at 0° C. was added drop wise a mixture of 3,5-dimethoxyphenylacetonitrile (56.2 mmol) and iodomethane (169.2 mmol) in dry DMF (40 ml). The reaction mixture was brought to room temperature after stirring at 0° C. for 15 min and stirred for additional 1.5 h. The reaction mixture was quenched with drop wise addition of saturated solution of NH$_4$Cl and diluted with ether. The organic layer was separated and aqueous layer extracted with ether 3 times. The combined organic layers were collected, washed with saturated brine solution, dried over magnesium sulfate and concentrated under vacuum to get crude product which was then chromatographed on silica gel eluting with 25% ethyl acetate/hexane to yield compound 1 as colorless oil (11.01 g, 95% yield). $^1$H NMR (500 MHz, Chloroform-d) δ ppm 1.71 (s, 6H) 3.82 (s, 6H) 6.40 (t, J=2.5 Hz, 1H) 6.61 (d, J=2.0 Hz, 2H).

2-(3, 5-dimethoxyphenyl)-2-methylpropanoic acid (2)

To the stirring mixture of 1 (19.48 mmol), n-butanol (29.23 mmol), sodium hydroxide (48.7 mmol) was added water (48.7 mmol) and the resulting reaction mixture was refluxed at 125° C. for 4 h. Excess of n-Butanol was removed under reduced pressure using rotavapor and the residue was acidified with drop wise addition of 2N HCl and the resulting mixture was diluted with ether. The organic layer separated and aqueous layer extracted with ether (20 ml) 3 times. The combined organic layers were collected washed with water, saturated brine solution, dried over magnesium sulfate and concentrated under vacuum to get crude product which was then chromatographed on silica gel eluting with 30% ether/hexane to give 2 (3.71 g, 93% yield) as white solid. $^1$H NMR (500 MHz, Chloroform-d) δ ppm 1.57 (s, 6H) 3.79 (s, 6H) 6.36 (t, J=2.0 Hz, 1H) 6.54 (d, J=2.5 Hz, 2H); HRMS calcd for $C_{12}H_{17}O_4$, 225.1127, found 225.1132. Melting point: 99° C.

2-(3,5-dihydroxyphenyl)-2-methylpropanoic acid (3)

To the stirring solution of 2 (3.03 mmol) in dry DCM (25 ml) in 50 ml RBF at −78° C. under argon was added borontribromide (10.61 mmol). The reaction mixture was brought to room temperature after stirring at same temperature for 20 min and stirred for additional 2 h. The reaction mixture was quenched with drop wise addition of 1N HCl and diluted with ether. The organic layer separated and aqueous layer extracted with ether (10 ml) 2 times. The combined organic layers were collected, washed with saturated brine solution and dried over magnesium sulfate to give crude product which was then chromatographed on silica gel to give 3 (3.2 g, 85%) as white solid. $^1$H NMR (500 MHz, Methanol d$_4$) δ ppm 1.48 (s, 6H) 6.15 (t, J=2.5 Hz, 1H) 6.33 (d, J=2.5 Hz, 2H). HRMS calcd for $C_{10}H_{13}O_4$, 197.0814, found 197.0806.

2-((6aS, 10aR)-6a,7, 10,10a-tetrahydro-1-hydroxy-6,6,9-trimethyl-6H-benzo[c]chromen-3-yl)-2-methylpropanoic acid (1.1)

The solution of 3 (1.01 mmol), p-menthadienol (1.12 mmol) and p-toluenesulfonic acid (0.2 mmol) in CHCl$_3$ (10 ml) was refluxed at 65° C. for 6 h. The reaction mixture was quenched with water and diluted with CHCl$_3$. The organic layer separated and aqueous layer extracted with CHCl$_3$ (10 ml) three times. The combined organic layers were collected, washed with water, dried over magnesium sulfate and concentrated under vacuum to give crude product which was then chromatographed on silica gel to give 4 (110 mg, 32% yield) as light yellowish solid. $^1$H NMR (500 MHz, CHLOROFORM-d) δ ppm 1.09 (s, 3H) 1.37 (s, 3H) 1.51 (d, J=9.0 Hz, 6H) 1.68 (s, 3H) 1.74-1.89 (m, 3H) 2.10-2.16 (m, 1H)

2.70 (td, J=11.0, 4.5 Hz, 1H) 3.19 (dd, J=16.5, 4.5 Hz, 1H), 5.42 (d, J=4.5 Hz, 1H) 6.29 (d, J=2.0 Hz, 1H) 6.45 (d, J=2.0 Hz, 1H); HRMS calcd for $C_{20}H_{27}O_4$, 331.1909, found 331.1901.

Example 2: Synthesis of Compounds 1.2, 1.3, 1.4, 1.5, 1.6, 1.7, 1.8, 1.9, 1.10, 1.24, 1.25, 1.34, 1.35, and 1.36

Tricyclic acid (1.1) was coupled with side chains using optimized microwave conditions to give respective compounds as shown in scheme 2 and 2a.

Typical Procedure

Alkyl side chain (1.5 equivalent) was added to the stirring mixture of 1.1 (1 equivalent) and sodium bicarbonate (1.5 equivalent) in dimethyl formamide (2 ml) in microwave vessel and the resulting solution was heated at 165° C. in microwave for 12 min. The reaction mixture was quenched with water and diluted with ethyl acetate. The organic layer separated and aqueous layer extracted 3 times with ethyl acetate. The combined organic layers were collected, washed with saturated brine, dried over magnesium sulfate and concentrated under vacuum to get crude product which was then chromatographed on silica gel to get pure product.

4-bromobutyl-2-((6aS, 10aR)-6a,7, 10, 10a-tetrahydro-1-hydroxy-6,6,9-trimethyl-6H-benzo chromen-3-yl)-2-methylpropanoate (1.2)

$^1$H NMR (500 MHz, Chloroform-d) δ ppm 1.1 (s, 3H) 1.38 (s, 3H) 1.68-1.86 (m, 7H) 1.70 (s, 3H) 1.51 (s, 6H) 2.1-2.2 (m, 1H) 2.69 (dt, J=11.0, 4.5 Hz, 1H) 3.20 (dd, J=16.5, 4.5 Hz, 1H) 3.32 (t, J=6.5, 2H) 4.09 (t, j=6.5, 2H) 5.18 (s, OH). 5.42 (d, J=4.5, 1H) 6.25 (d, J=2.0, 1H) 6.41 (d, J=2.0, 1H). HRMS calcd for $C_{24}H_{34}O_4Br$, 465.1640, found 465.1647.

Butyl-2-((6aS, 10aR)-6a, 7, 10, 10a-tetrahydro-1-hydroxy-6, 6, 9-trimethyl-6H-benzo[c]chromen-3-yl)-2-methylpropanoate (1.4)

$^1$H NMR (500 MHz, Chloroform-d) δ ppm 0.87 (t, J=7.32 Hz, 3H) 1.10 (s, 3H) 1.23-1.32 (m, 2H) 1.39 (s, 3H) 1.51 (s, 6H) 1.53-1.58 (m, 2H) 1.69 (s, 3H) 1.76-1.89 (m, 3H) 2.11-2.20 (m, 1H) 2.70 (td, J=11.0, 4.5 Hz, 1H) 3.21 (dd, J=16.0, 5.0 Hz, 1H) 4.07 (t, J=6.5 Hz, 2H) 5.11 (s, OH) 5.43 (d, J=4.5 Hz, 1H) 6.26 (s, 1H) 6.43 (d, J=2.0 Hz, 1H); HRMS calcd for $C_{24}H_{34}O_4$, 386.2457, found 386.2460.

Scheme 2

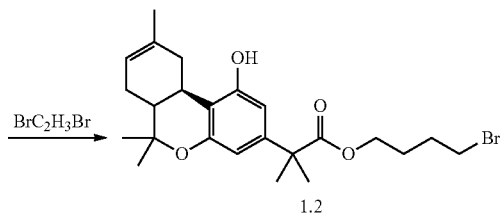

1.2

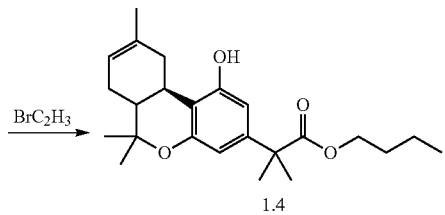

1.4

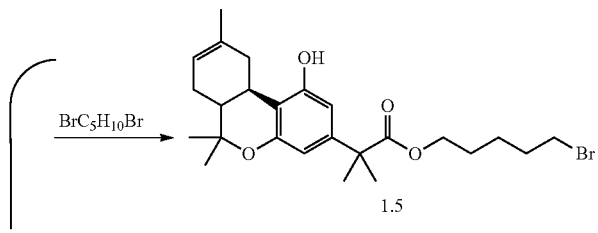

1.5

-continued
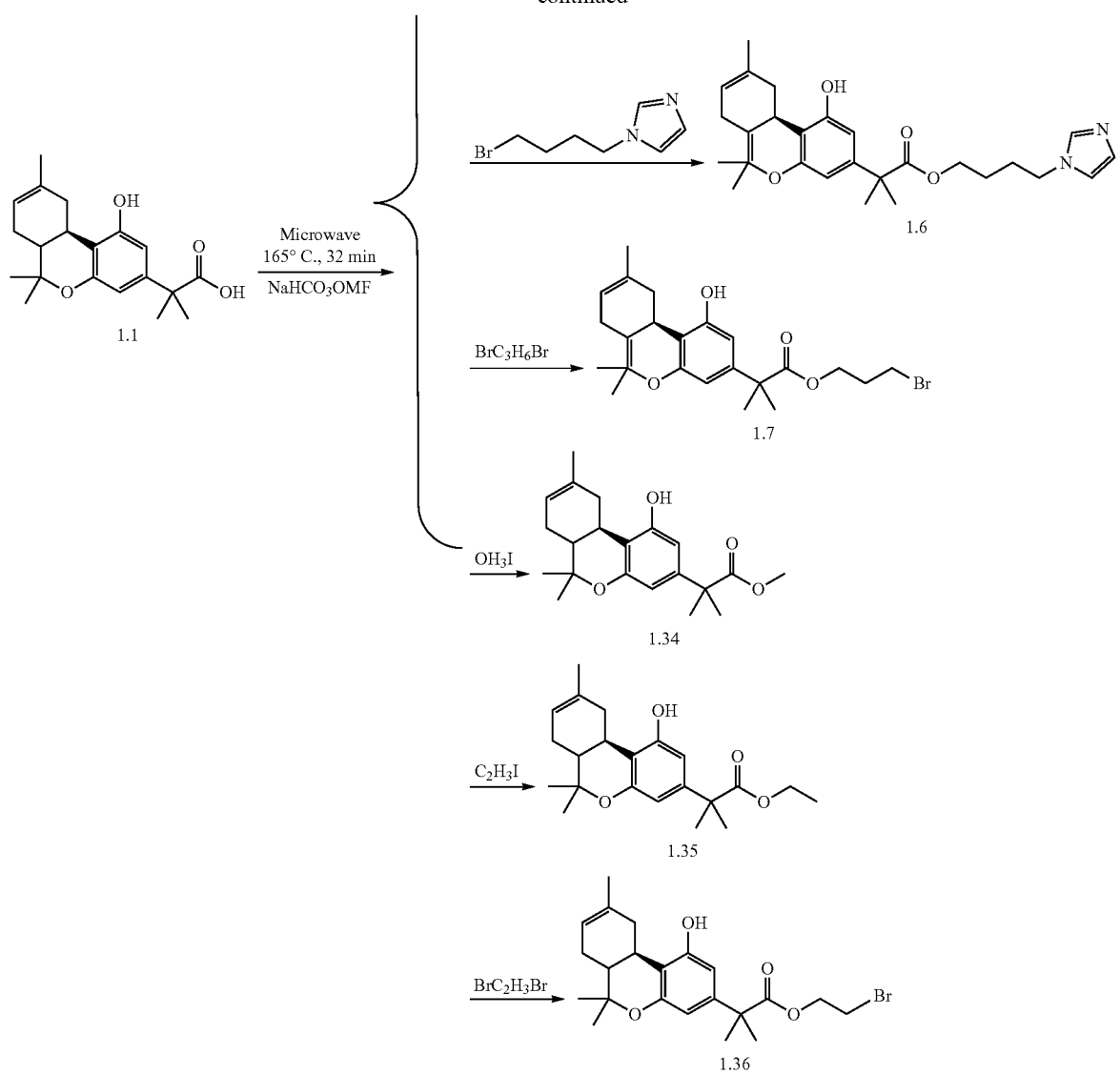
Scheme 2a
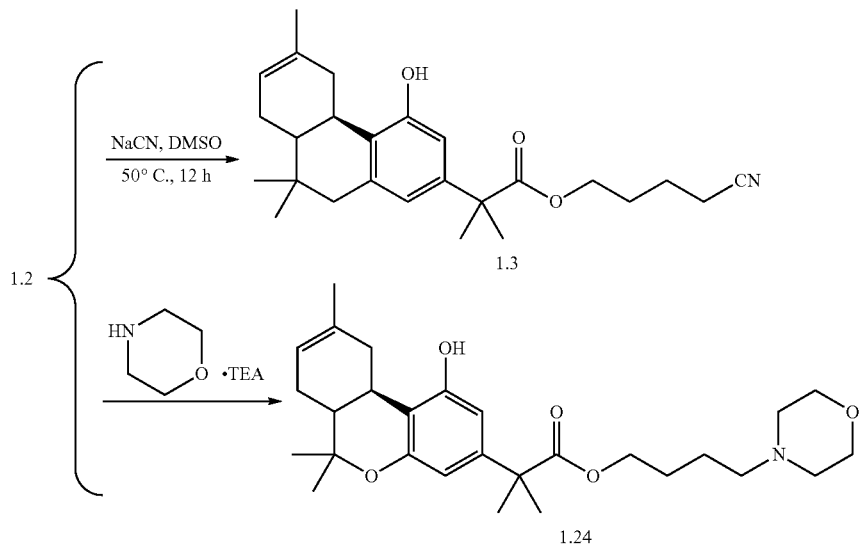

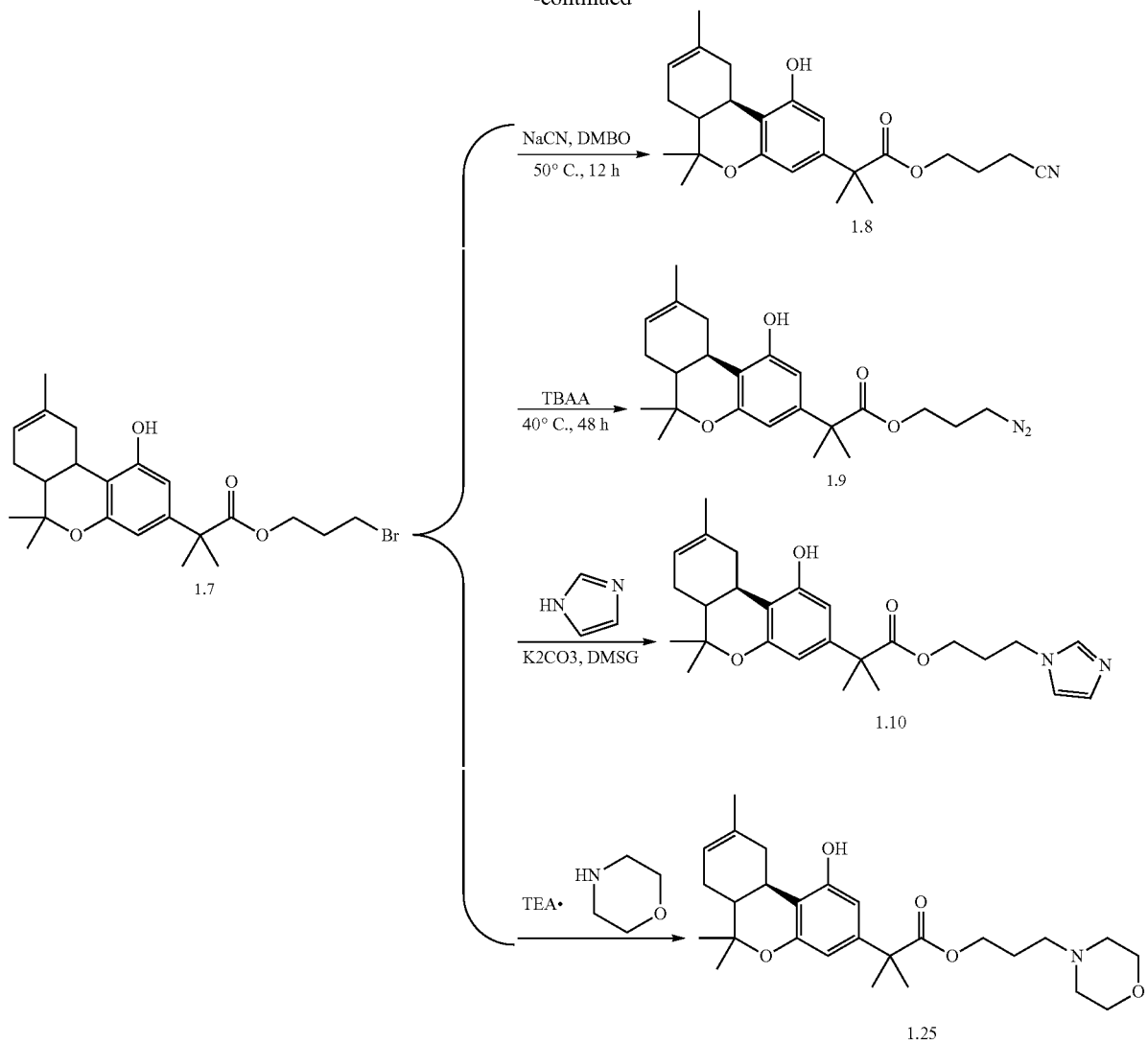

5-bromopentyl-2-((6aS, 10aR)-6a,7, 10, 10a-tetrahydro-1-hydroxy-6,6,9-trimethyl-6H-benzo[c]chromen-3-yl)-2-methylpropanoate (1.5)

$^1$H NMR (500 MHz, Chloroform-d) δ ppm 1.11 (s, 3H) 1.26 (br. s., 1H) 1.39 (s, 3H) 1.52 (s, 6H) 1.62-1.75 (m, 6H) 1.76-1.90 (m, 3H) 1.96-2.06 (m, 2H) 2.15 (d, J=15.0 Hz, 1H) 2.70 (td, J=10.5, 4.5 Hz, 1H) 3.20 (dd, J=16.0, 4.5 Hz, 1H) 4.07 (t, J=6.35 Hz, 2H) 4.91-5.01 (m, 2H) 5.44 (br. s., 1H) 5.67-5.81 (m, 1H) 6.25 (s, 1H) 6.44 (s, 1H); HRMS calcd for $C_{25}H_{35}O_4Br$, 478.1718, found 478.1715.

4-(1H-imidazol-1-yl)butyl 2-((6aR, 10aR)-6a,7, 10, 10a-tetrahydro-1-hydroxy-6,6,9-trimethyl-6H-benzo[c]chromen-3-yl)-2-methylpropanoate (1.6)

$^1$H NMR (500 MHz, Chloroform-d) δ ppm 1.09 (s, 3H) 1.38 (s, 3H) 1.47 (d, J=9.0 Hz, 6H) 1.69 (s, 3H) 1.70-1.82 (m, 7H) 2.10-2.16 (m, 1H) 2.72 (td, J=11.0, 5.0 Hz, 1H) 3.39 (dd, J=16.5, 4.0 Hz, 1H) 3.88 (td, J=6.5, 2.5 Hz, 2H) 3.96 (t, J=5.0 Hz, 2H) 5.42 (d, J=3.5 Hz, 1H) 6.23 (d, J=2.0 Hz, 1H) 6.36 (d, J=2 Hz, 1H) 6.86 (s, 1H) 7.10 (s, 1H) 7.50 (s, 1H).

3-bromopropyl-2-((6aR, 10aR)-6a, 7, 10, 10a-tetrahydro-1-hydroxy-6,6,9-trimethyl-6H-benzo[c]chromen-3-yl)-2-methylpropanoate (1.7)

$^1$H NMR (500 MHz, Chloroform-d) δ ppm 1.10 (s, 3H) 1.38 (s, 3H) 1.51 (s, 6H) 1.69 (s, 3H) 1.75-1.89 (m, 3H) 2.08 (t, J=6.50 Hz, 2H) 2.12-2.19 (m, 1H) 2.70 (dt, J=10.50, 4.50 Hz, 1H) 3.08-3.38 (m, 3H) 4.19 (t, J=6.5 Hz, 2H) 5.42 (d, J=5.0 Hz, 1H) 5.89 (s, 1H) 6.28 (d, J=1.5 Hz, 1H) 6.41 (d, J=1.5 Hz, 1H).

Methyl-2-((6aR, 10aR)-6a,7, 10, 10a-tetrahydro-1-hydroxy-6,6,9-trimethyl-6H-benzo[c] chromen-3-yl)-2-methylpropanoate (1.34)

$^1$H NMR (500 MHz, Chloroform-d) δ ppm 1.10 (s, 3H) 1.38 (s, 3H) 1.50 (s, 6H) 1.69 (s, 3H) 1.76-1.86 (m, 3H) 2.09-2.21 (m, 1H) 2.70 (dt, J=11.0, 5.0 Hz, 1H) 3.23 (dd, J=15.5, 4.5 Hz, 1H) 3.66 (s, 3H) 5.43 (d, J=4.5 Hz, 1H) 5.76 (s, 1H) 6.27 (d, J=2.0 Hz, 1H) 6.42 (d, J=2.0 Hz, 1H); HRMS calcd for $C_{21}H_{28}O_4$, 344.1988, found 344.1992.

Ethyl-2-((6aR, 10aR)-6a,7, 10, 10a-tetrahydro-1-hydroxy-6,6,9-trimethyl-6H-benzo[c] chromen-3-yl)-2-methylpropanoate (1.35)

$^1$H NMR (500 MHz, Chloroform-d) δ ppm 1.11 (s, 3H) 1.20 (t, J=6.5 Hz, 3H) 1.39 (s, 3H) 1.51 (s, 6H) 1.69 (s, 3H) 1.75-1.89 (m, 3H) 2.10-2.18 (m, 1H) 2.70 (td, J=11.0, 4.50 Hz, 1H) 3.23 (dd, J=16.0, 4.50 Hz, 1H) 4.11 (q, J=14.5, 7.0 Hz, 2H) 5.43 (d, J=5.0 Hz, 1H) 5.74 (d, J=2.0 Hz, 1H) 6.27 (d, J=1.0 Hz, 1H) 6.41 (d, J=1.0 Hz, 1H); HRMS calcd for $C_{22}H_{30}O_4$, 358.2144, found 358.2145.

2-bromoethyl-2-((6aR, 10aR)-6a,7,10, 10a-tetrahydro-1-hydroxy-6,6,9-trimethyl-6H-benzo[c]chromen-3-yl)-2-methylpropanoate (1.36)

$^1$H NMR (500 MHz, Chloroform-d) δ ppm 1.10 (s, 3H) 1.38 (s, 3H) 1.53 (s, 6H) 1.69 (s, 3H) 1.75-1.86 (m, 3H) 3.45 (t, J=6.0 Hz, 2H) 4.36 (td, J=2.0, 5.5 Hz, 2H) 5.04 (s, 1H) 5.43 (d, J=4.0 Hz, 1H) 6.27 (d, J=1.5 Hz, 11H) 6.42 (d, J=1.0 Hz, 11H); HRMS calcd for $C_{22}H_{29}O_4Br$, 436.1249, found 436.1250.

4-cyanobutyl-2-((6aS, 10aR)-6a, 7, 10, 10a-tetrahydro-1-hydroxy-6, 6, 9-trimethyl-6H-benzo[c] chromen-3-yl)-2-methylpropanoate (1.3)

To the stirring solution of 1.2 (0.043 mmol) in dry DMSO (3 ml) was added sodium cyanide (0.43 mmol). The resulting mixture was heated at 50° C. for 3 h, brought to room temperature, quenched with water and diluted with ethyl acetate. The organic layer separated and aqueous layer extracted with ethyl acetate (2 ml) 3 times. The combined organic extracts were collected, washed with saturated brine solution, dried over magnesium sulfate and concentrated under vacuum to give crude product which was then chromatographed on silica gel eluting with 20% ethyl acetate/hexane to give 1.3 (56% yield) as light yellowish gum. $^1$H NMR (500 MHz, Chloroform-d) δ ppm 1.1 (s, 3H) 1.38 (s, 3H) 1.51 (d, J=2.5 Hz, 6H) 1.59-1.90 (m, 7H) 1.69 (s, 3H) 2.12-2.15 (m, 1H) 2.27 (t, J=7.0 Hz, 2H) 2.70 (dt, J=11.0, 5.0 Hz, 1H) 3.20 (dd, J=16.0, 3.5 Hz, 1H) 4.11 (t, J=6.5 Hz, 2H) 5.26 (s, 1H) 5.42 (d, J=5.0 Hz, 1H) 6.26 (d, J=2.0 Hz, 1H) 6.41 (d, J=2.0 Hz, 1H); HRMS calcd for $C_{25}H_{34}NO_4$, 412.2488, found 412.2480.

3-cyanopropyl-2-((6aR, 10aR)-6a,7, 10, 10a-tetrahydro-1-hydroxy-6,6,9-trimethyl-6H-benzo[c]chromen-3-yl)-2-methylpropanoate (1.8)

Sodium cyanide (1.94 mmol) was added to the stirring solution of 1.7 (0.24 mmol) in dimethylsulfoxide (6 ml). The resulting solution was heated for 12 h at 50° C. The reaction mixture was quenched with water and diluted with ethyl acetate. The organic layer separated and aqueous layer extracted with ethyl acetate (2 ml) three times. The combined organic layers were collected, washed with saturated brine solution, dried over magnesium sulfate and concentrated under vacuum to get crude product which is then chromatographed on silica gel eluting with 25% ethyl acetate/hexane to give 1.8 (98% yield) as light yellowish gum. $^1$H NMR (500 MHz, Chloroform-d) δ ppm 1.10 (s, 3H) 1.38 (s, 3H) 1.51 (s, 6H) 1.69 (s, 3H) 1.75-1.87 (m, 3H) 1.89-1.96 (m, 2H) 2.10-2.18 (m, 1H) 2.21 (t, J=7.50 Hz, 2H) 2.70 (dt, J=11.0, 5.0 Hz, 1H) 3.23 (dd, J=16.0, 4.0 Hz, 1H) 4.13-4.18 (m, 2H) 5.42 (d, J=4.0 Hz, 1H) 5.82 (s, 1H) 6.29 (d, J=2.0 Hz, 1H) 6.40 (d, J=2.0 Hz, 1H); HRMS calcd for $C_{24}H_{31}NO_4$, 397.2253, found 397.2254.

3-azidopropyl-2-((6aR, 10aR)-6a,7, 10, 10a-tetrahydro-1-hydroxy-6,6,9-trimethyl-6H-benzo[c]chromen-3-yl)-2-methylpropanoate (1.9)

To the stirring solution of 1.7 (0.088 mmol) in dry dichloromethane (5 ml) under argon was added tetrabutylammoniumazide (0.88 mmol). The resulting mixture was heated at 40° C. for 48 h and quenched with water and diluted with ethyl acetate. The organic layer separated and aqueous layer extracted with ethyl acetate three times. The combined organic layers were collected washed with saturated brine solution, dried over magnesium sulfate and concentrated under vacuum to get crude product which was then chromatographed on silica gel eluting with 17% ethyl acetate/hexane to give 1.9 (70% yield) as light yellowish gum. $^1$H NMR (500 MHz, Chloroform-d) δ ppm 1.10 (s, 3H) 1.38 (s, 3H) 1.51 (s, 6H) 1.69 (s, 3H) 1.80-1.86 (m, 4H) 2.09-2.21 (m, 1H) 2.71 (dt, J=10.50, 4.50 Hz, 1H) 3.14-3.30 (m, 4H) 4.13-4.18 (m, 2H) 5.19 (s, 1H) 5.43 (d, J=4.50 Hz, 11H) 6.25 (d, J=2.0 Hz, 1H) 6.42 (d, J=2.0 Hz, 1H); HRMS calcd for $C_{23}H_{31}N_3O_4$, 413.2315, found 413.2317.

3-(1H-imidazol-1-yl) propyl-2-((6aR, 10aR)-6a,7, 10, 10a-tetrahydro-1-hydroxy-6,6,9-trimethyl-6H-benzo[c]chromen-3-yl)-2-methylpropanoate (1.10)

Imidazole (2.15 mmol) was added to the stirring suspension of 1.7 (0.43 mmol) and potassium carbonate (4.3 mmol) in dimethylsulfoxide (5 ml). The resulting mixture was stirred for 14 h at room temperature. The reaction mixture was quenched with water and diluted with ethyl acetate. The organic layer separated and aqueous layer extracted with ethyl acetate (2 ml) three times. The combined organic layers were collected washed with saturated brine solution, dried over magnesium sulfate and concentrated under vacuum to get crude product which was then chromatographed on silica gel eluting with 50% acetone/hexane to give 1.10 (41% yield) as light yellowish gum. $^1$H NMR (500 MHz, Chloroform-d) δ ppm 1.07 (s, 3H) 1.37 (s, 3H) 1.49 (d, J=4.0 Hz, 6H) 1.69 (s, 3H) 1.72-1.87 (m, 3H) 1.92-2.01 (m, 2H) 2.08-2.18 (m, 1H) 2.73 (dt, J=11.5, 4.5 Hz, 1H) 3.42 (dd, J=17.0, 4.0 Hz, 1H) 3.73 (t, J=7.0 Hz, 2H) 3.80-3.99 (m, 2H) 5.40 (d, J=5.0 Hz, 1H) 6.32 (d, J=2.0 Hz, 1H) 6.40 (d, J=2.0 Hz, 1H) 6.64 (s, 1H) 7.04 (s, 1H) 7.33 (s, 1H). HRMS calcd for $C_{26}H_{34}N_2O_4$, 438.2518, found 438.2518.

4-morpholinobutyl 2-((6aR, 10aR)-1-hydroxy-6,6,9-trimethyl-6a,7,10, 10a-tetrahydro-6H-benzo[c]chromen-3-yl)-2-methylpropanoate (1.24)

To the stirring solution of 1.2 (0.36 mmoles) in dry acetonitrile under argon at room temperature was added triethylamine (1.09 mmoles) and morpholine (3.6 mmoles). The resulting solution was stirred at same temperature for 24 h. The reaction mixture was quenched with water and diluted with ethyl acetate. The organic layer separated and aqueous layer extracted three times with ethyl acetate. The combined organic layers were collected, washed with saturated brine solution, dried over magnesium sulfate and concentrated under vacuum to get crude product which is then chromatographed on silicagel eluting with 48% acetone/hexane to get 1.24 (81% yield). $^1$H NMR (500 MHz, Chloroform-d) δ ppm 1.10 (s, 3H) 1.37 (s, 3H) 1.49 (d, J=7.5 Hz, 6H) 1.56-1.66 (m, 4H) 1.68 (s, 3H) 1.75-1.82 (m, 3H)

2.10-2.18 (m, 1H) 2.33-2.41 (m, 4H) 2.69 (dt, J=4.5, 11.0 Hz, 1H) 3.32 (dd, J=4.5, 16.0 Hz, 1H) 3.73-3.82 (m, 6H) 4.10-4.18 (m, 2H) 5.42 (d, J=4.0 Hz, 1H) 6.13 (d, J=2.0 Hz, 1H) 6.38 (d, J=1.5 Hz, 1H)

3-morpholinopropyl 2-((6aR, 10aR)-1-hydroxy-6,6,9-trimethyl-6a,7, 10, 10a-tetrahydro-6H-benzo[c]chromen-3-yl)-2-methylpropanoate (1.25)

To the stirring solution of 1.7 (0.58 mmoles) in dry acetonitrile under argon at room temperature was added triethylamine (1.76 mmoles) and morpholine (5.8 mmoles). The resulting solution was stirred at same temperature for 24 h. The reaction mixture was quenched with water and diluted with ethyl acetate. The organic layer separated and aqueous layer extracted three times with ethyl acetate. The combined organic layers were collected, washed with saturated brine solution, dried over magnesium sulfate and concentrated under vacuum to get crude product which is then chromatographed on silicagel eluting with 45% acetone/hexane to get 1.25 (78% yield). $^1$H NMR (500 MHz, Chloroform-d) δ ppm 1.10 (s, 3H) 1.37 (s, 3H) 1.49 (d, J=5.5 Hz, 6H) 1.67 (s, 3H) 1.75-1.83 (m, 5H) 2.11-2.18 (m, 1H) 2.24-2.36 (m, 2H) 2.41 (br, s, 4H) 2.68 (dt, J=4.5, 11.0 Hz, 1H) 3.26 (dd, J=4.5, 16.5 Hz, 1H) 3.71 (t, J=4.5 Hz, 4H) 4.12 (m, 2H) 5.41 (d, J=4.0 Hz, 1H) 6.23 (d, J=2.0 Hz, 1H) 6.38 (d, J=2.5 Hz, 1H); HRMS calcd for $C_{27}H_{39}NO_5$, 457.2828, found 457.2829.

Example 3: Synthesis of Compounds 1.11, 1.12, 1.13, 1.14, 1.15, and 1.16

The synthesis of compounds with monomethyl at 1' position is depicted in scheme 3, 3a and 3b.

Procedure 2-(3,5-dimethoxyphenyl)propanenitrile (4)

A solution of 3,5-dimethoxyphenylacetonitrile (28.2 mmoles) and iodomethane (42.3 mmoles) in dry DMF (30 ml) was added at 0° C. to a suspension of sodium hydride (33.8 mmoles, 60% dispersion in oil) in dry DMF (50 ml). The resulting mixture was brought to room temperature and stirred for additional 2 h. The reaction mixture was quenched with saturated ammonium chloride and diluted with ethyl acetate. The organic layer separated and aqueous layer extracted with ethyl acetate three times. The combined organic layers collected, washed with water, saturated brine solution and dried over magnesium sulfate solution to get crude product which is then chromatographed on silica gel eluting with 20% Ethyl acetate:Hexane mixture to get pure intermediate 4 (75% yield) as white solid. $^1$H NMR (500 MHz, Chloroform-d) S ppm 1.63 (d, J=7.5 Hz, 3H) 3.81 (s, 6H) 3.84 (q, J=7.0, 14.5 Hz, 1H) 6.41 (t, J=2.5 Hz, 1H) 6.54 (d, J=2.5 Hz, 2H).

Scheme 3

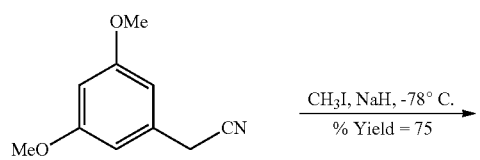

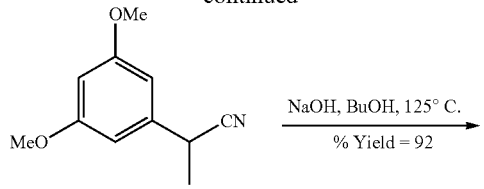

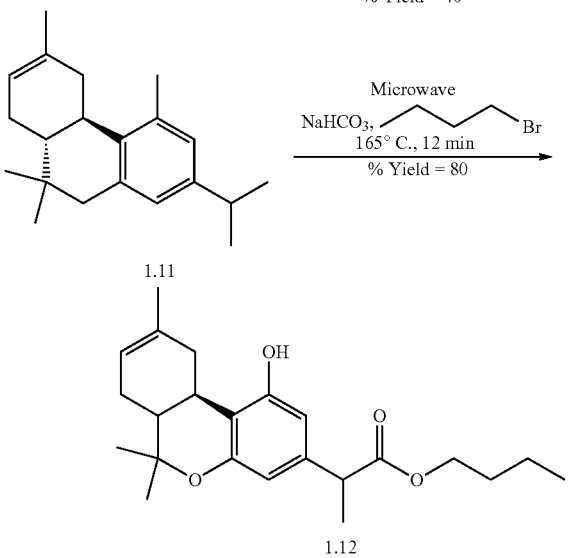

2-(3,5-dimethoxyphenyl)propanoic acid (5)

Sodium hydroxide (30.05 mmoles) was added to a mixture of 4 (12.02 mmoles), n-Butanol (18.04 mmoles) and water (30.05 mmoles). The resulting mixture was refluxed at 125° C. for 8 h and excess of n-butanol was removed under reduced pressure using rotavapor and the remaining reaction mixture was acidified using 1N HCl and diluted with ethyl acetate. The organic layer separated and aqueous layer was extracted with ethyl acetate three times. The combined organic layers was collected, washed with water, saturated brine, dried over magnesium sulfate and concentrated under vacuum to get crude product which is then chromatographed on silica gel eluting with 85% ethyl acetate:hexane to get pure intermediate 5 (92% yield) as white solid. $^1$H NMR (500 MHz, Chloroform-d) δ ppm 1.49 (d, J=7.5 Hz, 3H) 3.66 (q, J=7.0, 14.5 Hz, 1H) 3.77 (s, 6H) 6.37 (t, J=2.5 Hz, 1H) 6.47 (d, J=2.0 Hz, 2H).

2-(3,5-dihydroxyphenyl)propanoic acid (6)

Boron tribromide (38.45 mmoles, 1M Solution in DCM) was added at −78° C. to a solution of 5 (10.98 mmoles). The resulting mixture was brought to room temperature after stirring at same temperature for 1 h and stirred for additional 4 h. The reaction mixture was quenched with saturated sodium bicarbonate solution and diluted with ethyl acetate. The organic layer was separated and aqueous layer extracted with ethyl acetate three times. The combined organic layers were collected, washed with water, saturated brine, dried over magnesium sulfate and concentrated under vacuum to get crude product which is then chromatographed on silica gel eluting with 78% ethyl acetate/hexane to get pure intermediate 6 (78% yield). $^1$H NMR (500 MHz, Chloroform-d) δ ppm 1.40 (d, J=7.5 Hz, 3H) 3.56 (q, J=6.5, 14.0 Hz, 1H) 6.20 (t, J=2.0 Hz, 1H) 6.30 (d, J=2.5 Hz, 2H).

2-((6aR, 10aR)-1-hydroxy-6,6,9-trimethyl-6a,7,10,10a-tetrahydro-6H-benzo[c]chromen-3-yl)propanoic acid (1.11)

p toulenesulfonic acid (0.72 mmoles) was added to a solution of 6 (3.62 mmoles) and cis/trans paramentha dienol (3.98 mmoles) in chloroform (30 ml). The resulting mixture was refluxed at 65° C. for 6 h. The reaction mixture was quenched with water and diluted with DCM, the organic layer separated and aqueous layer was extracted with DCM three times. The combined organic layers was collected, washed with saturated brine and dried over magnesium sulfate to get crude product which had overlapping impurities and was used as such for next reaction without purification. HRMS calcd for $C_{19}H_{24}O_4$, 316.1675, found 316.1675.

Butyl 2-((6aR,10aR)-1-hydroxy-6,6,9-trimethyl-6a,7, 10,10a-tetrahydro-6H-benzo[c]chromen-3-yl)propanoate (1.12)

Sodium bicarbonate (0.66 mmoles) was added to a solution of 1.11 (0.55 mmoles) and bromobutane (0.82 mmoles) in DMF (2 ml) in microwave vessel. The resulting mixture was heated at 165° C. for 12 min. The reaction mixture was quenched with water and diluted with ethyl acetate, the organic layer was separated and aqueous layer extracted with ethyl acetate three times. The combined organic layers were collected, washed with saturated brine, dried over magnesium sulfate and concentrated under vacuum to get crude product which is then chromatographed on silica gel eluting with 12% ethyl acetate/hexane to get pure product 1.12 (80% yield). $^1$H NMR (500 MHz, Chloroform-d) δ ppm 0.87 (dt, J=2.0, 7.5 Hz, 3H) 1.09 (s, 3H) 1.25-1.35 (m, 2H) 1.37 (s, 3H), 1.44 (dd, J=1.5, 6.5 Hz, 3H) 1.52 (p, J=7.0, 14.5 Hz, 2H) 1.68 (s, 3H) 1.75-1.89 (m, 3H) 2.12 (d, J=145 Hz, 1H) 2.69 (dt, J=4.0, 10.5 Hz, 1H) 3.24 (d, J=19.5 Hz, 1H) 3.5-3.59 (m, 1H) 4.0-4.12 (m, 2H) 5.42 (d, J=4.0 Hz, 1H) 6.30 9s, 1H) 0.34 (s, 1H). HRMS calcd for $C_{23}H_{32}O_4$, 372.2301, found 372.2305.

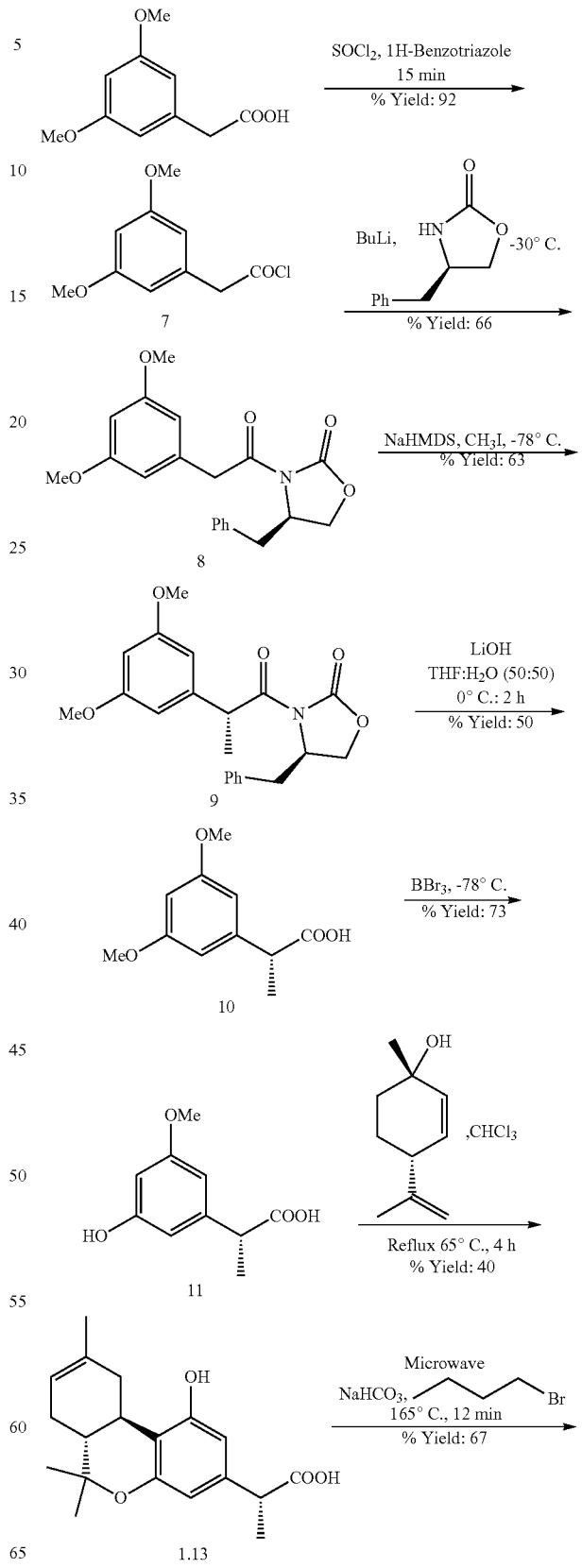

Scheme 3a

-continued

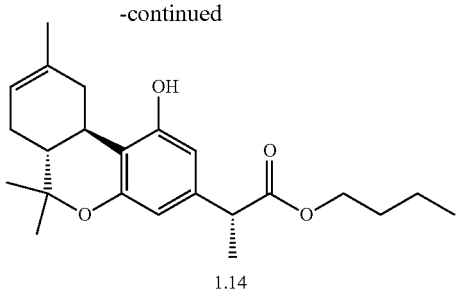

1.14

Procedure 2-(3,5-dimethoxyphenyl)acetyl chloride (7)

To the stirring solution of 3,5-dimethoxyphenylacetic acid (5.09 mmoles) in dry dichloromethane (40 ml) was added intermittently 4.24 ml of 1.5 M stock solution (thionyl chloride (5.46 ml) and benzotriazole (8.93 g) in 50 ml DCM). The reaction mixture was filtered through celite after stirring at room temperature for 20 min and diluted with dichloromethane. The organic layer was washed with dilute 1N HCl, saturated brine solution, dried over magnesium sulfate and concentrated under vacuum to give 57 (92% Yield) as crude product which was used as such for next reaction without purification.

(R)-4-benzyl-3-(2-(3,5-dimethoxyphenyl)acetyl) oxazolidin-2-one (8)

To the stirring solution of (R)-4-benzyl oxazolidin-2-one (4.18 mmoles) in dry THF (10 ml) at −30° C. was added drop wise n-butyl lithium (4.18 mmoles, 1.6 M solution in hexane) and the resulting mixture was stirred at same temperature for 30 min. To the resulting mixture was added solution of 7 (4.59 mmoles) in dry THF (3 ml) and the reaction mixture was stirred at same temperature for 4 h. The reaction mixture was quenched with sodium bisulfite and diluted with ethyl acetate. The organic layer separated and aqueous layer was extracted with ethyl acetate three times. The combined organic layers were collected washed with water, saturated brine solution, dried over magnesium sulfate and concentrated under vacuum to get crude product which is then chromatographed on silica gel eluting with 20% acetone:hexane to get pure product 8 (66% yield). $^1$H NMR (500 MHz, Chloroform-d) δ ppm 2.76 (dd, J=9.5, 14.0 Hz, 1H) 3.24 (dd, J=3.0, 13.5 Hz, 1H) 3.77 (s, 6H) 4.10-4.19 (m, 2H) 4.26 (q, J=15.5, 42.0 Hz, 2H) 4.64-4.70 (m, 1H) 6.39 (t, J=2.5 Hz, 1H) 6.5 (d, J=2.0 Hz, 2H) 7.13 (dd, J=1.5, 3.5 Hz, 2H) 7.21-7.31 (m, 3H).

(R)-4-benzyl-3-((R)-2-(3,5-dimethoxyphenyl)propanoyl)oxazolidin-2-one (9)

To the stirring solution of 8 (2.75 mmoles) in dry THF (20 ml) under argon at −78° C. was added drop wise sodium hexamethyldisilylamide (3.03 mmoles, 1M in THF) and the reaction mixture stirred at same temperature for 1 h. Iodomethane (13.75 mmoles) was added to the reaction mixture at −78° C. and the reaction mixture was stirred for additional 1 h and then allowed to warm to −30° C. and stirred for additional 1 h. The reaction mixture was quenched with acetic acid (30 ml) in ether (40 ml) and filtered over a celite pad. The filtrate was concentrated in vacuum and the crude product was chromatographed on silica gel eluting with 15% ethyl acetate:hexane mixture to get pure product 9 (63% yield) as viscous oil. $^1$H NMR (500 MHz, Chloroform-d) δ ppm 1.53 (d, J=7.0 Hz, 3H) 2.8 (dd, J=10.0, 13.5 Hz, 1H) 3.33 (dd, J=3.0, 13.5 Hz, 1H) 3.76 (s, 6H) 4.0-4.11 (m, 2H) 4.54-4.62 (m, 11H) 5.06 (q, J=7.5, 14.0 Hz, 111) 6.34 (t, J=2.0 Hz, 1H) 6.53 (d, J=2.5 Hz, 2H) 7.21 (d, J=7.5 Hz, 2H) 7.26 (t, J=7.5 Hz, 11H) 7.32 (t, J=8.0 Hz, 2H). HRMS calcd for $C_{21}H_{24}NO_5$, 370.1654, found 370.1669.

(R)-2-(3,5-dimethoxyphenyl)propanoic acid (10)

Mixture of 9 (0.27 mmoles) and lithium hydroxide (0.812 mmoles) was stirred at 0° C. in THF:H$_2$O (5 ml, 50:50 mixture) for 2 h. The solvent was removed under vacuum after warming to room temperature and the residue was washed with ethyl acetate. The combined organic layers were collected and acidified using 1N HCl and diluted with ethyl acetate. The organic layer separated and aqueous layer extracted with ethyl acetate. The combined organic layers were collected washed with brine, dried over magnesium sulfate and concentrated under vacuum to get crude product which is then chromatographed on silica gel eluting with 66% ethyl acetate:hexane to give pure product 10 (50% yield). $^1$H NMR (500 MHz, Chloroform-d) δ ppm 1.47 (d, J=7.5 Hz, 3H) 3.66 (q, J=14.5, 7.5 Hz, 1H) 3.77 (s, 6H) 6.37 (t, J=2.5 Hz, 1H) 6.47 (d, J=2.0 Hz, 2H).

(R)-2-(3,5-dihydroxyphenyl)propanoic acid (11)

Boron tribromide (4.8 mmoles, 1M solution in DCM) was added to the stirring solution of 10 (1.37 mmoles) in dry DCM (20 ml) at −78° C. and the reaction mixture stirred for 1 h at same temperature. The reaction mixture was brought to room temperature, stirred for additional 6 h and quenched with saturated sodium bicarbonate and diluted with chloroform. The organic layer separated and aqueous layer extracted with chloroform three times. The combined organic layers were collected, washed with water, saturated brine, dried over magnesium sulfate and concentrated under vacuum to get crude product which is then chromatographed on silica gel eluting with 55% acetone:hexane to get pure product 11 (73% yield). $^1$H NMR (500 MHz, Chloroform-d) δ ppm 1.38 (d, J=7.0 Hz, 3H) 3.53 (q, J=7.0, 14.5 Hz, 1H) 6.18 (t, J=2.0 Hz, 1H) 6.29 (d, J=2.0 Hz, 2H).

(R)-2-((6aR,10aR)-1-hydroxy-6,6,9-trimethyl-6a,7,10,10a-tetrahydro-6H-benzo[c]chromen-3-yl)propanoic acid (1.13)

p-toulenesulfonic acid (0.19 mmoles) was added to the stirring solution of 11 (0.98 mmoles) and paramentha dienol (1.08 mmoles) in chloroform (15 ml) and the resulting mixture was refluxed at 65° C. for 4 h. The reaction mixture was cooled to room temperature, quenched with water and diluted with chloroform. The organic layer separated and aqueous layer extracted with chloroform three times. The combined organic layers were collected, washed with brine, dried over magnesium sulfate and concentrated under vacuum to get crude product which is then chromatographed on silica gel eluting with 35% acetone; hexane to get 1.13 (40% yield). HRMS calcd for $C_{19}H_{24}O_4$, 316.1675, found

(R)-butyl 2-((6aR, 10aR)-1-hydroxy-6,6,9-trimethyl-6a,7,10,10a-tetrahydro-6H-benzo[c]chromen-3-yl)propanoate (1.14)

Bromobutane (0.36 mmoles) was added to a mixture of 1.13 (0.18 mmoles) and sodium bicarbonate (0.21 mmoles) in DMF (2 ml) in microwave vessel. The resulting mixture was heated at 165° C. for 12 min in microwave, the reaction mixture was cooled to room temperature and diluted with water and ethyl acetate. The organic layer was separated and aqueous layer was extracted with ethyl acetate three times. The combined organic layers were collected, washed with saturated brine solution, dried over magnesium sulfate and concentrated under vacuum to get crude product which was then chromatographed on silica gel eluting with 10% ethyl acetate:hexane mixture to get pure product 1.14 (46 mg, 67% yield). $^1$H NMR (500 MHz, Chloroform-d) δ ppm 0.87 (t, J=7.5 Hz, 3H) 1.09 (s, 3H) 1.29 (q, J=8.5 Hz, 15.5 Hz, 2H) 1.37 (s, 3H) 1.44 (dd, J=3.0, 6.5 Hz, 3H) 1.57 (p, J=7.0, 14.0 Hz, 2H) 1.68 (s, 3H) 1.75-1.88 (m, 3H) 2.11 (d, J=15.5 Hz, 1H) 2.69 (dt, J=4.5, 10.5 Hz, 1H) 3.24 (d, J=19.5 Hz, 1H) 3.55 (q, J=7.5 Hz, 14.5 Hz, 1H) 4.01-4.17 (m, 2H) 4.8 (s, 1H) 5.41 (s, 1H) 6.30 (s, 1H) 6.34 (s, 1H). HRMS calcd for $C_{23}H_{32}O_4$, 372.2301, found 372.2304.

Scheme 3b

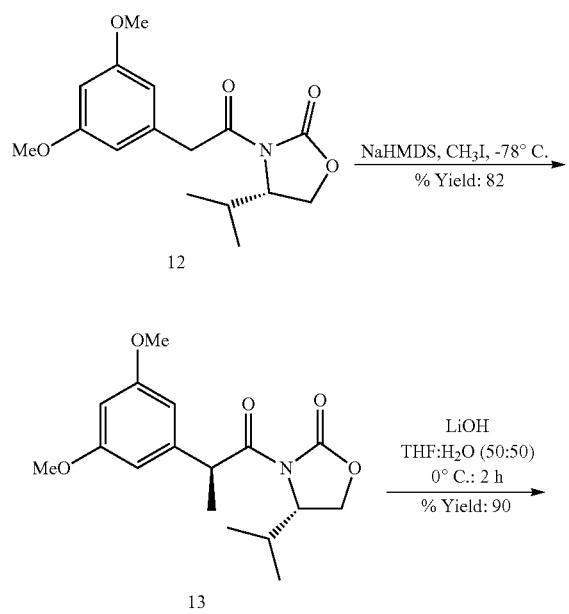

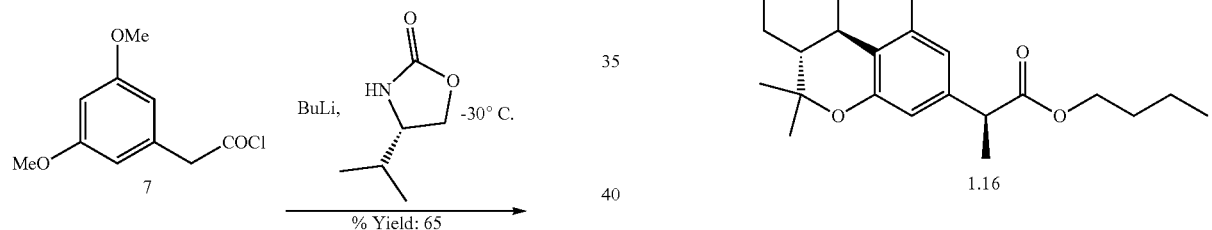

Procedure (S)-3-(2-(3,5-dimethoxyphenyl)acetyl)-4-isopropyloxazolidin-2-one (13)

To the stirring solution of (S)-4-isopropyl-oxazolidin-2-one (13.32 mmoles) in dry THF (15 ml) at −30° C. was added drop wise n-butyl lithium (13.32 mmoles, 1.6 M solution in hexane) and the resulting mixture was stirred at same temperature for 30 min. To the resulting mixture was added solution of 7 (12.11 mmoles) in dry THF (5 ml) and the reaction mixture was stirred at same temperature for 4 h. The reaction mixture was quenched with sodium bisulfite and diluted with ethyl acetate. The organic layer separated and aqueous layer was extracted with ethyl acetate three times. The combined organic layers were collected washed with water, saturated brine solution, dried over magnesium sulfate and concentrated under vacuum to get crude product which is then chromatographed on silica gel eluting with 20% acetone:hexane to get pure product 13 (65% yield). $^1$H NMR (500 MHz, Chloroform-d) δ ppm 0.89 (dd, J=7.0, 37.5 Hz, 6H) 2.3-2.4 (m, 1H) 3.76 (s, 6H) 4.13-4.22 (m, 2H) 4.27 (q, J=14.5, 23.5 Hz, 2H) 4.41-4.46 (m, 1H) 6.36 (t, J=2.5 Hz, 1H) 6.47 (d, J=2.0 Hz, 2H).

(S)-3-((S)-2-(3,5 dimethoxyphenyl)propanoyl)-4-isopropyloxazolidin-2-one (14)

To the stirring solution of 13 (15.06 mmoles) in dry THF (80 ml) under argon at −78° C. was added drop wise sodium hexamethyldisilylamide (16.57 mmoles, 1M in THF) and the reaction mixture stirred at same temperature for 1 h. Iodomethane (75.3 mmoles) was added to the reaction mixture at −78° C. and the reaction mixture was stirred for additional 1 h and then allowed to warm to −30° C. and stirred for additional 1 h. The reaction mixture was quenched with acetic acid (30 ml) in ether (40 ml) and filtered over a celite pad. The filtrate was concentrated in vacuum and the crude product was chromatographed on silica gel eluting with 15% ethyl acetate:hexane mixture to get pure product 14 (82% yield) as viscous oil. $^1$H NMR (500 MHz, Chloroform-d) δ ppm 0.9 (dd, J=6.5, 8.0 Hz, 6H) 1.48 (d, J=7.0 Hz, 3H) 2.38-2.49 (m, 1H) 3.76 (s, 6H) 4.13-4.27 (m, 2H) 4.33-4.4 (m, 1H) 5.08 (q, J=6.5, 14.0 Hz, 1H) 6.34 (t, J=2.0 Hz, 1H) 6.51 (d, J=2.0 Hz, 2H).

(S)-2-(3,5-dimethoxyphenyl)propanoic acid (15)

Mixture of 14 (11.53 mmoles) and lithium hydroxide (34.72 mmoles) was stirred at 0° C. in THF:H$_2$O (50:50 mixture) for 2 h. The solvent was removed under vacuum after warming to room temperature and the residue was washed with ethyl acetate. The combined organic layers were collected and acidified using 1N HCl and diluted with ethyl acetate. The organic layer separated and aqueous layer extracted with ethyl acetate. The combined organic layers were collected washed with brine, dried over magnesium sulfate and concentrated under vacuum to get crude product which is then chromatographed on silica gel eluting with 65% ethyl acetate:hexane to give pure product 15 (90% yield). $^1$H NMR (500 MHz, Chloroform-d) δ ppm 1.47 (d, J=7.0 Hz, 3H) 3.66 (q, J=10.0, 15.0 Hz, 1H) 3.75 (s, 6H) 6.36 (t, J=2.5 Hz, 1H) 6.47 (d, J=2.5 Hz, 2H) 11.91 (s, 1H).

(S)-2-(3,5-dihydroxyphenyl)propanoic acid (16)

Boron tribromide (32.46 mmoles, 1M solution in DCM) was added to the stirring solution of 15 (9.27 mmoles) in dry DCM (80 ml) at −78° C. and the reaction mixture stirred for 1 h at same temperature. The reaction mixture was brought to room temperature, stirred for additional 2 h and quenched with saturated sodium bicarbonate and diluted with chloroform. The organic layer separated and aqueous layer extracted with chloroform three times. The combined organic layers were collected, washed with water, saturated brine, dried over magnesium sulfate and concentrated under vacuum to get crude product which is then chromatographed on silica gel eluting with 65% ethyl acetate/hexane to get pure product 16 (90% yield). $^1$H NMR (500 MHz, Methanol-d) δ ppm 1.38 (d, J=7.5 Hz, 3H) 3.54 (q, J=7.5, 14.5 Hz, 1H) 6.17 (t, J=2.0 Hz, 1H) 6.28 (d, J=2.5 Hz, 2H).

(S)-2-((6aR, 10aR)-1-hydroxy-6,6,9-trimethyl-6a,7,10,10a-tetrahydro-6H-benzo[c]chromen-3-yl)propanoic acid (1.15)

p-toulenesulfonic acid (0.27 mmoles) was added to the stirring solution of 16 (1.37 mmoles) and paramentha dienol (1.5 mmoles) in chloroform (20 ml) and the resulting mixture was refluxed at 65° C. for 2 h. The reaction mixture was cooled to room temperature, quenched with water and diluted with chloroform. The organic layer separated and aqueous layer extracted with chloroform three times. The combined organic layers were collected, washed with brine, dried over magnesium sulfate and concentrated under vacuum to get crude product which is then chromatographed on silica gel eluting with 35% acetone:hexane to get 1.15 (32% yield) HRMS calcd for C$_{19}$H$_{24}$O$_4$, 316.1675, found 31.1670. (Note: The product could not be purified using column chromatography).

(S)-butyl 2-((6aR,10aR)-1-hydroxy-6,6,9-trimethyl-6a,7,10,10a-tetrahydro-6H-benzo[c]chromen-3-yl)propanoate (1.16)

Bromobutane (1.56 mmoles) was added to a mixture of 1.15 (0.78 mmoles) and sodium bicarbonate (0.94 mmoles) in DMF in microwave vessel. The resulting mixture was heated at 165° C. for 12 min in microwave, the reaction mixture was cooled to room temperature and diluted with water and ethyl acetate. The organic layer was separated and aqueous layer was extracted with ethyl acetate three times. The combined organic layers were collected, washed with saturated brine solution, dried over magnesium sulfate and concentrated under vacuum to get crude product which was then chromatographed on silica gel eluting with 12% ethyl acetate:hexane mixture to get pure product 1.16 (33% yield). $^1$H NMR (500 MHz, Chloroform-d) δ ppm 0.87 (t, J=7.5 Hz, 3H) 1.09 (s, 3H) 1.28-1.59 (m, 4H) 1.37 (s, 3H) 1.44 (d, J=6.5 Hz, 3H) 1.54-1.59 (m, 2H) 1.69 (s, 3H) 1.76-1.85 (m, 3H) 2.10-2.18 (m, 1H) 2.69 (dt, J=4.0, 10.5 Hz, 1H) 3.21 (dd, J=4.0, 16.0 Hz, 1H) 3.55 (q, j=7.0, 14.0 Hz, 1H) 4.05-4.12 (m, 2H) 5.23 (s, 1H) 5.42 (d, J=4.5 Hz, 1H) 6.27 (d, J=2.0 Hz, 11H) 6.36 (d, J=1.5 Hz, 1H). HRMS calcd for C$_{23}$H$_{32}$O$_4$, 372.2301, found 372.2299.

Example 4: Synthesis of Compounds 1.17, 1.18, 1.19, 1.20, and 1.21

Synthesis of cyclobutyl at 1 position with ester at 2' in side chain is depicted in scheme 4. Synthesis is accomplished by first forming cyclobutyl ring at 1' position of commercially available 3,5-dimethoxyphenylacetonitrile using 1,3-dibromopropane and potassium hexamethyl disilylamide as a base. The nitrile group of the resulting analog was hydrolyzed under basic conditions to generate carboxylic acid intermediate, which was demethylated using borontribromide at −78° C. The resulting resorcinol analog was coupled with paramenthadienol under standard acidic conditions to generate tricyclic carboxylic acid (1.19) with cyclobutyl ring at 1' position as a common intermediate which can be transformed to desired bromo analog (1.18) using 1,4 dibromobutane and sodium bicarbonate under microwave conditions. The resulting bromo analog was transformed to cyano analog (1.19) using sodium cyanide in DMSO over night, was transformed to azide (1.21) analog using tetrabutylamino azide and was transformed to unsubstituted alkyl chain (1.20) using bromobutane as shown in the experimental scheme 4.

Procedure

1-(3,5-dimethoxyphenyl)cyclobutanecarbonitrile (17)

To the stirring solution of commercially available 3,5-di methoxyphenylacetonitrile (28.21 mmoles) in dry THF (90 ml) at −16° C. was added potassium hexamethyl disilylamide (84.64 mmoles) and the reaction mixture was stirred at same temperature for 5 min. To the resulting mixture was added dibromopropane (31.03 mmoles) at same temperature and the reaction mixture was stirred for 2 h. Reaction mixture was quenched with saturated ammonium chloride and diluted with ethyl acetate. The organic layer was separated and aqueous layer extracted three times with ethyl acetate. The combined organic layers were collected, washed with water, saturated brine solution, dried over magnesium sulfate and concentrated under vacuum to get crude product which is then chromatographed on silica gel eluting with 12% acetone:hexane to get pure product 4 (1.8 g, 30% yield). $^1$H NMR (500 MHz, Chloroform-d) δ ppm 2.0-2.09 (m, 1H) 2.32-2.44 (m, 1H) 2.55-2.64 (m, 2H) 2.72-2.79 (in, 2H) 3.78 (s, 6H) 6.38 (t, J=2.0 Hz, 1H) 6.53 (d, J=2.0 Hz, 2H).

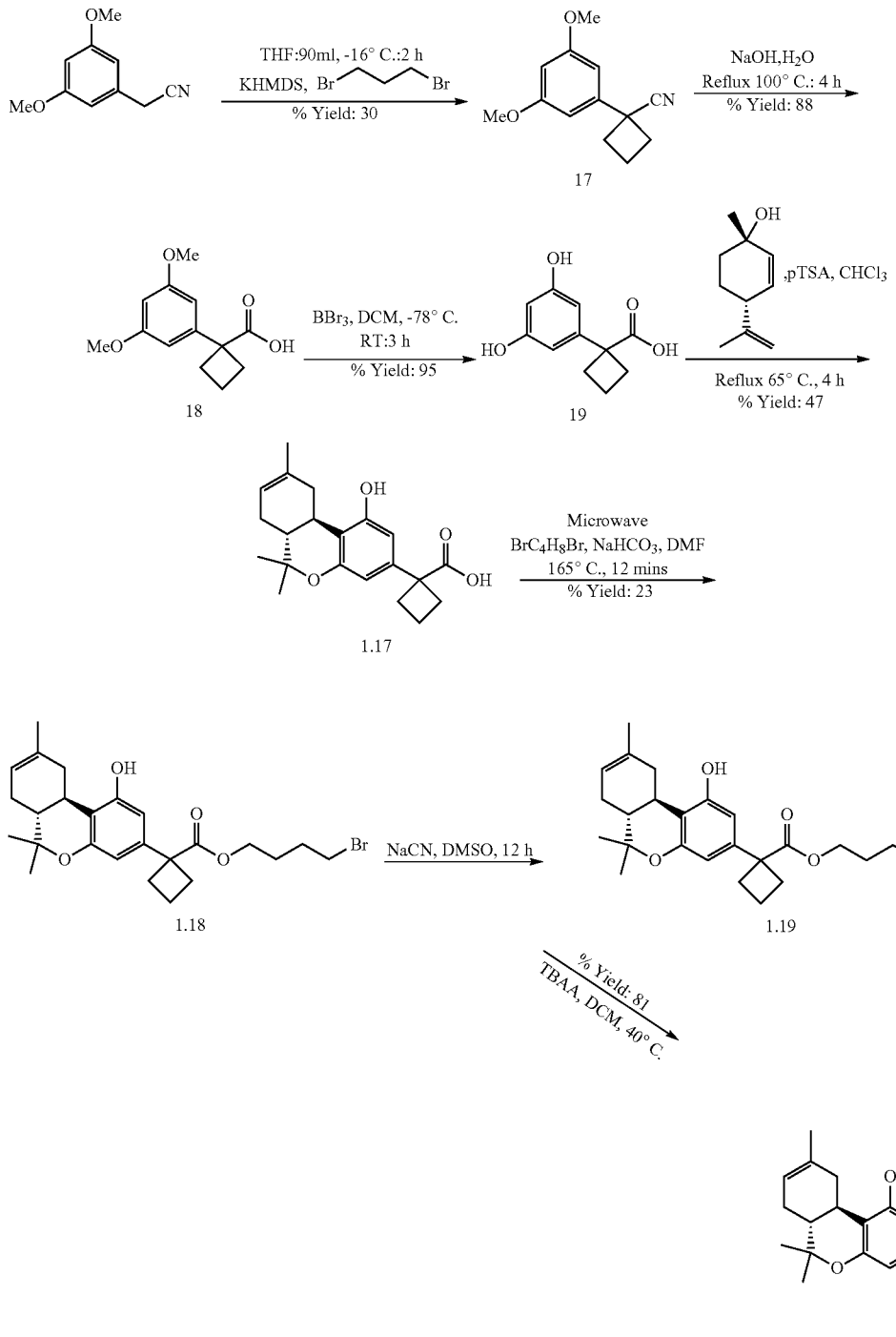

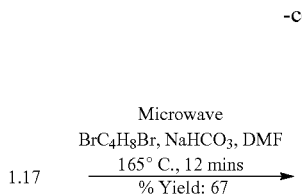
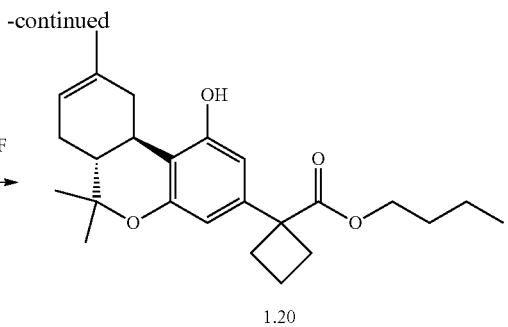

1.20

1-(3,5-dimethoxyphenyl)cyclobutanecarboxylic acid (18)

Sodium hydroxide (8.72 mmoles) was added to the stirring mixture of 4 (3.49 mmoles), n-butanol (388.92 mg, 5.24 mmoles) and water (156.96 mg, 8.72 mmoles) and the resulting mixture was refluxed at 100° C. for 4 h. The reaction mixture was cooled to room temperature and excess of n-butanol was removed under reduced pressure and the remaining crude was acidified using 1N HCl and diluted with ethyl acetate. The organic layer separated and aqueous layer was extracted with ethyl acetate 3 times. The combined organic layers were collected, washed with water, saturated brine solution, dried over magnesium sulfate and concentrated under vacuum to get crude product which is the chromatographed on silica gel eluting with 35% acetone:hexane to get pure product 5 (88% yield). $^1$H NMR (500 MHz, Chloroform-d) δ ppm 1.80-1.95 (m, 1H) 2.05-2.15 (m, 1H) 2.54 (q, J=9.0, 20.5 Hz, 2H) 2.80-2.90 (m, 2H) 3.82 (s, 6H) 6.40 (t, J=2.5 Hz, 1H) 6.5 (d, J=1.5 Hz, 2H) 12.16 (s, 1H); HRMS calcd for $C_{13}H_{17}O_4$, 237.1 127, found 237.1121.

1-(3,5-dihydroxyphenyl)cyclobutanecarboxylic acid (19)

Boron tribromide (11.85 mmoles, 1.0 M solution in DCM) was added to the solution of 71 (2.96 mmoles) in dry DCM (1 ml) under argon at −78° C. The resulting mixture was brought to room temperature after stirring at same temperature for 1 h and stirred for additional 3 h. The reaction mixture was quenched with saturated sodium bicarbonate solution and diluted with DCM, the organic layer separated and aqueous layer was extracted with DCM three times. The combined organic layers were collected, washed with water, saturated brine solution and dried over magnesium sulfate and concentrated under vacuum to get crude product which is then chromatographed on silica gel eluting with 45% acetone:hexane to get pure product 6 (95% yield). $^1$H NMR (500 MHz, Methanol-d) δ ppm 1.8-1.9 (m, 1H) 1.92-2.06 (m, 1H) 2.39-2.49 (m, 2H) 2.70-2.77 (m, 2H) 6.15 (t, J=2.5 Hz, 1H) 6.28 (d, J=2.0 Hz, 2H); HRMS calcd for $C_{11}H_{13}O_4$, 209.0814, found 209.0806.

1-((6aR, 10aR)-1-hydroxy-6,6,9-trimethyl-6a,7,10,10a-tetrahydro-6H-benzo[c]chromen-3-yl)cyclobutanecarboxylic acid (1.17)

p-toulenesulfonic acid (0.62 mmoles) was added to the stirring solution of 6 (3.12 mmoles) and paramentha dienol (3.43 mmoles) in chloroform (15 ml) and the resulting mixture was refluxed at 65° C. for 5 h. The reaction mixture was cooled to room temperature, quenched with water and diluted with chloroform. The organic layer separated and aqueous layer extracted with chloroform three times. The combined organic layers were collected, washed with brine, dried over magnesium sulfate and concentrated under vacuum to get crude product which is then chromatographed on silica gel eluting with 25% acetone; hexane to get pure product 1.19 (47% yield). $^1$H NMR (500 MHz, Chloroform-d) δ ppm 1.11 (s, 3H) 1.39 (s, 3H) 1.7 (S, 3H) 1.76-1.88 (m, 4H) 1.92-2.25 (m, 1H) 2.16 (dd, J=4.5, 12.5 Hz, 1H) 2.36-2.49 (m, 2H) 2.68-2.78 (m, 3H) 3.21 (dd, J=4.5, 16.0 Hz, 1H) 5.43 (d, J=4.5 Hz, 1H) 6.23 (d, J=2.0 Hz, 1H) 6.42 (d, J=1.5 Hz, 1H); HRMS calcd for $C_{21}H_{27}O_4$, 343.1909, found 343.1897.

4-bromobutyl 1-((6aR, 10aR)-1-hydroxy-6,6,9-trimethyl-6a,7,10,10a-tetrahydro-6H-benzo[c]chromen-3-yl)cyclobutanecarboxylate (1.18)

Dibromobutane (0.63 mmoles) was added to a mixture of 1.19 (0.42 mmoles) and sodium bicarbonate (0.46 mmoles) in DMF (1.5 ml) in microwave vessel. The resulting mixture was heated at 165° C. for 12 min in microwave, the reaction mixture was cooled to room temperature and diluted with water and ethyl acetate. The organic layer was separated and aqueous layer was extracted with ethyl acetate three times. The combined organic layers were collected, washed with saturated brine solution, dried over magnesium sulfate and concentrated under vacuum to get crude product which was then chromatographed on silica gel eluting with 12% acetone:hexane mixture to get pure product 1.20 (23% yield). $^1$H NMR (500 MHz, Chloroform-d) δ ppm 1.10 (s, 3H) 1.38 (s, 3H) 1.69 (s, 3H) 1.71-1.97 (m, 9H) 2.14 (dd, J=4.5, 11.5 Hz, 1H) 2.45 (p, J=10.0, 19.5 Hz, 2H) 2.66-2.77 (m, 3H) 324 (dd, J=4.0, 15.5 Hz, 1H) 3.31 (t, J=6.5 Hz, 2H) 4.10 (dt, J=1.5, 6.0 Hz, 2H) 5.42 (d, J=4.5 Hz, 1H) 5.85 (s, 1H) 6.24 (d, J=2.0 Hz, 1H) 6.39 (d, J=2.0 Hz, 1H); HRMS calcd for $C_{25}H_{34}O_4Br$, 477.1640, found 477.1636.

4-cyanobutyl 1-((6aR, 10aR)-1-hydroxy-6,6,9-trimethyl-6a,7,10,10a-tetrahydro-6H-benzo[c]chromen-3-yl)cyclo butanecarboxylate (1.19)

To the stirring solution of 1.20 (0.36 mmol) in dry DMSO (10 ml) was added sodium cyanide (2.93 mmol). The resulting mixture was heated at 40° C. for 12 h, brought to room temperature, quenched with water and diluted with ethyl acetate. The organic layer separated and aqueous layer extracted with ethyl acetate (2 ml) 3 times. The combined organic extracts were collected, washed with saturated brine solution, dried over magnesium sulfate and concentrated under vacuum to give crude product which was then chromatographed on silica gel eluting with 16% acetone/hexane to give 1.21 (62% yield). $^1$H NMR (500 MHz, Chloroform-d) δ ppm 1.09 (s, 3H) 1.38 (s, 3H) 1.54-1.63 (m, 2H) 1.69 (s, 3H) 1.70-1.99 (m, 8H) 2.11-2.18 (m, 1H) 2.26 (t, J=7.0 Hz, 2H) 2.41-2.50 (m, 2H) 2.67-2.79 (m, 3H) 3.26 (dd, J=5.0, 16.5 Hz, 1H) 4.11 (t, J=6.0 Hz, 2H) 5.42 (d, J=4.0 Hz, 11H) 5.94 (s, 1H) 6.26 (d, J=2.0 Hz, 11H) 6.37 (d, J=1.5 Hz, 11H); HRMS calcd for $C_{26}H_{34}NO_4$, 424.2488, found 424.2491.

4-azidobutyl 1-((6aR, 10aR)-1-hydroxy-6,6,9-trimethyl-6a,7,10,10a-tetrahydro-6H-benzo[c]chromen-3-yl)cyclo butanecarboxylate (1.21)

To the stirring solution of 1.20 (0.13 mmoles) in dry DCM (10 ml) under argon was added tetrabutyl ammonium azide (1.36 mmoles) and the resulting mixture was stirred at 40° C. for 48 h. The reaction mixture was quenched with water, diluted with ethyl acetate, the organic layer was separated and aqueous layer extracted with DCM three times. The combined organic layers were collected, washed with saturated brine solution, dried over magnesium sulfate and concentrated under vacuum to get crude product which is then chromatographed on silica gel eluting with 18% acetone:hexane to get pure product 1.23 (81% yield). $^1$H NMR (500 MHz, Chloroform-d) δ ppm 1.10 (s, 3H) 1.38 (s, 3H) 1.49-1.56 (m, 2H) 1.63-1.69 (m, 3H) 1.7 (s, 3H) 1.77-1.98 (m, 4H) 2.12-2.19 (m, 1H) 2.45 (t, J=9.0 Hz, 2H) 2.65-2.78 (m, 3H) 3.21 (t, J=7.0 Hz, 3H) 4.09 (td, J=1.5, 6.5 Hz, 2H) 5.35 (br, s, 1H) 5.43 (d, J=4.0 Hz, 1H) 6.21 (d, J=1.5 Hz, 1H) 6.39 (d, J=1.5 Hz, 1H); HRMS calcd for $C_{25}H_{34}N_3O_4$, 440.2549, found 440.2536.

butyl 1-((6aR,10aR)-1-hydroxy-6,6,9-trimethyl-6a,7,10,10a-tetrahydro-6H-benzo[c]chromen-3-yl)cyclobutane carboxylate (1.20)

Bromobutane (0.65 mmoles) was added to a mixture of 1.19 (0.26 mmoles) and sodium bicarbonate (0.47 mmoles) in DMF (1.5 ml) in microwave vessel. The resulting mixture was heated at 165° C. for 12 min in microwave, the reaction mixture was cooled to room temperature and diluted with water and ethyl acetate. The organic layer was separated and aqueous layer was extracted with ethyl acetate three times. The combined organic layers were collected, washed with saturated brine solution, dried over magnesium sulfate and concentrated under vacuum to get crude product which was then chromatographed on silica gel eluting with 15% acetone:hexane mixture to get pure product 1.22 (67% yield). $^1$H NMR (500 MHz, Chloroform-d) δ ppm 0.85 (t, J=7.5 Hz, 3H) 1.09 (s, 3H) 1.26 (m, 2H) 1.38 (s, 3H) 1.54 (m, 2H) 1.69 (s, 3H) 1.75-1.99 (m, 5H) 2.15 (dd, J=4.5, 11.5 Hz, 1H) 2.45 (p, J=9.5, 19.0 Hz, 2H) 2.65-2.79 (m, 3H) 3.21 (dd, J=4.0, 16.5 Hz, 1H) 4.03-4.10 (m, 2H) 5.42 (d, J=4.5 Hz, 11H) 6.01 (S, 1H) 6.26 (d, J=1.5 Hz, 1H) 6.39 (d, J=2.0 Hz, 1H); HRMS calcd for $C_{25}H_{35}O_4$, 399.2535, found 399.2536.

Example 5: Synthesis of Compounds 1.26, 1.27, 1.28, and 1.29

Synthesis of novel analogs without geminal dimethyl group at 1' position and ester group at 2' position is depicted in scheme 5. Common Intermediate 1.26 is synthesized by first hydrolyzing the nitrile group of commercially available 3,5-dimethoxyphenyl acetonitril to carboxylic acid intermediate 20. The intermediate 21 is obtained by demethylation of 20, followed by coupling with paramenthadienol to get desired common intermediate 1.26, which is coupled with respective side chains under standard microwave conditions as shown in scheme 5.

Procedure

2-(3,5-dimethoxyphenyl)acetic acid (20)

Sodium hydroxide (81.17 mmol) was added to a mixture of 3,5-dimethoxyphenylacetic acid (28.01 mmol), n-butanol (48.70 mmol) and water (81.17 mmol). The resulting mixture was refluxed for 4 h at 125° C. The reaction mixture was quenched with 1N HCl and diluted with ethyl acetate. The organic layer separated and aqueous layer extracted with ethyl acetate (20 ml) three times. The combined organic layers were collected, washed with water, saturated brine solution, dried over magnesium sulfate and concentrated under vacuum to get crude product which was then chromatographed on silica gel eluting with 35% ethyl acetate/hexane to get 20 (88% Yield) as colorless oil. 1H NMR (500 MHz, Chloroform-d) δ ppm 3.57 (s, 2H) 3.77 (s, 6H) 6.38 (t, J=2.0 Hz, 1H) 6.43 (d, J=2.5 Hz, 2H).

2-(3,5-dihydroxyphenyl)acetic acid (21)

To the stirring solution of 20 (1.78 mmol) in dry dichloromethane (15 ml) under argon at −78° C. was added boron tri bromide (6.24 mmol, IM solution in DCM). The reaction mixture was warmed to room temperature after stirring at same temperature for 1 h and stirred for additional 2 h. The reaction mixture was quenched with saturated sodium bicarbonate and diluted with ethyl acetate. The organic layer separated and aqueous layer extracted with ethyl acetate (10 ml) three times. The combined organic layers were collected washed with water, saturated brine solution, dried over magnesium sulfate, concentrated under vacuum to get crude product which was then chromatographed on silica gel eluting with 50% ethyl acetate/hexane to give 8 (88% Yield). $^1$H NMR (500 MHz, Methanol-d) δ ppm 3.4 (s, 2H) 6.18 (t, J=2.0 Hz, 1H) 6.21 (d, J=2.0 Hz, 2H).

Scheme 5

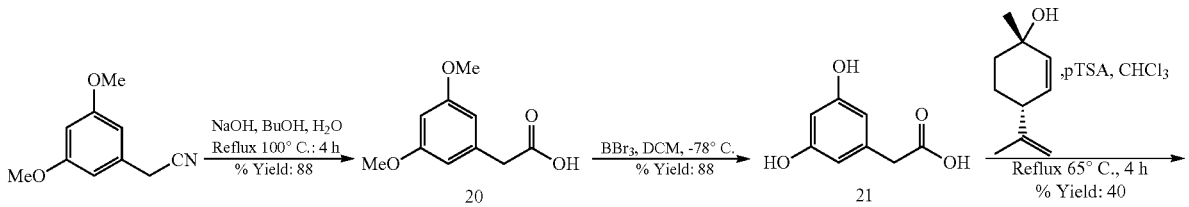

-continued

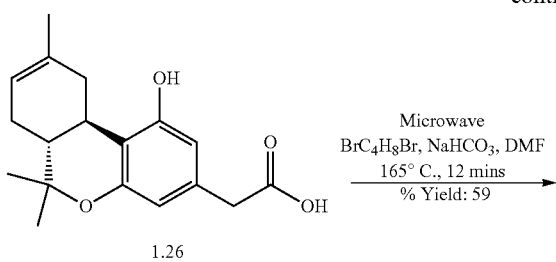

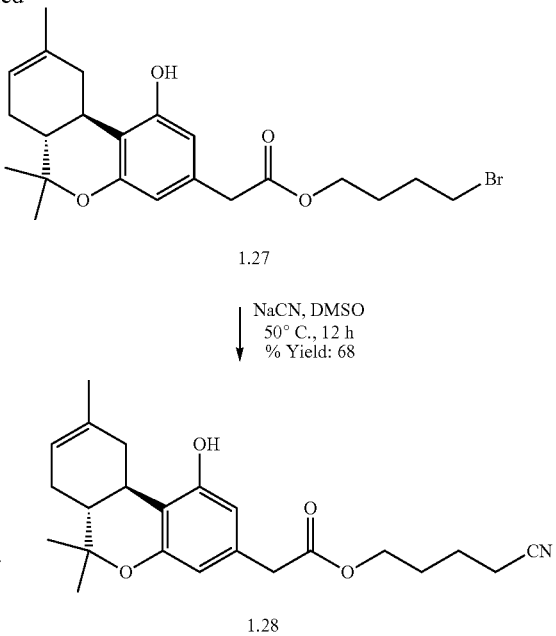

2-((6aR, 10aR)-6a,7,10,10a-tetrahydro-1-hydroxy-6, 6,9-trimethyl-6H-benzo[c]chromen-3-yl)acetic acid (1.26)

pTSA (1.18 mmol) was added to a solution of 20 (5.94 mmol), and paramenthadienol (6.54 mmol) in chloroform. The resulting mixture was refluxed at 65° C. for 6 h. The reaction mixture was quenched with water and diluted with ethyl acetate. The organic layer separated and the aqueous layer extracted with ethyl acetate (3 ml) three times. The combined organic layers were collected, washed with saturated brine solution, dried over magnesium sulfate, concentrated under vacuum to get crude product which was then chromatographed on silica gel eluting with 43% ethyl acetate/hexane to give 1.26 (40% yield) as a light yellowish oil. $^1$H NMR (500 MHz, Chloroform-d) δ ppm 1.06 (s, 3H) 1.36 (s, 3H) 1.67 (s, 3H) 1.73-1.85 (m, 3H) 2.08-2.18 (m, 1H) 2.64-2.23 (m, 1H) 3.19 (dd, J=4.5, 16 Hz, 1H) 3.44 (s, 2H) 5.41 (d, J=3.5 Hz, 1H) 6.18 (d, J=1.5 Hz, 1H) 6.33 (d, J=1.5 Hz, 1H); HRMS calcd for $C_{18}H_{22}O_4$, 302.1518, found 302.1522.

Butyl-2-((6aR, 10aR)-6a,7,10,10a-tetrahydro-1-hydroxy-6,6,9-trimethyl-6H-benzo[c]chromen-3-yl) acetate (1.29)

To the stirring solution of 1.28 (0.99 mmol) and sodium bicarbonate (1.48 mmol) in dimethylformamide (1.5 ml) was added 1-bromobutane (1.48 mmoles). The resulting mixture was heated at 165° C. for 12 min in microwave. The reaction mixture was quenched with water and diluted with ethyl acetate. The organic layer separated and aqueous layer extracted with ethyl acetate (3 ml) three times. The combined organic layers were collected washed with saturated brine solution, dried over magnesium sulfate and concentrated under vacuum to get crude product which was then chromatographed on silica gel eluting with 12% ethyl acetate/hexane to give 1.29 as light yellowish oil (52% yield). $^1$H NMR (500 MHz, Chloroform-d) S ppm 0.91 (t, J=7.5 Hz, 3H) 1.08 (s, 3H) 1.38 (s, 3H) 1.30-1.36 (m, 2H) 1.57-1.65 (m, 2H) 1.70 (s, 3H) 1.76-1.87 (m, 3H) 2.10-2.20 (m, 1H) 2.70 (td, J=11.0, 4.5 Hz, 1H) 3.20 (dd, J=16.0, 4.5 Hz, 1H) 3.46 (s, 2H) 4.09 (t, J=6.5 Hz, 2H) 5.4 (s, 1H) 5.42 (d, J=5.0 Hz, 1H) 6.25 (d, J=1.5 Hz, 1H) 6.32 (s, 1H); HRMS calcd for $C_{22}H_{30}O_4$, 358.2144, found 358.2143.

4-bromobutyl-2-((6aR, 10aR)-6a,7,10,10a-tetrahydro-1-hydroxy-6,6,9-trimethyl-6H-benzo[c] chromen-3-yl)acetate (1.27)

To the stirring solution of 1.28 (0.578 mmol) and sodium bicarbonate (0.868 mmol) in dimethylformamide (1.5 ml) was added 1, 4-dibromobutane (1.44 moles). The resulting mixture was heated at 165° C. for 12 min in microwave. The reaction mixture was quenched with water and diluted with ethyl acetate. The organic layer separated and aqueous layer extracted with ethyl acetate (2 ml) three times. The combined organic layers were collected washed with saturated brine solution, dried over magnesium sulfate and concentrated under vacuum to get crude product which was then chromatographed on silica gel eluting with 13% ethyl acetate/hexane to give 1.27 (59% yield). $^1$H NMR (500 MHz, Chloroform-d) δ ppm 1.10 (s, 3H) 1.36 (s, 3H) 1.70 (s, 3H) 1.74-1.86 (m, 4H) 1.86-1.96 (m, 3H) 2.09-2.22 (m, 1H) 2.70 (dt, J=11.0, 4.5 Hz, 1H) 3.18 (dd, J=4.5, 15 Hz, 1H) 3.40 (t, J=6.5 Hz, 2H) 3.46 (s, 2H) 4.14 (t, J=5.5 Hz, 2H) 5.24 (s, 1H) 5.43 (d, J=5.0 Hz, 1H) 6.25 (s, 1H) 6.33 (s, 1H); HRMS calcd for $C_{22}H_{29}O_4Br$, 436.1249, found 436.1252.

4-cyanobutyl-2-((6aR, 10aR)-6a,7,10,10a-tetrahydro-1-hydroxy-6,6,9-trimethyl-6H-benzo[c] chromen-3-yl)acetate (1.28)

To the stirring solution of 1.29 (0.178 mmol) in dimethylsulfoxide (5 ml) was added sodium cyanide (1.78 mmol). The resulting solution was stirred overnight at 50° C. and quenched with water. The organic layer separated and the aqueous layer extracted with ethyl acetate. The organic layers separated and the aqueous layer extracted with ethyl acetate (2 ml) three times. The combined organic layers were collected washed with saturated brine solution, dried over magnesium sulfate, concentrated under vacuum to get crude product which was then chromatographed on silica gel eluting with 15% ethyl acetate/hexane to give 1.28 (46 mg, 68% yield) as a light yellowish less gum. $^1$H NMR (500 MHz, Chloroform-d) δ ppm 1.09 (s, 3H) 1.37 (s, 3H) 1.64-1.87 (m, 10H) 2.09-2.20 (m, 1H) 2.36 (t, J=7.0 Hz, 2H) 2.70 (dt, J=11.0, 4.5 Hz, 1H) 3.22 (dd, J=16.0, 4.5 Hz, 1H) 3.47 (s, 2H) 4.14 (t, J=6.0 Hz, 2H) 5.42 (d, J=4.0 Hz, 1H) 5.72 (s, 1H) 6.27 (d, J=2.0 Hz, 1H) 6.31 (d, J=2.0 Hz, 1H); HRMS calcd for $C_{23}H_{29}NO_4$, 383.2096, found 383.2091.

Example 6: Synthesis of Compounds 1.22 and 1.23

The synthesis of β-lactone at 1' position is depicted in scheme 6.
Procedure 1-(3,5-dimethoxyphenyl)heptan-1-one (22)

To the stirring solution of commercially available 3,5-dimethoxybenzo nitrile (30.64 mmoles) in dry THF (50 ml) was added hexyl magnesium bromide (49.02 mmoles, 2M solution in ether) followed by copper bromide (3.06 mmoles) and the resulting solution was refluxed at 65° C. for 2 h. The reaction mixture was quenched with 1N HCl and diluted with ethyl acetate. The organic layer separated and aqueous layer was extracted with ethyl acetate three times. The combined organic layers were collected, washed with water, saturated brine solution and dried over magnesium sulfate to get crude product which is then chromatographed on silicagel eluting with 12% acetone/hexane to get pure product 22 (92% yield). $^1$H NMR (500 MHz, Chloroform-d) δ ppm 0.88 (t, J=7.5 Hz, 3H) 1.28-1.38 (m, 6H) 1.69 (p, J=7.5, 15.0 Hz, 2H) 2.88 (t, J=7.5 Hz, 2H) 3.79 (s, 6H) 6.60 (d, J=2.5 Hz, 2H) 7.0 (d, J=2.5 Hz, 2H).

Scheme 6

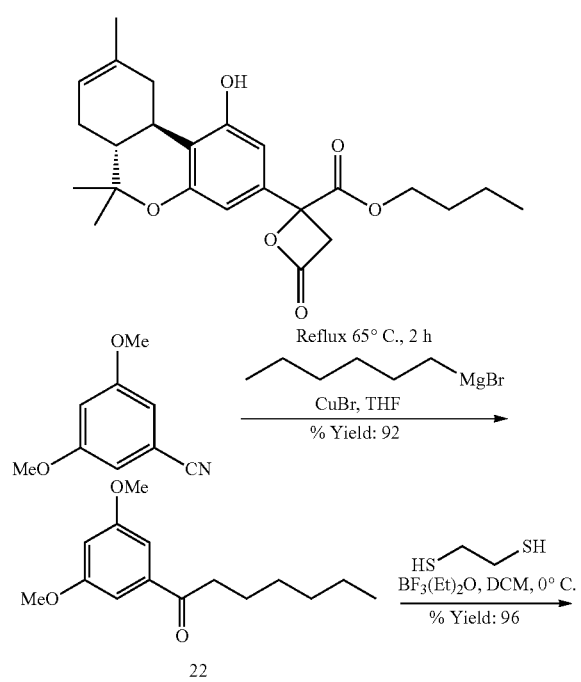

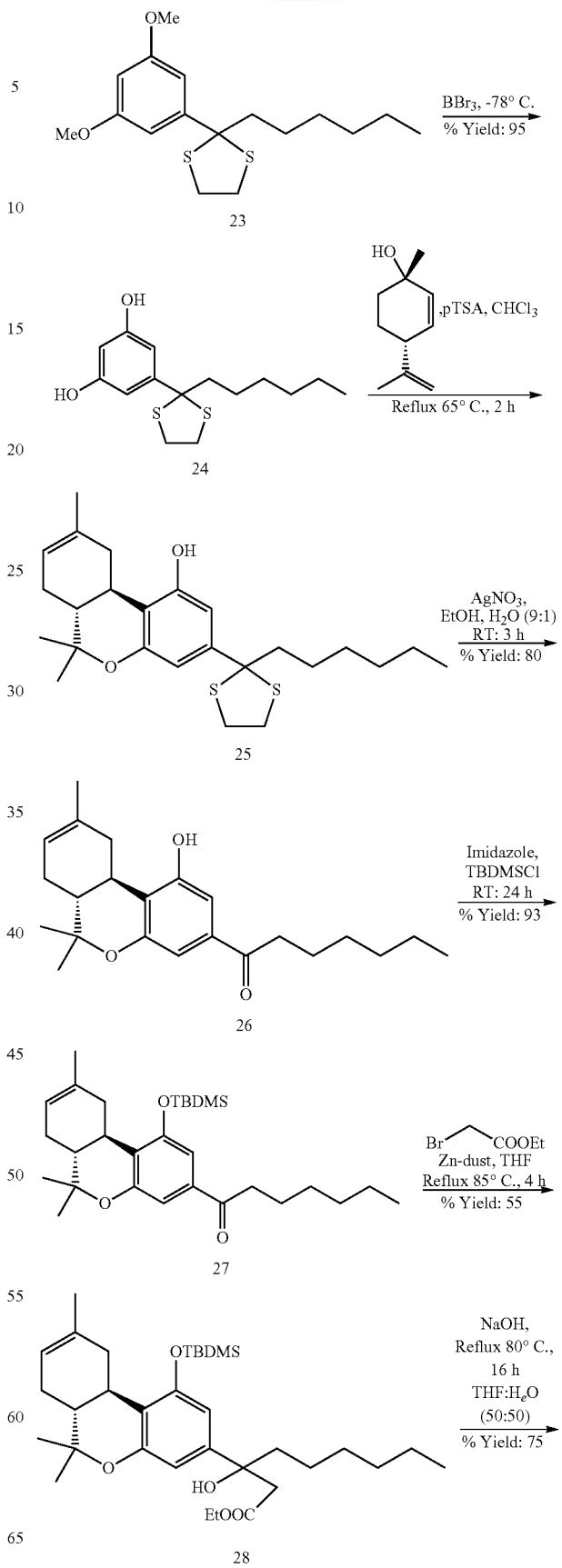

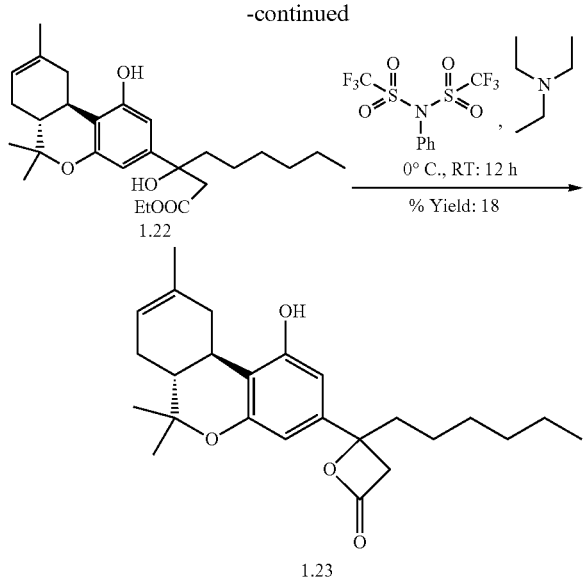

2-(3,5-dimethoxyphenyl)-2-hexyl-1,3-dithiolane (23)

To the stirring solution of 22 (9.98 mmoles) and ethane dithiol (24.96 mmoles) in dry DCM (40 ml) at 0° C. was added drop wise boron trifluoride diethyl etherate (1.99 mmoles) and the reaction mixture was stirred at same temperature for 3 h. The reaction mixture was quenched with saturated sodium bicarbonate and diluted with ethyl acetate. The organic layer separated and aqueous layer extracted with DCM three times. The combined organic layers were collected, washed with water, saturated brine solution, dried over magnesium sulfate and concentrated under vacuum to get crude product (96% Yield) which was sufficiently pure to be used for next reaction. 1H NMR (500 MHz, Chloroform-d) δ ppm 0.83 (t, J=7.0 Hz, 3H) 1.6-1.9 (m, 6H) 2.31 (t, J=8.0 Hz, 2H) 2.75 (dd, J=3.0, 4.5 Hz, 2H) 3.19-3.27 (m, 2H) 3.32-3.4 (m, 2H) 3.80 (s, 6H) 6.33 (t, J=2.5 Hz, 1H) 6.87 (d, J=2.0 Hz, 2H) 1

5-(2-hexyl-1,3-dithiolan-2-yl)benzene-1,3-diol (24)

Boron tribromide (27.95 mmoles, neat solution) was added to the solution of 23 (9.98 mmoles) in dry DCM (80 ml) under argon at −78° C. The resulting mixture was brought to room temperature after stirring at same temperature for 1 h and stirred for additional 7 h. The reaction mixture was quenched with saturated sodium bicarbonate solution and diluted with DCM, the organic layer separated and aqueous layer was extracted with DCM three times. The combined organic layers were collected, washed with water, saturated brine solution and dried over magnesium sulfate and concentrated under vacuum to get crude product 24 (95%) which was sufficiently pure and used as such for next reaction.

(6aR,10aR)-3-(2-hexyl-1,3-dithiolan-2-yl)-6,6,9-trimethyl-6a,7,10,10a-tetrahydro-6H-benzo[c]chromen-1-ol (25)

p-toulenesulfonic acid (0.80 mmoles) was added to the stirring solution of 24 (4.02 mmoles) and paramentha dienol (4.42 mmoles) in chloroform (40 ml) and the resulting mixture was refluxed at 65° C. for 5 h. The reaction mixture was cooled to room temperature, quenched with water and diluted with chloroform. The organic layer separated and aqueous layer extracted with chloroform three times. The combined organic layers were collected, washed with brine, dried over magnesium sulfate and concentrated under vacuum to get crude product 25 which was sufficiently pure to be used for next reaction.

1-((6aR, 10aR)-1-hydroxy-6,6,9-trimethyl-6a,7,10,10a-tetrahydro-6H-benzo[c]chromen-3-yl)heptan-1-one (26)

Silver nitrate (8.32 mmoles) was added to the stirring solution of 25 (2.77 mmoles) in 9:1 mixture of ethanol:water (50 ml) at room temperature and the resulting mixture was stirred at same temperature for 3 h. The reaction mixture was filtered through celite and filterate diluted with ethyl acetate, washed with water, saturated brine solution, dried over magnesium sulfate and concentrated under vacuum to get crude product which is then chromatographed on silica gel eluting with 15% acetone:hexane to get pure product 26 (80% yield). (Note: The reaction mixture could no go competition, so NMR still has some amount of starting material).

1-((6aR,10aR)-1-(tert-butyldimethylsilyloxy)-6,6,9-trimethyl-6a,7,10,10a-tetrahydro-6H-benzo[c]chromen-3-yl)heptan-1-one (27)

Imidazole (23.84 mmoles) was added to the stirring solution of 26 (2.38 mmoles) and TBDMSCl (11.9 mmoles) in dry DMF (5 ml) at room temperature and the resulting mixture was stirred at same temperature for 24 h. The reaction mixture was quenched with water, diluted with ethyl acetate. The organic layer separated and aqueous layer was extracted with ethyl acetate three times. The combined organic layers were collected, washed with saturated brine solution, dried over magnesium sulfate and concentrated under vacuum to get crude product which is then chromatographed on silica gel eluting with 5% acetone:hexane to get pure product 27 (93% yield). $^1$H NMR (500 MHz, Chloroform-d) δ ppm 0.18 (s, 3H) 0.32 (s, 3H) 0.89 (t, J=7.0 Hz, 3H) 1.02 (s, 9H) 1.09 (s, 3H) 1.30-1.38 (m, 4H) 1.40 (s, 3H) 1.68-1.89 (m, 7H) 2.16-2.19 (m, 1H) 2.65 (dt, J=4.0, 10.5 Hz, 1H) 2.87 (t, J=8.0 Hz, 2H) 3.27 (dd, J=4.5, 17.5 Hz, 1H) 5.42 (d, J=4.0 Hz, 1H) 7.0 (d, J=2.0 Hz, 1H) 7.06 (d, J=1.5 Hz, 1H).

Ethyl 3-((6aR,10aR)-1-(tert-butyldimethylsilyloxy)-6,6,9-trimethyl-6a,7,10,10a-tetrahydro-6H-benzo[c]chromen-3-yl)-3-hydroxynonanoate (28)

Zinc dust (0.95 mmoles) was added to the stirring solution of 27 (0.63 mmoles) and ethyl bromoacetoacetate (0.95 mmoles) in dry THF under argon. The resulting mixture was refluxed at 60° C. for 4 h (TLC shown completion of reaction). The reaction mixture was quenched with 1N HCl and diluted with ethyl acetate. The organic layer was separated and aqueous layer was extracted with ethyl acetate three times. The combined organic layers were collected, washed with water, saturated brine solution, dried over magnesium sulfate and concentrated under vacuum to get crude product which is the chromatographed on silica gel eluting with 7% acetone:hexane to give pure product 28 (55% yield). (Note: The reaction mixture had some inseparable impurities, so the product was carried for further reaction without purification).

3-hydroxy-3-((6aR,10aR)-1-hydroxy-6,6,9-trimethyl-6a,7,10,10a-tetrahydro-6H-benzo[c]chromen-3-yl)nonanoic acid (1.22)

The mixture of sodium hydroxide (1.14 mmoles) and 28 (0.28 mmoles) in 50:50 mixture of THF:Water (10 ml) was refluxed at 80° C. for 16 h. The reaction mixture was brought to room temperature and quenched with 1N HCl and diluted with ethyl acetate. The organic layer was separated and aqueous layer was extracted with ethyl acetate three times. The combined organic layers were collected, washed with water, saturated brine solution, dried over magnesium sulfate and concentrated under vacuum to get crude product which is then chromatographed on silica gel eluting with 28% acetone:hexane to get pure product 1.22 (75% yield) as yellowish gum.

4-hexyl-4-((6aR, 10aR)-1-hydroxy-6,6,9-trimethyl-6a,7,10,10a-tetrahydro-6H-benzo[c]chromen-3-yl)oxetan-2-one (1.23)

1,1,1-trifluoro-N-phenyl-N-(trifluoromethylsulfonyl)methanesulfonamide (0.24 mmoles) was added to the stirring solution of 1.22 (0.16 mmoles) and triethylamine (0.33 moles) in dry DCM at 0° C. The reaction mixture was brought to room temperature after stirring at same temperature for 1 h and stirred over night. The reaction mixture was quenched with saturated sodium bicarbonate and diluted with ethyl acetate. The organic layer was separated and aqueous layer was extracted with ethyl acetate three times. The combined organic layers were collected, washed with water, saturated brine solution, dried over magnesium sulfate and concentrated under vacuum to get crude product which is then chromatographed on silica gel; eluting with 24% acetone:hexane to get pure product 1.23 (18% yield) as light yellowish gum.

Example 7: Synthesis of Compounds 1.30, 1.31, 1.32, and 1.33

Synthesis of thioioester, amide and reverse ester is depicted in schemes 7 and 7a.
Procedure

2-((6aR,10aR)-6a,7,10,10a-tetrahydro-1-hydroxy-6,6,9-trimethyl-6H-benzo[c]chromen-3-yl)-2-methyl-propanoyl chloride (29)

To the stirring solution of 1.2 (0.30 mmol) in dry dichloromethane (20 ml) was added intermittently 1.5 M stock solution of thionyl chloride (5.46 ml) in 50 ml solution of benzotriazole (8.93 g) in 50 ml dichloromethane. The reaction mixture was filtered through celite after stirring at room temperature for 20 min and diluted with dichloromethane. The organic layer was washed with dilute 1N HCl, saturated brine solution, dried over magnesium sulfate and concentrated under vacuum to give 29 (86% Yield) as crude product which was sufficiently pure to be used for next reaction.

S-propyl-2-((6aR,10aR)-6a,7,10,10a-tetrahydro-1-hydroxy-6,6,9-trimethyl-6H-benzo[c] chromen-3-yl)-2-methylpropanethioate (1.30)

Pyridine was added under argon to the stirring solution of 29 (0.20 mmol) and propane thiol (0.24 mmol) in dry dichloromethane (5 ml). The reaction mixture is quenched with water after stirring the reaction mixture at room temperature for 3 h and diluted with ethyl acetate. The organic layer separated and aqueous layer extracted with ethyl acetate three times. The combined organic layers were collected, washed with saturated brine solution, dried over magnesium sulfate and concentrated under vacuum to get crude product which was then chromatographed on silica gel eluting with 16% ethyl acetate/hexane to give 1.30 (66% yield). $^1$H NMR (500 MHz, Chloroform-d) δ ppm 0.93 (t, J=7.5 Hz, 3H) 1.10 (s, 3H) 1.39 (s, 3H) 1.55 (s, 6H) 1.52-1.60 (m, 2H) 1.70 (s, 3H) 1.76-1.91 (m, 3H) 2.11-2.18 (m, 1H) 2.71 (td, J=10.5, 4.5 Hz, 1H) 2.79 (td, J=7.5, 2.5 Hz, 2H) 3.16-3.26 (m, 1H) 5.03 (s, 1H) 5.43 (d, J=4.5 Hz, 1H) 6.25 (d, J=2.0 Hz, 1H) 6.46 (d, J=2.0 Hz, 1H); HRMS calcd for $C_{23}H_{32}O_3S$, 388.2072, found 388.2075.

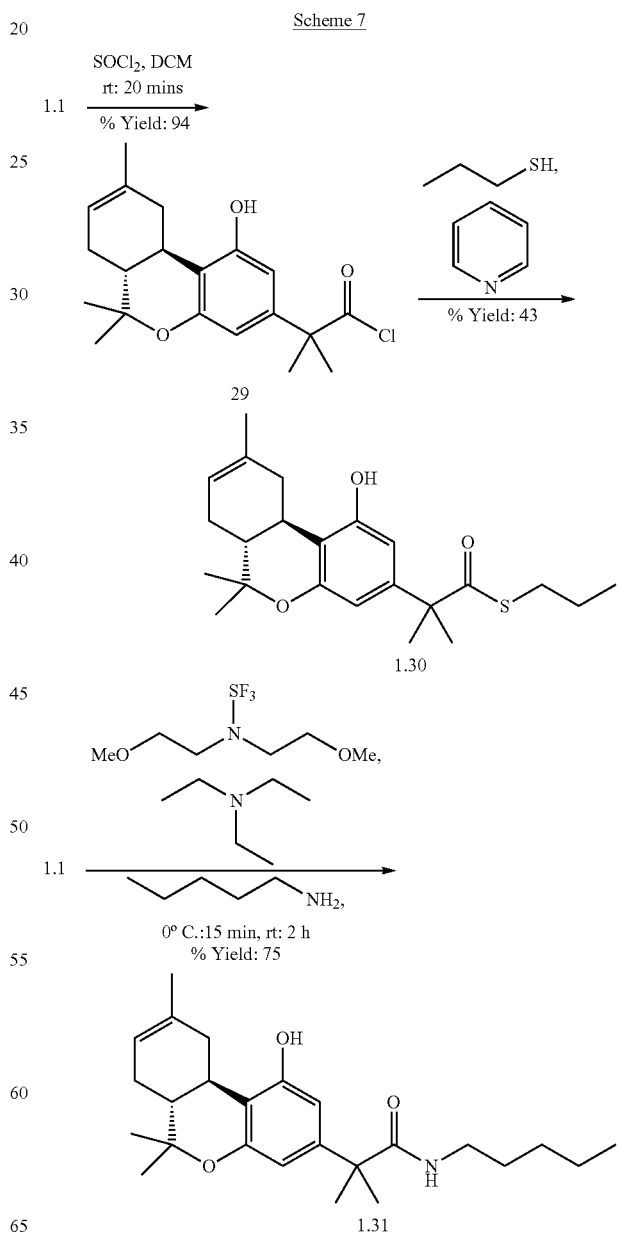

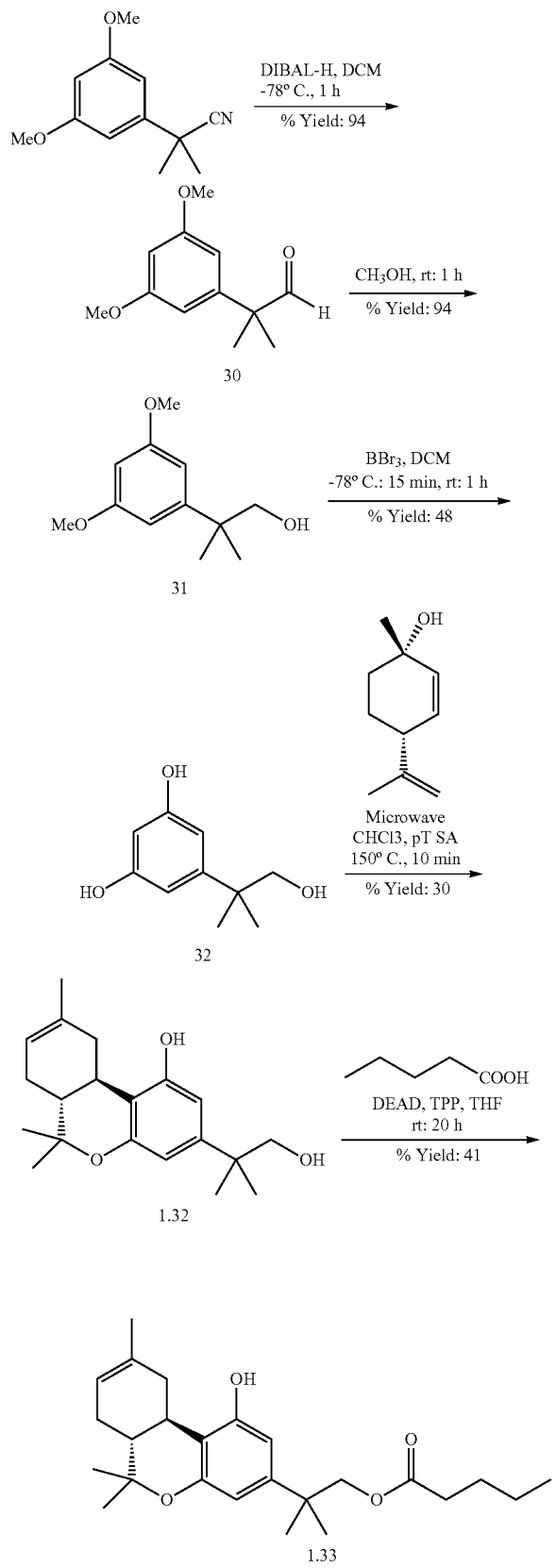

Scheme 7a 2-((6aR,10aR)-6a,7,10,10a-tetrahydro-1-hydroxy-6,6,9-trimethyl-6H-benzo[c]chromen-3-yl)-2-methyl-N-pentylpropanamide (1.31)

Deoxyfluor (0.72 mmol) was added under argon at 0° C. to a solution of 1.1 (0.60 mmol), triethylamine (0.90 mmol) and amylamine (0.90 mmol) in dry dichloromethane (6 ml). The reaction mixture was brought to room temperature after stirring at same temperature for 15 min and stirred for additional 2 h. The reaction mixture was quenched with saturated sodium bicarbonate and diluted with ethyl acetate. The organic layer separated and aqueous layer extracted with ethyl acetate (3 ml) three times. The combined organic layers were collected, washed with water, saturated brine solution, dried over magnesium sulfate and concentrated under vacuum to get crude product which was then chromatographed on silica gel eluting with 12% ethyl acetate/hexane to give 1.31 (75% Yield) as light yellowish gum. $^1$H NMR (500 MHz, Chloroform-I) δ ppm 0.81 (t, J=7.0 Hz, 3H) 1.08-1.14 (m, 2H) 1.13 (s, 3H) 1.84 (t, J=7.5 Hz, 2H) 1.35 (t, J=7.0 Hz, 3H) 1.40 (s, 3H) 1.49 (s, 6H) 1.70 (s, 3H) 1.81 (t, J=14.0 Hz, 2H) 2.14 (d, J=13.5 Hz, 1H) 2.74 (dt, J=4.5, 10.5 Hz, 1H) 3.13 (q, J=7.0, 13.0 Hz, 2H) 3.4 (dd, J=3.5, 16.5 Hz, 11H) 5.40 (s, 1H) 5.42 (d, J=5.5 Hz, 1H) 6.25 (d, J=2.0 Hz, 1H) 6.41 (d, J=1.5 Hz, 11H) 8.53 (s, 1H); HRMS calcd for $C_{25}H_{37}NO_3$, 399.2773, found 399.2777.

2-(3, 5-dimethoxyphenyl)-2-methylpropanal (30)

To the stirring solution of 1 (14.61 mmol) in dry DCM under argon at −78C was added drop wise diisobutylaluminium hydride (36.52 mmol). The reaction mixture was quenched with 10% solution of potassium sodium tartarate after stirring for 1 h and diluted with dichloromethane. The organic layer separated and aqueous layer was extracted with dichloromethane. The combined organic layers were collected, washed with water, saturated brine solution, dried over magnesium sulfate and concentrated under vacuum to give crude product which was chromatographed on silica gel eluting with 20% ethyl acetate/hexane mixture to give 30 as colorless oil (94%). $^1$H NMR (500 MHz, Chloroform-d) δ ppm 1.44 (s, 6H) 3.80 (s, 6H) 6.40 (t, J=2.5 Hz, 1H) 6.40-6.42 (m, 2H) 9.47 (s, 1H).

2-(3,5-dimethoxyphenyl)-2-methylpropan-1-ol (31)

To the stirring solution of 30 (8.40 mmol) in 40 ml methanol was added in small portions sodium borohydride (37.81 mmol). The reaction mixture was quenched with 1N HCl and diluted with ethyl acetate. The organic layer separated and aqueous layer extracted twice with ethyl acetate (10 ml) three times. The combined organic layers were collected, washed with water, saturated brine solution, dried over magnesium sulfate and concentrated under vacuum to give crude product which was chromatographed on silica gel elution with ethyl acetate/hexane (20:80) gave 31 (94%). $^1$H NMR (500 MHz, Chloroform-d) δ ppm 1.30 (s, 6H) 3.58 (s, 2H) 3.79 (s, 6H) 6.34 (t, J=1.5 Hz, 1H) 6.53 (d, J=2.0 Hz, 2H).

5-(1-hydroxy-2-methylpropan-2-yl) benzene-1,3-diol (32)

To the stirring solution of 31 (1.9 mmol) in dry dichloromethane (25 ml) under argon at −78C was added borontribromide (1M solution in DCM, 6.65 mmol). The reaction mixture was brought to room temperature after stirring at same temperature for 15 min and stirred for additional 1 h, quenched with 1N HCl and diluted with dichloromethane. The organic layer separated and aqueous layer was extracted 2-3 times with dichloromethane (10 ml). The combined organic layers were collected, washed with water, saturated brine solution, dried over magnesium sulfate and concentrated under vacuum to give crude product which was chromatographed on silica gel eluting with 60% ethyl acetate:hexane to give 32 (165 mg, 48%). $^1$H NMR (500 MHz, Chloroform-d) δ ppm 1.28 (s, 6H) 3.56 (d, J=6.0 Hz, 2H) 4.84 (s, 2H) 6.22 (t, J=2.0 Hz, 1H) 6.43 (d, J=2.5 Hz, 2H).

(6aR,10 aR)-3-(1-hydroxy-2-methylpropan-2-yl)-6,6,9-trimethyl-6a,7,10,10a-tetrahydro-6H-benzo[c]chromen-1-ol (1.32)

pTSA (0.27 mmol) was added to a solution of 32 (0.9 mmol) and para menthadienol (1.08 mmol) in chloroform (3 ml). The resulting mixture was heated at 150° C. for 10 min in microwave. The reaction mixture was quenched with water and diluted with chloroform. The organic layer separated and aqueous layer extracted with chloroform (10 ml) 3 times. The combined organic layers were collected, washed with saturated brine solution, dried over magnesium sulfate, and concentrated under vacuum to give crude product which is then chromatographed on silica gel eluting with 15% ethyl acetate/hexane mixture to give 1.32 (30%). $^1$H NMR (500 MHz, Chloroform-d) δ ppm 1.10 (s, 3H) 1.24 (s, 6H) 1.38 (s, 3H) 1.7 (s, 3H) 1.76-1.88 (m, 4H) 2.11-2.19 (m, 1H) 2.71 (dt, J=4.5, 10.5 Hz, 1H) 3.19 (dd, J=3.5, 15.5 Hz, 1H) 3.54 (s, 2H) 5.43 (d, J=4.5 Hz, 1H) 6.28 (d, J=1.5 Hz, 1H) 6.43 (d, J=1.5 Hz, 1H).

2-((6aR,10aR)-6a,7,10,10a-tetrahydro-1-hydroxy-6,6,9-trimethyl-6H-benzo[c]chromen-3-yl)-2-methyl propylpentanoate (1.33)

Triphenylphosphine (0.85 mmol) was added to the stirring solution of 1.32 (0.56 mmol) and valeric acid (85 mmol). To the resulting mixture was added drop wise at 0° C. diethylazodi-carboxylate (0.85 mmol). The reaction mixture was quenched with 1N HCl after stirring at room temperature for 20 h and diluted with ethyl acetate. The organic layer separated and aqueous layer extracted with ethyl acetate (10 ml) three times. The combined organic layers were collected, washed with water, saturated brine solution, dried over magnesium sulfate, concentrated under vacuum to get crude product which was chromatographed on silica gel, elution with ethyl acetate:hexane (25:75) gave 1.33 (41%). $^1$H NMR (500 MHz, Chloroform-d) δ ppm 0.88 (t, J=7.5 Hz, 3H) 1.28 (dd, J=15.0, 7.5 Hz, 2H) 1.34 (s, 6H) 1.55 (quin, J=7.5 Hz, 2H) 2.28 (t, J=7.5 Hz, 2H) 3.80 (s, 6H) 4.12 (s, 2H) 6.32-6.36 (m, 1H) 6.53 (d, J=2.5 Hz, 2H); HRMS calcd for $C_{25}H_{36}O_4$, 400.2614, found 400.2611.

Example 8: Preparation of Compounds with Molecular Formula 1b

Synthesis of compounds 2.1, 2.1 and 2.3 is depicted in scheme 8

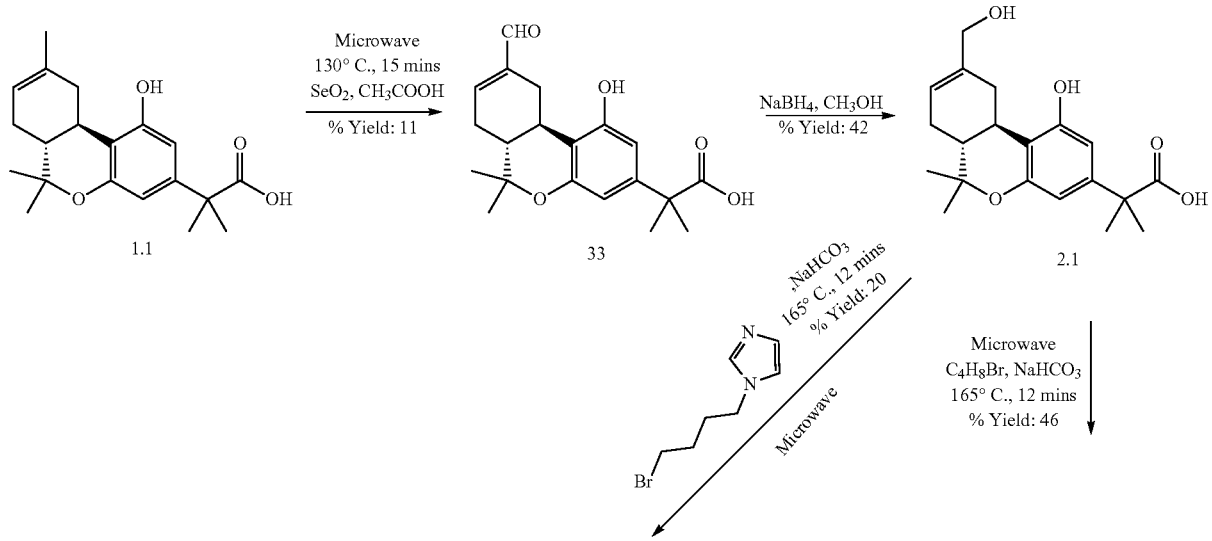

Scheme 8

-continued

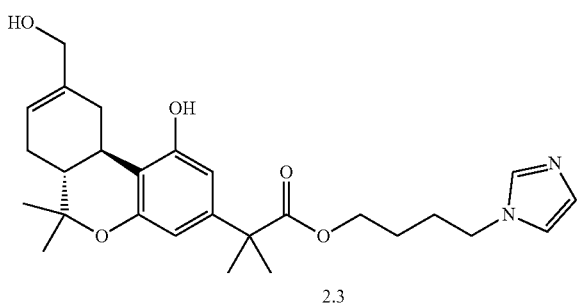

2.3

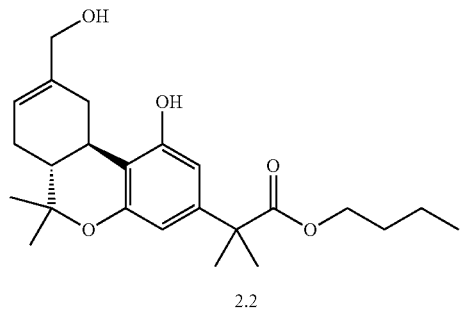

2.2

Procedure

2-((6aR,10aR)-9-formyl-6a,7,10,10a-tetrahydro-1-hydroxy-6,6-dimethyl-6H-benzo[c]chromen-3-yl)-2-methyl propanoic acid (33)

Selenium dioxide (0.9 mmol) was added to a solution of 1.1 (0.45 mmol) in acetic acid in microwave vessel and heated at 130° C. for 15 min in microwave. The reaction mixture was quenched with water and diluted with ethyl acetate, the organic layer separated and aqueous layer extracted with ethyl acetate (2 ml) three times. The combined organic layers were collected, washed with saturated brine solution, dried over magnesium sulfate and concentrated under vacuum to get crude product which was then chromatographed on silica gel eluting with 20% ethyl acetate/hexane to give 33 (11% Yield) as yellowish oil. $^1$H NMR (500 MHz, Chloroform-d) δ ppm 1.14 (s, 3H) 1.42 (s, 3H) 1.51 (d, J=5.5 Hz, 6H) 1.81-1.88 (m, 3H) 2.53-2.59 (m, 1H) 2.65 (dt, J=4.5, 11.0 Hz, 1H) 3.82-3.89 (m, 11H) 6.32 (d, J=2.0 Hz 1H) 6.45 (d, J=2.0 Hz, 1H) 6.85-6.86 (m, 1H) 9.47 (s, 1H).

2-((6aR,10aR)-6a,7,10,10a-tetrahydro-1-hydroxy-9-(hydroxymethyl)-6,6-dimethyl-6H-benzo[c]chromen-3-yl)-2-methylpropanoic acid (2.1)

To the stirring solution of 33 (0.21 mmol) in methanol was added in small portions sodium borohydride (0.97 mmol). The reaction mixture was quenched with 1N HCl and diluted with ethyl acetate. The organic layer separated and aqueous layer extracted with ethyl acetate (2 ml) three times. The combined organic layers were collected, washed with water, saturated brine solution, dried over magnesium sulfate, concentrated under vacuum to get crude product which was then chromatographed on silica gel eluting with 40% ethyl acetate/hexane to give 2.1 (42% Yield) as yellowish gum. $^1$H NMR (500 MHz, Chloroform-d) δ ppm 0.97 (s, 3H) 1.36 (d, J=20.5 Hz, 6H) 1.5 (s, 3H) 1.75-1.83 (m, 3H) 2.16-2.22 (m, 1H) 2.62-2.71 (m, 1H) 3.49-3.58 (m, 1H) 4.05 (dd, J=12.5, 31 Hz, 2H) 5.71 (s, 1H) 6.34 (s, 1H) 6.44 (s, 1H); HRMS calcd for $C_{20}H_{26}O_5$, 346.1780, found 346.1780.

Butyl-2-((6aR,10aR)-6a,7,10,10a-tetrahydro-1-hydroxy-9-(hydroxymethyl)-6,6-dimethyl-6H-benzo[c]chromen-3-yl)-2-methylpropanoate (2.2)

Bromobutane (0.49 mmol) was added to a solution of 2.1 (0.14 mmoles) and sodium bicarbonate (0.23 mmol) in dimethylformamide. The Resulting mixture was heated at 165° C. for 12 min in microwave. The reaction mixture was quenched with water and diluted with ethyl acetate. The organic layer separated and aqueous layer extracted with ethyl acetate three times. The combined organic layers were collected, washed with saturated brine solution, dried over magnesium sulfate, concentrated under vacuum to give crude product which was then chromatographed on silica eluting with 25% ethyl acetate/hexane to give 2.2 (48% yield) as light yellowish gum. $^1$H NMR (500 MHz, Chloroform-I) S ppm 0.87 (t, I=7.5 Hz, 3H) 1.11 (s, 3H) 1.24-1.32 (m, 3H) 1.40 (s, 3H) 1.51 (s, 6H) 1.53-1.62 (m, 4H) 1.78-1.94 (m, 3H) 2.24 (d, J=15.0 Hz, 1H) 2.71 (td, J=11.0, 4.5 Hz, 1H) 3.41 (dd, J=16.0, 4.0 Hz, 1H) 4.02-4.09 (m, 4H) 5.43 (s, 1H) 5.75 (d, J=5.0 Hz, 1H) 6.26 (d, J=2.0 Hz, 1H) 6.43 (d, J=2.0 Hz, 1H); HRMS calcd for $C_{24}H_{34}O_5$, 402.2406, found 402.2407.

Butyl-2-((6aR,10aR)-6a,7,10,10a-tetrahydro-1-hydroxy-9-(hydroxymethyl)-6,6-dimethyl-6H-4-(1H-imidazol-1-yl)-butyl-2-((6aR,10aR)-6a,7,10,10a-tetrahydro-1-hydroxy-9-(hydroxymethyl)-6,6-dimethyl-6H-benzo[c]chromen-3-yl)-2-methylpropanoate (2.3)

1-Bromobutane-4-imidazole (1.05 mmol) was added to a solution of 2.1 (0.60 mmol) and sodium bicarbonate (0.90 mmol) in dimethylformamide. The resulting mixture was heated at 165° C. degree for 12 min in microwave and diluted with ethyl acetate after quenching with water. The organic layer separated and aqueous layer extracted with ethyl acetate three times. The combined organic layers were collected, washed with saturated brine solution, dried over magnesium sulfate, concentrated under vacuum to give crude product which was then chromatographed on silica gel eluting with 15 ethyl acetate/hexane to give 2.3 (20% Yield) and yellowish gum. $^1$H NMR (500 MHz, Chloroform-d) δ ppm 1.09 (s, 3H) 1.36 (s, 3H) 1.47 (d, J=3.0 Hz, 6H) 1.52 (t, J=5.0, 2H) 1.6-1.87 (m, 5H) 2.15-2.24 (m, 1H) 2.71 (dt, J=4.0, 11.5 Hz, 1H) 3.58 (d, J=17.0 Hz, 1H) 3.74 (t, J=6.5 Hz 2H) 3.92-4.09 (m, 4H) 5.67 (s, 1H) 6.31 (s, 1H) 6.36 (s, 1H) 6.82 (s, 1H) 7.06 (s, 1H) 7.47 (s, 11H). HRMS calcd for $C_{27}H_{37}N_2O_5$, 469.2702, found 469.2707.

Example 9: Preparation of Compounds with Formula 1a

Synthesis of compounds 3.1, 3.2, 3.3, 3.4, 3.5, 3.6, 3.7, 3.8 is depicted in schemes 9, 9a and 9b
Procedure

Methyl 2-(3,5-dihydroxy-4-((1R,2R,5S)-6,6-dimethyl-4-ketobicyclo[3.1.1]heptan-2-yl) phenyl)acetate (34)

Para-toluenesulfonic acid (1.19 mmol) was added to a stirring solution of methyl 2-(3,5-dihydroxyphenyl) acetate (1.09 mmol) and nopinonediacetate mixture (1.92 mmol) in chloroform:acetone (9:1 mixture). The resulting mixture was quenched with water after stirring under dark for 5 days at room temperature and diluted with ethyl acetate. The organic layer separated and aqueous layer extracted with ethyl acetate (10 ml) three times. The combined organic layers were collected washed with saturated brine solution dried over magnesium sulfate, concentrated under vacuum to get crude product which was then chromatographed on silica gel eluting with 30% acetone/hexane to give 34 (54% yield). $^1$H NMR (500 MHz, Methanol-$d_4$) δ ppm 0.93 (s, 3H) 1.31 (s, 3H) 2.03-2.08 (m, 1H) 2.37-2.48 (m, 2H) 2.55 (t, J=5.5 Hz, 1H) 2.62 (d, J=10.5 Hz, 1H) 3.45 (t, J=9.0 Hz, 1H) 3.56 (d, J=6.5 Hz, 2H) 3.57 (m, 1H) 3.69 (s, 3H) 6.19 (d, J=2.5 Hz, 11H) 6.26 (d, J=2.0 Hz, 11H) 6.94 (br, s, 1H).

Methyl-2-((6aR,10aR)-6a,7,8,9,10,10a-hexahydro-1-hydroxy-6,6-dimethyl-9-oxo-6H-benzo[c]chromen-3-yl)acetate (35)

TMSOTf (0.89 mmol) was added at 0° C. to a stirring solution of 34 (2.98 mmol) in 3:1 mixture of DCM:Nitromethane. The reaction mixture was brought to room temperature after stirring at 0° C. for 1 h and stirred for additional 3 h. The reaction mixture was diluted with ethyl acetate after quenching with sodium bicarbonate, organic layer separated and aqueous layer extracted with ethyl acetate three times. The combined organic layers were collected, washed with water, saturated brine solution, dried over magnesium sulfate and concentrated under vacuum to get crude product which was then chromatographed on silica gel eluting with 18% ethyl acetate/hexane to give 35 (45% yield). $^1$H NMR (500 MHz, Chloroform-d) δ ppm 1.08 (s, 3H) 1.45 (s, 3H) 1.47-1.53 (m, 1H) 2.0 (dt, J=3.0, 12.5 Hz, 1H) 2.12-2.29 (m, 2H) 2.18-2.29 (m, 1H) 2.38-2.48 (m, 1H) 2.56-2.64 (m, 1H) 2.84 (dt, J=3.5, 11.0, 1H) 2.94-3.20 (m, 1H) 3.61 (q, J=16.5 Hz, 2H) 3.70 (s, 1H) 5.34 (br, s, 1H) 6.24 (d, J=2.5 Hz, 1H) 6.32 (d, J=2.5 Hz, 1H).

2-((6aR,10aR)-6a,7,8,9,10,10a-hexahydro-1-hydroxy-6,6-dimethyl-9-oxo-6H-benzo[c] chromen-3-yl)acetic acid (3.1)

Sodium hydroxide (0.77 mmol) was added to a solution of 35 (0.19 mmol) in 1:1 mixture of THF:water. The reaction mixture was quenched with diluted 1N HCl after stirring at room temperature for 3 h and diluted with ethyl acetate. The organic layer separated and aqueous layer extracted with ethyl acetate (3 ml) three times. The combined organic layers were collected washed with water, saturated brine solution, dried over magnesium sulfate, concentrated under vacuum to get crude product which was then chromatographed on silica gel eluting with 78% acetone/hexane to give 3.1 (79% Yield) as light yellowish gum. $^1$H NMR (500 MHz, Methanol-$d_4$) δ ppm 0.97 (s, 3H) 1.33 (s, 3H) 1.37-1.47 (m, 1H) 1.89 (dt, J=3.0, 13.0 Hz, 1H) 2.02-2.22 (m, 2H) 2.38-2.44 (m, 2H) 2.77-2.94 (m, 2H) 3.41-3.53 (m, 2H) 6.049 (d, J=2.5 Hz, 1H) 6.20 (d, J=2.50 Hz, 1H). HRMS calcd for $C_{17}H_{20}O_5$, 304.1311, found 304.1309.

Butyl-2-((6aR,10aR)-6a,7,8,9,10,10a-hexahydro-1-hydroxy-6,6-dimethyl-9-oxo-6H-benzo[c]chromen-3-yl)acetate (3.2)

To the stirring solution of 3.1 (0.27 mmol) and sodium bicarbonate (0.41 mmol) in dimethylformamide (1.5 ml) was added 1-bromobutane (0.67 mmol) in microwave vessel. The resulting mixture is heated at 165° C. for 12 min in microwave. The reaction mixture was quenched with water and diluted with ethyl acetate. The organic phase separated and aqueous layer extracted with ethyl acetate three times. The combined organic layers are collected, washed with brine, dried over magnesium sulfate and concentrated under vacuum to get crude product which was then chromatographed on silica gel eluting with 47% ethyl acetate/hexane to give 3.2 (54% yield). $^1$H NMR (500 MHz, Chloroform-d) δ ppm 0.91 (t, J=7.0 Hz, 3H) 1.08 (s, 3H) 1.31-1.39 (m, 2H) 1.45 (s, 3H) 1.50 (dd, J=5.5, 12.5 Hz, 1H) 1.57-1.64 (m, 2H) 2.0 (dt. J=2.5, 12.5 Hz, 1H) 2.10-2.29 (m, 2H) 2.38-2.47 (m, 1H) 2.59 (dd, J=5.5, 16.0 Hz, 1H) 2.85 (dt, J=3.0, 13.5 Hz, 1H) 3.00 (d, J=15.0 Hz, 1H) 3.60 (q, J=15.5, 34.0 Hz, 2H) 4.06-4.17 (m, 2H) 5.58 (s, 1H) 6.23 (d, J=2.50 Hz, 1H) 6.34 (d, J=2.50 Hz, 1H. HRMS calcd for $C_{21}H_{28}O_5$, 360.1937, found 360.1934.

Methyl 2-(3,5-dihydroxyphenyl)-2-methylpropanoate (36)

To the stirring solution of 3 (2.54 mmol) and sodium bicarbonate (3.82 mmol) in dimethylformamide (1.5 ml) was added iodomethane (6.35 mmol) in microwave vessel. The resulting mixture was heated at 165° C. for 12 min in microwave. The reaction mixture was quenched with water and diluted with ethyl acetate, the organic phase separated and aqueous layer extracted with ethyl acetate (5 ml) three times. The combined organic layers were collected, washed with saturated brine solution, dried over magnesium sulfate and concentrated under vacuum to get crude product which was then chromatographed on silica gel eluting with 34% ethyl acetate/hexane to give 36 (66% yield) as white amorphous solid. $^1$H NMR (500 MHz, Chloroform-d) δ ppm 1.47 (s, 6H) 3.61 (s, 3H) 6.25 (t, J=2.5 Hz, 1H) 6.41 (d, J=2.0 Hz, 2H) 6.90 (s, 2H).

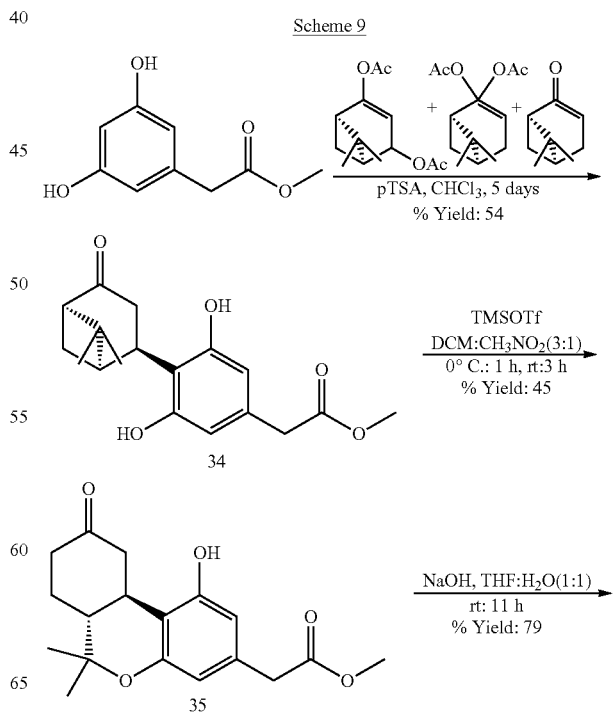

Scheme 9

-continued
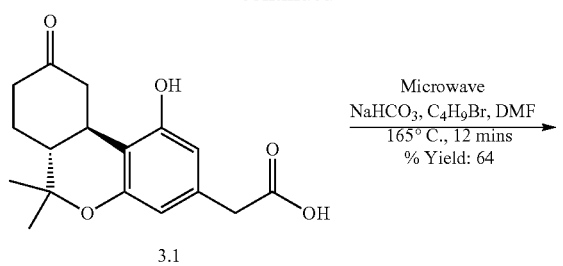
3.1
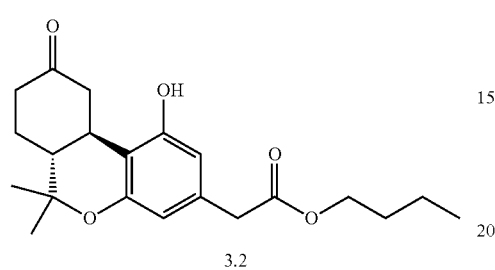
3.2
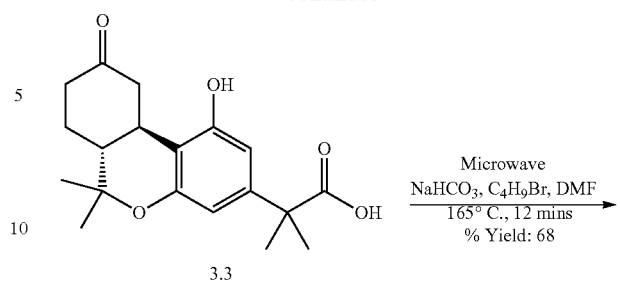
3.3
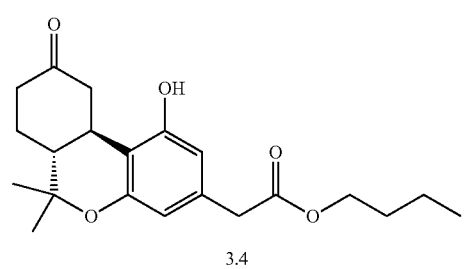
3.4
Scheme 9a
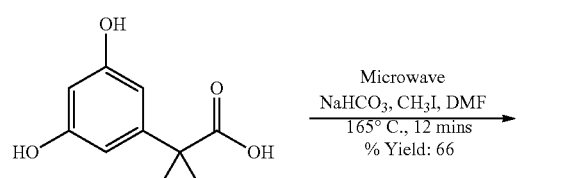
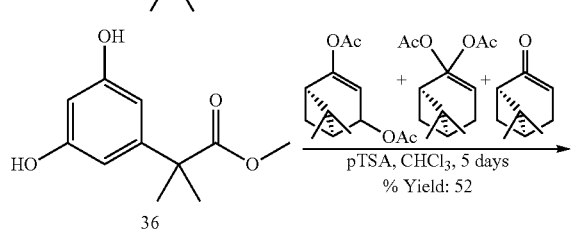
36
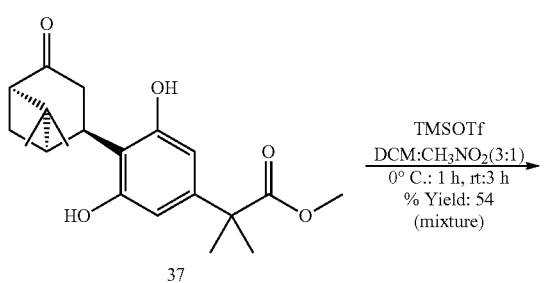
37
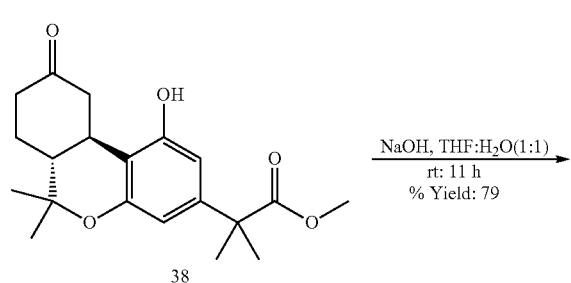
38
Scheme 9b
3.3
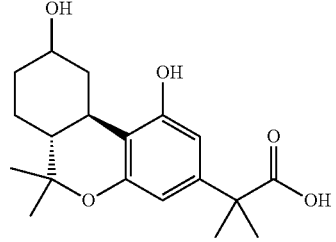
3.7
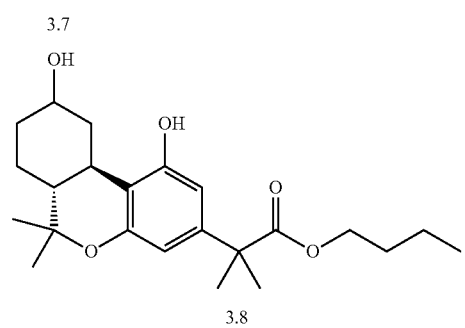
3.8
3.3
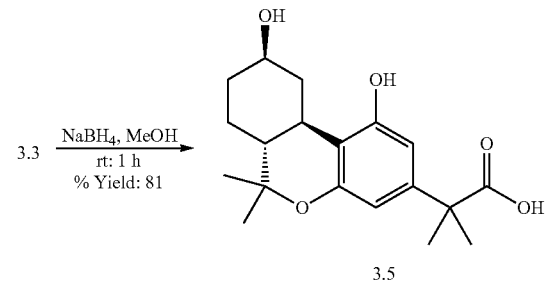
3.5

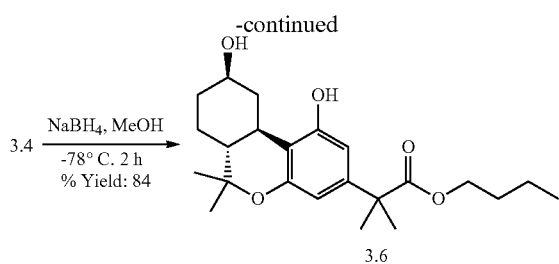

Methyl 2-(3,5-dihydroxy-4-((1R,2R,5S)-6,6-dimethyl-4-ketobicyclo[3.1.1]heptan-2-yl)phenyl)-2-methylpropanoate (37)

p-toluenesulfonic acid (1.82 mmol) was added to a stirring solution of 36 (1.66 mmol) and nopinone diacetate mixture (2.91 mmol) in chloroform. The resulting mixture was stirred at room temperature under dark for 5 days. The reaction mixture was quenched with water and diluted with ethyl acetate. The organic layer separated and aqueous layer extracted with ethyl acetate three times. The combined organic layers were collected, washed with saturated brine solution, dried over magnesium sulfate and concentrated under vacuum to get crude product which was then chromatographed on silica gel eluting with 18% ethyl acetate/hexane to give 37 (52% yield) as white amorphous powder. $^1$H NMR (500 MHz, Methanol-$d_4$) δ ppm 0.97 (s, 3H) 1.37 (s, 3H) 1.49 (s, 6H) 2.19 (t, J=5.50 Hz, 1H) 2.39-2.53 (m, 3H) 2.58-2.64 (m, 1H) 3.65 (s, 3H) 3.72 (dd, J=18.50, 7.0 Hz, 1H) 4.02 (t, J=8.0 Hz, 1H) 6.31 (s, 2H).

Methyl-2-((6aR,10aR)-6a,7,8,9,10,10a-hexahydro-1-hydroxy-6,6-dimethyl-9-oxo-6H-benzo[c]chromen-3-yl)-2-methylpropanoate (38)

TMSOTf (0.3 M solution in nitromethane, 0.19 mmol) was added at 0° C. to a stirring solution of 37 (0.63 mmol) in 3:1 mixture of DCM:Nitromethane (12 ml). The reaction mixture was brought to room temperature after stirring at 0° C. for 1 h and stirred for additional 3 h. (Note: the reaction doesn't go completion under these conditions). The reaction mixture was diluted with ethyl acetate after quenching with sodium bicarbonate, organic layer separated and aqueous layer extracted with ethyl acetate three times. The combined organic layers were collected, washed with water, saturated brine solution, dried over magnesium sulfate and concentrated under vacuum to get crude product which was then chromatographed on silica gel eluting with 12% ethyl acetate/hexane to give mixture of 37 and 38 (120 mg, 54% Yield) which is used as such for next reaction. HRMS calcd for $C_{20}H_{27}O_5$, 347.1858, found 347.1857.

2-((6aR, 10aR)-6a,7,8,9, 10,10a-hexahydro-1-hydroxy-6,6-dimethyl-9-oxo-6H-benzo[c] chromen-3-yl)-2-methylpropanoic acid (3.3)

Sodium hydroxide (0.69 mmol) was added to a solution of 38 (0.34 mmol) in 1:1 mixture of THF:water. The reaction mixture was quenched with diluted 1N HCl after stirring for 8 h and diluted with ethyl acetate. The organic layer separated and aqueous layer extracted with ethyl acetate (3 ml) three times. The combined organic layers were collected washed with water, saturated brine solution, dried over magnesium sulfate, concentrated under vacuum to get crude product which was then chromatographed on silica gel eluting with 48% acetone/hexane to give 3.3 (43% Yield) as light yellowish gum. $^1$H NMR (500 MHz, Methanol-$d_4$) δ ppm 1.10 (s, 3H) 1.46 (s, 3H) 1.48 (s, 6H) 1.98 (dt, J=12.0, 3.0 Hz, 1H) 2.06-2.22 (m, 3H) 2.48-2.54 (m, 2H) 2.79-2.87 (m, 1H) 3.87 (dd, J=15.0, 3.50 Hz, 1H) 6.32 (d, J=2.0, 1H) 6.37 (d, J=2.0 Hz, 1H); HRMS calcd for $C_{19}H_{25}O_5$, 333.1702, found 333.1700.

Butyl-2-((6aR, 10aR)-6a,7,8,9, 10,10a-hexahydro-1-hydroxy-6,6-dimethyl-9-oxo-6H-benzo[c]chromen-3-yl)-2-methylpropanoate (3.4)

To the stirring solution of 3.3 (0.15 mmol) and sodium bicarbonate (0.22 mmol) in dimethylformamide (1.5 ml) was added 1-bromobutane (0.40 mmol). The resulting mixture was heated at 165° C. for 12 min in microwave. The reaction mixture was quenched with water and diluted with ethyl acetate. The organic phase separated and aqueous layer extracted with ethyl acetate (3 ml) three times. The combined organic layers were collected, washed with saturated brine solution, dried over magnesium sulfate and concentrated under vacuum to get crude product which was then chromatographed on silica gel eluting with 20% ethyl acetate/hexane to give 3.4 (68% Yield) as light yellowish gum. $^1$H NMR (500 MHz, Chloroform-d) δ ppm 0.86 (t, J=7.5 Hz, 3H) 1.11 (s, 3H) 1.20-1.34 (m, 2H) 1.47 (s, 3H) 1.50 (s, 6H) 1.51-1.57 (m, 3H) 1.97 (dt, J=12.00, 3.0 Hz, 1H) 2.08-2.21 (m, 2H) 2.42-2.52 (m, 1H) 2.59-2.68 (m, 1H) 2.89 (dt, J=3.5, 13.0 Hz, 1H) 4.06 (dt, J=2.0, 6.5 Hz, 3H) 6.38 (q, J=1.5, 16 Hz, 2H) 6.36 (d, J=1.5 Hz, 1H) 6.39 (d, J=1.5 Hz, 1H) 7.37 (s, 1H); HRMS calcd for $C_{23}H_{32}O_5$, 388.2250, found 388.2246.

2-((6aR,9R,10aR)-6a,7,8,9, 10,10a-hexahydro-1,9-dihydroxy-6,6-dimethyl-6H-benzo[c]chromen-3-yl)-2-methylpropanoic acid (3.5)

To the stirring solution of 3.3 (0.16 mmol) in methanol was added in small portions sodiumborohydride (0.66 mmol). The reaction mixture was quenched with 1N HCl after stirring at room temperature for 1 h and diluted with ethyl acetate. The organic layer separated and aqueous layer extracted with ethyl acetate (3 ml) three times. The combined organic layers were collected washed with water, saturated brine solution, dried over magnesium sulfate, concentrated under vacuum to get crude product which was then chromatographed on silica gel eluting with 38% acetone/hexane to give 3.5 (81% yield). $^1$H NMR (500 MHz, Methanol-$d_4$) δ ppm 0.92-1.00 (m, 2H) 1.05 (s, 3H) 1.14-1.25 (m, 1H) 1.36 (s, 3H) 1.38-1.45 (m, 2H) 1.47 (s, 6H) 1.87-1.94 (m, 1H) 2.13 (dd, J=12.0, 2.0 Hz, 1H) 2.46 (dt, J=11.5, 2.5 Hz, 1H) 3.50-3.58 (m, 1H) 3.70-3.79 (m, 1H) 6.27 (d, J=2.0 Hz, 1H) 6.35 (d, J=2.0 Hz, 1H). HRMS calcd for $C_{19}H_{26}O_5$, 334.1780, found 334.1777.

Butyl-2-((6aR,9R, 10aR)-6a,7,8,9, 10, 10a-hexahydro-1,9-dihydroxy-6,6-dimethyl-6H-benzo[c]chromen-3-yl)-2-methylpropanoate (3.6)

To the stirring solution of 3.4 (0.097 mmol) in 3 ml of methanol at −78° C. was added in small portions sodium borohydride (0.097 mmol). The reaction mixture was stirred at same temperature for 2 h and quenched with 2N HCl and diluted with ethyl acetate. The organic layer separated and aqueous layer extracted with ethyl acetate (2 ml) three times. The combined organic layers were collected, washed with water, saturated brine solution, dried over magnesium sulfate and concentrated under vacuum to get crude product which was then chromatographed on silica gel eluting with 24% acetone/hexane to give 3.6 (84% yield) as light yellowish gum. $^1$H NMR (500 MHz, Chloroform-d) δ ppm 0.85 (t, J=7.5 Hz, 3H) 1.05 (s, 3H) 1.13-1.17 (m, 2H) 1.22-1.29 (m, 3H) 1.38 (s, 3H) 1.48 (s, 6H) 1.50-1.56 (m, 2H) 1.63 (s, br, 1H) 1.71-1.91 (m, 2H) 2.16 (d, J=11.0 Hz, 1H) 2.47 (dt, J=2.5, 11.5 Hz, 1H) 3.48-3.54 (m, 1H) 3.82-3.90 (m, 1H) 4.04 (t, J=6.5 Hz, 2H) 6.08 (s, br, 1H) 6.22 (d, J=2.0 Hz, 1H) 6.38 (d, J=1.5 Hz, 1H); HRMS calcd for $C_{23}H_{34}O_5$, 390.2406, found 390.2408.

2-((6aR,9S,10aR)-6a,7,8,9,10,10a-hexahydro-1,9-dihydroxy-6,6-dimethyl-6H-benzo[c]chromen-3-yl)-2-methylpropanoic acid (3.7)

K-Selectride (0.48 mmol) is added under argon to a solution of 3.3 (0.12 mmol) in dry tetrahydrofuran. The reaction mixture was quenched with 1N HCl after stirring at room temperature for 2 h and diluted with ethyl acetate. The organic layer separated and aqueous layer extracted with ethyl acetate (3 ml) three times. The combined organic layers were collected, washed with water, saturated brine solution, dried over magnesium sulfate and concentrated under vacuum to get crude product which was then chromatographed on silica gel eluting with 38% acetone/hexane to give 3.7 (95% yield). $^1$H NMR (500 MHz, Methanol-d$_4$) δ ppm 0.90-0.95 (m, 1H) 1.09 (s, 3H) 1.16-1.24 (m, 1H) 1.36 (s, 3H) 1.47 (s, 6H) 1.50-1.59 (m, 1H) 1.60-1.70 (m, 2H) 1.91-1.96 (m, 1H) 2.94 (dt, J=11.5, 3.0 Hz, 1H) 3.36-3.44 (m, 1H) 4.13 (t, J=3.0 Hz, 1H) 6.27 (d, J=2.0 Hz, 1H) 6.34 (d, J=1.5 Hz, 1H). HRMS calcd for $C_{19}H_{26}O_5$, 334.1780, found 334.1784.

Butyl-2-((6aR,9S,10aR)-6a,7,8,9,10,10a-hexahydro-1,9-dihydroxy-6,6-dimethyl-6H-benzo[c]chromen-3-yl)-2-methylpropanoate (3.8)

To the stirring solution of 3.7 (0.10 mmol) and sodium bicarbonate (0.16 mmol) in dimethyl formamide was added 1-bromobutane (0.25 mmol). The resulting mixture was heated at 165° C. for 12 min in microwave. The reaction mixture was quenched with water and diluted with ethyl acetate. The organic phase separated and aqueous layer extracted with ethyl acetate (2 ml) three times. The combined organic layers are collected, washed with saturated brine, dried over magnesium sulfate and concentrated under vacuum to get crude product which was then chromatographed on silica gel eluting with 23% acetone/hexane to give 3.8 (42% yield) as light yellowish gum. $^1$H NMR (500 MHz, Chloroform-d) δ ppm 0.87 (t, J=7.5 Hz, 3H) 1.07 (s, 3H) 1.25-1.31 (m, 4H) 1.39 (s, 3H) 1.44 (s, 1H) 1.51 (d, J=1.5, 6H) 1.52-1.58 (m, 3H) 1.62-1.71 (m, 2H) 1.96 (d, J=13.5 Hz, 1H) 2.96 (t, J=11.0 Hz, 1H) 3.24 (dd, J=14.0, 2.5 Hz, 1H) 4.07 (t, J=6.0 Hz, 2H) 4. HRMS calcd for $C_{23}H_{34}O_5$, 390.2406, found 390.2408.

Example 10: Synthesis of Compound 3.9

Experimental scheme for the synthesis of compound 3.9 in shown in Scheme 9c

Scheme 9c

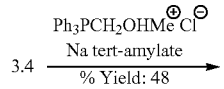

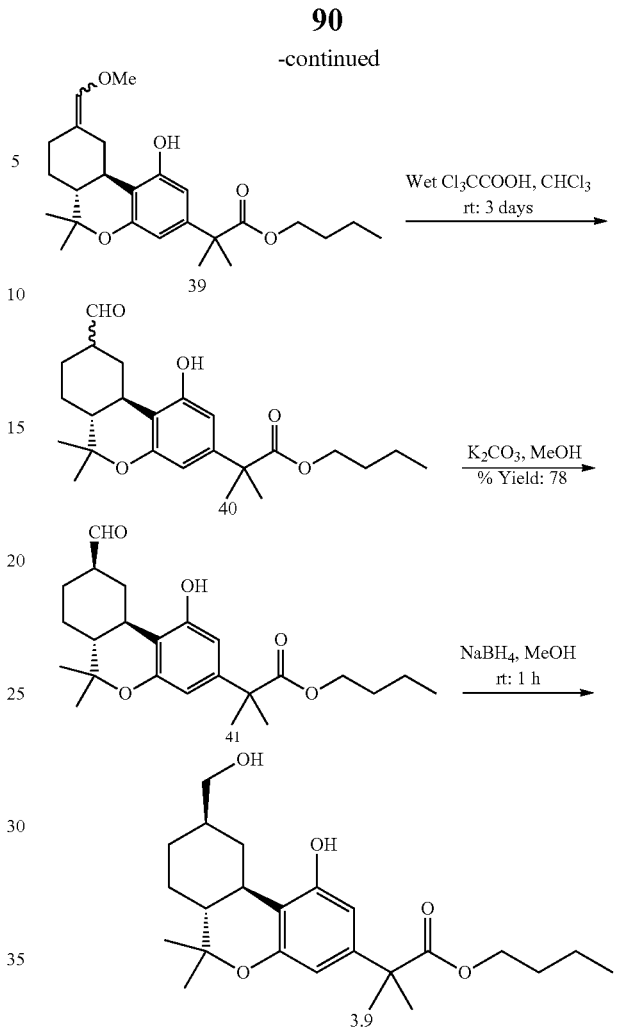

Procedure

Butyl 2-((6aR,10aS)-1-hydroxy-9-(methoxymethylene)-6,6-dimethyl-6a,7,8,9,10,10a-hexahydro-6H-benzo[c]chromen-3-yl)-2-methylpropanoate (39)

To the stirring solution of methoxymethyltriphenyl phosphonium chloride (5.53 mmoles) and sodium tert pentoxide (5.53 mmoles) in dry benzene was added 3.4 (11 mmoles). The reaction mixture was quenched with saturated ammonium chloride after stirring at room temperature for 8 h and diluted with ethyl acetate. The organic layer separated and aqueous layer was extracted with ethyl acetate three times. The combined organic layers were collected, washed with water, saturated brine solution, dried over magnesium sulfate and concentrated under vacuum to get crude product which is the chromatographed on silica gel eluting with 20% acetone hexane to give pure product 39 (48% yield). $^1$H NMR (500 MHz, Chloroform-d) δ ppm 0.84 (t, J=7.5 Hz, 3H) 1.05 (s, 3H) 1.09 (dt, J=4.5, 13.5 Hz, 1H) 1.25 (q, J=7.5, 15.0 Hz, 2H) 1.39 (s, 3H) 1.50 (s, 6H) 1.50-1.68 (m, 5H) 1.78 (dt, J=5.5, 14.0 Hz, 1H) 1.85-1.92 (m, 1H) 2.41 (dt, J=3.5, 11.0 Hz, 1H) 2.93 (dt, J=2.0 Hz, 1H) 3.5 (DD, J=2.0 Hz, 13.5 Hz, 1H) 3.56 (s, 3H) 4.05 (t, J=7.0 Hz, 2H) 5.91 (s, 1H) 6.22 (br, s, 1H) 6.28 (d, J=2.0 Hz, 1H) 6.39 (d, J=2.0 Hz, 1H).

Butyl 2-((6aR,10aS)-9-formyl-1-hydroxy-6,6-dimethyl-6a,7,8,9, 10,10a-hexahydro-6H-benzo[c]chromen-3-yl)-2-methylpropanoate (40)

To the stirring solution of 39 (0.24 mmoles) in chloroform was added wet trichloroacetic acid (1.92 mmoles) and stirred for 3 h at room temperature. The reaction mixture was quenched with saturated sodium bicarbonate and diluted with DCM. The organic layer separated and aqueous layer was extracted with DCM three times. The combined organic layers were collected, washed with water, saturated brine solution, dried over magnesium sulfate and concentrated under vacuum to get crude product which is then chromatographed on silica gel eluting with 20% acetone:hexane to give mixture of epimers 40 (93% yield) which was carried forward for next reaction without separating epimers.

Butyl 2-((6aR,9R, 10aS)-9-formyl-1-hydroxy-6,6-dimethyl-6a,7,8,9, 10, 10a-hexahydro-6H-benzo[c]chromen-3-yl)-2-methylpropanoate (41)

To the stirring solution of 40 (0.22 mmoles) in methanol was added potassium carbonate (1.56 mmoles) and the mixture was stirred at room temperature overnight. The reaction mixture was filtered, washed with water, saturated brine, dried over magnesium sulfate and concentrated under vacuum to get crude product which is then chromatographed on silicagel eluting with 15% acetone/hexane to get pure product 41 (78% yield). $^1$H NMR (500 MHz, Chloroform-d) δ ppm 0.84 (t, J=7.5 Hz, 3H) 1.08 (s, 3H) 1.20-1.28 (m, 4H) 1.39 (s, 3H) 1.48 (s, 6H) 1.49-1.57 (m, 6H) 1.78 (br, s, 1H) 1.96-2.01 (m, 2H) 2.12 (br, d, J=12.5 Hz, 1H) 2.44-2.6 (m, 2H) 3.54 (d, J=12.5 Hz, 11H) 4.05 (t, J=6.5 Hz, 2H) 6.28 (d, J=2.0 Hz, 1H) 6.29 (br, s, 1H) 6.40 (d, J=2.0 Hz, 1H) 9.65 (s, 11H).

Butyl 2-((6aR,9R, 10aS)-1-hydroxy-9-(hydroxymethyl)-6,6-dimethyl-6a,7,8,9,10, 10a-hexahydro-6H-benzo[c] chromen-3-yl)-2-methylpropanoate (3.9)

Sodium borohydride (1.04 mmoles) was added in small portions to the stirring solution of 41 (0.17 mmoles) in methanol at room temperature and the reaction mixture was stirred at same temperature for 1 h. The reaction mixture was quenched with 1N HCl and diluted with ethyl acetate. The organic layer separated and aqueous layer was extracted with ethyl acetate 3 times. The combined organic layers were collected, washed with water, saturated brine solution, dried over magnesium sulfate and concentrated under vacuum to get crude product which is the chromatographed on silica gel eluting with 15% acetone:hexane to get pure product 3.9 (72% yield). $^1$H NMR (500 MHz, Chloroform-d) δ ppm 0.72 (q, J=12.0, 24.0 Hz, 1H) 0.84 (t, J=7.0 Hz, 3H) 1.0 (s, 3H) 1.05-1.15 (m, 2H) 1.26 (p, J=7.5, 15.0 Hz, 2H) 1.35 (s, 3H) 1.47 (d, J=6.0 Hz, 6H) 1.53 (p, J=6.5, 14.0 Hz, 12H) 1.77 (br, s, 1H) 1.89 (m, 2H) 2.44 (dt, J=2.5, 10.5 Hz, 1H) 2.73 (br, s, 11H) 3.32 (d, J=12.5 Hz, 1H) 3.49 (m, 2H) 4.04 (r, J=6.5 Hz, 2H) 6.27 (d, J=2.0 Hz, 1H) 6.35 (d, J=2.0 Hz, 1H) 7.24 (br, s, 1H); HRMS calcd for $C_{24}H_{36}O_5$, 404.2563, found 404.2559.

Example 11: Synthesis of Compounds 3.10 and 3.11 is Shown in Scheme 9d

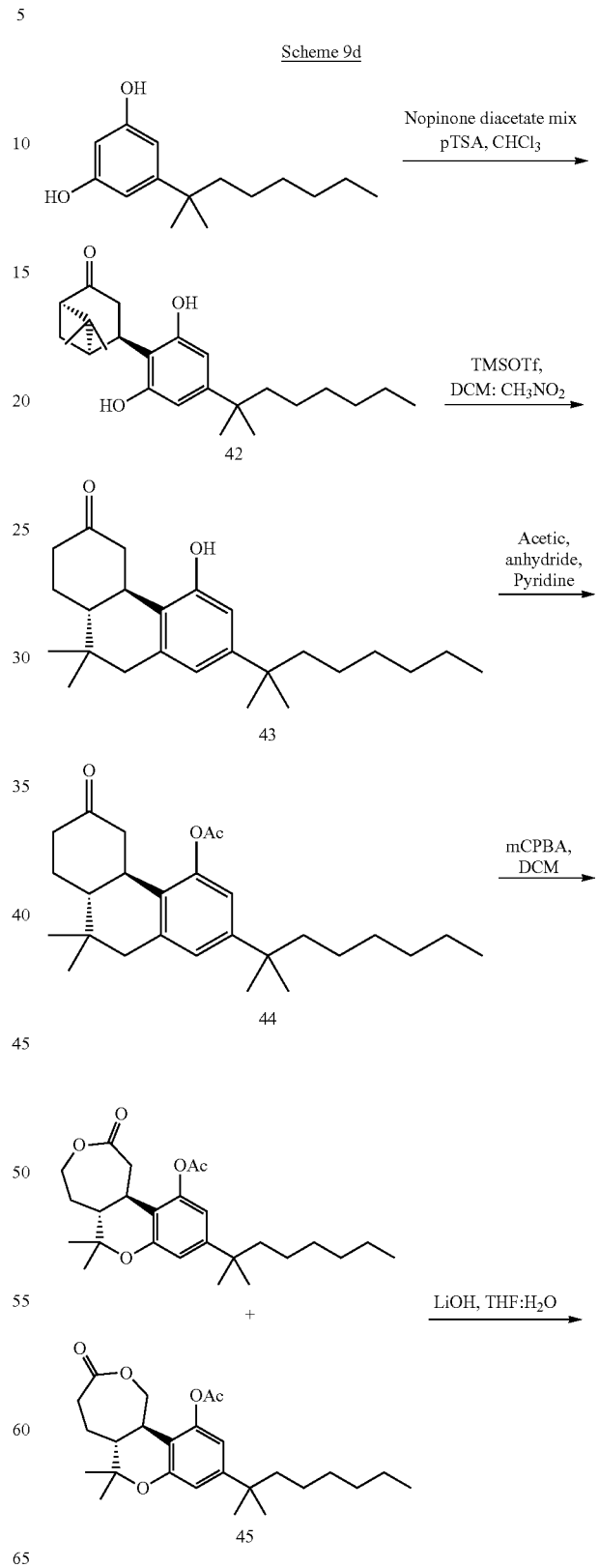

Scheme 9d

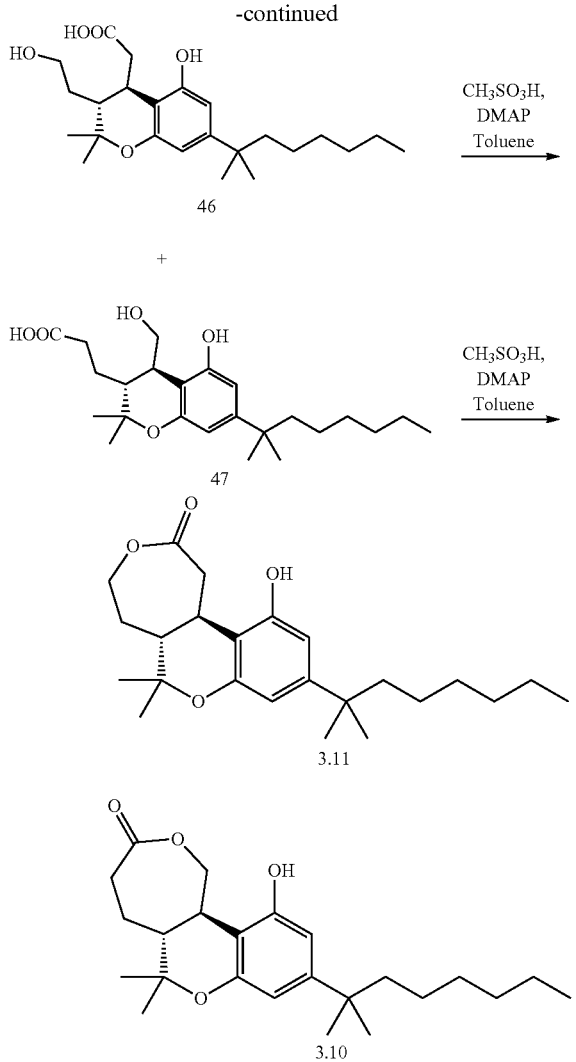

Procedure (1R,4R,5R)-4-(2,6-dihydroxy-4-(2-methyloctan-2-yl)phenyl)-6,6-dimethylbicyclo[3.1.1] heptan-2-one (42)

p-toluene sulfonic acid (2.78 mmoles) was added to the stirring solution of Dimethylheptyl resorcinol (2.53 mmoles) and nopinone diacetate mixture (3.04 mmoles) in chloroform. The resulting solution was stirred at room temperature under dark conditions and quenched with water after stirring for 3 days and diluted with dichloromethane. The organic layer separated and aqueous layer was extracted with dichloromethane three times. The combined organic layers were collected, washed with saturated brine solution, dried over magnesium sulfate and concentrated under vacuum to get crude product which was then chromatographed on silica gel eluting with 20% acetone:hexane to get pure product 42 (72% yield). $^1$H NMR (500 MHz, Chloroform-d) δ ppm 0.84 (t, J=7.0 Hz, 3H) 0.99 (s, 3H) 1.00-1.10 (m, 2H) 1.16-1.27 (m, 12H) 1.36 (s, 3H) 1.46-1.51 (m, 2H) 2.31 (t, J=5.5, 1H) 2.43-2.56 (m, 2H) 2.57-2.68 (m, 2H) 3.52 (q, J=7.5, 19.0 Hz, 1H) 3.94 (t, J=7.5 Hz, 1H) 5.12 (s, 2H) 6.28 9s, 2H).

(6aR, 10aR)-1-hydroxy-6,6-dimethyl-3-(2-methyloctan-2-yl)-7,8,10, 10a-tetrahydro-6H-benzo[c]chromen-9(6aH)-one (43)

TMSOTf (0.54 mmoles) was added to the stirring solution of 42 (1.81 mmoles) in 3:1 mixture of DCM:Nitromethane under argon at 0° C. and the reaction mixture was brought to room temperature after stirring at same temperature for 1 h and stirred for additional 4 h. The reaction mixture was quenched with saturated sodium bicarbonate and diluted with DCM. The organic layer separated and aqueous layer extracted three times with DCM. The combined organic layers were collected, washed with water, saturated brine solution, dried over magnesium sulfate and concentrated under vacuum to get crude product which is then chromatographed on silica gel eluting with 15 5 acetone:hexane to get pure product 43 (73% Yield). $^1$H NMR (500 MHz, Chloroform-d) δ ppm 0.83 (t, J=6.5 Hz, 3H) 1.01-1.08 (m, 2H) 1.13 (s, 3H) 1.15-1.26 (m, 12 h) 1.44-1.59 (m, 6H) 1.98 (dt, J=2.5, 12.0 Hz, 1H) 2.11-2.25 (m, 2H) 2.45-2.58 (m, 11H) 2.60-2.70 (m, 11H) 2.90 (dt, J=3.0, 12.5 Hz, 11H) 4.13-4.21 (m, 11H) 6.35 (d, J=1.5 Hz, 1H) 6.38 (d, J=1.0 Hz, 1H) 7.64 (s, 11H).

(6aR, 10aR)-6,6-dimethyl-3-(2-methyloctan-2-yl)-9-oxo-6a,7,8,9, 10, 10a-hexahydro-6H-benzo[c]chromen-1-yl acetate (44)

Acetic anhydride (0.26 mmoles) was added at 0° C. to the stirring solution of 43 (0.13 mmoles) and pyridine (0.65 mmoles) in dry DCM. To the resulting solution was added dimethylaminopyridine (0.65 mmoles) and the resulting solution stirred at room temperature for 3 h. The reaction mixture was quenched with saturated sodium bicarbonate and diluted with DCM. The organic layer separated and aqueous layer extracted with DCM three times. The combined organic layers were collected, washed with water, saturated brine solution, dried over magnesium sulfate and concentrated under vacuum to get crude product which is then chromatographed on silica gel eluting with 9% acetone hexane to get pure product 44 (90% yield). $^1$H NMR (500 MHz, Chloroform-d) δ ppm 0.84 (t, J=7.0 Hz, 3H) 1.0-1.09 (m, 2H) 1.12 (s, 3H) 1.16-1.28 (m, 12 h) 1.44-1.54 (m, 6H) 1.98 (dt, J=2.5, 12.0 Hz, 1H) 2.11-2.25 (m, 2H) 2.32 (s, 3H) 2.37-2.76 (m, 3H) 3.24-3.31 (m, 1H) 6.52 (d, J=1.5 Hz, 1H) 6.70 (d, J=2.0 Hz, 1H).

(5aR, 11bR)-6,6-dimethyl-9-(2-methyloctan-2-yl)-3-oxo-3,4,5,5a,6,11b-hexahydro-1H-oxepino[4,3-c]chromen-11-yl acetate (45)

To the stirring solution of 44 (0.072 mmoles) in dry DCM was added a solution of metachloro peroxybenzoic acid (0.36 mmoles) in dry dichloromethane at 0° C. dropwise. The reaction mixture was brought to room temperature after stirring at 0° C. for 1 h and stirred for additional 12 h. The reaction mixture was quenched with saturated sodium bicarbonate and diluted with DCM. The organic layer separated and aqueous layer was extracted with DC three times. The combined organic layers were collected, washed with water, dried over magnesium sulfate and concentrated under vacuum to get crude product which is the chromatographed on silicagel eluting with 10% acetone:hexane to get pure product 45 (95% yield). (Note: The product is mixture of inseparable isomers, so the reaction was carried forward to next reaction as such.)

2-((3R,4R)-5-hydroxy-3-(2-hydroxyethyl)-2,2-dimethyl-7-(2-methyloctan-2-yl)chroman-4-yl)acetic acid (46)

3-((3R,4R)-5-hydroxy-4-(hydroxymethyl)-2,2-dimethyl-7-(2-methyloctan-2-yl)chroman-3-yl)propanoic acid (47)

Lithium hydroxide (0.55 mmole) was added to the stirring solution of 45 (0.069 mmoles) in 50:50 mixture of THF: water at room temperature and stirred for 5 h. The reaction mixture was quenched with 2N HCl and diluted with ethyl acetate, The organic layer separated and aqueous layer extracted three times with ethyl acetate. The combined organic layers were collected washed with water, saturated brine solution, dried over magnesium sulfate and concentrated under vacuum to get crude product which is chromatographed on silica gel eluting with 45 5 acetone hexane to get pure products 46 (50% yield) and 47 (35% yield). NMR of intermediate 46 could not be isolated in very pure form, carried for cyclization without purification. NMR of intermediate 47: $^1$H NMR (500 MHz, Chloroform-d) δ ppm 0.83 (t, J=6.5 Hz, 3H) 1.0-1.10 (m, 2H) 1.15-1.28 (m, 16H) 1.33 (s, 3H) 1.47-1.59 (m, 4H) 1.64-2.0 (m, 6H) 2.4-2.58 (m, 2H) 2.80 (m, 1H) 3.82-3.93 (m, 2H) 6.35 (d, J=2.0 Hz, 1H) 6.47 (d, J=1.0 Hz, 1H).

(5aR, 11bR)-11-hydroxy-6,6-dimethyl-9-(2-methyloctan-2-yl)-4,5,5a,6-tetrahydro-1H-oxepino[4,5-c]chromen-2(11bH)-one (3.11)

Methanesulfonic acid (0.08 mmoles) was added to the stirring solution of 46 (0.029 mmoles) in toluene followed by dimethylamino pyridine (0.08 mmoles) at room temperature. The reaction mixture was quenched with saturated sodium bicarbonate after stirring at room temperature for 1 h and diluted with ethyl acetate. The organic layer separated and aqueous layer was extracted with ethyl acetate three times. The combined organic layer were collected, washed with water, saturated brine solution, dried over magnesium sulfate and concentrated under vacuum to get crude product which is then chromatographed on silica gel eluting with 23% acetone:hexane to get pure product 3.11 (75% yield). $^1$H NMR (500 MHz, Chloroform-d) δ ppm 0.84 (t, J=6.5 Hz, 3H) 1.0-1.10 (m, 2H) 1.16-1.28 (m, 17H) 1.47 (s, 3H) 1.49-1.6 (m, 2 h) 1.72-1.79 (m, 1H) 2.29 (t, J=15.0 Hz, 1H) 2.81 (ddd, J=4, 11.5 Hz, 1H) 3.06 (dd, J=4.0, 15.5 Hz, 1H) 3.66-3.79 (m, 2H) 6.58 (s, 1H) 6.59 (s, 1H).

(5aR, 11bR)-11-hydroxy-6,6-dimethyl-9-(2-methyloctan-2-yl)-4,5,5a,6-tetrahydro-1H-oxepino[4,3-c]chromen-3(11bH)-one (3.10)

Methanesulfonic acid (0.08 mmoles) was added to the stirring solution of 47 (0.029 mmoles) in toluene followed by dimethylamino pyridine (0.08 mmoles) at room temperature. The reaction mixture was quenched with saturated sodium bicarbonate after stirring at room temperature for 1 h and diluted with ethyl acetate. The organic layer separated and aqueous layer was extracted with ethyl acetate three times. The combined organic layer were collected, washed with water, saturated brine solution, dried over magnesium sulfate and concentrated under vacuum to get crude product which is then chromatographed on silica gel eluting with 26% acetone:hexane to get pure product 3.10 (78% yield). $^1$H NMR (500 MHz, Chloroform-d) δ ppm 0.86 (t, J=6.5 Hz, 3H) 1.03-1.10 (m, 5H) 1.18-1.30 (m, 14H) 1.42 (s, 3H) 1.48-1.54 (m, 1 h) 1.95 (dt, J=3.0, 12.5 Hz, 1H) 2.10-2.16 (m, 1H) 2.70-2.90 (m, 3H) 4.40 (q, J=7.5, 12.0 Hz, 1 Hz) 4.94 (br, s, 1H) 5.31 (dd, J=1.5, 12.0 Hz, 1H) 6.28 (d, J=2.0 Hz, 1H) 6.41 9d, J=2.0 Hz, 1H)

Example 12: Preparation of Compounds with Molecular Formula Lie

Synthesis of compounds 4.1, 4.2, 4.3, 4.4, 4.5, 4.6, 4.7, 4.8 are shown in scheme 10 and 10b.

Scheme 10

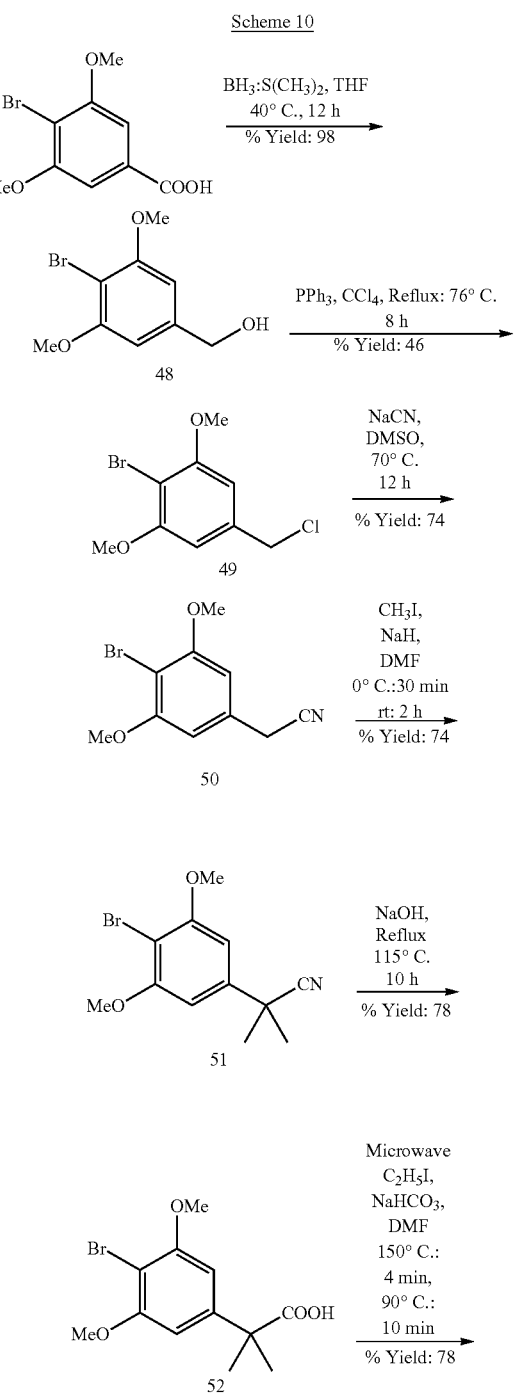

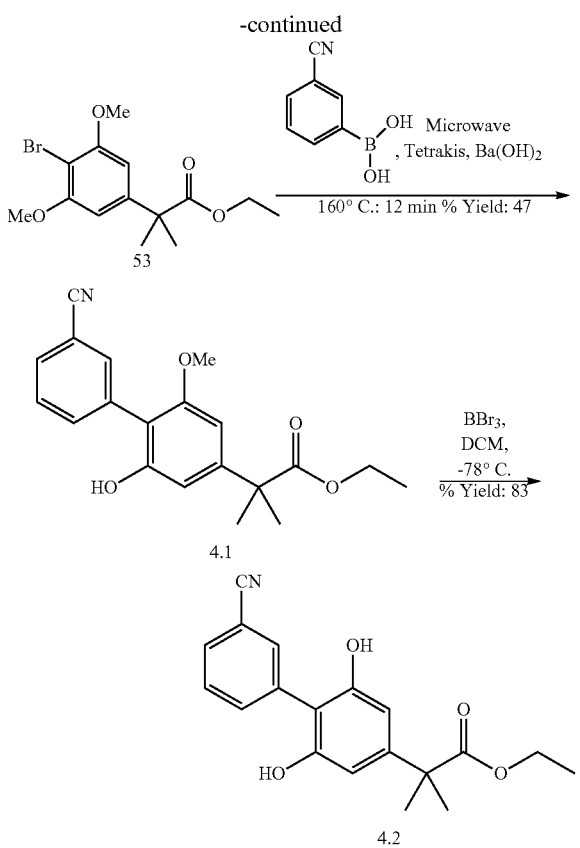

Procedure 4-bromo-3,5-dimethoxyphenyl)methanol (48)

To the stirring solution of 3,5-dimethoxy bromobenzoic acid (57.45 mmoles) in dry THF under argon was added drop wise borane dimethyl sulfide solution (114.91 mmoles, 2M solution in THF). The resulting solution was heated at 40° C. for 12 h, quenched with 1N HCl and diluted with ethyl acetate. The organic layer separated and aqueous layer was extracted with ethyl acetate three times. The combined organic layers were collected, washed with water, saturated brine solution, dried over magnesium sulfate, concentrated under vacuum to get crude product which is then chromatographed on silicagel eluting with 20% ethy acetate/hexane to get pure product 48 (98% Yield). $^1$H NMR (500 MHz, Chloroform-d) δ ppm 1.88 (s, 1H) 3.90 (s, 6H) 4.67 (d, J=4.0 Hz, 2H) 6.58 (s, 2H).

2-bromo-5-(chloromethyl)-1,3-dimethoxybenzene (49)

To the stirring solution of 48 (20.23 mmoles) in dry DCM was added solution of triphenyl phosphine (70.82 mmoles) in carbon tetrachloride and the resulting mixture was refluxed at 76° C. for 8 h. The reaction mixture was concentrated under vacuum to get crude product 49 which was sufficiently pure and carried forward for next reaction without purification.

2-(4-bromo-3,5-dimethoxyphenyl)acetonitrile (50)

To the stirring solution of 49 (18.07 mmoles) in DMSO was added sodium cyanide (180.77 mmol) and the resulting mixture was heated at 70° C. for 12 h, quenched with water and diluted with ethyl acetate. The organic layer was separated and aqueous layer was extracted with ethyl acetate three times. The combined organic layers were collected, washed with saturated brine solution, dried over magnesium sulfate and concentrated under vacuum to get crude product which is then chromatographed on silica gel eluting with 18% ethyl acetate/hexane to get 50 (74% yield). $^1$H NMR (500 MHz, Chloroform-d) δ ppm 3.73 (s, 2H) 3.91 (s, 6H) 6.52 (s, 2H).

2-(4-bromo-3,5-dimethoxyphenyl)-2-methylpropanenitrile (51)

To the stirring suspension of sodium hydride (37.5 mmoles) in dry DMF under argon at 0° C. was added drop wise a mixture 50 (12.5 mmol) and iodomethane (37.5 mmoles) in dry DMF (40 ml).

The reaction mixture was brought to room temperature after stirring at 0° C. for 30 min and stirred for additional 2 h. The reaction mixture was quenched with drop wise addition of saturated solution of ammonium chloride and diluted with ether. The organic layer was separated and aqueous layer extracted with ether 3 times. The combined organic layers were collected, washed with saturated brine solution, dried over magnesium sulfate and concentrated under vacuum to get crude product which was then chromatographed on silica gel eluting with 25% ethyl acetate/hexane to yield compound 51 (74% yield). $^1$H NMR (500 MHz, Chloroform-d) δ ppm 1.74 (s, 6H) 3.93 (s, 6H) 6.66 (s, 2H).

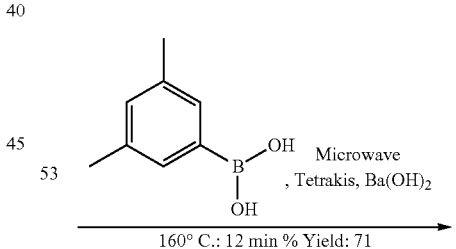

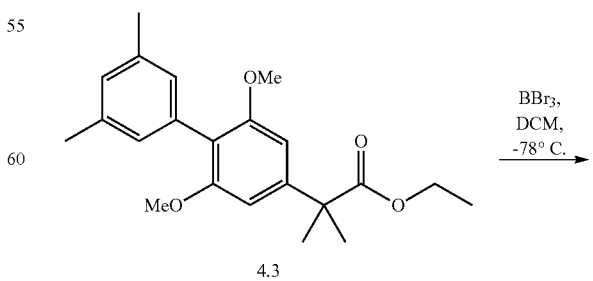

-continued

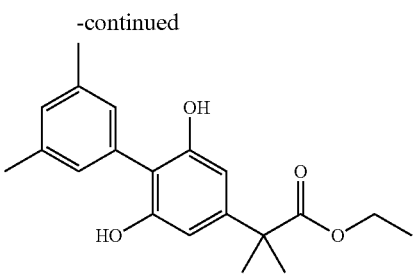

4.4

+

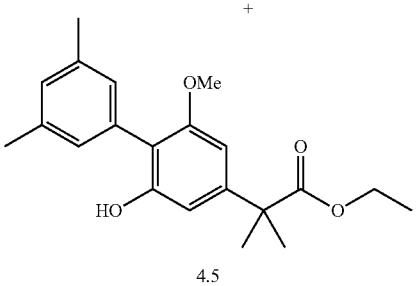

4.5

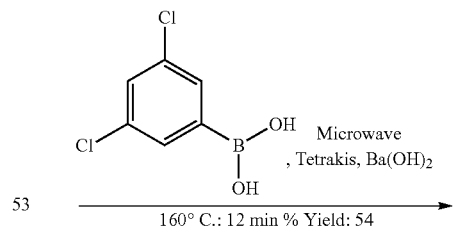

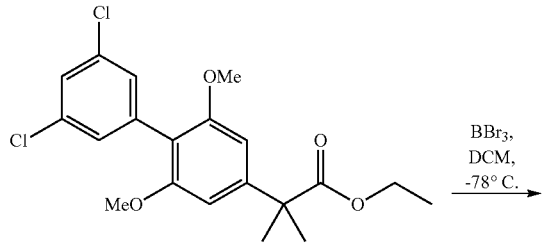

4.6

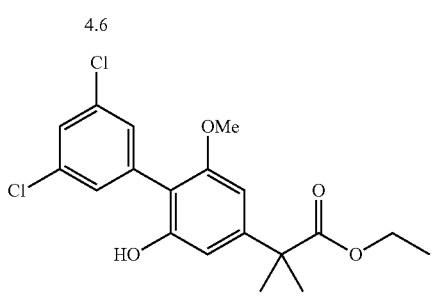

4.7

+

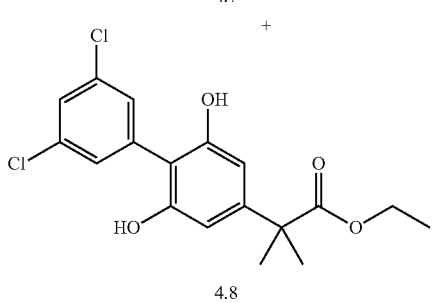

4.8

2-(4-bromo-3,5-dimethoxyphenyl)-2-methylpropanoic acid (52)

35% sodium hydroxide solution was added to the stirring solution of 51 (3.5 mmoles) in ethanol:methanol (80:20) mixture and the resulting solution was refluxed at 115° C. for 10 h. The reaction mixture was acidified with 2N HCl and diluted with ether. The organic layer was separated and aqueous layer was extracted with ether three times. The combined organic layers were collected, washed with saturated brine solution, dried over magnesium sulfate, concentrated under vacuum to get crude product which is then chromatographed on silica gel eluting with 50 ethyl acetate/hexane to get pure product 52 (78% yield). $^1$H NMR (500 MHz, Chloroform-d) δ ppm 1.61 (s, 6H) 3.89 (s, 6H) 6.60 (s, 2H).

Ethyl 2-(4-bromo-3,5-dimethoxyphenyl)-2-methylpropanoate (53)

Ethyl iodide (21.04 mmoles) was added to a mixture of 52 (2.63 mmoles) and sodium bicarbonate (7.91 mmoles) in DMF in microwave vessel. The resulting mixture was heated at 165° C. for 12 min in microwave, the reaction mixture was cooled to room temperature and diluted with water and ethyl acetate. The organic layer was separated and aqueous layer was extracted with ethyl acetate three times. The combined organic layers were collected, washed with saturated brine solution, dried over magnesium sulfate and concentrated under vacuum to get crude product which was then chromatographed on silicagel eluting with 8% ethyl acetate:hexane mixture to get pure product 53 (83% yield). $^1$H NMR (500 MHz, Chloroform-d) δ ppm 1.2 (t, J=7.0 Hz, 3H) 1.57 (s, 6H) 3.89 (s, 6H) 4.14 (q, J=6.0, 12.5 Hz, 2H) 6.55 (s, 2H); HRMS calcd for $C_{14}H_{20}O_4Br$, 331.0545, found 331.0543.

Ethyl 2-(3'-cyano-2,6-dimethoxybiphenyl-4-yl)-2-methylpropanoate (4.1)

3-cyanophenyl boronic acid (1.81 mmoles) was added to the stirring solution of 53 (1.5 mmoles) in 4.0 ml of DME in microwave vessel and the resulting mixture was degassed for 10 min. Water (0.5 ml) was added to the resulting mixture and the reaction mixture further degassed for 10 min. To the resulting mixture was added barium hydroxide (2.25 mmoles) and palladium tetrakis (0.3 mmoles) and the reaction mixture degassed for additional 10 min. The degassed reaction mixture was heated in microwave for 12 min at 160° C., quenched with water and diluted with ether. The organic layer was separated and aqueous layer was extracted with ether three times. The combined organic layers were collected, washed with saturated brine solution, dried over magnesium sulfate and concentrated under vacuum to get crude product which is then chromatographed on silicagel eluting with 10% ethyl acetate/hexane mixture to get pure product 4.1 (47% yield). $^1$H NMR (500 MHz, Chloroform-d) δ ppm 1.25 (t, J=7.0 Hz, 3H) 1.62 (s, 6H) 3.74 (s, 6H) 4.18 (q, J=7.0 Hz, 2H) 6.62 (s, 2H) 7.46 (t, J=8.0 Hz, 1H) 7.57 (tt, J=1.5, 7.5 Hz, 2H) 7.65 (t, J=1.5 Hz, 1H). HRMS calcd for $C_{21}H_{24}NO_4$, 354.1705, found 354.1717.

Ethyl 2-(3'-cyano-2,6-dihydroxybiphenyl-4-yl)-2-methylpropanoate (4.2)

To the stirring solution of 4.1 (0.098 mmoles) in dry DCM at −78° C. was added 1M solution of boron tribromide (0.58 mmoles) and the resulting solution was brought to room temperature after stirring at −78° C. for 1 h and stirred for additional 8 h. The reaction mixture was quenched with saturated sodium bicarbonate solution and diluted with DCM. The organic layer was separated and aqueous layer was extracted with DCM three times. The combined organic layers were collected, washed with water, saturated brine solution and dried over magnesium sulfate to get crude product which is then chromatographed on silica gel eluting with 35% ethyl acetate/hexane to give 4.2 (31% yield). $^1$H NMR (500 MHz, Chloroform-d) δ ppm 1.23 (t, J=7.0 Hz, 3H) 1.78 (s, 6H) 4.15 (q, J=7.0, 14.5 Hz, 2H) 6.11 (s, 2H) 6.54 (s, 2H) 7.56 (t, J=7.5 Hz, 1H) 7.65 (m, 1H) 7.72 (m, 1H) 7.77 (s, 1H); HRMS calcd for $C_{19}H_{20}NO_4$, 326.1392, found 326.1388.

Ethyl 2-(2,6-dimethoxy-3',5'-dimethylbiphenyl-4-yl)-2-methylpropanoate (4.3)

3,5-dimethylphenylboronic acid (1.5 mmoles) was added to the stirring solution of 53 (0.78 mmoles) in DME in microwave vessel and the resulting mixture was degassed for 10 min. Water was added to the resulting mixture and the reaction mixture further degassed for 10 min. To the resulting mixture was added barium hydroxide (1.24 mmoles) and palladium tetrakis (0.15 mmoles) and the reaction mixture degassed for additional 10 min. The degassed reaction mixture was heated in microwave for 12 min at 165° C., quenched with water and diluted with ether. The organic layer was separated and aqueous layer was extracted with ether three times. The combined organic layers were collected, washed with saturated brine solution, dried over magnesium sulfate and concentrated under vacuum to get crude product which is then chromatographed on silicagel eluting with 8% acetone/hexane mixture to get pure product 4.3 (71% yield). $^1$H NMR (500 MHz, Chloroform-d) δ ppm 1.23 (t, J=7.0 Hz, 3H) 1.61 (s, 6H) 2.32 (s, 6H) 3.71 (s, 6H) 4.17 (q, J=7.0, 14.5 Hz, 2H) 6.60 (s, 2H) 6.93 (s, 3H); HRMS calcd for $C_{22}H_{29}O_4$, 357.2066, found 357.2065.

Ethyl 2-(2,6-dihydroxy-3',5'-dimethylbiphenyl-4-yl)-2-methylpropanoate (4.4)

To the stirring solution of 4.3 (0.45 mmoles) in dry DCM at −78° C. was added 1M solution of boron tribromide (1.79 mmoles) and the resulting solution was stirred at same temperature for 2 h. The reaction mixture was quenched with saturated sodium bicarbonate solution and diluted with DCM. The organic layer was separated and aqueous layer was extracted with DCM three times. The combined organic layers were collected, washed with water, saturated brine solution and dried over magnesium sulfate to get crude product which is a mixture of 4.4 and Ethyl 2-(2-hydroxy-6-methoxy-3',5'-dimethylbi phenyl-4-yl)-2-methylpropanoate (4.5). The crude mixture of 102 and 103 was separated using column chromatography using 15 5 acetone/hexane mixture to get pure product 4.4 (51% yield) and 4.5 (28% yield).
$^1$H NMR (500 MHz, Chloroform-d) S ppm (4.4): 1.23 (t, J=7.0 Hz, 3H) 1.55 (s, 6H) 2.36 (s, 6H) 4.16 (q, J=7.0, 14.5 Hz, 2H) 4.98 (s, 2H) 6.56 (s, 2H) 7.0 (s, 2H) 7.09 (s, 1H); HRMS calcd for $C_{20}H_{25}O_4$, 329.1753, found 329.1745.
$^1$H NMR (500 MHz, Chloroform-d) δ ppm (4.5): 1.23 (t, J=7.5 Hz, 3H) 1.58 (s, 6H) 2.35 (s, 3H) 4.17 (q, J=7.5, 14.5 Hz, 2H) 5.08 (s, 1H) 6.49 (d, J=1.5 Hz, 1H) 6.65 (d, J=1.5 Hz, 1H) 6.96 (s, 2H) 7.02 (s, 1H); HRMS calcd for $C_{21}H_{27}O_4$, 343.1909, found 343.1898.

Ethyl 2-(3',5'-dichloro-2,6-dimethoxybiphenyl-4-yl)-2-methylpropanoate (4.6)

3,5-dichlorophenylboronic acid (1.29 mmoles) was added to the stirring solution of 53 (0.64 mmoles) in DME in microwave vessel and the resulting mixture was degassed for 10 min. Water was added to the resulting mixture and the reaction mixture further degassed for 10 min. To the resulting mixture was added barium hydroxide (1.02 mmoles) and palladium tetrakis (0.12 mmoles) and the reaction mixture degassed for additional 10 min. The degassed reaction mixture was heated in microwave for 12 min at 165° C., quenched with water and diluted with ether. The organic layer was separated and aqueous layer was extracted with ether three times. The combined organic layers were collected, washed with saturated brine solution, dried over magnesium sulfate and concentrated under vacuum to get crude product which is then chromatographed on silicagel eluting with 12% acetone/hexane mixture to get pure product 4.6 (54% yield). $^1$H NMR (500 MHz, Chloroform-d) δ ppm 1.23 (t, J=7.0 Hz, 3H) 1.61 (s, 6H) 3.73 (s, 6H) 4.16 (q, J=6.5, 14.0 Hz, 2H) 6.59 (s, 2H) 7.22 (d, J=1.5 Hz, 1H) 7.27 (t, J=1.5 Hz, 11H); HRMS calcd for $C_{20}H_{23}O_4 Cl_2$, 397.0973, found 397.0961.

Ethyl 2-(3',5'-dichloro-2,6-dihydroxybiphenyl-4-yl)-2-methylpropanoate (4.7)

To the stirring solution of 4.6 (0.35 mmoles) in dry DCM at −78° C. was added 1M solution of boron tribromide (1.05 mmoles) and the resulting solution was stirred at same temperature for 4 h. The reaction mixture was quenched with saturated sodium bicarbonate solution and diluted with DCM. The organic layer was separated and aqueous layer was extracted with DCM three times. The combined organic layers were collected, washed with water, saturated brine solution and dried over magnesium sulfate to get crude product which is a mixture of 4.7 and ethyl 2-(3',5'-dichloro-2-hydroxy-6-methoxybi phenyl-4-yl)-2-methylpropanoate (4.8). The crude mixture of 105 and 106 was separated using column chromatography using 16% acetone/hexane mixture to get pure product 4.7 (29% yield) and 4.8 (31% yield).
$^1$H NMR (500 MHz, Chloroform-d) δ ppm (4.7): 1.22 (t, J=6.5 Hz, 3H) 1.53 (s, 6H) 1.57 (br, s, 2H) 4.13 (q, J=6.0, 14.0 Hz, 2H) 6.48 (s, 2H) 7.32-7.38 (m, 3H) 7.36 (m, 1H). HRMS calcd for $C_{19}H_{21}O_4Cl_2$, 383.0817, found 383.0809.
$^1$H NMR (500 MHz, Chloroform-d) δ ppm (4.8): 1.23 (t, J=7.5 Hz, 3H) 1.57 (s, 6H) 3.73 (s, 6H) 4.17 (q, J=7.0, 14.0 Hz, 2H) 6.50 (s, 1H) 6.61 (d, J=1.0 Hz, 1H) 7.26 (d, J=2.0 Hz, 2H) 7.36 (s, 1H); HRMS calcd for $C_{18}H_{19}O_4Cl_2$, 369.0660, found 369.0659.

Example 13: Biochemical Pharmacology (a) Membrane Preparations from Tissue Culture Sources
HEK293 cells expressing hCB1 or hCB2 or mCB2 receptor are used for membrane preparations according to Abadji et al. *The resulting pellet is resuspended in* 10 mM Tris-chloride, pH 7.4, with 5 mM $MgCl_2$ and 2 mM EDTA (TME), rapidly frozen in liquid nitrogen and stored at −80° C. for no longer than two months. Protein content is assayed by using the Bio-Rad protein assay according to the manufacturer's protocol.

(b) Membrane Preparations from Tissue Sources

Frozen rat brains (CB1 source) are obtained from Pel-Freeze Biologicals (Rogers, AK) and stored at −80° C. until use. Membranes are prepared according to the method described by Dodd et al. and used in our laboratory as reported.

(c) rCB 1, mCB2, and hCB2 Binding Assays

All the cannabinoids discussed in this invention are tested for their ability to bind to CB 1 and CB2 receptors using membranes from rat brain or HEK293 cells expressing either mCB2 or hCB2, respectively via competition-equilibrium binding using [$^3$H]CP-55,940. Results are analyzed using nonlinear regression to determine ligand IC$_{50}$ (Prism by GraphPad Software, Inc.), and Ki values are calculated from the IC$_{50}$. IC$_{50}$ and Ki values are determined from at least three independent experiments.

(d) Stability in Plasma and Buffer

The designed compounds carry a side chain that is susceptible to plasma esterase activity, inviting their rapid deactivation. Thus, it is important to characterize the rate of compound metabolism in isolated rat or monkey plasma. As a preliminary predictor of oral stability, this assay will also be done in buffers at pH 2 (to emulate the stomach) and pH 7.4 (physiological pH). Compounds (10 mM in DMSO) are diluted in plasma, acetonitrile or buffer to a concentration of 200 µM and incubated in a 37° shaking water bath for 2 hours. Samples are taken periodically, diluted 1:4 with acetonitrile and centrifuged to precipitate protein. The resulting supernatant is analyzed by HPLC to predict expected in vivo plasma half-lives.

(e) Preliminary Distribution and the Blood Brain Barrier

Mice (CD-I, weighing 25-30 g) are dosed intravenously or by oral gavage with 0.1-2 mg/kg of the compound dissolved in appropriate vehicle. Fifteen minutes post-injection or 30 and 60 minutes post-gavage, the animals are sacrificed humanely by decapitation followed by blood collection (~500 µL) and tissue dissection; samples are flash-frozen with liquid nitrogen to prevent post-mortem degradation of the compounds or endogenous ligands. Tissues (plasma or brain) are extracted following published procedures (*J. Biol. Chem.* 1957, 226, (1), 497-509; herein incorporated by reference in its entirety) and analyzed in SRM mode using a Thermo-Finnigan Quantum Ultra triple quadruple mass spectrometer with an Agilent 1 100 HPLC front-end. Chromatographic separation is achieved using a Phenomenex Gemini column (2×50 mm, 5µ). Hardware consists of a Finnigan TSQ Quantum Ultra triple quad mass spectrometer with both an APCI and ESI source and an Agilent 1100 front end. The mass spec is run in APCI mode with mobile phase consisting of 0.1% formic acid in water (A) and 0.1% formic acid in methanol (B) in the following gradient: the first two minutes were held at 95% A before transitioning in a linear gradient to 5% A and held for seven minutes before returning to initial conditions. The run time is 15 minutes and the flow rate is 0.3 mL/min. The mass spec is in SRM mode and internal standards are used for quantitation.

Example 14: Biological Profiles of Exemplary Compounds

TABLE 5

Compounds of Formula (I)a:

(I)a

| No. | R$^1$, R$^2$, R$^3$ | rCB1 Ki (nM) | mCB2 Ki (nM) | hCB2 Ki (nM) | tPSA | cLogp | t1/2 (min) |
|---|---|---|---|---|---|---|---|
| 1.1 | (COOH) | >10,000 | >10,000 | >10,000 | 66.7 | 4.6 | |
| 1.2 | (C(=O)O(CH$_2$)$_4$Br) | 1.2 | 0.6 | 0.8 | 55.7 | 6.4 | 15 |
| 1.3 | (C(=O)O(CH$_2$)$_4$CN) | 0.7 | 0.5 | 0.8 | 79.5 | 4.9 | 40 |

TABLE 5-continued

Compounds of Formula (I)a:

(I)a

| No. | R¹ R² R³ | rCB1 Ki (nM) | mCB2 Ki (nM) | hCB2 Ki (nM) | tPSA | cLogp | t1/2 (min) |
|---|---|---|---|---|---|---|---|
| 1.4 | (butyl ester of dimethyl) | 0.6 | 0.6 | 0.7 | 55.7 | 6.5 | |
| 1.5 | (5-bromopentyl ester of dimethyl) | 1.2 | 0.5 | 0.6 | 55.7 | 6.9 | |
| 1.6 | (4-imidazolylbutyl ester of dimethyl) | 29.1 | 11.6 | 8.7 | 71.3 | 5.3 | 120 |
| 1.7 | (3-bromopropyl ester of dimethyl) | 0.8 | 1.1 | 0.6 | 55.7 | 6.0 | |
| 1.8 | (3-cyanopropyl ester of dimethyl) | 0.5 | 0.7 | 1.4 | 79.5 | 4.9 | |
| 1.9 | (3-azidopropyl ester of dimethyl) | 1.0 | 0.7 | 0.8 | 104.5 | 6.4 | |
| 1.10 | (3-imidazolylpropyl ester of dimethyl) | 3.4 | 2.0 | 1.2 | 71.3 | 5.2 | 240 |
| 1.11 | (carboxylic acid of methyl) | >10,000 | >10,000 | >10,000 | 66.7 | 4.2 | |

TABLE 5-continued

Compounds of Formula (I)a:

(I)a

| No. | R¹ R² R³ | rCB1 Ki (nM) | mCB2 Ki (nM) | hCB2 Ki (nM) | tPSA | cLogp | t1/2 (min) |
|---|---|---|---|---|---|---|---|
| 1.12 | (isopropyl-C(=O)-O-butyl) | 0.7 | 1.2 | 1.0 | 55.7 | 6.1 | 3 |
| 1.13 | (gem-dimethyl, CH(CH₃)-COOH) | >10,000 | >10,000 | >10,000 | 66.7 | 4.2 | |
| 1.14 | (gem-dimethyl, CH(CH₃)-C(=O)-O-butyl) | 0.9 | 1.4 | 1.4 | 55.7 | 6.1 | 7 |
| 1.15 | (CH(CH₃)-COOH) | >10,000 | >10,000 | >10,000 | 66.7 | 4.2 | |
| 1.16 | (CH(CH₃)-C(=O)-O-butyl) | 2.4 | 1.3 | 1.5 | 55.7 | 6.1 | 6 |
| 1.17 | (1-cyclobutyl-COOH with methyl) | >10,000 | >10,000 | >10,000 | 66.7 | 4.7 | |
| 1.18 | (1-cyclobutyl-C(=O)-O-(CH₂)₄-Br) | 0.3 | 3.7 | 0.7 | 55.7 | 6.6 | 50 |
| 1.19 | (1-cyclobutyl-C(=O)-O-(CH₂)₄-CN) | 0.9 | 1.5 | 1.8 | 79.5 | 5.0 | 107 |

TABLE 5-continued

Compounds of Formula (I)a:

(I)a

| No. | R¹ R² R³ | rCB1 Ki (nM) | mCB2 Ki (nM) | hCB2 Ki (nM) | tPSA | cLogp | t1/2 (min) |
|---|---|---|---|---|---|---|---|
| 1.20 | [cyclobutyl with methyl and C(=O)O-butyl] | 0.7 | 0.7 | 0.4 | 55.7 | 6.7 | 40 |
| 1.21 | [cyclobutyl with methyl and C(=O)O-(CH2)4-N3] | 0.9 | 1.9 | 2.7 | 104.5 | 7.0 | |
| 1.22 | [C(CH3)(CH2OH)(COOH)-pentyl] | 600 | 1000 | 1000 | 86.9 | 4.7 | |
| 1.23 | [β-lactone with pentyl and methyl] | 15.9 | 40.7 | 55.5 | 55.7 | 5.2 | |
| 1.24 | [C(CH3)2-C(=O)O-(CH2)4-morpholine] | 33.8 | 71.8 | 39.9 | 68.2 | 5.5 | 68 |
| 1.25 | [C(CH3)2-C(=O)O-(CH2)3-morpholine] | 15.2 | 104 | 8.7 | 68.2 | 5.5 | 200 |
| 1.26 | [C(CH3)2-CH2-COOH] | >10,000 | >10,000 | >10,000 | 66.7 | 3.8 | |
| 1.27 | [C(CH3)2-C(=O)O-(CH2)4-Br] | 2.2 | 11.6 | 7.1 | 55.7 | 5.7 | 3 |

TABLE 5-continued

Compounds of Formula (I)a:

(I)a

| No. | R¹ R² R³ | rCB1 Ki (nM) | mCB2 Ki (nM) | hCB2 Ki (nM) | tPSA | cLogp | t1/2 (min) |
|---|---|---|---|---|---|---|---|
| 1.28 | ester-CH₂-C(=O)-O-(CH₂)₄-CN | 14.3 | 2.1 | 1.2 | 79.5 | 4.2 | 4.8 |
| 1.29 | -CH₂-C(=O)-O-butyl | 40.3 | 27.0 | 8.2 | 55.7 | 5.8 | 5 |
| 1.30 | -C(CH₃)₂-C(=O)-S-propyl | 0.5 | — | 0.7 | 46.5 | 6.8 | |
| 1.31 | -C(CH₃)₂-C(=O)-NH-pentyl | 6.3 | 9.2 | 2.8 | 58.5 | 5.9 | |
| 1.32 | -C(CH₃)₂-CH₂-OH | 447 | — | — | 49.6 | 4.6 | |
| 1.33 | -C(CH₃)₂-CH₂-O-C(=O)-butyl | 0.5 | — | 1.0 | 55.7 | 7.1 | |
| 1.34 | -C(CH₃)₂-C(=O)-O-methyl | 83.1 | 34.5 | 36.8 | 55.7 | 5.0 | 60 |
| 1.35 | -C(CH₃)₂-C(=O)-O-ethyl | 2.7 | 0.5 | 1.5 | 55.7 | 5.5 | |
| 1.36 | -C(CH₃)₂-C(=O)-O-CH₂CH₂Br | 2.9 | 3.2 | 7.7 | 55.7 | 5.7 | |

TABLE 6
Compounds of Formula (I)b:
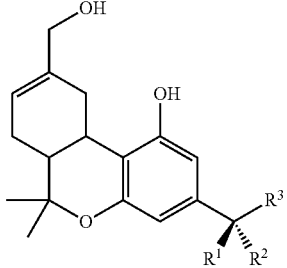
| No. | R¹ R² R³ | rCB1 Ki (nM) | mCB2 Ki (nM) | hCB2 Ki (nM) | tPSA | cLogp | t1/2 (min) |
|---|---|---|---|---|---|---|---|
| 2.1 | ![structure with -C(CH3)2-COOH] | >10,000 | >10,000 | >10,000 | 86.9 | 3.0 | |
| 2.2 | ![structure with -C(CH3)2-C(O)O-butyl] | 0.6 | 1.5 | 0.8 | 75.9 | 4.8 | 5 |
| 2.3 | ![structure with imidazole ester] | 25.3 | 11.6 | 8.7 | 91.5 | 3.2 | 120 |
| 2.4 | ![structure with -C(O)O-propyl-Br] | 1 | 1 | 1 | | | |
| 2.5 | ![structure with -C(O)O-propyl-CN] | 1 | 1 | 1 | | | |
| 2.6 | ![structure with imidazole propyl ester] | 1 | 1 | 1 | | | |
| 2.7 | ![structure with morpholine propyl ester] | 1 | 1 | 1 | | | |

TABLE 7

Compounds of Formula (I)c:

(I)c

| No. | X | R¹ R² R³ group | rCB1 Ki (nM) | mCB2 Ki (nM) | hCB2 Ki (nM) | tPSA | cLogp | t1/2 (min) |
|---|---|---|---|---|---|---|---|---|
| 3.1 | C(O) | -CH₂-C(O)OH | >10,000 | >10,000 | >10,000 | 83.8 | 1.9 | |
| 3.2 | C(O) | -CH₂-C(O)O-butyl | 1,000 | 1,000 | 1,000 | 72.8 | 3.4 | |
| 3.3 | C(O) | -C(CH₃)₂-C(O)OH | >10,000 | >10,000 | >10,000 | 83.2 | 3.2 | |
| 3.4 | C(O) | -C(CH₃)₂-C(O)O-butyl | 2.2 | 7.2 | 6.2 | 72.8 | 4.7 | |
| 3.5 | CH(OH) | -C(CH₃)₂-C(O)OH | >10,000 | >10,000 | >10,000 | 86.9 | 3.0 | |
| 3.6 | CH(OH) | -C(CH₃)₂-C(O)O-butyl | 0.1 | 0.2 | 0.2 | 75.9 | 4.5 | 3 |
| 3.7 | CH(OH) | -C(CH₃)₂-C(O)OH | >10,000 | >10,000 | >10,000 | 86.9 | 3.0 | |
| 3.8 | CH(OH) | -C(CH₃)₂-C(O)O-butyl | 3.1 | 0.6 | 4.5 | 75.9 | 4.5 | 8 |
| 3.9 | CH-CH₂OH | -C(CH₃)₂-C(O)O-butyl | 2.4 | 4.3 | 6.5 | 75.9 | 4.9 | |
| 3.10 | —C(O)O— | -C(CH₃)₂-pentyl | | | | 55.7 | 5.8 | 15 |

TABLE 7-continued

Compounds of Formula (I)c:

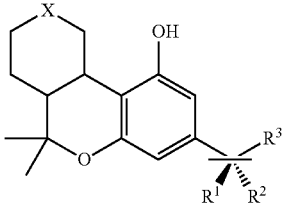

(I)c

| No. | X | R¹ R² R³ | rCB1 K$i$ (nM) | mCB2 K$i$ (nM) | hCB2 K$i$ (nM) | tPSA | cLogp | t$1/2$ (min) |
|---|---|---|---|---|---|---|---|---|
| 3.11 | —O(O)C— | | 99 | 8.0 | | 55.7 | 5.8 | |

TABLE 8

Compounds of Formula (II):

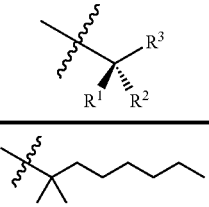

(II)

| No. | R⁷ | R⁸ | R⁹ | R¹⁰ | rCB1 K$i$ (nM) | mCB2 K$i$ (nM) | hCB2 K$i$ (nM) |
|---|---|---|---|---|---|---|---|
| 4.1 | OCH₃ | OCH₃ | H | CN | >1,000 | >1,000 | >1,000 |
| 4.2 | OH | OH | H | CN | 3.664 | — | 94.8 |
| 4.3 | OCH₃ | OCH₃ | CH₃ | CH₃ | 1,000 | 1,000 | 1,000 |
| 4.4 | OH | OH | CH₃ | CH₃ | 941 | 36 | 48.8 |
| 4.5 | OCH₃ | OH | CH₃ | CH₃ | 1,000 | 108 | 375 |
| 4.6 | OCH₃ | OCH₃ | Cl | Cl | 1,000 | 1,000 | 1,000 |
| 4.7 | OCH₃ | OH | Cl | Cl | 1,000 | 1,000 | 700 |
| 4.8 | OH | OH | Cl | Cl | 191 | 10.3 | 20.9 |

Example 15: Hypothermia Test

Figure 1B:
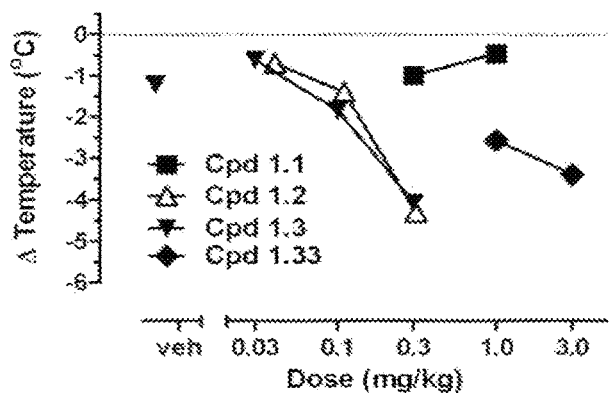
Figure 1C:
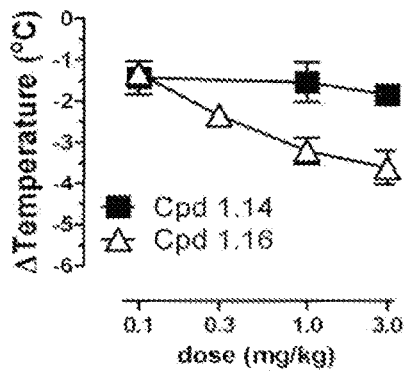
Figure 1D:
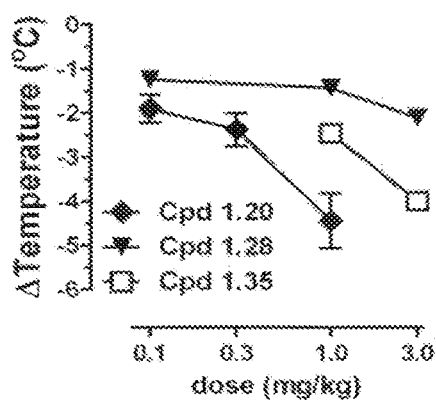
Figure 1E:
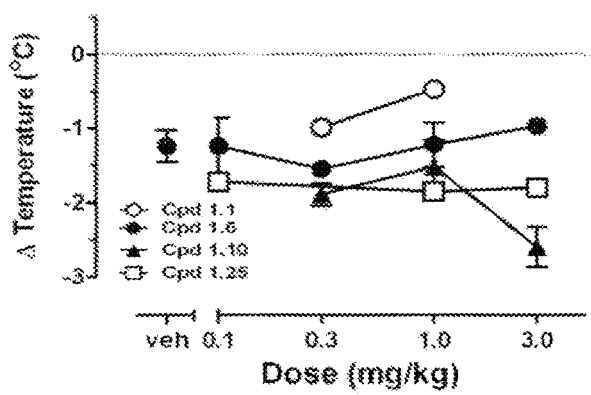

The hypothermia test determines the ability of a test compound to act as a central CB 1 agonist and decrease body temperature. A dose range from 0.01 mg/kg to 3 mg/kg was examined subcutaneously (s.c), initially based on in vitro CB receptor agonist potency, so as to facilitate characterization of potency in vivo and onset/offset of action. Rat core temperature is monitored with a thermistor probe for up to 6 h. Compounds were initially dissolved in a solution of 20% EtOH, 20% Alkamuls, and 60% saline and further diluted with saline. Injections were administered s.c. in a volume of 0.5-2 mL/kg. Two temperature values recorded prior to injection were averaged to obtain a single baseline temperature. Temperature recorded after injection was expressed as change from baseline. Group means and SEM were calculated, and time-or dose-effect functions were analyzed using standard ANOVA or paired t-test procedures with significance set as $p<0.05$. Wherever appropriate, ANOVA was followed by Bonferroni's post-hoc test or by Dunnet's multiple comparison t-test. In all cases, statistical significance was set at $p<0.05$. FIG. 1A shows results for Compounds 2.2, 3.6, and 3.9. FIG. 1B shows results for Compounds 1.1, 1.2, 1.3, and 1.33. FIG. 1C shows results for Compounds 1.14 and 1.16. FIG. 1D shows results for Compounds 1.20, 1.28, and 1.35. FIG. 1E shows results for Compounds 1.1, 1.6, 1.10, and 1.25.

Example 16: Antinociception Tail Flick Test

Figure 2:
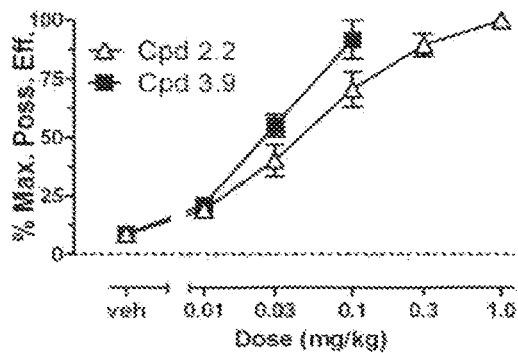
FIG. 2 shows rat tail flick test results for compounds 2.2 and 3.9.
Figure 3A:
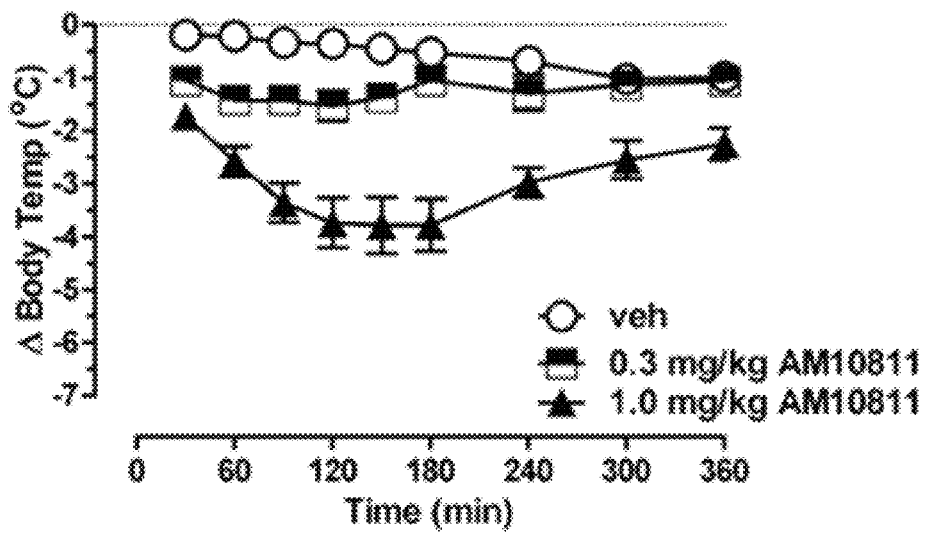
FIG. 3A shows a comparison of the hypothermic effects of AM10843 (bottom) and the more polar agonist, AM10811 (top), in rats. Abscissa, time after injection; ordinate, change in body temperature. The more polar (compare c Log P and tPSA values) and the more potent (compare cAMP data) agonist AM10811 is shorter acting when compared to AM10843.
Figure 3A:
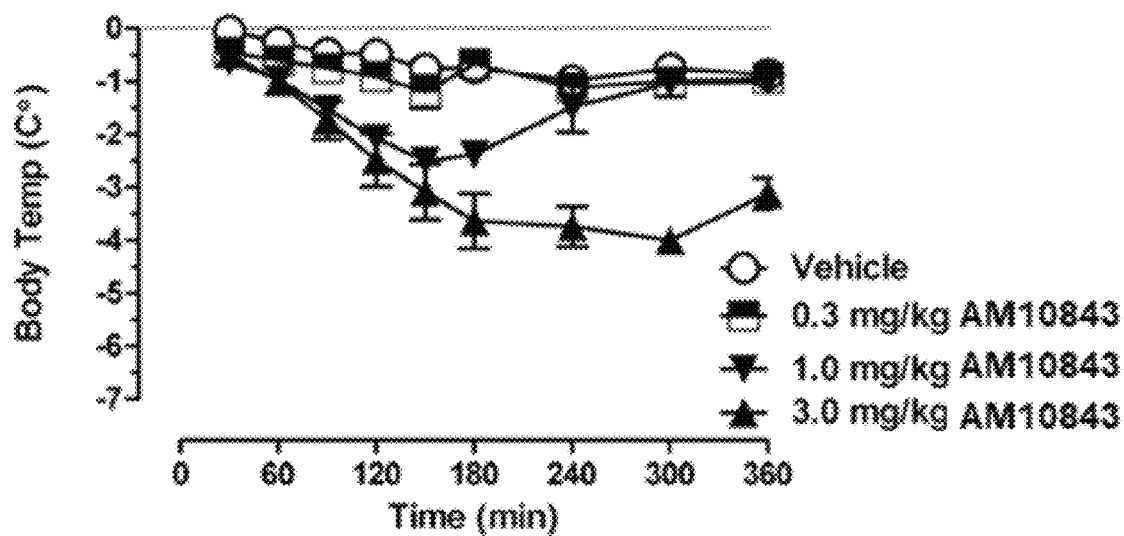
Figure 3B:
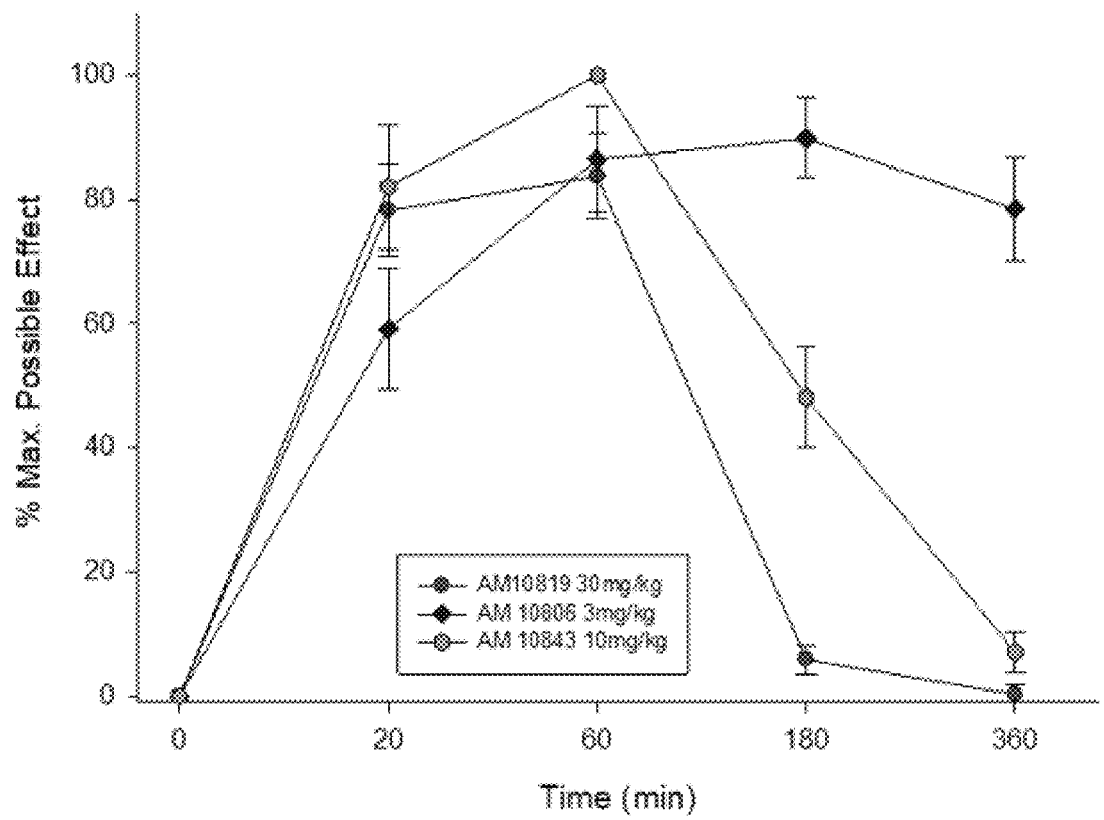
FIG. 3B shows a comparison of the analgesic effects (tail flick in mice, at iso-active doses) of the drug nabilone (AM10806), AM10843, and AM10819. AM10819 with steric bulk further away (beta) to the metabolically labile ester is shorter acting.

Compounds with hypothermic activity were tested in the rat tail flick test for antinociception. The tail flick test measures spinal nociception as sensitivity of the animal to increasing temperature and indicates the ability of a test compound to activate cannabinergic signaling in vivo and thereby reduce nociceptive pain at the pharmacologically relevant doses. The animals were enclosed in polypropylene chamber with an opening through which its tail is exposed. In the test, the distal third of the rat's tail was exposed to a heat source and the time the animal takes to move its tail away from the heat source was measured. The response is expressed as a percentage of maximum possible effect (% MPE). Dose-effect functions were constructed using the maximum effect recorded in each rat at a given dose of compound. FIG. 2 shows rat tail flick test results for Compounds 2.2 and 3.9.

Example 17: Compounds of Formula (Ie)

Some disclosed compounds were tested for CB1 and CB2 receptor binding affinity, which can be represented by a Ki value. The Ki value is the affinity constant and describes the affinity of the compound for the receptor. The lower the Ki value, the higher the affinity of the compound for the receptor. A detailed description of the methods used to test binding affinity of compounds is given in US 2007/0135388 and in Papahatjis, et al., *J. Med. Chem.* (2007) 4048, the content of each of which is hereby incorporated by reference. Table 9 lists the Ki values for certain compounds of Formula (Ie).

The polarity or polar characteristics of a compound refers to the calculated log P (c log P) and total polar surface area (tPSA) of each respective compound. These values have been calculated using the ChemBioDraw Ultra 14.0 software. It has been found that the polar characteristics/polarity of a compound are important parameters that determine in vivo efficacy, potency, water solubility, tissue exposure and retention, and in some cases toxicity. See Nikas, et al. *J. Med. Chem.* (2015) 58, 609. Generally, the lower the c log P and the higher the tPSA values of a compound the higher the polarity/polar character of that compound. More polar compounds may exhibit enhanced druggability profiles including, for instance, better water solubility, absorption, oral bioavailability, excretion and detoxification. Table 9 lists the c Log P and tPSA of certain compounds of Formula (Ie).

TABLE 9

Structures of Further Compounds of Formula (Ie) and Their Affinities For CB1 and CB2 and Calculated (ChemDraw Software) cLogP and tPSA values:

| No. | R | rCB1 (Ki, nM) | mCB2 (Ki, nM) | hCB2 (Ki, nM) | cLogP | tPSA |
|---|---|---|---|---|---|---|
| 34a | –C(CH$_3$)$_2$C(O)OEt | 36.7 ± 5.6 | 89.7 ± 18.1 | 67.5 ± 13.4 | 3.82 | 72.83 |
| 34b | –C(CH$_3$)$_2$C(O)O-n-Pr | 4.8 ± 0.8 | 32.0 ± 5.2 | 8.3 ± 3.1 | 3.69 | 72.83 |
| 34c | –C(CH$_3$)$_2$C(O)O-n-Bu | 0.4 ± 0.01 | 6.1 ± 1.1 | 11.5 ± 1.6 | 4.75 | 72.83 |
| 34d | –C(CH$_3$)$_2$C(O)O-n-pentyl | 5.9 ± 1.2 | 30.0 ± 7.3 | 15.1 ± 2.2 | 5.28 | 72.83 |
| 34e | –C(CH$_3$)$_2$C(O)O-(S)-sec-butyl | 3.0 ± 0.5 | 54.0 ± 10.6 | 12.4 ± 2.5 | 5.04 | 72.83 |
| 34f | –C(CH$_3$)$_2$C(O)O-(R)-sec-butyl | 4.0 ± 0.7 | 36.4 ± 12.4 | 7.0 ± 2.1 | 5.04 | 72.83 |
| 7 | –C(CH$_3$)$_2$C(O)O(CH$_2$)$_3$I | 0.1 ± 0.04 | 1.2 ± 0.6 | 5.3 ± 0.9 | 4.08 | 72.83 |
| 8 AM10811 | –C(CH$_3$)$_2$C(O)O(CH$_2$)$_3$CN | 0.7 ± 0.03 | 1.1 ± 0.4 | 6.2 ± 2.7 | 2.65 | 96.62 |

TABLE 9-continued
Structures of Further Compounds of Formula (Ie) and Their Affinities For CB1 and CB2 and Calculated (ChemDraw Software) cLogP and tPSA values:
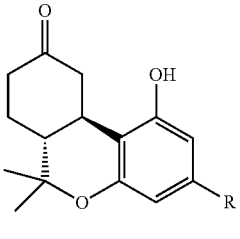
(Ie)
| No. | R | rCB1 | mCB2 | hCB2 | cLogP | tPSA |
|---|---|---|---|---|---|---|
| | | | (Ki, nM) | | | |
| 34g | 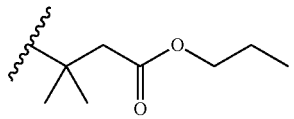 [SMILES: *C(C)(C)CC(=O)OCCC] | 17.0 ± 3.5 | 91.7 ± 20.4 | 18.2 ± 4.1 | 3.18 | 85.30 |
| 18 AM10819 | 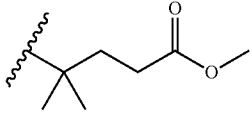 [SMILES: *C(C)(C)CCC(=O)OC] | 11 ± 1.4 | 26 ± 3.6 | 90 ± 11.3 | 4.09 | 72.83 |
| 23 | 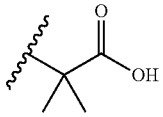 [SMILES: *C(C)(C)C(=O)O] | 270 ± 34.6 | 540 ± 46.7 | 560 ± 64.3 | 3.56 | 72.81 |
| 32 | 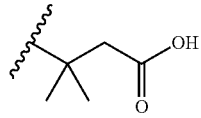 [SMILES: *C(C)(C)CC(=O)O] | >1000 | >1000 | >1000 | 3.21 | 83.83 |
| 19 | 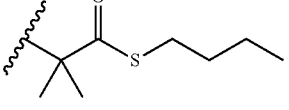 | >1000 | >1000 | >1000 | 3.16 | 83.83 |
| 34h | 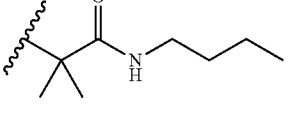 | 0.70 ± 0.03 | 5.0 ± 1.4 | 16.0 ± 2.4 | 5.02 | 63.60 |
| 34i | 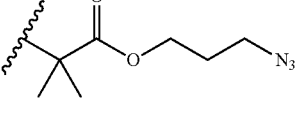 | 115 ± 21.6 | >1000 | >1000 | 4.05 | 77.70 |
| 9 | 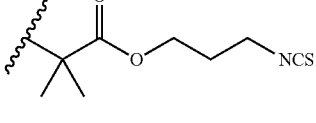 | 0.13 | 4 | 3.1 | 4.10 | 121 |
| 10 | | 7.9 | 20 | 22 | 3.9 | 85 |

TABLE 9-continued

Structures of Further Compounds of Formula (Ie) and Their Affinities For
CB1 and CB2 and Calculated (ChemDraw Software) cLogP and tPSA values:

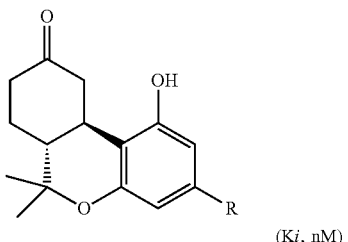

(Ie)

| No. | R | (Ki, nM) | | | cLogP | tPSA |
|---|---|---|---|---|---|---|
| | | rCB1 | mCB2 | hCB2 | | |
| 36 | —C(CH₃)₂C(O)O(CH₂)₄Br | .002 | 1.8 | — | 4.87 | 72.83 |
| 37 | —C(CH₃)₂C(O)O(CH₂)₄N₃ | 1.7 | 4.5 | 1.7 | 4.30 | 121.53 |
| 38 | —C(CH₃)₂C(O)O(CH₂)₄NCS | 4.9 | 21.4 | 5.2 | 4.33 | 85.19 |
| 39 | —C(CH₃)₂C(O)O(CH₂)₄ONO₂ | 0.2 | 2.2 | 2.6 | 4.73 | 133.87 |
| AM8137 | cyclopentyl-C(O)O-butyl | 0.4 ± 0.01 | 10.3 ± 1.1 | — | 4.98 | 72.8 |
| AM8139 | cyclopentyl-C(O)OH | >1000 | >1000 | >1000 | 3.55 | 83.83 |

Functional characterization of some of the disclosed compounds was performed by using the cyclic adenosine monophosphate (cAMP) assay. The functional potency of the compound in the cAMP assay is represented by the $EC_{50}$ value. The lower the $EC_{50}$ value, the higher the functional potency. A detailed description of the cyclic adenosine monophosphate (cAMP) assay is given in Nikas et al. *J. Med. Chem.* (2010) 6996, the content of which is incorporated herein by reference. Table 10 lists the $EC_{50}$ values of certain compounds of Formula (Je) in the cAMP assay.

TABLE 10

Structures of Compounds of Formula (Ie) and cAMP Data for CB1 and CB2 Cannabinoid Receptors

| No. | R | rCB1 EC$_{50}$ (nM) | rCB1 E$_{max}$ (%) | hCB2 EC$_{50}$ (nM) | hCB2 E$_{max}$ (%) |
|---|---|---|---|---|---|
| 34c | –C(CH$_3$)$_2$C(O)O-pentyl | 8.9 ± 2.3 | 94 | 8.4 ± 1.8 | 46 |
| AM 10843 | –C(CH$_3$)$_2$C(O)O-butyl | 1.0 ± 0.3 | 83 | 1.1 ± 2.3 | 80 |
| 8 AM10811 | –C(CH$_3$)$_2$C(O)O-(CH$_2$)$_3$CN | 0.4 ± 0.06 | 87 | 0.1 ± 0.03 | 77 |
| 18 AM10819 | –C(CH$_3$)$_2$CH$_2$C(O)O-propyl | 15.9 ± 3.6 | 90 | 0.2 ± 0.09 | 82 |
| 34h | –C(CH$_3$)$_2$C(O)S-butyl | 0.2 ± 0.04 | 89 | 83.4 ± 4.7 | 72 |
| 9 | –C(CH$_3$)$_2$C(O)O-(CH$_2$)$_3$N$_3$ | 0.2 | 52 | 2.1 | 87 |
| 10 | –C(CH$_3$)$_2$C(O)O-(CH$_2$)$_3$NCS | 13.8 | 38 | — | — |
| 34g | –C(CH$_3$)$_2$C(O)O-(CH$_2$)$_3$-morpholinyl | 4.2 | 78 | — | — |
| 34e | –C(CH$_3$)$_2$C(O)O-(S)-pentan-2-yl | 2.9 | 58 | — | — |
| 34f | –C(CH$_3$)$_2$C(O)O-(R)-pentan-2-yl | 94.5 | 71 | — | — |

Some of the disclosed compounds were tested in vivo using two well defined rodent assays for cannabinergic activity, the analgesia and the hypothermia assays. The analgesia assay (tail immersion test) determines the ability of a test compound to activate cannabinergic signaling, through modulation of cannabinoid receptors, and thereby reduce nociceptive pain. The hypothermia test determines the ability of a test compound to act as a central CB1 agonist and decrease the body temperature. A peripherally acting cannabinergic compound does not show effects in the hypothermia test. The details of both assays are described below.

Materials. All reagents and solvents were purchased from Aldrich Chemical Co., unless otherwise specified, and were used without further purification. All anhydrous reactions were performed under a static argon atmosphere in flame-dried glassware using scrupulously dry solvents. Flash column chromatography employed silica gel 60 (230-400 mesh). All compounds were demonstrated to be homogeneous by analytical TLC on pre-coated silica gel TLC plates (Merck, 60 $F_{245}$ on glass, layer thickness 250 μm), and chromatograms were visualized by phosphomolybdic acid staining. Melting points were determined on a micromelting point apparatus and are uncorrected. IR spectra were recorded on a Perkin Elmer Spectrum One FT-IR spectrometer. NMR spectra were recorded in $CDCl_3$, unless otherwise stated, on a Bruker Ultra Shield 400 WB plus ($^1H$ at 400 MHz, $^{13}C$ at 100 MHz) or on a Varian INOVA-500 ($^1H$ at 500 MHz, $^{13}C$ at 125 MHz) spectrometer, and chemical shifts are reported in units of δ relative to internal TMS standard. Multiplicities are indicated as br (broadened), s (singlet), d (doublet), t (triplet), q (quartet), m (multiplet) and coupling constants (J) are reported in hertz (Hz). Low and high-resolution mass spectra were performed in School of Chemical Sciences, University of Illinois at Urbana-Champaign. Mass spectral data are reported in the form of m/z (intensity relative to base=100). LC/MS analysis was performed by using a Waters MicroMass ZQ system [electrospray-ionization (ESI) with Waters-2525 binary gradient module coupled to a Photodiode Array Detector (Waters-2996) and ELS detector (Waters-2424) using a XTerra MS C18, 5 μm, 4.6 mm×50 mm column and acetonitrile/water.

Scheme 1: Synthesis of the chiral terpene synthon (References: Nikas, S. P. et al. *Tetrahedron*, 2007, 63, 8112-8123; Nikas, S. P. et al. *J. Med. Chem.*, 2010, 53, 6996-7010; Nikas, S. P. et al. *J. Med. Chem.* 2015, 58, 665-681; Kulkarni, S. et al. *J. Med. Chem.* 2016, 59, 6903-6919).

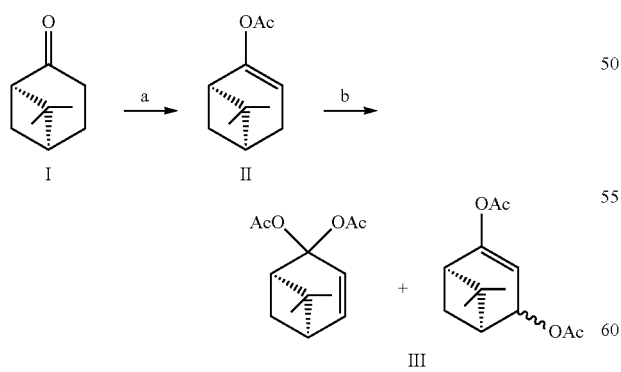

Reagents and conditions: (a) isopropenyl acetate, p-TSA, reflux, 95%; (b) benzene, Lead (IV) acetate, 80° C., 85%.

Scheme 2: Synthesis of C2' ester analogs. (References: Nikas, S. P. et al. *Tetrahedron*, 2007, 63, 8112-8123; Nikas, S.P. et al. *J. Med. Chem.*, 2010, 53, 6996-7010; Nikas, S. P. et al. *J. Med. Chem.* 2015, 58, 665-681; Kulkarni, S. et al. *J. Med. Chem.* 2016, 59, 6903-6919; Hua, T. et. al. *Nature*, 2017, 547, 468-471; Hua, T. et. al. *Cell*, 2020, 180, 1-11).

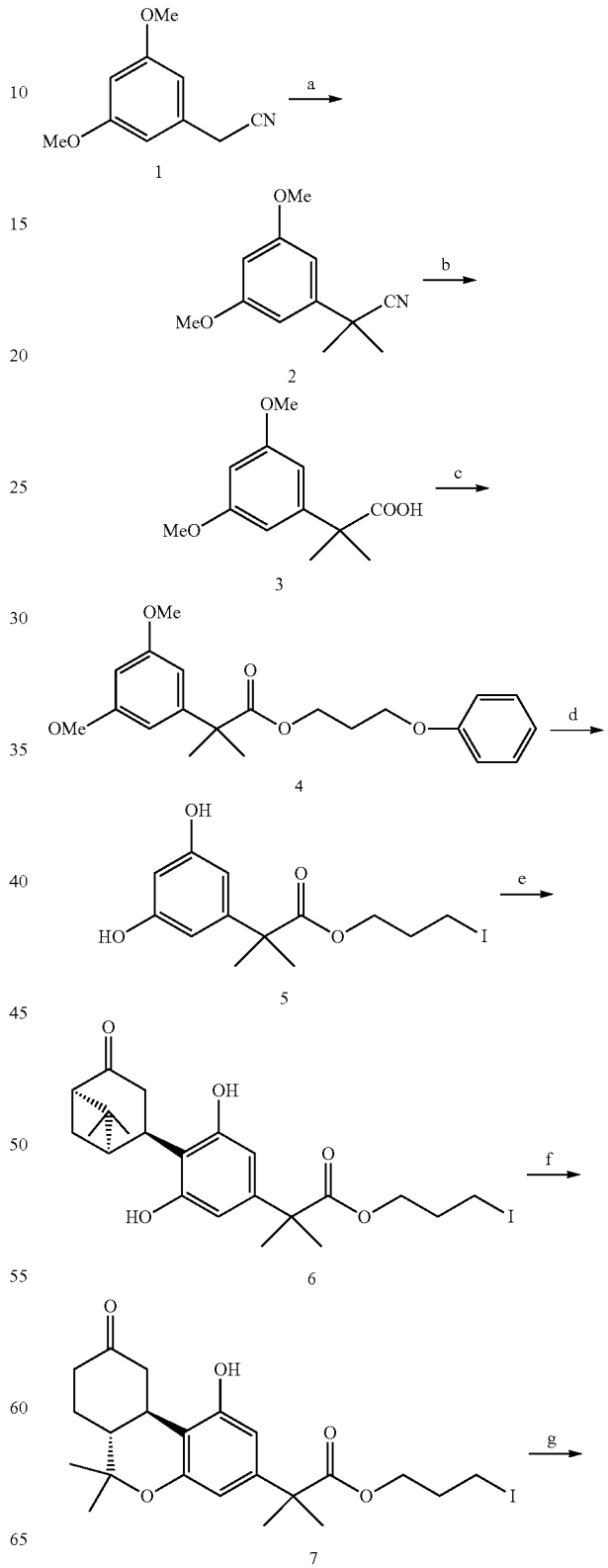

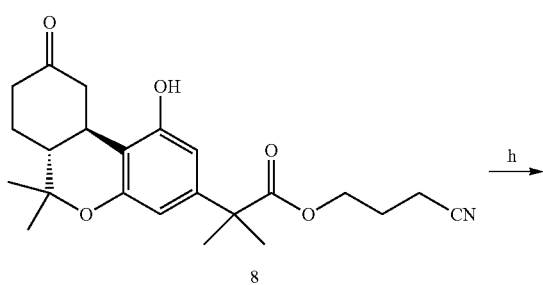
8
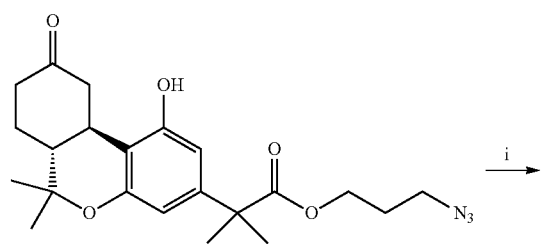
9
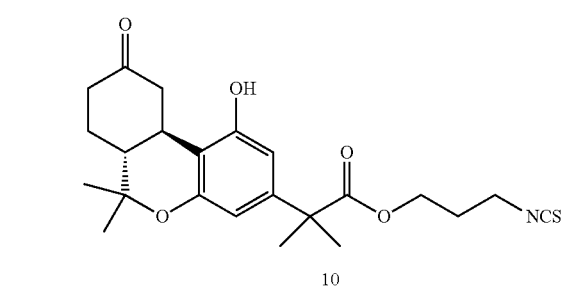
10
Reagents and contitions: (a) CH₃I, NaH, DMF, 0° C. to rt, 2 h, 97%; (b) NaOH, n-BuOH, H₂O, 50° C., reflux, 90%; (c) NaHCO₃, Phenoxy-propyl bromide, DMF, 165° C., MW, 12 min, 90%; (d) 9-I-9-BBN, Hexane, 0° C. to rt, 3.5 h, 85%; (e) III, p-TSA, CHCl₃, 0° C. to rt, 4 days, 22%; (f) TMSOTf, CH₂Cl₂, MeNO₂, 0° C. to rt, 7 h, 65%; (g) NaCN, DMSO, 20 °C - rt, 1 h, 50%; (h) n-Bu₄N⁺N₃⁻, CH₂Cl₂, CH₃NO₂, 70° C., 24 h, 75%; (i) PPh₃, CS₂, THF, rt, 12 h, 78%.
Scheme 3: Synthesis of C3' ester analogs
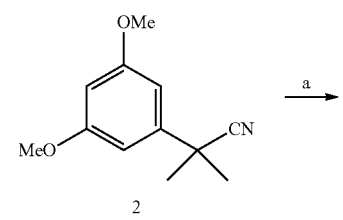
2
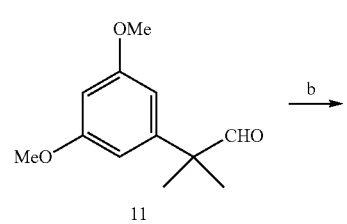
11
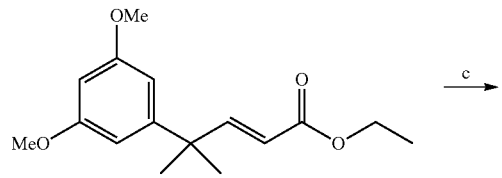
12
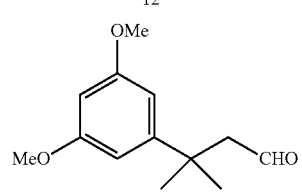
13
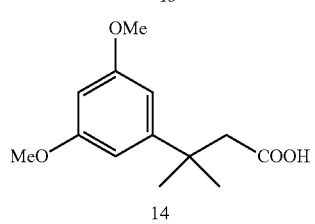
14
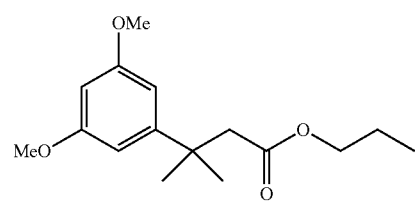
15
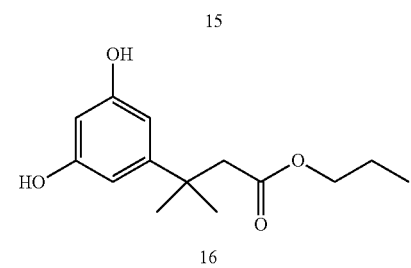
16
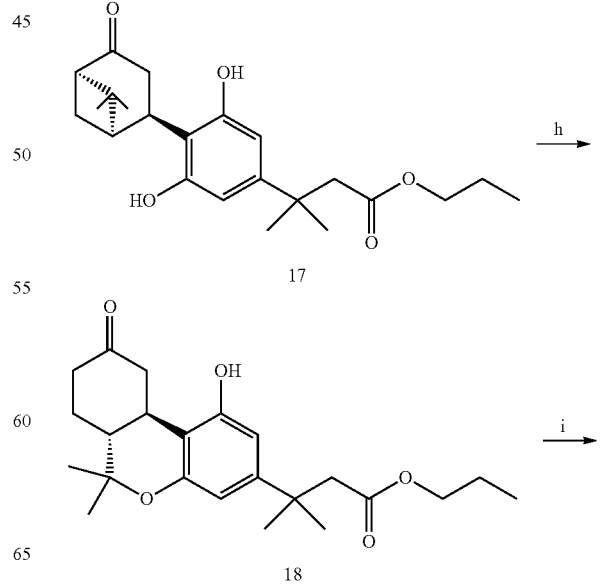
17
18

131

-continued

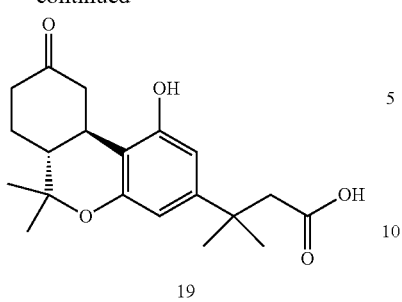

19

Reagents and conditions: (a) DIBAL—H, CH₂Cl₂, -78° C., 0.5 h, 82%; (b) Ph₃PClCH₂OEt, (Me₃Si)₂NK, THF, 0° C. to rt, 3 h, 80%; (c) HCl, Dioxane, rt, 2 h, 80%; (d) Oxone, DMF, rt, 90%; (e) NaHCO₃, 1-Bromopropane, DMF, 165° C., MW, 12 min, 90%; (f) 9-I-9-BBN, Hexane, 0° C. to rt, 3.5 h, 85%; (g) III, p-TSA, CHCl₃, 0° C. to rt, 2 days, 22%; (h) TMSOTf, CH₂Cl₂, MeNO₂, 0° C. to rt, 4 h, 65%; (i) LiOH, Dioxane/H₂O, 24 h, rt, 75%.

132

-continued

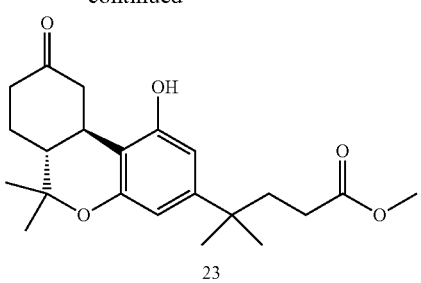

23

Reagents and conditions: (a) Mg, MeOH, 0° C. to rt, 3 h, 85%; (b) 9-I-9-BBN, Hexane, 0° C. to rt, 3.5 h, 70%; (c) III, p-TSA, CHCl₃, 0° C. to rt, 4 days, 25%; (d) TMSOTf, CH₂Cl₂, MeNO₂, 0° C. to rt, 4 h, 60%.

Scheme 5: Synthesis of the advanced intermediate aldehyde 30.

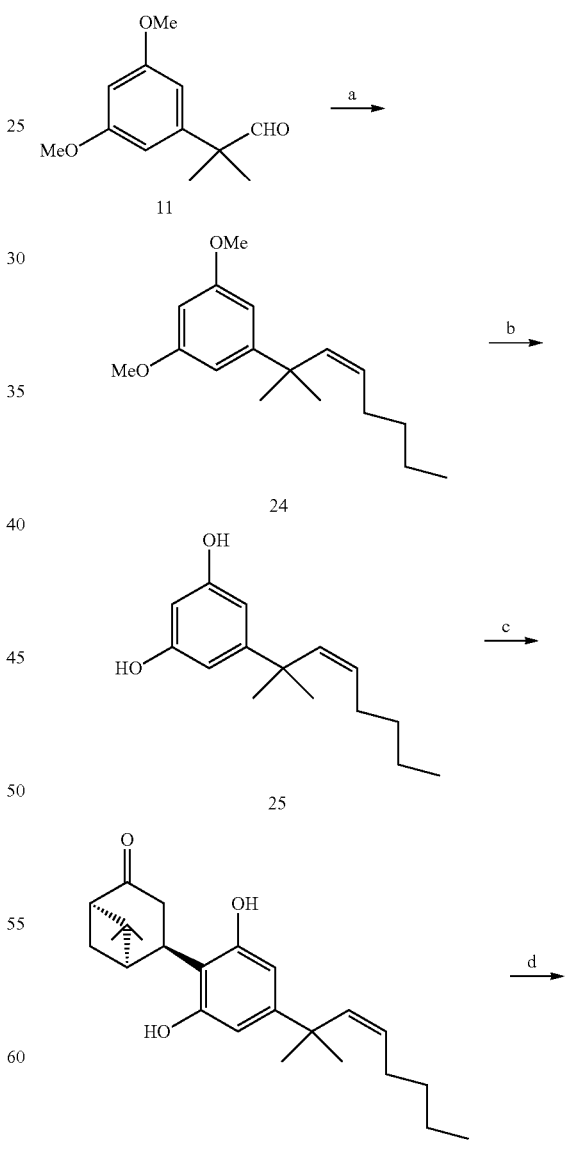

Scheme 4: Synthesis of C4′ ester analogs

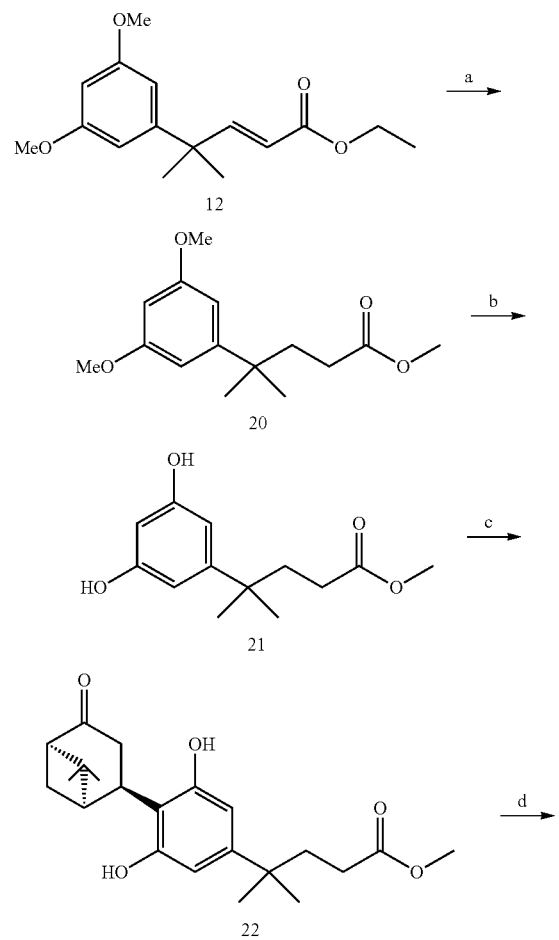

133
-continued

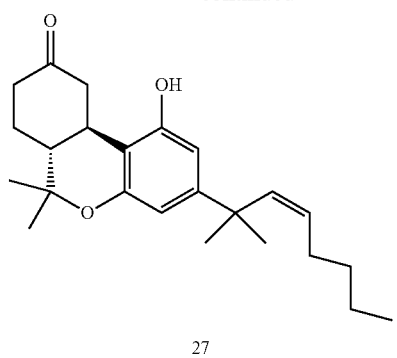

27

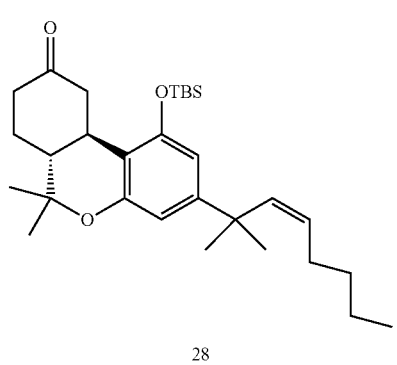

28

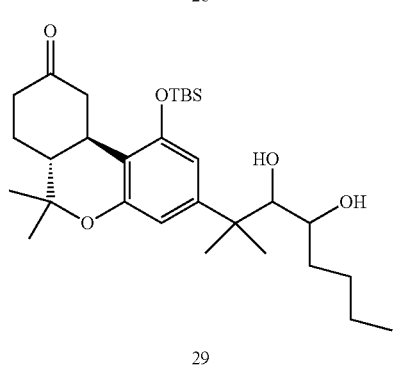

29

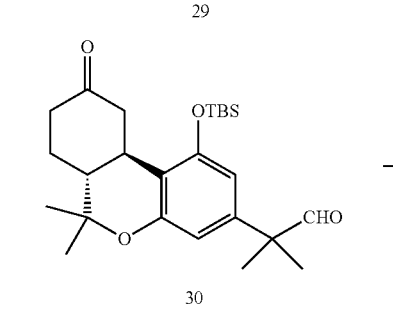

30

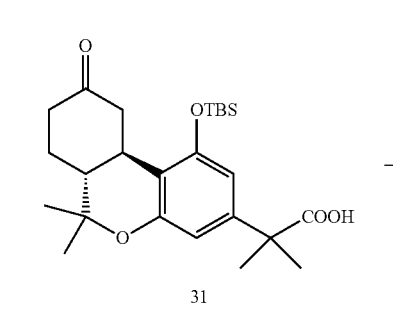

31

134
-continued

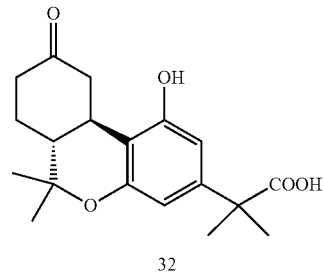

32

Reagent and conditions: (a) Br P+Ph3(CH2)4CH3, (Me3Si)2NK, THF, 0° C. to R.T, 2 h, 93%; (b) 9-I-BBN, Hexane, 0° C. to rt, 3.5 h, 85%; (c) III, p-TSA, CHCl3, 0° C. to rt, 4 days, 55%; (d) TMSOTf, CH2Cl2, MeNO2, 0° C. to rt, 7 h, 65%; (e) TBDMSCl, Imidazole, DMAP, DMF, rt, 12 h, 90%; (f) NMO, OsO4, 2,6-lutidine, Acetone, Water, rt, 3 h; (g) (Diacetoyiodo)benzene, rt, 2 h, 80% (2 steps); (h) NaClO2, NaH2PO4, 2-methyl-2-butene, t-BuOH, 0° C. to rt, 4 h, 80%; (i) TBAF, THF, -40° C., 30 min, 90%.

Scheme 6: Synthesis of functionalized side-chain analogs

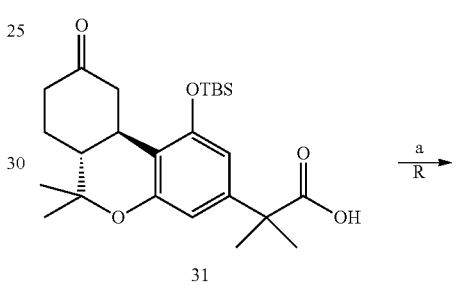

31

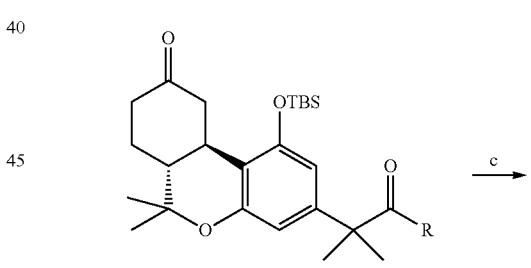

33 (a-i)

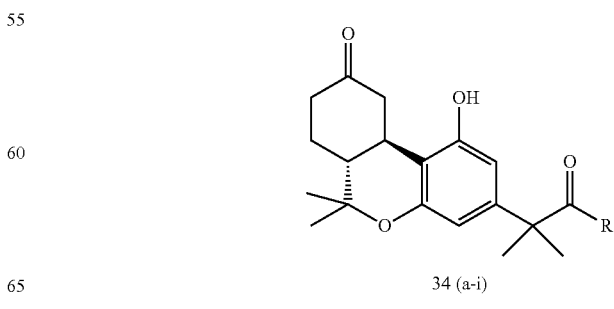

34 (a-i)

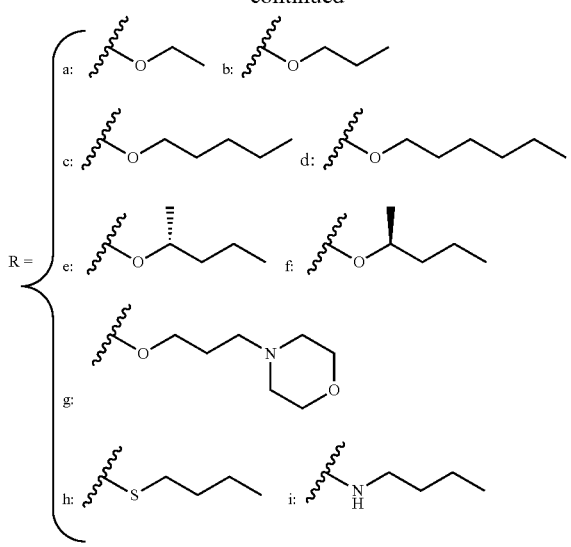

Reagents and conditions: (a) EDCI, DMAP, R—OH or R—SH, or R—NH₂, CH₂Cl₂, 0° C. to rt, 24 h, 65-75%; (b) TBAF, THF, -40° C., 30 min, 84-92%

Scheme 7: Synthesis of compounds carrying covalent groups (e.g.: NCS, N₃) or , mioeties with tight binding abilities (e.g.: ONO₂). (References: Hua, T. et. al. *Nature*, 2017, *547*, 468-471; Hua, T. et. al. *Cell*, 2020, 180, 1-11; Makriyannis, A. *J. Med. Chem.* 2014, 57, 3891-3911).

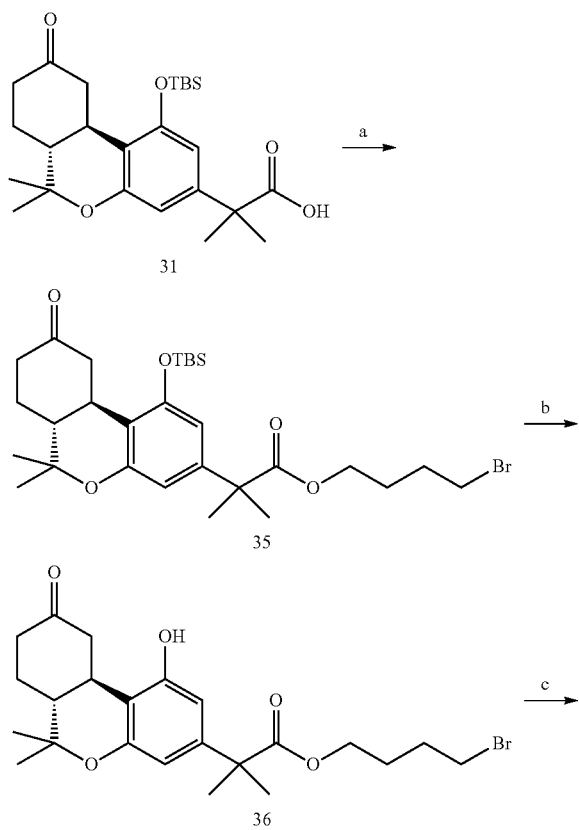

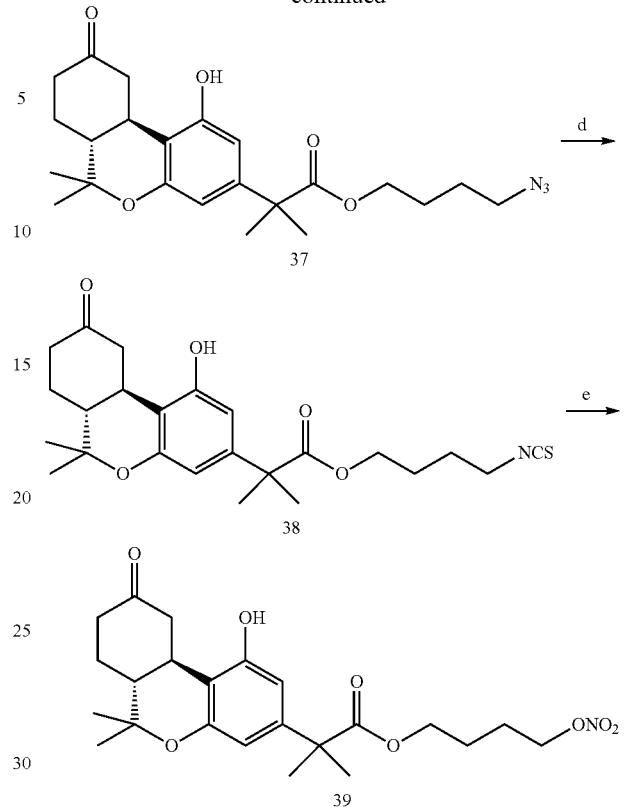

Reagents and conditions: (a) DMAP, EDCI, 4-bromo-1-butanol, CH₂Cl₂, 0° C.-rt, 24 h, 77%; (b) TBAF, THF, -50° C., 95%; (c) n-Bu₄N⁺N₃⁻, CH₂Cl₂, CH₃NO₂, 70° C., 24 h, 80%; (d) PPh₃, CS₂, THF, rt, 12 h, 71%; (e) Silver nitrate, CH₃CN, 70° C., 24 h, 75%.

2-(3,5-Dimethoxyphenyl)-2-methylpropanenitrile (2)

To a stirred suspension of sodium hydride (6.7 g, 169.0 mmol) in dry DMF (40 mL) at 0° C. under an argon atmosphere was added dropwise a solution of 3,5-dimethoxyphenyl)acetonitrile (10.0 g, 56.4 mmol) and iodomethane (10.5 mL, 169.0 mmol) in dry DMF (40 mL). The reaction temperature rose to 25° C. over a 15 min period and stirring was continued for 2 h. The reaction mixture was quenched with saturated aqueous NH4Cl solution and extracted with diethyl ether. The organic layer was separated, and the aqueous layer was extracted with diethyl ether. The combined organic layer was washed with water and brine, dried (MgSO₄), and concentrated in vacuo. Purification by flash column chromatography on silica gel (25% ethyl acetate in hexane) gave the title compound (11.0 g, 95% yield) as colorless oil. ¹H NMR (500 MHz, CDCl3) δ 6.61 (d, J=2.0 Hz, 2H, ArH), 6.40 (t, J=2.0 Hz, 1H, ArH), 3.81 (s, 6H, —OCH3), 1.71 (s, 6H, —C(CH3)2-); mass spectrum (ESI) m/z (relative intensity) 206 (M++H, 100).

2-(3,5-Dimethoxyphenyl)-2-methylpropanoic Acid (3)

A stirred mixture of (3,5-dimethoxyphenyl)-2-methylpropanenitrile (2, 5.7 g, 32.2 mmol) and NaOH (3.2 g, 80 mmol) in n-butanol/water (5 mL, 2:1 ratio) was refluxed for 4 h under argon. Volatiles were removed under reduced pressure, and the residue was acidified with 2 N HCl and diluted with diethyl ether. The organic layer was separated, and the aqueous layer was extracted with diethyl ether. The combined organic layer was washed with water and brine, dried (MgSO$_4$), and concentrated in vacuo. Purification by flash column chromatography on silica gel (30% ethyl acetate in hexane) gave 3 (5.61 g, 89% yield) as a white solid. $^1$H NMR (500 MHz, CDCl3) δ 6.54 (d, J=2.5 Hz, 2H, ArH), 6.37 (t, J=2.5 Hz, 1H, ArH), 3.79 (s, 6H, —OCH3), 1.57 (s, 6H, —C(CH3)2-); mass spectrum (ESI) m/z (relative intensity) 225 (M++H, 10), 190 (7), 179 (33), 149 (100).

3-Phenoxypropyl 2-(3,5-dimethoxyphenyl)-2-methylpropanoate (4)

The synthesis was carried out as described for 5 starting from 3 (1 g, 4.46 mmol) in anhydrous DMF (4.65 ml), 3-phenoxypropyl bromide (1.44 g, 6.70 mmol) and sodium bicarbonate (450 mg, 5.35 mmol) to give 4 as a colorless oil (1.4 g, 90% yield). $^1$H NMR (500 MHz, CDCl$_3$) δ 7.25 (tt, J=8.0 Hz, J=6.0 Hz, 2H, O-Ph), 6.92 (tt, J=7.5 Hz, J=6.0 Hz, 1H, O-Ph), 6.80 (dt, J=8.0 Hz, J=2 Hz, 2H, O-Ph), 6.47 (d, J=2.0 Hz, 2H, ArH), 6.31 (t, J=2.5 Hz, 1H, ArH), 4.25 (t, J=6.5 Hz, 2H, 4'-H), 3.84 (t, J=6.5 Hz, 2H, 6'-H), 3.73 (s, 6H, (OCH$_3$)$_2$), 2.03 (q, 2H, 5'-H), 1.54 (s, 6H, —C(CH$_3$)$_2$—). LC/MS analysis (Waters MicroMass ZQ system) showed purity 99.5% and retention time 4.0 min for the title compound.

3-Iodopropyl 2-(3,5-dihydroxyphenyl)-2-methylpropanoate (5)

To a solution of 17 (4.4 g, 12.30 mmol) in dry Hexane (245 mL) at 0° C. under an argon atmosphere was added 9-I-9-BBN (52 ml, 52 mmol). Following the addition, the reaction temperature was gradually raised to room temperature. Stirring was continued at that temperature until completion of the reaction (3 h). The reaction mixture was evaporated and then anhydrous Et$_2$O (50 ml) was added. Then ethanolamine (3.4 mg, 8.9 mmol) in anhydrous THF (20 ml) was added to the solution and stirred vigorously for 30 min. The white precipitate formed was filtered out and the filtrate was concentrated and purified. Purification by flash column chromatography (25% ethyl acetate-petroleum ether) afforded 3.8 g (85% yield) of the compound 5 as a colorless oil. $^1$H NMR (500 MHz, CDCl$_3$) δ 6.39 (d, J=2.0 Hz, 2H, ArH), 6.24 (t, J=2.5 Hz, 1H, ArH), 5.08 (s, 1H, OH), 4.14 (t, J=6.5 Hz, 2H, 4'-H), 3.05 (t, J=6.5 Hz, 2H, 6'-H), 2.05 (m, 2H, 5'-H), 1.52 (s, 6H, —C(CH$_3$)$_2$—). LC/MS analysis (Waters MicroMass ZQ system) showed purity 98.7% and retention time 4.2 min for the title compound.

3-Iodopropyl-2-(4-((1R,2R,5R)-6,6-dimethyl-4-oxo-bicyclo[3.1.1]heptan-2-yl)-3,5-dihydroxyphenyl)-2-methylpropanoate (6)

To a degassed solution of 5 (2.9 g, 7.96 mmol), diacetates III (6.6 g, ca. 80% pure by $^1$H NMR, 27.88 mmol) at 0° C., under an argon atmosphere, was added p-toluenesulfonic acid monohydrate (2.12 g, 11.15 mmol) in CHCl$_3$ (80 ml). The mixture was warmed to room temperature and stirred for 4 days to ensure complete formation of the product. The reaction mixture was diluted with diethyl ether and washed sequentially with water, saturated aqueous NaHCO$_3$, and brine. The organic phase was dried over MgSO$_4$, and the solvent was removed under reduced pressure. The residue was chromatographed on silica gel (43% diethyl ether in hexane) to give 900 mg (22% yield) of 6. $^1$H NMR (500 MHz, CDCl$_3$) δ 6.31 (s, 2H, ArH), 5.50 (s, 2H, OH), 4.14 (t, J=7.5 Hz, 1H, 4'-H), 3.95 (t, J=7.0 Hz, 1H, 4-H), 3.51 (dd, J=11.0 Hz, J=8.0 Hz, 1H, 3α-H), 3.05 (t, J=6.5 Hz, 2H, 6'-H), 2.64-2.57 (m, 2H, 3β-H, 1-H), 2.51 (m, 1H, 7α-H), 2.46 (d, J=10.5 Hz, 1H, 7β-H), 2.29 (t, J=4.5 Hz, 1H, 5-H), 2.06 (m, 2H, 5'-H), 1.50 (s, 6H, —C(CH$_3$)$_2$—), 1.36 (s, 3H, 6β-Me), 1.00 (s, 3H, 6α-Me). Mass spectrum (ESI) m/z (relative intensity) 501 (M$^+$+H, 100). Exact mass (ESI) calculated for C$_{22}$H$_{30}$O$_5$I (M$^+$+H), 501.1138; found 501.1139. LC/MS analysis (Waters MicroMass ZQ system) showed purity 98.5% and retention time 4.7 min for the title compound.

3-Iodopropyl-2-((6aR,10aR)-1-hydroxy-6,6-dimethyl-9-oxo-6a,7,8,9,10,10a-hexahydro-6H-benzo[c]chromen-3-yl)-2-methylpropanoate (7)

To a stirred solution of 6 (300 mg, 0.6 mmol), in anhydrous CH$_2$Cl$_2$/CH$_3$NO$_2$ (3:1 mixture, 12 mL) at 0° C., under an argon atmosphere was added trimethylsilyl trifluoromethanesulfonate (0.6 mL, 0.3 M solution in CH$_3$NO$_2$, 0.18 mmol). Stirring was continued for 3 h while the temperature was allowed to rise to 25° C. The reaction mixture was quenched using 1:1 solution of saturated NaHCO$_3$ and brine and extracted with diethyl ether. The organic layer was washed with brine, dried (MgSO$_4$), and concentrated under reduced pressure. Purification by flash column chromatography on silica gel (30% acetone in hexane) gave 200 mg (65% yield) of 7 as a white crystalline solid. $^1$H NMR (500 MHz, CDCl$_3$) δ 6.41 (d, J=2.0 Hz, 1H, Ar—H), 6.29 (d, J=2.0 Hz, 1H, Ar—H), 6.25 (s, 1H, OH), 4.12 (t, J=7.5 Hz, 1H, 4'-H), 3.96 (ddd, J=15.0 Hz, J=3.5 Hz, J=2.0 Hz, 1H, 10eq-H), 3.02 (t, J=7.0 Hz, 2H, 6'-H), 2.88 (td, J=11.5 Hz, J=4.0 Hz, 1H, 10a-H), 2.64-2.58 (m, 1H, 8eq-H), 2.50-2.41 (m, 1H, 8ax-H), 2.19-2.13 (m, 2H, 10ax-H, 7eq-H), 2.06 (m, 2H, 5'-H), 2.00-1.93 (td, J=11.5 Hz, J=4.0 Hz, 1H, 6a-H), 1.55-1.53 (m, 1H, 7ax-H), 1.51 (s, 6H, —C(CH$_3$)$_2$—), 1.48 (s, 3H, 6β-Me), 1.12 (s, 3H, 6α-Me). Mass spectrum (ESI) m/z (relative intensity) 501 (M$^+$+H, 100). Exact mass (ESI) calculated for C$_{22}$H$_{30}$O$_5$I (M$^+$+H), 501.1138; found 501.1141. LC/MS analysis (Waters MicroMass ZQ system) showed purity 99.2% and retention time 4.9 min for the title compound.

3-Cyanopropyl-2-((6aR,10aR)-1-hydroxy-6,6-dimethyl-9-oxo-6a,7,8,9,10,10a-hexahydro-6H-benzo[c]chromen-3-yl)-2-methylpropanoate (8)

To a stirred solution of 7 (27 mg, 0.054 mmol) in anhydrous DMSO (1.1 ml) at room temperature, sodium cyanide (13 mg, 0.27 mmol) was added under an argon atmosphere. The reaction mixture was stirred at the same temperature for 16 h. The reaction was quenched using H$_2$O and extracted using Et$_2$O. The organic layer was concentrated under vacuum and the residue was chromatographed on silica gel (35% ethyl acetate in hexane) to give 8 (11 mg, 52% yield). $^1$H NMR (500 MHz, CDCl$_3$) δ 6.22 (d, J=2.0 Hz, 1H, Ar—H), 6.31 (d, J=2.0 Hz, 1H, Ar—H), 6.19 (s, 1H, OH), 4.17 (t, J=7.5 Hz, 1H, 4'-H), 3.94 (ddd, J=15.0 Hz, J=3.5 Hz, J=2.0 Hz, 1H, 10eq-H), 2.88 (td, J=11.5 Hz, J=4.0 Hz, 1H, 10a-H), 2.64-2.58 (m, 1H, 8eq-H), 2.50-2.41 (m, 1H, 8ax-H), 2.24 (t, J=7.0 Hz, 2H, 6'-H), 2.19-2.13 (m, 2H, 10ax-H, 7eq-H), 2.00-1.90 (m, 3H, 5'-H, 6a-H), 1.55-1.53 (m, 1H, 7ax-H), 1.51 (d, J=1.5 Hz, 6H, —C(CH$_3$)$_2$—), 1.48 (s, 3H, 6β-Me), 1.12 (s, 3H, 6α-Me). Mass spectrum (ESI) m/z (relative intensity) 400 (M$^+$+H, 100). Exact mass (ESI) calculated for C$_{23}$H$_{30}$NO$_5$ (M$^+$+H), 400.2124; found 400.2117. LC/MS analysis (Waters MicroMass ZQ system) showed purity 98.6% and retention time 4.5 min for the title compound.

3-Azidopropyl-2-((6aR,10aR)-1-hydroxy-6,6-dimethyl-9-oxo-6a,7,8,9,10,10a-hexahydro-6H-benzo[c]chromen-3-yl)-2-methylpropanoate (9)

To a stirred solution of 7 (50 mg, 0.10 mmol) in anhydrous $CH_2Cl_2/CH_3NO_2$ (3:1 mixture, 2 mL) at 70° C., tetrabutylammonium azide (850 mg, 3.0 mmol) was added. The reaction was stirred at same temperature for 24 h. The reaction mixture was quenched by brine and extraction was done using $Et_2O$. The organic layer was concentrated under vacuum and the residue was chromatographed on silica gel (40% ethyl acetate in hexane) to give 9 (35 mg, 75% yield). $^1H$ NMR (500 MHz, $CDCl_3$) δ 6.56 (s, 1H, OH), 6.40 (d, J=2.0 Hz, 1H, Ar—H), 6.31 (d, J=2.0 Hz, 1H, Ar—H), 4.15 (t, J=7.5 Hz, 1H, 4'-H), 3.99 (ddd, J=15.0 Hz, J=3.5 Hz, J=2.0 Hz, 1H, 10eq-H), 3.20 (t, J=7.0 Hz, 1H, 6'-H), 2.88 (td, J=11.5 Hz, J=4.0 Hz, 1H, 10a-H), 2.64-2.58 (m, 1H, 8eq-H), 2.50-2.41 (m, 1H, 8ax-H), 2.20-2.12 (m, 2H, 10ax-H, 7eq-H), 2.00-1.92 (m, 1H, 6a-H), 1.84 (m, 2H, 5'-H), 1.56-1.52 (m, 1H, 7ax-H), 1.51 (d, J=1.5 Hz, 6H, —C(CH$_3$)$_2$—), 1.47 (s, 3H, 6β-Me), 1.12 (s, 3H, 6α-Me). Mass spectrum (ESI) m/z (relative intensity) 416 ($M^+$+H, 100). Exact mass (ESI) calculated for $C_{22}H_{30}N_3O_5$ ($M^+$+H), 416.2185; found 416.2179. LC/MS analysis (Waters MicroMass ZQ system) showed purity 99.5% and retention time 4.8 min for the title compound.

3-Isothiocyanatopropyl-2-((6aR,10aR)-1-hydroxy-6,6-dimethyl-9-oxo-6a,7,8,9,10,10a-hexahydro-6H-benzo[c]chromen-3-yl)-2-methylpropanoate (10)

To a stirred solution of 9 (20 mg, 0.05 mmol) in anhydrous THF (0.5 ml) at room temperature, triphenyl phosphine (63 mg, 0.12 mmol) and carbon disulfide (110 mg, 0.75 mmol) was added. The reaction was stirred continuously for 12 h. The reaction mixture was diluted with $Et_2O$ and then evaporated under vacuum. The crude was chromatographed on silica gel (35% ethyl acetate in hexane) to give 10 (14 mg, 78% yield) $^1H$ NMR (500 MHz, $CDCl_3$) δ 6.40 (d, J=2.0 Hz, 1H, Ar—H), 6.35 (s, 11H, OH), 6.29 (d, J=2.0 Hz, 1H, Ar—H), 4.17 (t, J=7.5 Hz, 1H, 4'-H), 3.98 (ddd, J=15.0 Hz, J=3.5 Hz, J=2.0 Hz, 1H, 10eq-H), 3.40 (t, J=7.0 Hz, 1H, 6'-H), 2.89 (td, J=11.5 Hz, J=4.0 Hz, 1H, 10a-H), 2.64-2.58 (m, 1H, 8eq-H), 2.51-2.42 (m, 1H, 8ax-H), 2.20-2.12 (m, 2H, 10ax-H, 7eq-H), 2.00-1.91 (m, 3H, 5'-H, 6a-H), 1.55-1.53 (m, 1H, 7ax-H), 1.51 (d, J=1.5 Hz, 6H, —C(CH$_3$)$_2$—), 1.48 (s, 3H, 6β-Me), 1.12 (s, 3H, 6α-Me). Mass spectrum (ESI) m/z (relative intensity) 432 ($M^+$+H, 100). Exact mass (ESI) calculated for $C_{23}H_{30}NO_5S$ ($M^+$+H), 432.1845; found 432.1838. LC/MS analysis (Waters MicroMass ZQ system) showed purity 99.2% and retention time 4.9 min for the title compound.

2-(3,5-Dimethoxyphenyl)-2-methylpropanal (11)

To a solution of 2 (4.0 g, 17.2 mmol), in dry $CH_2Cl_2$ (174 mL) at −78° C. under an argon atmosphere, was added diisobutylaluminum hydride (43.4 mL, 1 M solution in hexanes) over a period of 15 min. The reaction mixture was stirred at the same temperature for 1 h and then quenched by dropwise addition of potassium sodium tartrate (10% solution in water). The resulting mixture was warmed to room temperature, stirred vigorously for 40 min, and then diluted with EtOAc. The organic phase was separated and the aqueous phase extracted with EtOAc. The combined organic layer was washed with brine and dried over $MgSO_4$, and the solvent was evaporated under reduced pressure. The crude product was purified by flash column chromatography on silica gel using 15% diethyl ether-petroleum ether as eluent to give compound 11 as a white solid in 82% yield (3.5 g). $^1H$ NMR (500 MHz, $CDCl_3$) δ 9.46 (s, 1H), 6.40 (d, J=1.7 Hz, 2H, ArH), 6.38 (t, J=1.7 Hz, 1H, ArH), 3.79 (s, 6H), 1.71 (s, 6H, —C(CH$_3$)$_2$—). LC/MS analysis (Waters MicroMass ZQ system) showed purity 98.2% and retention time 4.4 min for the title compound.

Ethyl-4-(3,5-dimethoxyphenyl)-4-methylpent-2-enoate (12)

To a suspension of methoxymethyltriphenylphosphonium bromide (23.8 g, 57.7 mmol) in dry THF (193 mL) at 0° C., under an argon atmosphere, was added potassium bis(trimethylsilyl)amide (11.25 g, 56.56 mmol). The mixture was stirred for 15 min to ensure complete formation of the orange ylide. To the resulting slurry, at the same temperature, was added dropwise a solution of 11 (2.4 g, 11.54 mmol) in dry THF (17 mL). The reaction was stirred for 90 min and upon completion was quenched by the addition of saturated aqueous $NH_4Cl$. The organic layer was separated, and the aqueous phase was extracted with diethyl ether. The combined organic layer was washed with brine and dried over MgSO4, and the solvent was evaporated under reduced pressure. The residue was purified through a column of silica gel using 5% diethyl ether-petroleum ether as eluent to afford the compound 12 as a colorless liquid in 80% yield (2.2 g). $^1H$ NMR (500 MHz, $CDCl_3$) δ 7.09 (d, J=15.5 Hz, 1H, 2'-H), 6.44 (d, J=2.5 Hz, 2H, Ar—H), 6.33 (t, J=2.0 Hz, 2H, Ar—H), 5.81 (d, J=13 Hz, 1H, 3'-H), 4.18 (q, J=7 Hz, 2H, 6'-H), 3.78 (s, 3H, OMe), 1.43 (s, 6H, —C(CH$_3$)$_2$—), 1.28 (t, J=7 Hz, 3H, 7'-H). LC/MS analysis (Waters MicroMass ZQ system) showed purity 99.3% and retention time 4.9 min for the title compound.

3-(3,5-Dimethoxyphenyl)-3-methylbutanal (13)

To a stirred solution of 12 (1.1 g, 3.96 mmol) in dioxane (10 ml) was added 6.5 ml of 1 M HCl under an argon atmosphere. The reaction mixture was stirred vigorously at room temperature for 16 h. The reaction was quenched using $H_2O$ and extracted using $Et_2O$. The organic layer was concentrated under vacuum and then purified by flash column chromatography using (10% ethyl acetate in hexane) to give 13 (750 mg) as a colorless oil with 80% yield. $^1H$ NMR (500 MHz, $CDCl_3$) δ 9.50 (t, J=3.0 Hz, 1H, CHO), 6.52 (d, J=1.5 Hz, 2H, Ar—H), 6.33 (t, J=2.5 Hz, 1H, Ar—H), 3.79 (s, 6H, (OMe)$_2$), 2.63 (d, J=2.5 Hz, 2H, 2'-H), 1.42 (s, 6H, —C(CH$_3$)$_2$—). LC/MS analysis (Waters MicroMass ZQ system) showed purity 98.5% and retention time 4.4 min for the title compound.

3-(3,5-Dimethoxyphenyl)-3-methylbutanoic acid (14)

To a solution of 13 (300 mg, 1.35 mmol) in anhydrous DMF (13.5 ml) at room temperature under an argon atmosphere was added oxone (1.67 g, 2.70 mmol). The reaction was complete in 4 h. The reaction was quenched using $H_2O$ and extracted using $Et_2O$. The organic layer was concentrated under vacuum and then purified by flash column chromatography using (30% ethyl acetate in hexane) to give 14 (375 mg) as a colorless oil with 90% yield. $^1$H NMR (500 MHz, CDCl$_3$) δ 6.52 (d, J=1.5 Hz, 2H, Ar—H), 6.32 (t, J=2.5 Hz, 1H, Ar—H), 3.78 (s, 6H, (OMe)$_2$), 2.63 (s, 2H, 2'-H), 1.43 (s, 6H, —C(CH$_3$)$_2$—). LC/MS analysis (Waters MicroMass ZQ system) showed purity 99.5% and retention time 4.1 min for the title compound.

Propyl-3-(3,5-dimethoxyphenyl)-3-methylbutanoate (15)

To a stirred suspension of 14 (370 mg, 1.55 mmol) in anhydrous DMF (4 ml), bromopropane (287 mg, 2.33 mmol) and sodium bicarbonate (156 mg, 1.86 mmol) was added and heated at 165° C. for 12 min using microwave irradiation. The reaction mixture was cooled to room temperature and diluted with water and ethyl acetate. The organic layer was separated and the aqueous layer was extracted with ethyl acetate (3×5 mL). The combined organic layer was washed with water and brine, dried (MgSO$_4$) and concentrated under vacuo. The residue was chromatographed on silica gel to give 15 (330 mg, 90% yield) as a colorless oil. $^1$H NMR (500 MHz, CDCl$_3$) δ 6.52 (d, J=1.5 Hz, 2H, Ar—H), 6.31 (t, J=2.5 Hz, 1H, Ar—H), 3.91 (t, J=6.5 Hz, 2H, 5'-H), 3.78 (s, 6H, (OMe)$_2$), 2.59 (s, 2H, 2'-H), 1.52 (q, 2H, 6'H), 1.42 (s, 6H, —C(CH$_3$)$_2$—), 0.84 (t, J=7.0 Hz, 3H, 7'H). LC/MS analysis (Waters MicroMass ZQ system) showed purity 99.6% and retention time 4.9 min for the title compound.

Propyl-3-(3,5-dihydroxyphenyl)-3-methylbutanoate (16)

To a solution of 15 (280 mg, 1 mmol) in dry Hexane (20 mL) at 0° C. under an argon atmosphere was added 9-I-9-BBN (3.2 mL, 1 M solution in Hexane). Following the addition, the reaction temperature was gradually raised to room temperature. Stirring was continued at that temperature until completion of the reaction (3 h). The reaction mixture was evaporated and then anhydrous Et$_2$O (20 ml) was added. Then ethanolamine (213 mg, 3.5 mmol) in anhydrous THF (8 ml) was added to the solution and stirred vigorously for 30 min. The white precipitate formed was filtered out and the filtrate was concentrated and purified. Purification by flash column chromatography (25% ethyl acetate-petroleum ether) afforded 190 mg (85% yield) of the compound 16 as a colorless oil. $^1$H NMR (500 MHz, CDCl$_3$) δ 6.43 (d, J=1.5 Hz, 2H, Ar—H), 6.16 (t, J=2.0 Hz, 1H, Ar—H), 5.99 (s, 2H, OH), 3.91 (t, J=6.5 Hz, 2H, 5'-H), 2.59 (s, 2H, 2'-H), 1.52 (sextet, J=7.0 Hz, 2H, 6'-H), 1.38 (s, 6H, —C(CH$_3$)$_2$—), 0.84 (t, J=7.0 Hz, 3H, 7'H). LC/MS analysis (Waters MicroMass ZQ system) showed purity 99.8% and retention time 4.0 min for the title compound.

Propyl-3-(4-((1R,2R,5R)-6,6-dimethyl-4-oxobicyclo[3.1.1]heptan-2-yl)-3,5-dihydroxyphenyl)-3-methylbutanoate (17)

The synthesis was carried out as described for 6 starting from 16 (75 mg, 0.30 mmol), diacetates III (188 mg, ca. 80% pure by $^1$H NMR, 0.75 mmol) and p-toluenesulfonic acid monohydrate (80 mg, 0.42 mmol) in CHCl$_3$ (3 ml) and gave 28 mg (22% yield) of 17 as a white crystalline solid. $^1$H NMR (500 MHz, CDCl$_3$) δ 6.31 (s, 2H, ArH), 4.98 (s, 2H, OH), 3.94 (t, J=7.5 Hz, 1H, 4-H), 3.91 (t, J=7.0 Hz, 2H, 5'-H), 3.49 (dd, J=11.0 Hz, J=8.0 Hz, 1H, 3α-H), 2.60-2.55 (m, 2H, 3β-H, 1-H), 2.53 (s, 2H, 2'-H), 2.49 (m, 1H, 7α-H), 2.46 (d, J=10.0 Hz, 1H, 7β-H), 2.26 (t, J=4.5 Hz, 1H, 5-H), 1.51 (quintet, J=7.5 Hz, 2H, 6'-H), 1.37 (s, 6H, —C(CH$_3$)$_2$—), 1.36 (s, 3H, 6β-Me), 0.99 (s, 3H, 6α-Me), 0.83 (t, J=7.5 Hz, 3H, 7'H). Mass spectrum (ESI) m/z (relative intensity) 389 (M$^+$+H, 100). Exact mass (ESI) calculated for C$_{23}$H$_{33}$O$_5$ (M$^+$+H), 389.2328; found 389.2321. LC/MS analysis (Waters MicroMass ZQ system) showed purity 99.0% and retention time 4.6 min for the title compound.

Propyl-3-((6aR,10aR)-1-hydroxy-6,6-dimethyl-9-oxo-6a,7,8,9,10,10a-hexahydro-6H-benzo[c]chromen-3-yl)-3-methylbutanoate (18)

The synthesis was carried out as described for 7 starting from 17 (26 mg, 0.07 mmol), trimethylsilyl trifluoromethanesulfonate (0.07 mL, 0.3 M solution in CH$_3$NO$_2$, 0.02 mmol) in anhydrous CH$_2$Cl$_2$/CH$_3$NO$_2$ (3:1 mixture, 1.4 mL) gave 16 mg (65% yield) of 18 as a white crystalline solid. $^1$H NMR (500 MHz, CDCl$_3$) δ 6.42 (d, J=2.0 Hz, 1H, Ar—H), 6.32 (d, J=2.0 Hz, 1H, Ar—H), 6.03 (s, 1H, OH), 3.95 (ddd, J=15.0 Hz, J=3.5 Hz, J=2.0 Hz, 11H, 10eq-H), 3.91 (t, J=7.0 Hz, 2H, 5'-H), 2.87 (td, J=11.5 Hz, J=4.0 Hz, 1H, 10a-H), 2.63-2.57 (m, 1H, 8eq-H), 2.54 (s, 2H, 2'-H), 2.48-2.39 (m, 1H, 8ax-H), 2.19-2.08 (m, 2H, 10ax-H, 7eq-H), 1.98-1.91 (td, J=11.5 Hz, J=4.0 Hz, 1H, 6a-H), 1.55-1.48 (m, 3H, 7ax-H, 6'-H), 1.47 (s, 3H, 6β-Me), 1.38 (s, 6H, —C(CH$_3$)$_2$—), 1.11 (s, 3H, 6α-Me), 0.83 (t, J=7.5 Hz, 3H, 7'H). Mass spectrum (ESI) m/z (relative intensity) 389 (M$^+$+H, 100). Exact mass (ESI) calculated for C$_{23}$H$_{33}$O$_5$ (M$^+$+H), 389.2328; found 389.2322. LC/MS analysis (Waters MicroMass ZQ system) showed purity 99.5% and retention time 4.8 min for the title compound.

3-((6aR,10aR)-1-Hydroxy-6,6-dimethyl-9-oxo-6a,7,8,9,10,10a-hexahydro-6H-benzo[c]chromen-3-yl)-3-methylbutanoic acid (19)

To a stirred solution of 18 (20 mg, 0.05 mmol) in dioxane/H$_2$O (1:1 ratio, 3 mL) at room temperature, under an argon atmosphere, was added lithium hydroxide (12 mg, 0.5 mmol). Stirring was continued for 8 h and then the reaction mixture was quenched with 1N HCl and diluted with ethyl acetate. The organic layer was separated and the aqueous layer was extracted with ethyl acetate. The combined organic phase was washed with water and brine, dried (MgSO$_4$), and concentrated under vacuo. The crude product was chromatographed on silica gel (48% acetone in hexane) to give 19 (14 mg, 80% yield) as a white solid. $^1$H NMR (500 MHz, CDCl$_3$+CD$_3$OD) δ 6.40 (d, J=2.0 Hz, 1H, ArH), 6.33 (d, J=2.0 Hz, 1H, ArH), 6.30 (br s, 1H, OH), 4.00 (ddd, J=15.0, J=3.5 Hz, J=2.0 Hz, 1H, 10eq-H), 2.88 (m as td, J=12.5, J=3.5 Hz, 1H, 10a-H), 2.65-2.60 (m, 1H, 8eq-H), 2.56 (s, 1H, 2'-H), 2.52-2.42 (m, 1H, 8ax-H), 2.19-2.10 (m, 2H, 10ax-H, 7eq-H), 1.96 (m as td, J=12.2, J=3.0 Hz, 1H, 6a-H), 1.58-1.50 (m, 1H, 7ax-H), 1.47 (s, 3H, 6β-Me), 1.39 (s, 6H, —C(CH$_3$)$_2$—), 1.21 (s, 3H, 6α-Me). Mass spectrum (ESI) m/z (relative intensity) 347 (M$^+$+H, 100). Exact mass (ESI) calculated for C$_{20}$H$_{27}$O$_5$ (M$^+$+H), 347.1858; found 347.1851. LC/MS analysis (Waters MicroMass ZQ system) showed purity 98.7% and retention time 4.3 min for the title compound.

Methyl-4-(3,5-dimethoxyphenyl)-4-methylpentanoate (20)

To a stirred solution of 12 (480 mg, 2.16 mmol) in dry MeOH (22 ml) at 0° C., under an argon atmosphere was added Magnesium (800 mg, 32.4 mmol). Following the addition, the reaction temperature was gradually raised to room temperature. Stirring was continued at that temperature until completion of the reaction (15 h). The reaction mixture was first evaporated and then dissolved in $H_2O$ to dissolve the white precipitate. To this mixture, $Et_2O$ was added and stirred vigorously. 5% HCl was added drop wise to make a clear solution and then extraction was done using $Et_2O$. The organic layer was concentrated and the residue was chromatographed on silica gel (30% $Et_2O$ in hexane) to yield 20 with 85% yield (300 mg) as a colorless oil. $^1H$ NMR (500 MHz, $CDCl_3$) δ 6.47 (d, J=1.5 Hz, 2H, Ar—H), 6.30 (t, J=2.5 Hz, 1H, Ar—H), 3.79 (s, 6H, $(OMe)_2$), 3.60 (s, 3H, 6'-H), 2.10-2.05 (m, 2H, 3'-H), 1.96-1.91 (m, 2H, 2'H), 1.28 (s, 6H, —$C(CH_3)_2$—). LC/MS analysis (Waters MicroMass ZQ system) showed purity 98.4% and retention time 4.7 min for the title compound.

Methyl-4-(3,5-dihydroxyphenyl)-4-methylpentanoate (21)

The synthesis was carried out as described for 16 starting from 20 (250 mg, 0.90 mmol), 9-I-9-BBN (2.7 ml, 2.7 mmol) in anhydrous hexane (15 ml) and gave 170 mg (85% yield) of 21 as a colorless oil. IR (neat): 3339, 2958, 1710, 1595, 1439, 1239, 1161, 1026 cm. $^1H$ NMR (500 MHz, $CDCl_3$) δ 6.37 (d, J=2.0 Hz, 2H, Ar—H), 6.20 (t, J=2.0 Hz, 1H, Ar—H), 5.27 (s, 2H, OH), 3.61 (s, 3H, 6'-H), 2.12-2.06 (m, 2H, 3'-H), 1.94-1.88 (m, 2H, 2'H), 1.25 (s, 6H, —$C(CH_3)_2$—). $^{13}C$ NMR (100 MHz $CDCl_3$) δ 176.0 (—C(O)O—), 156.8 (ArC-1 and ArC-5), 151.4 (tertiary aromatic), 106.0 (ArC-2 and ArC-4), 100.7 (tertiary aromatic), 52.0 (—$OCH_3$—), 38.9, 37.5, 30.2, 28.9. LC/MS analysis (Waters MicroMass ZQ system) showed purity 99.0% and retention time 3.7 min for the title compound.

Methyl-4-(4-((1R,2R,5R)-6,6-dimethyl-4-oxobicyclo[3.1.1]heptan-2-yl)-3,5-dihydroxyphenyl)-4-methylpentanoate (22)

The synthesis was carried out as described for 6 starting from 21 (150 mg, 0.80 mmol), diacetates III (505 mg, ca. 80% pure by $^1H$ NMR, 1.28 mmol) and p-toluenesulfonic acid monohydrate (243 mg, 1.28 mmol) in $CHCl_3$ (8 ml) and gave 90 mg (25% yield) of 22 as a white crystalline solid. $^1H$ NMR (500 MHz, $CDCl_3$) δ 6.26 (s, 2H, ArH), 5.30 (s, 1H, OH), 3.95 (t, J=7.5 Hz, 1H, 4-H), 3.62 (s, 3H, 6'-H), 3.50 (dd, J=12.0 Hz, J=7.5 Hz, 1H, 3α-H), 2.64-2.57 (m, 2H, 3β-H, 1-H), 2.54-2.44 (m, 2H, 7α-H, 7β-H), 2.28 (t, J=4.5 Hz, 1H, 5-H), 2.12-2.07 (m, 2H, 3'-H), 1.91-1.85 (m, 2H, 2'H), 1.36 (s, 3H, 6β-Me), 1.22 (s, 6H, —$C(CH_3)_2$—), 1.00 (s, 3H, 6α-Me). Mass spectrum (ESI) m/z (relative intensity) 375 ($M^++H$, 100). Exact mass (ESI) calculated for $C_{22}H_{31}O_5$ ($M^++H$), 375.2171; found 375.2166. LC/MS analysis (Waters MicroMass ZQ system) showed purity 99.2% and retention time 4.5 min for the title compound.

Methyl-4-((6aR,10aR)-1-hydroxy-6,6-dimethyl-9-oxo-6a,7,8,9,10,10a-hexahydro-6H-benzo[c]chromen-3-yl)-4-methylpentanoate (23)

The synthesis was carried out as described for 7 starting from 22 (20 mg, 0.05), trimethylsilyl trifluoromethanesulfonate (0.06 mL, 0.3 M solution in $CH_3NO_2$, 0.016 mmol) in anhydrous $CH_2Cl_2/CH_3NO_2$ (3:1 mixture, 1 mL) and gave 12 mg (60% yield) of 23 as a white crystalline solid. $^1H$ NMR (500 MHz, $CDCl_3$) δ 6.36 (d, J=2.0 Hz, 1H, Ar—H), 6.28 (d, J=2.0 Hz, 1H, Ar—H), 6.25 (s, 1H, OH), 3.98 (ddd, J=15.0 Hz, J=3.5 Hz, J=2.0 Hz, 1H, 10eq-H), 3.61 (s, 3H, 6'-H), 2.88 (td, J=11.5 Hz, J=4.0 Hz, 1H, 10a-H), 2.64-2.58 (m, 1H, 8eq-H), 2.50-2.41 (m, 1H, 8ax-H), 2.19-2.06 (m, 4H, 3'-H, 10ax-H, 7eq-H), 1.99-1.92 (td, J=11.5 Hz, J=4.0 Hz, 1H, 6a-H), 1.91-1.85 (m, 2H, 2'H), 1.56-1.49 (m, 1H, 7ax-H), 1.47 (s, 3H, 6β-Me), 1.24 (s, 6H, —$C(CH_3)_2$—), 1.12 (s, 3H, 6α-Me). Mass spectrum (ESI) m/z (relative intensity) 375 ($M^++H$, 100). Exact mass (ESI) calculated for $C_{22}H_{31}O_5$ ($M^++H$), 375.2171; found 375.2166. LC/MS analysis (Waters MicroMass ZQ system) showed purity 99.5% and retention time 4.6 min for the title compound.

1,3-Dimethoxy-5-(2-methyldec-3-en-2-yl)benzene (24)

To a suspension of pentyltriphenylphosphonium bromide (15.0 g, 36.3 mmol) in dry THF (200 mL) at 0° C., under an argon atmosphere, was added potassium bis(trimethylsilyl)amide (7.01 g, 35.6 mmol). The mixture was stirred for 15 min to ensure complete formation of the orange (butylmethylene)triphenylphosphorane. To the resulting slurry, at the same temperature, was added dropwise a solution of 11 (1.7 g, 7.26 mmol) in dry THF (17 mL). The reaction was stirred for 90 min and upon completion was quenched by the addition of saturated aqueous $NH_4Cl$. The organic layer was separated, and the aqueous phase was extracted with diethyl ether. The combined organic layer was washed with brine and dried over MgSO4, and the solvent was evaporated under reduced pressure. The residue was purified through a short column of silica gel using 5% diethyl ether-petroleum ether as eluent to afford the compound 24 as a colorless liquid in 93% yield (2.0 g). $^1H$ NMR (500 MHz, $CDCl_3$) δ 6.55 (d, J=2.0 Hz, 2H, ArH), 6.28 (t, J=2.0 Hz, 1H, ArH), 5.60 (dt, J=11.5 Hz, J=2.0 Hz, 1H, 2'H), 5.28 (dt, J=11.5 Hz, J=7.5 Hz, 1H, 3'H), 3.78 (s, 6H, OMe), 1.65 (ddt, J=2.0 Hz, J=7.5 Hz, J=7.5 Hz, 2H, 4'H), 1.39 (s, 6H, —$C(CH_3)_2$—), 1.15-1.07 (m, 4H, 5'H, 6'H), 0.74 (t, J=7.5 Hz, 3H, 7'H). LC/MS analysis (Waters MicroMass ZQ system) showed purity 98.3% and retention time 5.6 min for the title compound.

5-(2-Methyldec-3-en-2-yl)benzene-1,3-diol (25)

To a solution of 24 (8 g, 30.5 mmol) in dry $CH_2Cl_2$ (305 mL) at 0° C. under an argon atmosphere was added 9-I-9-BBN (85 mL, 1 M solution in $CH_2Cl_2$). Following the addition, the reaction temperature was gradually raised to room temperature. Stirring was continued at that temperature until completion of the reaction (3 h). The reaction mixture was evaporated and then anhydrous $Et_2O$ (100 ml) was added. Then ethanolamine (8.4 g, 137.4 mmol) in anhydrous THF (45 ml) was added to the solution and stirred vigorously for 30 min. The white precipitate formed was filtered out and the filtrate was concentrated and purified. Purification by flash column chromatography (25% ethyl acetate-petroleum ether) afforded 6.5 g (85% yield) of the compound 25 as a slightly brown oil. $^1H$ NMR (500 MHz, $CDCl_3$) δ 6.44 (d, J=2.0 Hz, 2H, ArH), 6.16 (t, J=2.0 Hz, 1H, ArH), 5.58 (dt, J=11.5 Hz, 1H, 2'H), 5.27 (dt, J=11.5 Hz, J=7.5 Hz, 1H, 3'H), 4.73 (s, 1H, OH), 1.65 (ddt, J=2.0 Hz, J=7.5 Hz, J=7.5 Hz, 2H, 4'H), 1.36 (s, 6H, —$C(CH_3)_2$—), 1.16-1.09 (m, 4H, 5'H, 6'H), 0.76 (t, J=7.5 Hz, 3H, 7'H). LC/MS analysis (Waters MicroMass ZQ system) showed purity 99.6% and retention time 4.6 min for the title compound.

(1R,4R,5R)-4-(2,6-Dihydroxy-4-(2-methyloct-3-en-2-yl)phenyl)-6,6-dimethylbicyclo[3.1.1]heptan-2-one (26)

To a degassed solution of 25 (1.25 g, 4.81 mmol) and diacetates (2.14 g, ca. 80% pure by $^1$H NMR, 8.99 mmol) in CHCl$_3$ (48 mL) at 0° C., under an argon atmosphere, was added p-toluenesulfonic acid monohydrate (1.28 g, 6.73 mmol). The mixture was warmed to room temperature and stirred for 3 days to ensure complete formation of the product. The reaction mixture was diluted with diethyl ether and washed sequentially with water, saturated aqueous NaHCO$_3$, and brine. The organic phase was dried over MgSO$_4$, and the solvent removed under reduced pressure. The residue was chromatographed on silica gel (43% diethyl ether in hexane), and fractions containing almost pure product (TLC) were combined and evaporated. Further purification by recrystallization from CHCl$_3$ and hexane gave 26 as a white crystalline solid (1.01 g, 53% yield). $^1$H NMR (500 MHz, CDCl$_3$) δ 6.33 (s, 2H, ArH), 5.55 (dt, J=11.0 Hz, J=1.5 Hz, 1H, 2'-H), 5.27 (dt, J=11.5 Hz, J=7.0 Hz, 1H, 3'-H), 4.93 (s, 2H, OH), 3.95 (t, J=8.5 Hz, 1H, 4-H), 3.49 (dd, J=18.8 Hz, J=7.8 Hz, 1H, 3α-H), 2.62-2.55 (m, 2H, 3β-H, 1-H), 2.54-2.45 (m, 2H, 7α-H, 7β-H), 2.27 (t, J=5.5 Hz, 1H, 5-H), 1.70-1.63 (m, 2H, 4'-H), 1.58 (s, 3H, 6-Me), 1.36 (d, J=6.5 Hz, 6H, —C(CH$_3$)$_2$—), 1.17-1.06 (m, 4H, 5'-H, 6'-H), 1.00 (s, 3H, 6-Me), 0.74 (t, J=6.5 Hz, 3H, 7'-H). LC/MS analysis (Waters MicroMass ZQ system) showed purity 99.4% and retention time 5.1 min for the title compound.

(6aR,10aR)-1-Hydroxy-6,6-dimethyl-3-(2-methyloct-3-en-2-yl)-6,6a,7,8,10,10a-hexahydro-9H-benzo[c]chromen-9-one (27)

To a stirred solution of 26 (467 mg, 1.18 mmol) in anhydrous CH$_2$Cl$_2$/CH$_3$NO$_2$ (3:1 mixture, 24 mL) at 0° C., under an argon atmosphere was added trimethylsilyl trifluoromethanesulfonate (1.2 mL, 0.3 M solution in CH$_3$NO$_2$, 0.36 mmol). The reaction mixture was stirred at 0° C. for 1 h and then gradually brought to room temperature till the reaction was complete (3 h). The reaction mixture was quenched using 1:1 solution of sat. NaHCO$_3$ and Brine and extracted using Et$_2$O. The organic layer was concentrated and the residue was chromatographed on silica gel (30% acetone in hexane) to yield 27 as a white solid with 61% yield (284 mg). $^1$H NMR (500 MHz, CDCl$_3$) δ 6.45 (d, J=2.0 Hz, 1H, Ar—H), 6.35 (d, J=2.0 Hz, 1H, Ar—H), 6.10 (s, 1H, OH), 5.56 (dt, J=11.0 Hz, J=1.5 Hz, 1H, 2'H), 5.24 (dt, J=11.0 Hz, J=7.5 Hz, 1H, 3'H), 3.99 (ddd, J=15.0 Hz, J=3.5 Hz, J=2.0 Hz, 1H, 10eq-H), 2.88 (td, J=11.5 Hz, J=4.0 Hz, 1H, 10a-H), 2.65-2.58 (m, 1H, 8eq-H), 2.50-2.41 (m, 1H, 8ax-H), 2.20-2.10 (m, 2H, 10ax-H, 7eq-H), 2.00-1.92 (td, J=11.5 Hz, J=2.5 Hz, 1H, 6a-H), 1.69-1.63 (m, 2H, 4'H), 1.54-1.49 (m, 1H, 7ax-H), 1.47 (s, 3H, 6-Me), 1.35 (d, J=2.0 Hz, 6H, —C(CH$_3$)$_2$—), 1.14-1.05 (m, 7H, 5'H, 6'H, 6-Me, especially 1.11, s, 6-Me), 0.72 (t, J=7.0 Hz, 3H, 7'H). LC/MS analysis (Waters MicroMass ZQ system) showed purity 99.1% and retention time 5.4 min for the title compound.

(6aR,10aR)-1-((tert-Butyldimethylsilyl)oxy)-6,6-dimethyl-3-(2-methyloct-3-en-2-yl)-6,6a,7,8,10,10a-hexahydro-9H-benzo[c]chromen-9-one (28)

To a solution of 27 (1.1 g, 3.10 mmol) in anhydrous DMF (21 ml) under an argon atmosphere, imidazole (1 g, 15.54 mmol), DMAP (189 mg, 1.55 mmol) and TBDMSCl (2.28 g, 15.2 mmol) was added. The reaction mixture was stirred at room temperature for 12 h. The reaction mixture was quenched using brine and extracted using Et$_2$O. The organic layer was evaporated and the residue was chromatographed on silica gel (20% Et$_2$O in hexane) to afford 1.190 g of 28 as a colorless oil with 80% yield. $^1$H NMR (500 MHz, CDCl$_3$) δ 6.49 (d, J=2.0 Hz, 1H, Ar—H), 6.40 (d, J=1.5 Hz, 1H, Ar—H), 5.55 (dt, J=11.5 Hz, J=2.0 Hz, 1H, 2'H), 5.24 (dt, J=11.5 Hz, J=7.5 Hz, 1H, 3'H), 3.77 (ddd, J=15.0 Hz, J=3.5 Hz, J=2.0 Hz, 1H, 10eq-H), 2.71 (td, J=11.5 Hz, J=4.0 Hz, 1H, 10a-H), 2.60-2.52 (m, 1H, 8eq-H), 2.46-2.35 (m, 1H, 8ax-H), 2.18-2.05 (m, 2H, 10ax-H, 7eq-H), 1.99-1.90 (td, J=11.5 Hz, J=4.0 Hz, 1H, 6a-H), 1.68-1.62 (m, 2H, 4'H), 1.53-1.48 (m, 1H, 7ax-H), 1.46 (s, 3H, 6-Me), 1.35 (d, J=4.0 Hz, 6H, —C(CH$_3$)$_2$—), 1.14-1.06 (m, 7H, 5'H, 6'H, 6-Me, especially 1.08, s, 6-Me), 1.00 (s, 9H, Si(Me)$_2$CMe$_3$), 0.74 (t, J=7.5 Hz, 3H, 7'H), 0.23 (s, 3H, Si(Me)$_2$CMe$_3$), 0.14 (s, 3H, Si(Me)$_2$CMe$_3$). LC/MS analysis (Waters MicroMass ZQ system) showed purity 99.0% and retention time 6.9 min for the title compound.

2-((6aR,10aR)-1-((tert-Butyldimethylsilyl)oxy)-6,6-dimethyl-9-oxo-6a,7,8,9,10,10a-hexahydro-6H-benzo[c]chromen-3-yl)-2-methylpropanal (30)

To a stirred solution of 28 (1.14 g, 2.35 mmol) in Acetone:H$_2$O (10:1) (28 ml) under an argon atmosphere, NMO (504 mg, 4.70 mmol), 2,6-lutidine (413 mg, 3.52 mmol) and 0.0 (75 mg, 0.28 mmol) was added at room temperature. The reaction was complete in 4 h to form 1,2-diol 29 (Rf=0.05). This diol without isolation was treated with (diacetoxyiodo)benzene (1.14 g, 3.52 mmol) at room temperature for 30 min. The reaction was quenched using Na$_2$S$_2$O$_3$ and extraction was done using Et$_2$O. The organic layer was washed with saturated CuSO$_4$ and then concentrated. Purification by flash column chromatography (15% ethyl acetate in hexane) afforded 700 mg (80% yield) of 30 as a colorless oil. $^1$H NMR (500 MHz, CDCl$_3$) δ 9.43 (s, 1H, CHO), 6.42 (d, J=2.0 Hz, 1H, Ar—H), 6.23 (d, J=2.0 Hz, 11H, Ar—H), 3.75 (ddd, J=13.5 Hz, J=3.5 Hz, J=2.0 Hz, 1H, 10eq-H), 2.72 (td, J=11.5 Hz, J=4.0 Hz, 1H, 10a-H), 2.60-2.52 (m, 1H, 8eq-H), 2.46-2.36 (m, 1H, 8ax-H), 2.19-2.07 (m, 2H, 10ax-H, 7eq-H), 1.98-1.89 (td, J=11.5 Hz, J=4.0 Hz, 1H, 6a-H), 1.55-1.48 (m, 1H, 7ax-H), 1.47 (s, 3H, 6-Me), 1.38 (d, J=2.0 Hz, 6H, —C(CH$_3$)$_2$—), 1.10 (s, 3H, 6-Me), 0.99 (s, 9H, Si(Me)$_2$CMe$_3$), 0.24 (s, 3H, Si(Me)$_2$CMe$_3$), 0.16 (s, 3H, Si(Me)$_2$CMe$_3$). Mass spectrum (ESI) m/z (relative intensity) 431 (M$^+$+H, 100). Exact mass (ESI) calculated for C$_{25}$H$_{39}$O$_4$Si (M$^+$+H), 431.2618; found 431.2611. LC/MS analysis (Waters MicroMass ZQ system) showed purity 98.2% and retention time 5.2 min for the title compound.

2-((6aR,10aR)-1-((tert-Butyldimethylsilyl)oxy)-6,6-dimethyl-9-oxo 6a,7,8,9,10,10a-hexahydro-6H-benzo[c]chromen-3-yl)-2-methylpropanoic acid (31)

To a stirred solution of 30 (700 mg, 1.63 mmol) in t-BuOH (33 ml) and 2-methyl-2-propene (52 ml) under an argon atmosphere was added a solution of NaClO$_2$ (2.4 g, 21.16) and NaH$_2$PO$_4$ (2.14 g, 17.93 mmol) in 33 ml of H$_2$O. The reaction mixture was stirred at 0° C. for 45 min and then gradually brought to room temperature till the reaction was complete (2 h). The reaction mixture was quenched using Na$_2$SO$_3$ and extracted using Et$_2$O. The organic layer was quickly passed through a pad of silica equilibrated using 20% ethyl acetate in hexane. The organic layer was then concentrated under vacuum and then purified by flash column chromatography (20% ethyl acetate in hexane) to afford 550 mg (70% yield) of 31 as a white crystalline solid. $^1$H NMR (500 MHz, CDCl$_3$) δ 6.50 (d, J=2.0 Hz, 1H, Ar—H), 6.41 (d, J=2.0 Hz, 1H, Ar—H), 3.76 (ddd, J=15.0 Hz, J=3.5 Hz, J=2.0 Hz, 1H, 10eq-H), 2.72 (td, J=11.5 Hz, J=4.0 Hz, 1H, 10a-H), 2.60-2.39 (m, 1H, 8eq-H), 2.46-2.36 (m, 1H, 8ax-H), 2.18-2.06 (m, 2H, 10ax-H, 7eq-H), 1.97-1.88 (td, J=11.5 Hz, J=4.0 Hz, 1H, 6a-H), 1.54-1.47 (m, 7H, 7ax-H, —C(CH$_3$)$_2$—, especially, 1.52, d, J=2.0 Hz, —C(CH$_3$)$_2$—), 1.46 (s, 3H, 6-Me), 1.09 (s, 3H, 6-Me), 0.99 (s, 9H, Si(Me)$_2$CMe$_3$), 0.23 (s, 3H, Si(Me)$_2$CMe$_3$), 0.16 (s, 3H, Si(Me)$_2$CMe$_3$). Mass spectrum (ESI) m/z (relative intensity) 447 (M$^+$+H, 100). Exact mass (ESI) calculated for C$_{25}$H$_{39}$O$_4$Si (M++H), 447.2567; found 447.2556. LC/MS analysis (Waters MicroMass ZQ system) showed purity 99.5% and retention time 5.2 min for the title compound.

2-[(6aR,10aR)-6a,7,8,9,10,10a-Hexahydro-1-hydroxy-6,6-dimethyl-9-oxo-6H-benzo[c] chromen-3-yl]-2-methylpropanoic acid (32)

To a stirred solution of 31 (25 mg, 0.05 mmol) in dry THF at −50° C. under an argon atmosphere, tetra-butyl ammonium fluoride (0.1 ml, 0.1 mmol) was added. Stirring was continued for 30 min and then the reaction mixture was quenched with saturated solution of ammonium chloride and diluted with diethyl ether. The organic layer was separated and the aqueous layer was extracted with diethyl ether. The crude product was chromatographed on silica gel (20% ethyl acetate in hexane) to give 32 (232 mg, 90% yield) as a white solid. $^1$H NMR (500 MHz, CDCl$_3$+CD$_3$OD) δ 6.39 (d, J=1.5 Hz, 1H, ArH), 6.34 (d, J=1.5, 1H, ArH), 4.35 (br s, 1H, OH), 3.94 (ddd, J=15.0, J=3.5 Hz, J=2.0 Hz, 1H, 10eq-H), 2.86 (m as td, J=12.5, J=3.5 Hz, 1H, 10a-H), 2.62-2.58 (m, 1H, 8eq-H), 2.48-2.41 (m, 1H, 8ax-H), 2.19-2.04 (m, 2H, 10ax-H, 7eq-H), 1.94 (m as td, J=12.2, J=3.0 Hz, 1H, 6a-H), 1.57-1.48 (m, s and s, overlapping, 7H, 7ax-H, —C(CH$_3$)$_2$—, especially 1.50, s, and 1.49, s, —C(CH$_3$)$_2$—), 1.47 (s, 3H, 6-CH$_3$), 1.11 (s, 3H, 6-CH$_3$). Mass spectrum (ESI) m/z (relative intensity) 333 (M$^+$+H, 100). Exact mass (ESI) calculated for C$_{19}$H$_{25}$O$_5$ (M$^+$+H), 333.1702; found 333.1700. HPLC (4.6×250 mm, Supelco discovery column, acetonitrile/water) showed purity 97.5% and retention time 6.5 min for the title compound.

Ethyl 2-((6aR,10aR)-1-((tert-butyldimethylsilyl)oxy)-6,6-dimethyl-9-oxo-6a,7,8,9,10,10a-hexahydro-6H-benzo[c]chromen-3-yl)-2-methylpropanoate (33a)

To a solution of 31 (50 mg, 0.11 mmol) in dry CH$_2$Cl$_2$ (1 ml) at 0° C. under an argon atmosphere, DMAP (33 mg, 0.27 mmol) and EDCI (39 mg, 0.2 mmol) was added. The reaction was stirred for 20 min at 0° C. and then ethanol (8.5 mg, 0.11 mmol) was added. The mixture was warmed to room temperature and stirred for 24 h to ensure complete formation of the product. The reaction mixture was diluted with diethyl ether and washed sequentially with 5% HCl, saturated aqueous NaHCO$_3$, and brine. The organic phase was dried over MgSO$_4$, and the solvent was removed under reduced pressure. The crude product was chromatographed on silica gel (20% ethyl acetate in hexane) to give 33a (35 mg, 75% yield) as a colorless oil. $^1$H NMR (500 MHz, CDCl$_3$) δ 6.46 (d, J=1.5 Hz, 1H, Ar—H), 6.34 (br d, J=2.0 Hz, 1H, Ar—H), 4.16-4.06 (m 2H, 4'-H), 3.76 (ddd, J=15.0 Hz, J=3.5 Hz, J=2.0 Hz, 1H, 10eq-H), 2.71 (m as td, J=12.5 Hz, J=3.5 Hz, 1H, 10a-H), 2.60-2.52 (m, 1H, 8eq-H), 2.45-2.36 (m, 1H, 8ax-H), 2.18-2.06 (m, 2H, 10ax-H, 7eq-H), 1.93 (m as td, J=12.0 Hz, J=3.0 Hz, 1H, 6a-H), 1.52-1.48 (m, 7H, 7ax-H, —C(CH$_3$)$_2$—, especially, 1.50, s, 3H, —C(CH$_3$)$_2$— and 1.48, s, 3H, —C(CH$_3$)$_2$—), 1.46 (s, 3H, 6-Me), 1.19 (t, J=7.0 Hz, 3H, 5'-H), 1.09 (s, 3H, 6-Me), 0.99 (s, 9H, Si(Me)$_2$CMe), 0.23 (s, 3H, Si(Me)$_2$CMe$_3$), 0.15 (s, 3H, Si(Me)$_2$CMe$_3$). LC/MS analysis (Waters MicroMass ZQ system) showed purity 99.3% and retention time 5.9 min for the title compound.

Propyl 2-((6aR,10aR)-1-((tert-butyldimethylsilyl)oxy)-6,6-dimethyl-9-oxo-6a,7,8,9,10,10a-hexahydro-6H-benzo[c]chromen-3-yl)-2-methylpropanoate (33b)

The synthesis was carried out as described for 33a using 31 (40 mg, 0.10 mmol), DMAP (73 mg, 0.60 mmol), EDCI (76 mg, 0.40 mmol), propanol (25 mg, 0.40 mmol) and dry CH$_2$Cl$_2$ (1 ml). Purification by flash column chromatography on silica gel (20% ethyl acetate in hexane) gave title compound 33b (35 mg, 80% yield) as a colorless oil. $^1$H NMR (500 MHz, CDCl$_3$) δ 6.47 (d, J=2.0 Hz, 1H, Ar—H), 6.35 (d, J=1.5 Hz, 1H, Ar—H), 4.06-3.94 (m, 2H, 4'-H), 3.75 (ddd, J=15.0 Hz, J=3.5 Hz, J=2.0 Hz, 1H, 10eq-H), 2.71 (m as td, J=12.5 Hz, J=3.5 Hz, 1H, 10a-H), 2.60-2.52 (m, 1H, 8eq-H), 2.45-2.36 (m, 1H, 8ax-H), 2.18-2.04 (m, 2H, 10ax-H, 7eq-H), 1.93 (m as td, J=12.0 Hz, J=3.0 Hz, 1H, 6a-H), 1.62-1.57 (m, 3H, 7ax-H, 5'-H), 1.50 (s, 3H, —C(CH$_3$)$_2$—), 1.49 (s, 3H, —C(CH$_3$)$_2$—), 1.46 (s, 3H, 6-Me), 1.08 (s, 3H, 6-Me), 0.99 (s, 9H, Si(Me)$_2$CMe), 0.83 (t, J=7.0 Hz, 3H, 6'-H), 0.23 (s, 3H, Si(Me)$_2$CMe$_3$), 0.15 (s, 3H, Si(Me)$_2$CMe$_3$). LC/MS analysis (Waters MicroMass ZQ system) showed purity 98.2% and retention time 6.0 min for the title compound.

Pentyl 2-((6aR,10aR)-1-((tert-butyldimethylsilyl)oxy)-6,6-dimethyl-9-oxo-6a,7,8,9,10,10a-hexahydro-6H-benzo[c]chromen-3-yl)-2-methylpropanoate (33c)

The reaction was carried out as described for 33a using 31 (70 mg, 0.18 mmol), DMAP (132 mg, 1.07 mmol), EDCI (138 mg, 0.72 mmol), pentanol (70 mg, 0.40 mmol) and dry CH$_2$Cl$_2$ (1.4 ml). Purification by flash column chromatography on silica gel (20% ethyl acetate in hexane) gave title compound 33c (48 mg, 60% yield) as a colorless oil. $^1$H NMR (500 MHz, CDCl$_3$) δ 6.46 (d, J=1.5 Hz, 1H, Ar—H), 6.35 (d, J=2.0 Hz, 1H, Ar—H), 4.09-3.97 (m, 2H, 4'-H), 3.76 (ddd, J=15.0 Hz, J=3.5 Hz, J=2.0 Hz, 1H, 10eq-H), 2.71 (m as td, J=12.5 Hz, J=3.5 Hz, 11H, 10a-H), 2.60-2.52 (m, 1H, 8eq-H), 2.45-2.36 (m, 1H, 8ax-H), 2.18-2.04 (m, 2H, 10ax-H, 7eq-H), 1.93 (m as td, J=12.0 Hz, J=3.0 Hz, 1H, 6a-H), 1.60-1.52 (m, 3H, 7ax-H, 5'-H), 1.50 (s, 3H, —C(CH$_3$)$_2$—), 1.49 (s, 3H, —C(CH$_3$)$_2$—), 1.46 (s, 3H, 6-Me), 1.31-1.20 (m, 4H, 6'-H, 7'-H), 1.09 (s, 3H, 6-Me), 0.99 (s, 9H, Si(Me)$_2$CMe), 0.85 (t, J=7.5 Hz, 3H, 8'-H), 0.23 (s, 3H, Si(Me)$_2$CMe$_3$), 0.15 (s, 3H, Si(Me)$_2$CMe$_3$). LC/MS analysis (Waters MicroMass ZQ system) showed purity 98.3% and retention time 6.3 min for the title compound.

Hexyl 2-((6aR,10aR)-1-((tert-butyldimethylsilyl)oxy)-6,6-dimethyl-9-oxo-6a,7,8,9,10,10a-hexahydro-6H-benzo[c]chromen-3-yl)-2-methylpropanoate (33d)

The synthesis was carried out as described for 33a using 31 (70 mg, 0.18 mmol), DMAP (132 mg, 1.07 mmol), EDCI (138 mg, 0.72 mmol), pentanol (81 mg, 0.40 mmol) and dry CH$_2$Cl$_2$ (1.4 ml). Purification by flash column chromatography on silica gel (20% ethyl acetate in hexane) gave title compound 33d (44 mg, 58% yield) as a colorless oil. 1H NMR (500 MHz, CDCl$_3$) δ 6.46 (d, J=2.0 Hz, 11H, Ar—H), 6.34 (d, J=2.0 Hz, 11H, Ar—H), 4.09-3.98 (m, 2H, 4'-H), 3.76 (ddd, J=15.0 Hz, J=3.5 Hz, J=2.0 Hz, 1H, 10eq-H), 2.71 (m as td, J=12.5 Hz, J=3.5 Hz, 11H, 10a-H), 2.60-2.52 (m, 1H, 8eq-H), 2.46-2.36 (m, 1H, 8ax-H), 2.18-2.04 (m, 2H, 10ax-H, 7eq-H), 1.93 (m as td, J=12.0 Hz, J=3.0 Hz, 1H, 6a-H), 1.57-1.51 (m, 3H, 7ax-H, 5'-H), 1.50 (s, 3H, —C(CH$_3$)$_2$—), 1.49 (s, 3H, —C(CH$_3$)$_2$—), 1.46 (s, 3H, 6-Me), 1.30-1.20 (m, 6H, 6'-H, 7'-H, 8'-H), 1.09 (s, 3H, 6-Me), 0.99 (s, 9H, Si(Me)$_2$CMe), 0.87 (t, J=7.0 Hz, 3H, 9'-H), 0.23 (s, 3H, Si(Me)$_2$CMe$_3$), 0.15 (s, 3H, Si(Me)$_2$CMe$_3$). LC/MS analysis (Waters MicroMass ZQ system) showed purity 98.1% and retention time 6.5 min for the title compound.

(S)-Pentan-2-yl 2-((6aR,10aR)-1-((tert-butyldimethylsilyl)oxy)-6,6-dimethyl-9-oxo-6a,7,8,9,10,10a-hexahydro-6H-benzo[c]chromen-3-yl)-2-methylpropanoate (33e)

The synthesis was carried out as described for 33a using 31 (50 mg, 0.11 mmol), DMAP (88 mg, 0.72 mmol), EDCI (92 mg, 0.48 mmol), (S)-2-pentanol (43 mg, 0.48 mmol) and dry CH$_2$Cl$_2$ (1 ml). Purification by flash column chromatography on silica gel (20% ethyl acetate in hexane) gave title compound 33e (40 mg, 70% yield) as a colorless oil. 1H NMR (500 MHz, CDCl$_3$) δ 6.48 (d, J=1.5 Hz, 11H, Ar—H), 6.37 (d, J=2.0 Hz, 11H, Ar—H), 4.88-4.79 (m, 1H, 4'-H), 3.75 (ddd, J=15.0 Hz, J=3.5 Hz, J=2.0 Hz, 11H, 10eq-H), 2.71 (m as td, J=12.5 Hz, J=3.5 Hz, 1H, 10a-H), 2.60-2.52 (m, 1H, 8eq-H), 2.46-2.36 (m, 1H, 8ax-H), 2.18-2.04 (m, 2H, 10ax-H, 7eq-H), 1.93 (m as td, J=12.0 Hz, J=3.0 Hz, 1H, 6a-H), 1.54-1.44 (m, 12H, 7ax-H, 5'-H, —C(CH$_3$)$_2$—, 6-Me, especially, 1.49, s, 3H, —C(CH$_3$)$_2$— and 1.48, s, 3H, —C(CH$_3$)$_2$— and 1.46, s, 3H, 6-Me), 1.22-1.160 (m, 2H, 6'-H), 1.10 (s, 3H, —O—CH—CH$_3$), 1.07 (s, 3H, 6-Me), 0.99 (s, 9H, Si(Me)$_2$CMe$_3$), 0.81 (t, J=7.0 Hz, 3H, 6'-H), 0.23 (s, 3H, Si(Me)$_2$CMe$_3$), 0.15 (s, 3H, Si(Me)$_2$CMe$_3$). LC/MS analysis (Waters MicroMass ZQ system) showed purity 99.3% and retention time 6.3 min for the title compound.

(R)-Pentan-2-yl 2-((6aR,10aR)-1-((tert-butyldimethylsilyl)oxy)-6,6-dimethyl-9-oxo-6a,7,8,9,10,10a-hexahydro-6H-benzo[c]chromen-3-yl)-2-methylpropanoate (33f)

The synthesis was carried out as described for 33a using 31 (50 mg, 0.11 mmol), DMAP (88 mg, 0.72 mmol), EDCI (92 mg, 0.48 mmol), (R)-2-pentanol (43 mg, 0.48 mmol) and dry CH$_2$Cl$_2$ (1 ml). Purification by flash column chromatography on silica gel (20% ethyl acetate in hexane) gave title compound 33f (40 mg, 70% yield) as a colorless oil. LC/MS analysis (Waters MicroMass ZQ system) showed purity 99.0% and retention time 6.3 min for the title compound.

3-Morpholinopropyl 2-((6aR,10aR)-1-((tert-butyldimethylsilyl)oxy)-6,6-dimethyl-9-oxo-6a,7,8,9,10,10a-hexahydro-6H-benzo[c] chromen-3-yl)-2-methylpropanoate (33g)

The synthesis was carried out as described for 33a using 31 (100 mg, 0.11 mmol), DMAP (164 mg, 1.35 mmol), EDCI (168 mg, 0.88 mmol), 4-(3-Hydroxypropyl)morpholine (128 mg, 0.88 mmol) and dry CH$_2$Cl$_2$ (2 ml). Purification by flash column chromatography on silica gel (20% ethyl acetate in hexane) gave title compound 33g (90 mg, 70% yield) as a colorless oil. $^1$H NMR (500 MHz, CDCl$_3$) δ 6.45 (d, J=1.5 Hz, 1H, Ar—H), 6.33 (d, J=2.0 Hz, 1H, Ar—H), 4.20-4.06 (m, 11H, 4'-H), 3.74 (ddd, J=15.0 Hz, J=3.5 Hz, J=2.0 Hz, 11H, 10eq-H), 3.67 (t, J=5.0 Hz, 4H, morpholine —CH$_2$—O—CH$_2$—), 2.71 (m as td, J=12.5 Hz, J=3.5 Hz, 1H, 10a-H), 2.61-2.52 (m, 1H, 8eq-H), 2.46-2.32 (m, 5H, 8ax-H, morpholine —CH$_2$—N—CH$_2$), 2.28 (t, J=7.5 Hz, 2H, 6'-H), 2.16-2.02 (m, 2H, 10ax-H, 7eq-H), 1.93 (m as td, J=12.0 Hz, J=3.0 Hz, 11H, 6a-H), 1.75 (p, J=7.5 Hz, 2H, 5'-H) 1.54-1.44 (m, 10H, 7ax-H, —C(CH$_3$)$_2$—, 6-Me, especially, 1.50, s, 3H, —C(CH$_3$)$_2$— and 1.49, s, 3H, —C(CH$_3$)$_2$— and 1.46, s, 3H, 6-Me), 1.09 (s, 3H, 6-Me), 0.99 (s, 9H, Si(Me)$_2$CMe), 0.23 (s, 3H, Si(Me)$_2$CMe$_3$), 0.16 (s, 3H, Si(Me)$_2$CMe$_3$). LC/MS analysis (Waters MicroMass ZQ system) showed purity 98.3% and retention time 6.7 min for the title compound.

S-Butyl 2-((6aR,10aR)-1-((tert-butyldimethylsilyl)oxy)-6,6-dimethyl-9-oxo-6a,7,8,9,10,10a-hexahydro-6H-benzo[c]chromen-3-yl)-2-methylpropanethioate (33 h)

The synthesis was carried out as described for 33a using 31 (80 mg, 0.18 mmol), DMAP (132 mg, 1.07 mmol), EDCI (138 mg, 0.72 mmol), butanethiol (72 mg, 0.40 mmol) and dry CH$_2$Cl$_2$ (1.6 ml). Purification by flash column chromatography on silica gel (20% ethyl acetate in hexane) gave title compound 33h (75 mg, 80% yield) as a colorless oil. $^1$H NMR (500 MHz, CDCl$_3$) δ 6.49 (d, J=1.5 Hz, 1H, Ar—H), 6.34 (d, J=2.0 Hz, 1H, Ar—H), 3.76 (ddd, J=15.0 Hz, J=3.5 Hz, J=2.0 Hz, 1H, 10eq-H), 2.79 (t, J=7.5 Hz, 2H, 4'-H), 2.72 (m as td, J=12.5 Hz, J=3.5 Hz, 1H, 10a-H), 2.60-2.52 (m, 1H, 8eq-H), 2.46-2.36 (m, 1H, 8ax-H), 2.18-2.04 (m, 2H, 10ax-H, 7eq-H), 1.94 (m as td, J=12.0 Hz, J=3.0 Hz, 1H, 6a-H), 1.54-1.45 (m, 12H, 7ax-H, 5'-H, —C(CH$_3$)$_2$—, 6-Me, especially, 1.53, s, 3H, —C(CH$_3$)$_2$— and 1.52, s, 3H, —C(CH$_3$)$_2$— and 1.46, s, 3H, 6-Me), 1.33 (sextet, J=7.5 Hz, 2H, 6'-H), 1.10 (s, 3H, 6-Me), 0.99 (s, 9H, Si(Me)$_2$CMe), 0.88 (t, J=7.0 Hz, 3H, 7'-H), 0.23 (s, 3H, Si(Me)$_2$CMe$_3$), 0.15 (s, 3H, Si(Me)$_2$CMe$_3$). LC/MS analysis (Waters Micro-Mass ZQ system) showed purity 98.7% and retention time 6.4 min for the title compound.

N-Butyl-2-((6aR,10aR)-1-((tert-butyldimethylsilyl)oxy)-6,6-dimethyl-9-oxo-6a,7,8,9,10,10a-hexahydro-6H-benzo[c]chromen-3-yl)-2-methylpropanamide (33i)

To a stirred solution of 31 (54 mg, 0.12 mmol) in dry THF (1 ml), CDI (77 mg, 0.48 mmol) was added. The reaction was stirred at room temperature for 2 h followed by addition of butylamine (44 mg, 0.60 mmol) and the reaction continued for additional 4 h. Upon completion, the reaction mixture was diluted using ethyl acetate and quenched using 5% HCl. The organic phase was dried over MgSO$_4$, and the solvent was removed under reduced pressure. The crude product was chromatographed on silica gel (30% ethyl acetate in hexane) to give 33i (45 mg, 75% yield) as a colorless oil. $^1$H NMR (500 MHz, CDCl$_3$) δ 6.50 (d, J=2.0 Hz, 1H, Ar—H), 6.34 (d, J=1.5 Hz, 1H, Ar—H), 3.76 (ddd, J=15.0 Hz, J=3.5 Hz, J=2.0 Hz, 1H, 10eq-H), 3.19 (sextet, J=7.0 Hz, 1H, 4'-H), 3.10 (sextet, J=7.0 Hz, 1H, 4'-H), 2.73 (m as td, J=12.5 Hz, J=3.5 Hz, 1H, 10a-H), 2.61-2.54 (m, 1H, 8eq-H), 2.47-2.37 (m, 1H, 8ax-H), 2.20-2.05 (m, 2H, 10ax-H, 7eq-H), 1.94 (m as td, J=12.0 Hz, J=3.0 Hz, 1H, 6a-H), 1.54-1.50 (m, 1H, 7ax-H), 1.49 (s, 6H, —C(CH$_3$)$_2$—), 1.48 (s, 3H, 6-Me), 1.40-1.31 (m, 2H, 5'-H), 1.21 (sextet, J=7.5 Hz, 2H, 6'-H), 1.11 (s, 3H, 6-Me), 0.99 (s, 9H, Si(Me)$_2$CMe), 0.85 (t, J=7.5 Hz, 3H, 7-H), 0.23 (s, 3H, Si(Me)$_2$CMe$_3$), 0.16 (s, 3H, Si(Me)$_2$CMe$_3$). LC/MS analysis (Waters MicroMass ZQ system) showed purity 99.2% and retention time 5.6 min for the title compound.

Ethyl 2-((6aR,10aR)-1-hydroxy-6,6-dimethyl-9-oxo-6a,7,8,9,10,10a-hexahydro-6H-benzo[c]chromen-3-yl)-2-methylpropanoate (34a)

The synthesis was carried out as described for 32 using 33a (40 mg, 0.08 mmol), tetrabutylammonium fluoride (0.13 ml, 0.13 mmol) and dry THF (2 ml). Purification by flash column chromatography on silica gel (30% ethyl acetate in hexane) gave title compound 34a (25 mg, 84% yield) as a white solid. $^1$H NMR (500 MHz, CDCl$_3$) δ 6.41 (d, J=2.0 Hz, 1H, Ar—H), 6.29 (d, J=2.0 Hz, 1H, Ar—H), 4.06 (q, J=7.5 Hz, 2H, 4'-H), 3.94 (ddd, J=15.0 Hz, J=3.5 Hz, J=2.0 Hz, 1H, 10eq-H), 2.87 (m as td, J=12.5 Hz, J=4.0 Hz, 1H, 10a-H), 2.64-2.57 (m, 1H, 8eq-H), 2.49-2.39 (m, 1H, 8ax-H), 2.20-2.09 (m, 2H, 10ax-H, 7eq-H), 1.95 (m as td, J=12.0 Hz, J=3.0 Hz, 1H, 6a-H), 1.53-1.46 (m, 10H, 7ax-H, —C(CH$_3$)$_2$—, 6-Me, especially, 1.49, s, —C(CH$_3$)$_2$— and 1.47, s, 6-Me), 1.20 (t, J=7.0 Hz, 3H, 5'-H), 1.12 (s, 3H, 6-Me). Mass spectrum (ESI) m/z (relative intensity) 361 (M$^+$+H, 100). Exact mass (ESI) calculated for C$_{21}$H$_{29}$O$_5$ (M$^+$+H), 361.2015; found 361.2005. LC/MS analysis (Waters MicroMass ZQ system) showed purity 98.8% and retention time 4.6 min for the title compound.

Propyl 2-((6aR,10aR)-1-hydroxy-6,6-dimethyl-9-oxo-6a,7,8,9,10,10a-hexahydro-6H-benzo[c]chromen-3-yl)-2-methylpropanoate (34b)

The synthesis was carried out as described for 32 using 33b (25 mg, 0.06 mmol), tetrabutylammonium fluoride (0.10 ml, 0.10 mmol) and dry THF (1.5 ml). Purification by flash column chromatography on silica gel (30% ethyl acetate in hexane) gave title compound 34b (15 mg, 82% yield) as a white solid. $^1$H NMR (500 MHz, CDCl$_3$) δ 6.69 (s, 1H, OH), 6.41 (d, J=1.5 Hz, 1H, Ar—H), 6.33 (d, J=2.0 Hz, 1H, Ar—H), 4.05-3.97 (m, 3H, 10eq-H, 4'-H), 2.87 (m as td, J=12.5 Hz, J=4.0 Hz, 1H, 10a-H), 2.65-2.58 (m, 1H, 8eq-H), 2.50-2.40 (m, 1H, 8ax-H), 2.20-2.09 (m, 2H, 10ax-H, 7eq-H), 1.95 (m as td, J=12.0 Hz, J=3.0 Hz, 1H, 6a-H), 1.70-1.56 (m, 3H, 7ax-H, 5'-H), 1.50 (s, 6H, —C(CH$_3$)$_2$—), 1.47 (s, 3H, 6-Me), 1.16 (s, 3H, 6-Me), 0.84 (t, J=7.0 Hz, 3H, 6'-H). Mass spectrum (ESI) m/z (relative intensity) 375 (M$^+$+H, 100). Exact mass (ESI) calculated for C$_{22}$H$_{31}$O$_5$ (M$^+$+H), 375.2171; found 375.2162. LC/MS analysis (Waters MicroMass ZQ system) showed purity 99.0% and retention time 4.8 min for the title compound.

Pentyl 2-((6aR,10aR)-1-hydroxy-6,6-dimethyl-9-oxo-6a,7,8,9,10,10a-hexahydro-6H-benzo[c]chromen-3-yl)-2-methylpropanoate (34c)

The synthesis was carried out as described for 32 using 33c (30 mg, 0.06 mmol), tetrabutylammonium fluoride (0.10 ml, 0.10 mmol) and dry THE (1.5 ml). Purification by flash column chromatography on silica gel (30% ethyl acetate in hexane) gave title compound 34c (15 mg, 90% yield) as a white solid. $^1$H NMR (500 MHz, CDCl$_3$) δ 6.99 (s, 11H, OH), 6.40 (d, J=1.5 Hz, 1H, Ar—H), 6.34 (d, J=1.5 Hz, 1H, Ar—H), 4.09-3.99 (m, 3H, 10eq-H, 4'-H), 2.88 (m as td, J=12.5 Hz, J=4.0 Hz, 1H, 10a-H), 2.65-2.57 (m, 1H, 8eq-H), 2.51-2.41 (m, 1H, 8ax-H), 2.20-2.09 (m, 211, 10ax-H, 7eq-H), 1.95 (m as td, J=12.0 Hz, J=3.0 Hz, 1H, 6a-H), 1.61-1.51 (m, 3H, 7ax-H, 5'-H), 1.50 (s, 6H, —C(CH$_3$)$_2$—), 1.47 (s, 3H, 6-Me), 1.30-1.19 (m, 4H, 6'-H, 7'-H), 1.12 (s, 3H, 6-Me), 0.85 (t, J=7.0 Hz, 3H, 8'-H). Mass spectrum (ESI) m/z (relative intensity) 403 (M$^+$+H, 100). Exact mass (ESI) calculated for C$_{24}$H$_{35}$O$_5$ (M$^+$+H), 403.2484; found 402.2476. LC/MS analysis (Waters MicroMass ZQ system) showed purity 99.5% and retention time 5.1 min for the title compound.

Hexyl 2-((6aR,10aR)-1-hydroxy-6,6-dimethyl-9-oxo-6a,7,8,9,10,10a-hexahydro-6H-benzo[c]chromen-3-yl)-2-methylpropanoate (34d)

The synthesis was carried out as described for 32 using 33d (32 mg, 0.06 mmol), tetrabutylammonium fluoride (0.10 ml, 0.10 mmol) and dry THF (1.5 ml). Purification by flash column chromatography on silica gel (30% ethyl acetate in hexane) gave title compound 34d (20 mg, 90% yield) as a white solid. $^1$H NMR (500 MHz, CDCl$_3$) δ 6.39 (d, J=1.5 Hz, 1H, Ar—H), 6.35 (d, J=2.0 Hz, 11H, Ar—H), 4.08-4.00 (m, 3H, 10eq-H, 4'-H), 2.88 (m as td, J=12.5 Hz, J=4.0 Hz, 1H, 10a-H), 2.67-2.58 (m, 1H, 8eq-H), 2.51-2.40 (m, 1H, 8ax-H), 2.22-2.09 (m, 2H, 10ax-H, 7eq-H), 1.95 (m as td, J=12.0 Hz, J=3.0 Hz, 1H, 6a-H), 1.60-1.52 (m, 3H, 7ax-H, 5'-H), 1.50 (s, 6H, —C(CH$_3$)$_2$—), 1.47 (s, 3H, 6-Me), 1.32-1.18 (m, 6H, 6'-H, 7'-H, 8'-H), 1.11 (s, 3H, 6-Me), 0.85 (t, J=7.5 Hz, 3H, 9'-H). Mass spectrum (ESI) m/z (relative intensity) 417 (M$^+$+H, 100). Exact mass (ESI) calculated for C$_{25}$H$_{37}$O$_5$ (M$^+$+H), 417.2641; found 417.2634. LC/MS analysis (Waters MicroMass ZQ system) showed purity 99.1% and retention time 5.2 min for the title compound.

(S)-pentan-2-yl 2-((6aR,10aR)-1-hydroxy-6,6-dimethyl-9-oxo-6a,7,8,9,10,10a-hexahydro-6H-benzo[c]chromen-3-yl)-2-methylpropanoate (34e)

The synthesis was carried out as described for 32 using 33e (30 mg, 0.06 mmol), tetrabutylammonium fluoride (0.10 ml, 0.10 mmol) and dry THE (1.4 ml). Purification by flash column chromatography on silica gel (30% ethyl acetate in hexane) gave title compound 34e (20 mg, 86% yield) as a white solid. $^1$H NMR (500 MHz, CDCl$_3$) δ 7.24 (s, 1H, OH), 6.41 (d, J=2.0 Hz, 1H, Ar—H), 6.35 (d, J=2.0 Hz, 11H, Ar—H), 4.91-4.83 (m, 3H, 4'-H), 4.04 (ddd, J=15.0 Hz, J=3.5 Hz, J=2.0 Hz, 11H, 10eq-H), 2.88 (m as td, J=12.5 Hz, J=4.0 Hz, 11H, 10a-H), 2.65-2.57 (m, 1H, 8eq-H), 2.48-2.40 (m, 11H, 8ax-H), 2.20-2.11 (m, 2H, 10ax-H, 7eq-H), 1.95 (m as td, J=12.0 Hz, J=3.0 Hz, 11H, 6a-H), 1.55-1.45 (m, 9H, 7ax-H, 5'-H, 6-Me, —C(CH$_3$)$_2$—, especially 1.49, s, —C(CH$_3$)$_2$— and 1.46, s, 6-Me), 1.42-1.34 (m, 1H, 6'-H), 1.26-1.09 (m, 7H, 6'-H, —O—CH—CH$_3$, especially 1.13, s, —O—CH—CH$_3$, and 1.11, s, 6-Me), 0.81 (t, J=7.5 Hz, 3H, 7'-H). Mass spectrum (ESI) m/z (relative intensity) 403 (M$^+$+H, 100). Exact mass (ESI) calculated for C$_{24}$H$_{35}$O$_5$ (M$^+$+H), 403.2484; found 403.2470. LC/MS analysis (Waters MicroMass ZQ system) showed purity 99.5% and retention time 5.0 min for the title compound.

(R)-Pentan-2-yl 2-((6aR,10aR)-1-hydroxy-6,6-dimethyl-9-oxo-6a,7,8,9,10,10a-hexahydro-6H-benzo[c]chromen-3-yl)-2-methylpropanoate (34f)

The synthesis was carried out as described for 32 using 33f (30 mg, 0.06 mmol), tetrabutylammonium fluoride (0.10 ml, 0.10 mmol) and dry THF (1.4 ml). Purification by flash column chromatography on silica gel (30% ethyl acetate in hexane) gave title compound 34f (20 mg, 86% yield) as a white solid. LC/MS analysis (Waters MicroMass ZQ system) showed purity 99.0% and retention time 5.0 min for the title compound.

3-Morpholinopropyl 2-((6aR,10aR)-1-hydroxy-6,6-dimethyl-9-oxo-6a,7,8,9,10,10a-hexahydro-6H-benzo[c]chromen-3-yl)-2-methylpropanoate (34g)

The synthesis was carried out as described for 32 using 33g (45 mg, 0.08 mmol), tetrabutylammonium fluoride (0.11 ml, 0.11 mmol) and dry THF (1.5 ml). Purification by flash column chromatography on silica gel (30% ethyl acetate in hexane) gave title compound 34g (32 mg, 90% yield) as a white solid. $^1$H NMR (500 MHz, CDCl$_3$) δ 6.40 (d, J=1.5 Hz, 1H, Ar—H), 6.24 (d, J=2.0 Hz, 1H, Ar—H), 4.17 (t, J=6.0 Hz, 2H, 4'-H), 3.90 (ddd, J=15.0 Hz, J=3.5 Hz, J=2.0 Hz, 1H, 10eq-H), 3.71 (t, J=5.0 Hz, 4H, morpholine —CH$_2$—O—CH$_2$—), 2.86 (m as td, J=12.5 Hz, J=3.5 Hz, 1H, 10a-H), 2.62-2.56 (m, 1H, 8eq-H), 2.49-2.34 (m, 7H, 8ax-H, 6'-H, morpholine —CH$_2$—N—CH$_2$), 2.18-2.08 (m, 2H, 10ax-H, 7eq-H), 1.93 (m as td, J=12.0 Hz, J=3.0 Hz, 1H, 6a-H), 1.78 (p, J=7.5 Hz, 2H, 5'-H) 1.55-1.45 (m, 10H, 7ax-H, —C(CH$_3$)$_2$—, 6-Me, especially, 1.50, s, 3H, —C(CH$_3$)$_2$— and 1.49, s, 3H, —C(CH$_3$)$_2$— and 1.47, s, 3H, 6-Me), 1.12 (s, 3H, 6-Me). Mass spectrum (ESI) m/z (relative intensity) 460 (M$^+$+H, 100). Exact mass (ESI) calculated for C$_{26}$H$_{38}$NO$_6$ (M$^+$+H), 460.2699; found 460.2692. LC/MS analysis (Waters MicroMass ZQ system) showed purity 98.7% and retention time 3.9 min for the title compound.

S-Butyl 2-((6aR,10aR)-1-hydroxy-6,6-dimethyl-9-oxo-6a,7,8,9,10,10a-hexahydro-6H-benzo[c]chromen-3-yl)-2-methylpropanethioate (34 h)

The synthesis was carried out as described for 32 using 33 h (32 mg, 0.06 mmol), tetrabutylammonium fluoride (0.10 ml, 0.10 mmol) and dry THF (1.5 ml). Purification by flash column chromatography on silica gel (30% ethyl acetate in hexane) gave title compound 34h (22 mg, 92% yield) as a colorless oil. $^1$H NMR (500 MHz, CDCl$_3$) δ 6.44 (d, J=1.5 Hz, 11H, Ar—H), 6.28 (d, J=1.5 Hz, 11H, Ar—H), 5.82 (s, 1H, OH), 3.93 (ddd, J=15.0 Hz, J=3.5 Hz, J=2.0 Hz, 1H, 10eq-H), 2.88 (m as td, J=12.5 Hz, J=3.5 Hz, 1H, 10a-H), 2.80 (t, J=7.5 Hz, 2H, 4'-H), 2.64-2.56 (m, 1H, 8eq-H), 2.50-2.39 (m, 1H, 8ax-H), 2.20-2.10 (m, 2H, 10ax-H, 7eq-H), 1.96 (m as td, J=12.0 Hz, J=3.0 Hz, 1H, 6a-H), 1.56 (s, 3H, —C(CH$_3$)$_2$—), 1.54 (s, 3H, —C(CH$_3$)$_2$—), 1.52-1.45 (m, 5H, 7ax-H, 5'-H, 6-Me, 1.47, s, 3H, 6-Me), 1.34 (sextet, J=7.5 Hz, 2H, 6'-H), 1.12 (s, 3H, 6-Me), 0.88 (t, J=7.0 Hz, 3H, 7-H). Mass spectrum (ESI) m/z (relative intensity) 405 (M$^+$+H, 100). Exact mass (ESI) calculated for C$_{23}$H$_{33}$O$_4$S (M$^+$+H), 405.2100; found 405.2089. LC/MS analysis (Waters MicroMass ZQ system) showed purity 99.2% and retention time 5.1 min for the title compound.

N-Butyl-2-((6aR,10aR)-1-hydroxy-6,6-dimethyl-9-oxo-6a,7,8,9,10,10a-hexahydro-6H-benzo[c]chromen-3-yl)-2-methylpropanamide (34i)

The synthesis was carried out as described for 32 using 33i (32 mg, 0.07 mmol), tetrabutylammonium fluoride (0.10 ml, 0.10 mmol) and dry THF (1.5 ml). Purification by flash column chromatography on silica gel (30% ethyl acetate in hexane) gave title compound 34i (22 mg, 91% yield) as a colorless oil. $^1$H NMR (500 MHz, CDCl$_3$) δ 6.43 (d, J=2.0 Hz, 1H, Ar—H), 6.28 (d, J=1.5 Hz, 1H, Ar—H), 3.97 (ddd, J=15.0 Hz, J=3.5 Hz, J=2.0 Hz, 1H, 10eq-H), 3.19-3.09 (m, 2H, 4'-H), 2.90 (m as td, J=12.5 Hz, J=3.5 Hz, 1H, 10a-H), 2.64-2.56 (m, 1H, 8eq-H), 2.49-2.39 (m, 1H, 8ax-H), 2.16-2.07 (m, 2H, 10ax-H, 7eq-H), 1.96 (m as td, J=12.0 Hz, J=3.0 Hz, 1H, 6a-H), 1.58-1.44 (m, 10H, 7ax-H, —C(CH$_3$)$_2$—, 6-Me, especially 1.49, s, —C(CH$_3$)$_2$— and 1.48, s, —C(CH$_3$)$_2$— and 1.47, s, 6-Me), 1.40-1.31 (m, 2H, 5'-H), 1.20 (sextet, J=7.5 Hz, 2H, 6'-H), 1.14 (s, 3H, 6-Me), 0.82 (t, J=7.5 Hz, 3H, 7-H).). Mass spectrum (ESI) m/z (relative intensity) 388 (M$^+$+H, 100). Exact mass (ESI) calculated for C$_{23}$H$_{34}$NO$_4$ (M$^+$+H), 388.2428; found 388.2480. LC/MS analysis (Waters MicroMass ZQ system) showed purity 98.9% and retention time 4.5 min for the title compound.

4-Bromobutyl 2-((6aR,10aR)-1-((tert-butyldimethylsilyl)oxy)-6,6-dimethyl-9-oxo-6a,7,8,9,10,10a-hexahydro-6H-benzo[c]chromen-3-yl)-2-methylpropanoate (35)

The synthesis was carried out as described for 33a using 31 (200 mg, 0.45 mmol), DMAP (330 mg, 2.70 mmol), EDCI (345 mg, 1.80 mmol), 4-bromo-1-butanol (275 mg, 1.80 mmol) and dry CH$_2$Cl$_2$ (6.5 ml). Purification by flash column chromatography on silica gel (20% ethyl acetate in hexane) gave title compound 35 (200 mg, 77% yield) as a colorless oil. $^1$H NMR (500 MHz, CDCl$_3$) δ 6.45 (d, J=2.0 Hz, 1H, Ar—H), 6.33 (d, J=2.0 Hz, 1H, Ar—H), 4.14-4.01 (m, 2H, 4'-H), 3.75 (ddd, J=15.0 Hz, J=3.5 Hz, J=2.0 Hz, 1H, 10eq-H), 3.31 (t, J=7.0 Hz, 3H, 7'-H), 2.71 (m as td, J=12.5 Hz, J=3.5 Hz, 1H, 10a-H), 2.60-2.52 (m, 1H, 8eq-H), 2.46-2.36 (m, 1H, 8ax-H), 2.18-2.04 (m, 2H, 10ax-H, 7eq-H), 1.93 (m as td, J=12.0 Hz, J=3.0 Hz, 1H, 6a-H), 1.84-1.79 (m, 2H, 5'-H), 1.78-1.68 (m, 2H, 6'-H), 1.52-1.48 (m, 7H, 7ax-H, —C(CH$_3$)$_2$—, especially, 1.50, s, —C(CH$_3$)$_2$— and 1.49, s, —C(CH$_3$)$_2$—), 1.46 (s, 3H, 6-Me), 1.09 (s, 3H, 6-Me), 0.99 (s, 9H, Si(Me)$_2$CMe), 0.24 (s, 3H, Si(Me)$_2$CMe$_3$), 0.16 (s, 3H, Si(Me)$_2$CMe$_3$). LC/MS analysis (Waters MicroMass ZQ system) showed purity 98.9% and retention time 6.1 min for the title compound.

4-Bromobutyl 2-((6aR,10aR)-1-hydroxy-6,6-dimethyl-9-oxo-6a,7,8,9,10,10a-hexahydro-6H-benzo[c]chromen-3-yl)-2-methylpropanoate (36)

The synthesis was carried out as described for 32 using 35 (100 mg, 0.17 mmol), tetrabutylammonium fluoride (0.26 ml, 0.26 mmol) and dry THF (4.3 ml). Purification by flash column chromatography on silica gel (30% ethyl acetate in hexane) gave title compound 36 (78 mg, 95% yield) as a white solid. 1H NMR (500 MHz, CDCl$_3$) δ 6.52 (s, 1H, OH), 6.40 (d, J=1.5 Hz, 1H, Ar—H), 6.31 (d, J=2.0 Hz, 1H, Ar—H), 4.09 (t, J=6.0 Hz, 2H, 4'-H), 3.99 (ddd, J=15.0 Hz, J=3.5 Hz, J=2.0 Hz, 1H, 10eq-H), 3.32 (t, J=6.5 Hz, 3H, 7'-H), 2.88 (m as td, J=12.5 Hz, J=3.5 Hz, 1H, 10a-H), 2.66-2.58 (m, 1H, 8eq-H), 2.52-2.41 (m, 1H, 8ax-H), 2.21-2.11 (m, 2H, 10ax-H, 7eq-H), 1.97 (m as td, J=12.0 Hz, J=3.0 Hz, 1H, 6a-H), 1.84-1.77 (m, 2H, 5'-H), 1.76-1.70 (m, 2H, 6'-H), 1.53-1.49 (m, 7H, 7ax-H, —C(CH$_3$)$_2$—, especially, 1.51, s, —C(CH$_3$)$_2$— and 1.50, s, —C(CH$_3$)$_2$—), 1.47 (s, 3H, 6-Me), 1.12 (s, 3H, 6-Me). LC/MS analysis (Waters MicroMass ZQ system) showed purity 99.6% and retention time 4.9 min for the title compound.

4-Azidobutyl 2-((6aR,10aR)-1-hydroxy-6,6-dimethyl-9-oxo-6a,7,8,9,10,10a-hexahydro-6H-benzo[c]chromen-3-yl)-2-methylpropanoate (37)

The synthesis was carried out as described for 9 using 36 (40 mg, 0.11 mmol), $CH_2Cl_2/CH_3NO_2$ (3:1 mixture, 1.8 ml) and tetrabutylammonium azide (915 mg, 3.21 mmol). Purification by flash column chromatography on silica gel (40% ethyl acetate in hexane) gave title compound 37 (28 mg, 80% yield) as a white solid. $^1$H NMR (500 MHz, $CDCl_3$) δ 6.41 (d, J=2.0 Hz, 1H, Ar—H), 6.28 (d, J=2.0 Hz, 1H, Ar—H), 4.10 (t, J=6.0 Hz, 2H, 4'-H), 3.95 (ddd, J=15.0 Hz, J=3.5 Hz, J=2.0 Hz, 1H, 10eq-H), 3.23 (t, J=7.0 Hz, 3H, 7'-H), 2.88 (m as td, J=12.5 Hz, J=3.5 Hz, 1H, 10a-H), 2.65-2.57 (m, 1H, 8eq-H), 2.51-2.40 (m, 1H, 8ax-H), 2.21-2.10 (m, 2H, 10ax-H, 7eq-H), 1.96 (m as td, J=12.0 Hz, J=3.0 Hz, 1H, 6a-H), 1.72-1.64 (m, 2H, 5'-H), 1.57-1.48 (m, 9H, 7ax-H, 6'-H, —C(CH$_3$)$_2$—, especially, 1.51, s, —C(CH$_3$)$_2$— and 1.50, s, —C(CH$_3$)$_2$—), 1.47 (s, 3H, 6-Me), 1.12 (s, 3H, 6-Me). Mass spectrum (ESI) m/z (relative intensity) 430 (M$^+$+H, 100). Exact mass (ESI) calculated for $C_{23}H_{32}N_3O_5$ (M$^+$+H), 430.2342; found 430.2330. LC/MS analysis (Waters MicroMass ZQ system) showed purity 99.1% and retention time 4.9 min for the title compound.

4-Isothiocyanatobutyl 2-((6aR,10aR)-1-hydroxy-6,6-dimethyl-9-oxo-6a,7,8,9,10,10a-hexahydro-6H-benzo[c]chromen-3-yl)-2-methylpropanoate (38)

The synthesis was carried out as described for 10 using 37 (28 mg, 0.06 mmol), triphenyl phosphine (86 mg, 0.32 mmol), carbon disulfide (137 mg, 1.80 mmol) and dry THF (1.2 ml). Purification by flash column chromatography on silica gel (35% ethyl acetate in hexane) gave title compound 38 (20 mg, 71% yield) as a white solid. $^1$H NMR (500 MHz, $CDCl_3$) δ 7.11 (s, 1H, OH), 6.39 (d, J=2.0 Hz, 1H, Ar—H), 6.34 (d, J=2.0 Hz, 1H, Ar—H), 4.10 (m as td, J=6.5 Hz, J=2.0 Hz, 2H, 4'-H), 4.05 (ddd, J=15.0 Hz, J=3.5 Hz, J=2.0 Hz, 1H, 10eq-H), 3.40 (t, J=7.0 Hz, 3H, 7'-H), 2.90 (m as td, J=12.5 Hz, J=3.5 Hz, 1H, 10a-H), 2.67-2.58 (m, 1H, 8eq-H), 2.55-2.43 (m, 1H, 8ax-H), 2.23-2.10 (m, 2H, 10ax-H, 7eq-H), 1.99 (m as td, J=12.0 Hz, J=3.0 Hz, 1H, 6a-H), 1.75-1.67 (m, 2H, 5'-H), 1.66-1.59 (m, 2H, 6'-H), 1.58-1.49 (m, 7H, 7ax-H, —C(CH$_3$)$_2$—, especially, 1.52, s, —C(CH$_3$)$_2$— and 1.51, s, —C(CH$_3$)$_2$—), 1.48 (s, 3H, 6-Me), 1.12 (s, 3H, 6-Me). Mass spectrum (ESI) m/z (relative intensity) 446 (M$^+$+H, 100). Exact mass (ESI) calculated for $C_{24}H_{32}NO_5S$ (M$^+$+H), 446.2001; found 446.1992. LC/MS analysis (Waters MicroMass ZQ system) showed purity 98.8% and retention time 5.0 min for the title compound.

4-(Nitrooxy)butyl 2-((6aR,10aR)-1-hydroxy-6,6-dimethyl-9-oxo-6a,7,8,9,10,10a-hexahydro-6H-benzo[c]chromen-3-yl)-2-methylpropanoate (39)

To a stirred solution of 36 (22 mg, 0.05 mmol) in acetonitrile (1.25 ml) at 70° C., silver nitrate (120 mg, 0.70 mmol) was added. The reaction was stirred continuously for 24 h at the same temperature. Upon completion, the reaction mixture was diluted with acetonitrile and filtered. The solute was concentrated under vacuum followed by addition of ethyl acetate and water. The organic layer was concentrated under vacuum and the residue was chromatographed on silica gel (40% ethyl acetate in hexane) to give 39 (16 mg, 75% yield) as a white solid. $^1$H NMR (500 MHz, $CDCl_3$) δ 6.40 (d, J=1.5 Hz, 1H, Ar—H), 6.27 (d, J=1.5 Hz, 1H, Ar—H), 6.00 (s, 1H, OH), 4.36 (t, J=6.0 Hz, 2H, 4'-H), 4.13-4.08 (m, 2H, 7'-H), 3.94 (ddd, J=15.0 Hz, J=3.5 Hz, J=2.0 Hz, 1H, 10eq-H), 2.88 (m as td, J=12.5 Hz, J=3.5 Hz, 1H, 10a-H), 2.64-2.56 (m, 1H, 8eq-H), 2.50-2.40 (m, 1H, 8ax-H), 2.20-2.11 (m, 2H, 10ax-H, 7eq-H), 1.95 (m as td, J=12.0 Hz, J=3.0 Hz, 1H, 6a-H), 1.73-1.63 (m, 4H, 5'-H, 6'-H), 1.54-1.49 (m, 7H, 7ax-H, —C(CH$_3$)$_2$—, especially, 1.51, s, —C(CH$_3$)$_2$— and 1.50, s, —C(CH$_3$)$_2$—), 1.47 (s, 3H, 6-Me), 1.11 (s, 3H, 6-Me). Mass spectrum (ESI) m/z (relative intensity) 450 (M$^+$+H, 100). Exact mass (ESI) calculated for $C_{23}H_{32}NO_8$ (M$^+$+H), 450.2128; found 450.2122. LC/MS analysis (Waters MicroMass ZQ system) showed purity 99.3% and retention time 4.9 min for the title compound.

Analgesia Assay. C57BL6/J mice (Jackson Laboratories, Bar Harbor Maine) were single housed at least 1 h before start of experiment. Food and water were removed immediately before the first injection.

The test compounds were dissolved in a solution of ethanol:emulphor:saline (1:1:18) in several concentrations. $\Delta^9$-THC was dissolved in a solution of ethanol:emulphor:saline (1:1:18) in concentrations of 0.3 mg/ml (i.e., 3 mg/kg), 0.7 mg/ml, (i.e., 7 mg/kg), 2 mg/ml (i.e., 20 mg/kg), and 7 mg/ml (i.e., 70 mg/kg), which resulted in cumulative doses of 3, 10, 30, and 100 mg/kg. Route of administration=i.p. Volume=1 mL/100 g body weight.

Tail withdrawal test: 52° C. water bath (use bags). Bag was made of stapled surgery sheets to form a small pocket the size of a mouse. Mouse was placed head first into bag gently and the bag was pinched securely to ensure the mouse did not turn around, but not forcefully enough to be squeezing the mouse. The tip of the mouse's tail was dipped into the warm water, with 1 cm submerged. Time for the mouse to flick its tail or exhibit a gross tail movement such that it is no longer submerged was recorded; gross body movements were not considered a tail-flick.

Hypothermia Assay. C57BL/6 J mice (Charles River Breeding Laboratories, Wilmington, MA, USA) weighing 30 to 35 g were group housed five to a cage, in a temperature-controlled (20° C.) animal facility. Mice were habituated to the animal facility for at least 1 week prior to experiments with a 12-h light/dark cycle (lights are on at 7:00 AM). Mice were given free access to food and water. Experimentally naïve mice were used for each dose condition, and the mice were tested during the light phase.

Rectal temperature was measured in mice using a rectal probe of a digital laboratory thermometer, RET-3-ISO, type T thermocouple (Physitemp Instruments Inc, Clifton, NJ). The lubricated probe was inserted approximately 2.0 cm into the rectum for approximately 30 seconds prior to each recording. Rectal temperature recordings were taken from each mouse prior to dosing along with 20, 60, 180, 240, 360 and 1440-min post injection.

Discussion. The compounds of Formula (Ie) can bind to and modulate (e.g., activate) the cannabinoid CB1/CB2 receptors and, thus, they are specific ligands for these receptors. Some of the compounds that bound to cannabinoid CB1 and CB2 receptors also exhibited agonist activities for these receptors.

Compounds of Formula (Ie) exhibit "controlled deactivation" because they possess structural features that allow precise control of metabolic breakdown of the molecule as well as its polar characteristics (another major parameter responsible for tissue distribution and retention of the drug molecule), and, therefore, these structural features allow control of duration of the pharmacological effects elicited by that molecule via its interaction with cannabinoid receptors.

The structural features encompassed in the "controlled deactivation" cannabinoids are at least threefold. Thus, the compounds of Formula (Ie) possess a "metabolically vulnerable" group that is subjected to cleavage (hydrolysis) by hydrolyzing enzymes (for example, esterases, found in the body of an individual or animal, or tissue preparation). Variable A of Formulas (Id) and (Ie) corresponds to the "metabolically vulnerable" group in compounds of Formulas (Id) and (Ie). Compounds of Formula (Ie) also possess a "steric environment" in the vicinity of the "metabolically vulnerable" group. Changes to the steric environment can speed up or slow down the hydrolysis of the "metabolically vulnerable" group by enzymes. See and compare, for example, the steric environments surrounding the "metabolically vulnerable" ester group in compounds 34e, 34f, 18, 23, AM8137, and 3.4. Finally, many compounds of Formula (Ie) possess groups with increased polarity (for example, CN, ONO$_2$, and morpholino groups, see analogs 8, 39, 34g and compare their c Log P and tPSA values). These groups, when incorporated into the structure of the parent molecule decreased the lipophilicity of the parent cannabinoid and, thus, enhanced the druggability profile of the molecule because higher polarity of a drug molecule is connected to higher water solubility and higher exposure and effectiveness of the drug. Higher polarity of a drug also affected the duration of the action of the drug. For example, higher polarity reduced the depot effect (residency in adipose tissue, and plasma) and, therefore, the duration of the action of the cannabinoid drug.

Combinations of the above structural features in one molecule did not impair the biological activity and the in vitro pharmacological potency of that molecule for the cannabinoid CB1 and CB2 receptors. In contrast, they increased binding affinities and agonist potencies, as can be seen from the Ki and EC$_{50}$ values of the compounds presented in Tables 9 and 10.

Thus, it is expected from at least the in vivo data in the rodent models, that when administered in a therapeutically effective amount to an individual or animal, compounds of Formula (Ie) will result in a sufficiently high level of that compound in the individual or animal to cause a physiological response. The physiological response may be useful to treat a number of (patho)physiological conditions, such as those disclosed herein, as well as others in which the cannabinoid system is implicated.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention. Those skilled in the art will recognize, or be able to ascertain, using no more than routine experimentation, numerous equivalents to the specific embodiments described specifically in this disclosure. Such equivalents are intended to be encompassed in the scope of the following claims.

All publications, patent applications, patents, and other references mentioned herein are incorporated by reference in their entirety. The patent and scientific literature referred to herein establishes knowledge that is available to those skilled in the art. The issued patents, applications, and other publications that are cited herein are hereby incorporated by reference to the same extent as if each was specifically and individually indicated to be incorporated by reference. In the case of inconsistencies, the present disclosure will prevail.

The invention claimed is:

1. A compound of Formula (Ic):

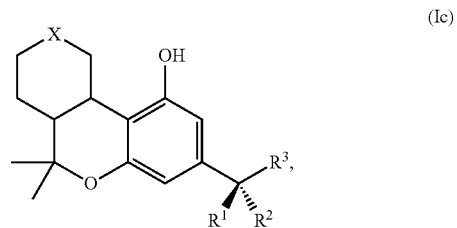

or a pharmaceutically acceptable salt thereof, wherein:
X is —C(O)—, —CH(OH)—, —C(O)O—, —OC(O)— or —CH(CH$_2$OH)—;
R$^1$ and R$^2$ are independently H or methyl, or R$^1$ and R$^2$ together with the carbon to which they are attached form a —(C$_3$-C$_6$)-cycloalkyl;
R$^3$ is —C(O)OR$^4$, —(C$_1$-C$_3$ alkyl)-C(O)OR$^4$, —C(O)SR$^4$, —C(O)N(R$^6$)R$^4$, —OC(O)R$^4$ or —(C$_1$-C$_3$ alkyl)-OC(O)R$^4$;
R$^4$ is —(C$_1$-C$_8$)-alkyl-R$^5$, —(C$_1$-C$_8$)-alkenyl-R$^5$, or —(C$_1$-C$_8$)-alkynyl-R$^5$;
R$^5$ is H, halogen, —OH, —O—(C$_1$-C$_6$)-alkyl, —O—(C$_1$-C$_6$)-alkenyl, —O—(C$_1$-C$_6$)-alkynyl, —CN, —N$_3$, —NCS, —SO$_2$NH$_2$, —SO$_2$CF$_3$, imidazole, oxazole, isoxazole, 1,2,3-triazole, 1,2,4-triazole, morpholine, thiomorpholine,

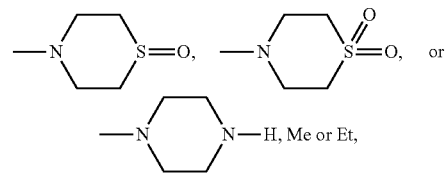

wherein —O—(C$_1$-C$_6$)-alkyl, —O—(C$_1$-C$_6$)-alkenyl, and —O—(C$_1$-C$_6$)-alkynyl are optionally substituted with —CN, —N$_3$ or —NCS; and
R$^6$ is H or —(C$_1$-C$_2$)-alkyl.

2. The compound of claim 1, wherein X is —C(O)—.

3. The compound of claim 1, wherein R$^1$ and R$^2$ are each methyl.

4. The compound of claim 1, wherein R$^1$ and R$^2$ together with the carbon to which they are attached for a —(C$_3$-C$_6$)-cycloalkyl.

5. The compound of claim 1, wherein R$^3$ is —C(O)OR$^4$ or —(C$_1$-C$_3$ alkyl)-C(O)OR$^4$.

6. The compound of claim 1, wherein R$^3$ is —C(O)OR$^4$.

7. The compound of claim 1, wherein R$^4$ is —(C$_1$-C$_8$)-alkyl-R$^5$.

8. The compound of claim 1, wherein R$^5$ is halogen, —OH, —O—(C$_1$-C$_6$)-alkyl, —O—(C$_1$-C$_6$)-alkenyl, —O—(C$_1$-C$_6$)-alkynyl, —CN, —N$_3$, —NCS, —SO$_2$NH$_2$, —SO$_2$CF$_3$, imidazole oxazole, isoxazole, 1,2,3-triazole, 1,2,4-triazole, morpholine, thiomorpholine,

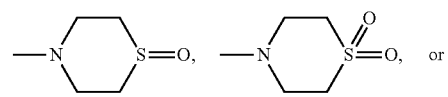

-continued

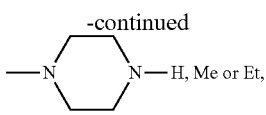

wherein —O—($C_1$-$C_6$)-alkyl, —O—($C_1$-$C_6$)-alkenyl, and —O—($C_1$-$C_6$)-alkynyl are optionally substituted with —CN, —$N_3$ or —NCS.

9. The compound of claim 7, wherein $R^5$ is halogen, —CN, —$N_3$, imidazole, oxazole, isoxazole, 1,2,3-triazole, or 1,2,4-triazole.

10. A pharmaceutical formulation comprising a compound of claim 1, or a pharmaceutically acceptable salt thereof, and a pharmaceutically acceptable carrier.

11. A method of modulating a cannabinoid receptor in a subject, comprising administration of a compound of claim 1, or a pharmaceutically acceptable salt thereof, to the subject.

12. A method of treating cannabinoid dependence, pain, inflammation, a neuropathy, a neurodegenerative disease, an anxiety disorder, a motor function disorder, a fertility disorder, a gastrointestinal disorder, an appetite disorder, a metabolic disorder, a movement disorder, or cancer in a subject comprising administration of a therapeutically effective amount of a compound of claim 1, or a pharmaceutically acceptable salt thereof, to the subject.

13. A method of treating brain trauma or post-traumatic stress disorder in a subject, comprising administration of a therapeutically effective amount of a compound of claim 1, or a pharmaceutically acceptable salt thereof, to the subject.

14. A method of treating a sleep disorder in a subject, comprising administration of a therapeutically effective amount of a compound of claim 1, or a pharmaceutically acceptable salt thereof, to the subject.

15. A compound of Formula (Id):

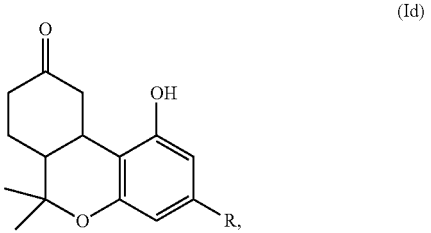

or a pharmaceutically acceptable salt thereof, wherein:
R is

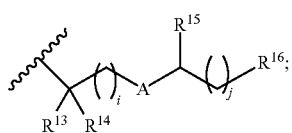

A is —C(O)—O—, —O—C(O)—, —C(O)—S—, —S—C(O)—, —C(O)—NH—, —NH—C(O)—, —NHSO$_2$—, or —SO$_2$—NH—;
$R^{13}$ and $R^{14}$ are independently H, methyl or fluoro, or $R^{13}$ and $R^{14}$ together with the carbon to which they are attached form a ($C_3$-$C_6$)cycloalkyl or ($C_3$-$C_6$)heterocyclyl containing one or two heteroatoms independently selected from O, S or N, wherein each N, when present, is optionally and independently substituted with methyl;

$R^{15}$ is H, fluoro, methyl or ethyl;
$R^{16}$ is H, halo, ($C_1$-$C_3$)alkyl, ($C_1$-$C_3$)haloalkyl, —NCS, —$N_3$, —CN, —$NO_2$, —$ONO_2$, —$SO_2F$, —OH, —O—($C_1$-$C_6$)alkyl, —SH, —S—($C_1$-$C_6$)alkyl, —$NH_2$, —N(H)($C_1$-$C_6$)alkyl, —N[($C_1$-$C_6$)alkyl]2, or ($C_3$-$C_6$) heterocyclyl;
i is 0, 1, 2, 3, 4 or 5; and
j is 0, 1, 2, 3, 4, 5 or 6.

16. The compound of claim 15, having Formula (Ie):

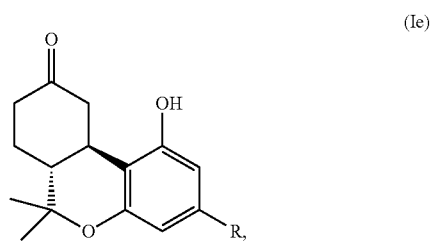

or a pharmaceutically acceptable salt thereof.

17. The compound of claim 15, wherein $R^{13}$ and $R^{14}$ are each methyl.

18. The compound of claim 15, wherein $R^{13}$ and $R^{14}$ together with the carbon to which they are attached form a —($C_3$-$C_6$)-cycloalkyl.

19. The compound of claim 15, wherein $R^{15}$ is H or methyl.

20. The compound of claim 15, wherein $R^{16}$ is halo, ($C_1$-$C_3$)alkyl, ($C_1$-$C_3$)haloalkyl, —NCS, —$N_3$, —CN, —$NO_2$, —$ONO_2$, —$SO_2F$, —OH, —O—($C_1$-$C_6$)alkyl, —SH, —S—($C_1$-$C_6$)alkyl, —$NH_2$, —N(H)($C_1$-$C_6$)alkyl, —N[($C_1$-$C_6$)alkyl]$_2$, or ($C_3$-$C_6$)heterocyclyl.

21. The compound of claim 15, wherein $R^{16}$ is H, halo, —NCS, —$N_3$, —CN, —$ONO_2$, or saturated ($C_3$-$C_6$)heterocyclyl.

22. The compound of claim 15, wherein $R^{16}$ is halo, —NCS, —$N_3$, —CN, —$ONO_2$, or saturated ($C_3$-$C_6$)heterocyclyl.

23. The compound of claim 15, wherein i is 0.

24. The compound of claim 15, wherein j is 1, 2, 3, 4 or 5.

25. The compound of claim 15, wherein A is —C(O)—O— or —C(O)—S—.

26. The compound of claim 25, wherein A is —C(O)—O—.

27. A pharmaceutical formulation comprising a compound of claim 15, or a pharmaceutically acceptable salt thereof, and a pharmaceutically acceptable carrier.

28. A method of modulating a cannabinoid receptor in a subject, comprising administration of a compound of claim 15, or a pharmaceutically acceptable salt thereof, to the subject.

29. A method of treating pain; central pain; peripheral pain; neuropathic pain; a neuropathy; inflammatory pain; diabetes; a neurodegenerative disease; multiple sclerosis; Parkinson's disease; Huntington's chorea; Alzheimer's disease; amyotrophic lateral sclerosis; a mental disorder; schizophrenia; depression; a mood disorder; an addiction disorder; a sleep disorder; a memory disorder; a gastrointestinal motility disorder; irritable bowel syndrome; diarrhea; dyskinesia; migraine; headache; brain injury; traumatic brain injury; post-traumatic stress disorder, osteoporosis; osteoarthritis; high blood pressure disease or hypertension; peripheral vascular disease; coronary artery disease; abnormal heart rate; cardiac insufficiency; pulmonary hypertension; ocular hypertension or glaucoma; endotoxic shock; hypotensive shock; an appetite disorder; an immune system disorder; a fertility disorder; a disease associated with motor dysfunction; Tourette's syndrome; inflammation; a neurological disorder; epilepsy; nausea; nausea associated with cancer chemotherapy; AIDS wasting syndrome; or cancer in a subject, comprising administration of a therapeutically effective amount of a compound of claim 15, or a pharmaceutically acceptable salt thereof, to the subject.

30. A compound having the following structural formula:

AM10811

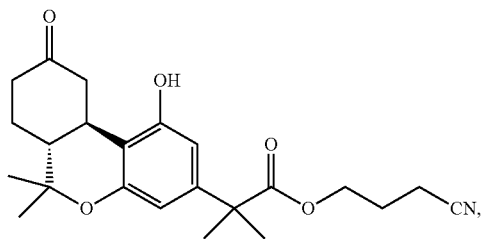

or a pharmaceutically acceptable salt thereof.

* * * * *